US007449576B1

(12) United States Patent
Pennell et al.

(10) Patent No.: US 7,449,576 B1
(45) Date of Patent: Nov. 11, 2008

(54) SUBSTITUTED PIPERAZINES

(75) Inventors: Andrew M.K. Pennell, San Francisco, CA (US); James B. Aggen, Burlingame, CA (US); J.J. Kim Wright, Redwood City, CA (US); Subrabrata Sen, Sunnyvale, CA (US); Brian E. McMaster, Mountain View, CA (US); Daniel Joseph Dairaghi, Palo Alto, CA (US)

(73) Assignee: ChemoCentryx, Inc., Mountain View, CA (US)

( * ) Notice: Subject to any disclaimer, the term of this patent is extended or adjusted under 35 U.S.C. 154(b) by 0 days.

(21) Appl. No.: 11/491,540

(22) Filed: Jul. 21, 2006

Related U.S. Application Data

(62) Division of application No. 10/460,752, filed on Jun. 11, 2003, now Pat. No. 7,157,464.

(60) Provisional application No. 60/453,711, filed on Jun. 12, 2002.

(51) Int. Cl.
*C07D 401/12* (2006.01)
*C07D 403/12* (2006.01)

(52) U.S. Cl. ................ 544/238; 544/295; 544/357; 544/364

(58) Field of Classification Search ................ None
See application file for complete search history.

(56) References Cited

U.S. PATENT DOCUMENTS

| | | |
|---|---|---|
| 3,362,956 A | 1/1968 | Archer |
| 3,478,032 A | 11/1969 | Arya |
| 3,491,098 A | 1/1970 | Archer |
| 3,723,433 A | 3/1973 | Ueno et al. |
| 3,950,354 A | 4/1976 | Wenzelburger et al. |
| 3,994,890 A | 11/1976 | Fujimura et al. |
| 4,166,452 A | 9/1979 | Generales, Jr. |
| 4,174,393 A | 11/1979 | Van Daalen et al. |
| 4,256,108 A | 3/1981 | Theeuwes |
| 4,265,874 A | 5/1981 | Bonsen et al. |
| 4,310,429 A | 1/1982 | Lai |
| 4,442,102 A | 4/1984 | Heinemann et al. |
| 4,547,505 A | 10/1985 | Oepen et al. |
| 4,559,341 A | 12/1985 | Petersen et al. |
| 4,562,189 A | 12/1985 | Tomcufcik et al. |
| 4,672,063 A | 6/1987 | Jasserand et al. |
| 4,772,604 A | 9/1988 | van Wijngaarden et al. |
| 4,880,809 A | 11/1989 | Sugihara et al. |
| 4,997,836 A | 3/1991 | Sugihara et al. |
| 5,011,928 A | 4/1991 | Venero et al. |
| 5,177,078 A | 1/1993 | Ward et al. |
| 5,215,989 A | 6/1993 | Baldwin et al. |
| 5,227,486 A | 7/1993 | Merce-Vidal et al. |
| 5,292,739 A | 3/1994 | Merce-Vidal et al. |
| 5,346,896 A | 9/1994 | Ward et al. |
| 5,382,586 A | 1/1995 | Merce-Vidal et al. |
| 5,464,788 A | 11/1995 | Bock et al. |
| 5,580,985 A | 12/1996 | Lee et al. |
| 5,607,936 A | 3/1997 | Chiang et al. |
| 5,646,151 A | 7/1997 | Kruse et al. |
| 5,681,954 A | 10/1997 | Yamamoto et al. |
| 5,719,156 A | 2/1998 | Shue et al. |
| 5,756,504 A | 5/1998 | Bock et al. |
| 5,760,028 A | 6/1998 | Jadhav et al. |
| 5,760,225 A | 6/1998 | Yuan |
| 5,780,475 A | 7/1998 | Baker et al. |
| 5,798,359 A | 8/1998 | Shue et al. |
| 5,968,938 A | 10/1999 | Williams et al. |
| 6,043,246 A | 3/2000 | Fukami et al. |
| 6,114,334 A | 9/2000 | Kerrigan et al. |
| 6,191,159 B1 | 2/2001 | Pinto |
| 6,207,665 B1 | 3/2001 | Bauman et al. |
| 6,288,083 B1 | 9/2001 | Luly et al. |
| 6,329,385 B1 | 12/2001 | Luly et al. |
| 6,372,746 B1 * | 4/2002 | Corbera-Arjona et al. .............. 514/252.14 |
| 6,384,035 B1 | 5/2002 | Hutchings et al. |
| 6,451,399 B1 | 9/2002 | Boyce |
| 6,455,544 B1 | 9/2002 | Friedhoff et al. |

(Continued)

FOREIGN PATENT DOCUMENTS

EP      0 479 546 A2     4/1992

(Continued)

OTHER PUBLICATIONS

Badran, M. et al., "Indazole derivatives (part III): synthesis of pyrazolo-[1,2-a]indazole-1,9-dione,[1,2,4]triazino[1,2-a]indazole-1, 10-dione, 3-(Indazol-1-yl)propionic acid amides and hydrazides possessing potential biological activity" *Alex. J. Pharm. Sci.* (1999) 13(2):101-106.

Bebernitz, G. et al., "The effect of 1,3-diaryl-[1H]-pyrazole-4-acetamides on glucose utilization in on/ob mice" *J. Med. Chem.* (2001) 44:2601-2611.

Czarnocka_Janowicz, A. et al., "Synthesis and pharmacological activity of 5-substituted-s-triazole-3-thiols" *Pharmazie* (1991) 46:109-112.

Database Crossfire Beilstein 'Online! Beilstein Institut zur Forderung der Chemischen Wissenschaften, Frankfurt am Main, DE; Database accession No. BRN 6982047 XP002254060 abstract & Varasi et al., Farmaco Ed. Sci. (1987) 42(6):425-436.

(Continued)

*Primary Examiner*—Emily Bernhardt
(74) *Attorney, Agent, or Firm*—Townsend and Townsend and Crew LLP

(57) ABSTRACT

Compounds are provided that act as potent antagonists of the CCR1 receptor, and which have been further confirmed in animal testing for inflammation, one of the hallmark disease states for CCR1. The compounds are generally aryl piperazine derivatives and are useful in pharmaceutical compositions, methods for the treatment of CCR1-mediated diseases, and as controls in assays for the identification of competitive CCR1 antagonists.

7 Claims, 20 Drawing Sheets

U.S. PATENT DOCUMENTS

| | | | |
|---|---|---|---|
| 6,469,041 | B2 | 10/2002 | Yuan |
| 6,492,375 | B2 | 12/2002 | Snutch |
| 6,518,273 | B1 | 2/2003 | Chapman et al. |
| 6,979,686 | B1 | 12/2005 | Naraian et al. |
| 7,157,464 | B2 | 1/2007 | Pennell et al. |
| 2002/0022624 | A1 | 2/2002 | Dinnell et al. |
| 2002/0040020 | A1 | 4/2002 | Bretenbucher et al. |
| 2002/0045613 | A1 | 4/2002 | Pauls et al. |
| 2002/0045749 | A1 | 4/2002 | Lai |
| 2002/0049205 | A1 | 4/2002 | Li et al. |
| 2002/0077321 | A1 | 6/2002 | Khanna et al. |
| 2002/0107255 | A1 | 8/2002 | Bllumberg et al. |
| 2002/0119961 | A1 | 8/2002 | Blumberg et al. |
| 2003/0087917 | A1 | 5/2003 | Starck et al. |
| 2003/0139425 | A1 | 7/2003 | Bauman et al. |
| 2003/0149021 | A1 | 8/2003 | Li et al. |
| 2004/0082571 | A1 | 4/2004 | Pennell et al. |
| 2004/0162282 | A1 | 8/2004 | Pennell et al. |
| 2005/0256130 | A1 | 11/2005 | Pennell et al. |
| 2006/0122234 | A1 * | 6/2006 | Archer et al. ............... 514/342 |
| 2007/0010530 | A1 | 1/2007 | Beavers et al. |

FOREIGN PATENT DOCUMENTS

| | | |
|---|---|---|
| EP | 1 006 110 A1 | 6/2000 |
| WO | WO 97/10219 A1 | 3/1997 |
| WO | WO 97/44329 A1 | 11/1997 |
| WO | WO 98/25617 A1 | 6/1998 |
| WO | WO 98/39000 A1 | 9/1998 |
| WO | WO 98/56771 A2 | 12/1998 |
| WO | WO 99/07351 A2 | 2/1999 |
| WO | WO 99/09984 A1 | 3/1999 |
| WO | WO 99/25686 A1 | 5/1999 |
| WO | WO 99/32468 A1 | 7/1999 |
| WO | WO 99/37619 A1 | 7/1999 |
| WO | WO 99/37651 A1 | 7/1999 |
| WO | WO 00/31032 A1 | 6/2000 |
| WO | WO 00/46195 A1 | 8/2000 |
| WO | WO 00/46196 A1 | 8/2000 |
| WO | WO 00/46197 A1 | 8/2000 |
| WO | WO 00/46198 A1 | 8/2000 |
| WO | WO 00/46199 A1 | 8/2000 |
| WO | WO 00/47539 A1 | 8/2000 |
| WO | WO 00/53600 A1 | 9/2000 |
| WO | WO 00/69815 A1 | 11/2000 |
| WO | WO 00/69820 A1 | 11/2000 |
| WO | WO 00/69848 A1 | 11/2000 |
| WO | WO 02/08221 A3 | 1/2002 |
| WO | WO 02/14314 A2 | 2/2002 |
| WO | WO 02/070523 A1 | 9/2002 |
| WO | WO 03/008395 A1 | 1/2003 |
| WO | WO 03/024450 A1 | 3/2003 |
| WO | WO 03/051842 A2 | 6/2003 |
| WO | WO 03/105853 A1 | 12/2003 |
| WO | WO 2004/009550 A1 | 1/2004 |

OTHER PUBLICATIONS

Database Crossfire Beilstein 'Online! Beilstein Institut zur Forderung der Chemischen Wissenschaften, Frankfurt am Main, DE; Database accession No. BRN 1159762 XP002254062 abstract & Zotta et al. Farmacia (1977) 25:129-134.

Database Crossfire Beilstein 'Online! Beilstein Institut zur Forderung der Chemischen Wissenschaften, Frankfurt am Main, DE; Database accession No. BRN 6000843 XP002254061 abstract & Toja et al., Heterocycles (1987) 26(8):2129-2138.

Database Crossfire Beilstein 'Online! Beilstein Institut zur Forderung der Chemischen Wissenschaften, Frankfurt am Main, DE; Database accession No. BRN 9229443 XP002254063 abstract & Vovk, et al., Russ. J. Org. Chem. (2001) 37(12).

Devries, M. et al., "On the edge: the physiological and pathophysiological role of chemokines during inflammatory and immunological responses" *Sem. Immun.* (1999) 11:95-104.

Fischer, F. et al., "Modulation of experimental autoimmune encephalomyelitis: effect of altered peptide ligand on chemokine and chemokine receptor expression" *J. Neuroimmun.* (2000) 110:195-208.

Foks, H. et al., "Synthesis of new 5-substituted 1,2,4-triazole-3-thione derivatives" *Phosphorus, Sulfur and Silicon* (2000) 164:67-81.

Hayao, S. et al., "New antihypertensive aminoalkyltetrazoles" *J. Med. Chem.* (1967) 10:400-402.

Hcaplus; Accession No. 1984:630511, Document No. 101:230511; Japanese Patent No. 59130890, issued Jul. 27, 1984; Abstract, 4 pages.

Hesselgesser, J. et al., "Identification and characterization of small molecule functional antagonists of the CCR1 chemokine receptor" *J. Biol. Chem.* (1998) 273(25):15687-15692.

Izikson, L. et al., "Resistance to experimental autoimmune encephalomyelitis in mice lacking the CC chemokine receptor $(CCR)_2$" *J. Exp. Med.* (2000) 192(7):1075-1080.

Kennedy, K. et al., "Role of chemokines in the regulation of Th1/Th2 and autoimmune encephalomyelitis" *J. Clin. Immunol.* (1999) 19(5):273-279.

Liang, M. et al., "Species selectivety of a small molecule antagonist for the CCR1 chemokine receptor" *Eur. J. Pharmacol.* (2000) 389:41-49.

Liang, M. et al., "Identification and characterization of a potent, selective, and orally active antagonist of the CC chemokine receptor" *J. Biol. Chem.* (2000) 275(25):19000-19008.

Ng, H. et al., "Discovery of novel non-peptide CCR1 receptor antagonists" *J. Med. Chem.* (1999) 42:4680-4694.

Nicolai, E. et al., "Synthesis and angiotesin II receptor antagonist activity of C-linkedpyrazole derivatives" *Chem. Pharm. Bull.* (1994) 42(8):1617-1630.

Patent Abstracts of Japan, vol. 007, No. 139 (C-171), Jun. 17, 1983 & JP 58 052256 A (Nippon Noyaku KK), Mar. 28, 1983 abstract.

Plater-Zyberk, C. et al., "Effect of a CC chemokine receptor antagonist on collagen induced arthritis in DBA/1 mice" *Ummun. Lett.* (1997) 57:117-120.

Rottman, J. et al., "Leukocyte recruitment during onset of experimental allergic encephalomyelitis is CCR1 dependent" *Eur. J. Immunol.* (2000) 30:2372-2377.

SciFinder Report; Piperazine, 1-[(4-nitro-1H-imidazol-1-yl)acetyl]-4phenyl-(9CI); Registry No. 312707-74-7; Catalogs: STN Chemcats, Exploratory Library, Interchim Intermediates, AsinEx Express Gold Collection, and Pharma Library Collection; report dated Sep. 30, 2003; 7 pages.

SciFinder Report; Piperazine, 1-[(3,5-dimethyl-4-nitro-1H-pyrazol-1-yl)acetyl]-4-(4-fluorophenyl)-(9CI); Registry No. 356039-23-1; Catalogs: STN Chemcats, Exploratory Library, ChemDiv, Inc. Product Library; report dated Sep. 30, 2003; 4 pages.

SciFinder Report; Piperazine, 1-[2-(3,5-dimethyl-4-nitro-1H-pyrazol-1-yl)-1-oxopropyl]-4-phenyl-; Registry No. 489449-56-1; Catologs: Compounds for Screening, Interchim Intermediates; report dated Sep. 30, 2003; 3 pages.

SciFinder Report; Piperazine, 1-[(2,4-dinitro-1H-Imidazol-1-yl)acetyl]-4-(4-fluorophenyl)-; Registry No. 313987-12-1; Catalogs: Exploratory Library, Interchim Intermediates, ChemDiv, Inc. Product Library, AsinEx Express Gold Collection, Pharma Library Collection; report dated Sep. 30, 2003; 7 pages.

SciFinder Report; Piperazine, 1-[(2,4-dinitro-1H-imidazol-1-yl)acetyl]4-phenyl-; Registry No. 313987-13-2; Catalogs: Exploratory Library, Interchim Intermediates, Compounds for Screening, ChemDic, Inc. Product Library, AsinEx Express Gold Collection, Pharma Library Collection; report dated Sep. 30, 2003; 7 pages.

Walsh, D. et al., "Synthesis and antiallergy activity of N-[2-(dimethylamino)ethyl]-4-aryl-1-piperazinecarboxamide derivatives" *J. Med. Chem.* (1990) 33:2028-2032.

U.S. Appl. No. 10/732,897, filed Dec. 9, 2003, Pennell et al.

Anders et al., "A chemokine receptor CCR-1 antagonist reduces renal fibrosis after unilateral ureter ligation." *J Clin Invest.* (2002) 109(2):251-9.

Bendele et al., "Animal models of arthritis: relevance to human disease." Toxicologic Pathol. (1999) 27: 143-142.

Berge et al., "Pharmaceutical Salts." Journal of Pharmaceutical Sciences (1977) 66: 1-19.

Chemcats Database, Chemical Abstracting Service, Accession No. 2003:2855298, Jan. 1, 2004 for CAS Registry No. 492422-98-7.

Chemcats Database, Chemical Abstracting Service, Accession No. 2001:2759474, Oct. 20, 2003 for CAS Registry No. 351986-92-0.

Gao et al., "Targeting of the chemokine receptor CCR1 suppresses development of acute and chronic cardiac allograft rejection." J Clin Invest. (2000) 105(1):35-44.

Monteclaro et al., "The amino-terminal domain of CCR2 is both necessary and sufficient for high affinity binding of monocyte chemoattractant protein 1. Receptor activation by a pseudo-tethered ligand." J Biol Chem. (1997), 272(37): 23186-90.

Podolin et al., "A potent and selective nonpeptide antagonist of CXCR2 inhibits acute and chronic models of arthritis in the rabbit." J Immunol. (2002) 169(11):6435-6444.

Rossi et al., "The biology of chemokines and their receptors." Annu Rev Immunol. (2000) 18:217-42.

Saeki et al., "CCR1 chemokine receptor antagonist." Curr Pharm Des. (2003) 9:1201-1208.

Trentham et al., "Autoimmunity to type II collagen an experimental model of arthritis." J Exp Med (1977) 146(3):857-868.

Tokuda et al., "Pivotal role of CCR1-positive leukocytes in bleomycin-induced lung fibrosis in mice." J Immunol. (2000) 164(5):2745-51.

* cited by examiner

SUBSTITUTED PIPERAZINES

REFERENCE TO RELATED APPLICATIONS

This application is a divisional of U.S. patent application Ser. No. 10/460,752, filed Jun. 11, 2003, now U.S. Pat. No. 7,157,464, which claims the benefit of U.S. Ser. No. 60/453,711, filed Jun. 12, 2002, the disclosures of which are incorporated herein by reference.

STATEMENT AS TO RIGHTS TO INVENTIONS MADE UNDER FEDERALLY SPONSORED RESEARCH OR DEVELOPMENT

This application was supported in part by DARPA Grant No. N65236-99-1-5420. The government of the United States may have certain rights in this application.

REFERENCE TO A "SEQUENCE LISTING," A TABLE, OR A COMPUTER PROGRAM LISTING APPENDIX SUBMITTED ON A COMPACT DISK

Not applicable

BACKGROUND OF THE INVENTION

The present invention provides compounds, pharmaceutical compositions containing one or more of those compounds or their pharmaceutically acceptable salts, which are effective in inhibiting the binding of various chemokines, such as MIP-1α, leukotactin, MPIF-1 and RANTES, to the CCR1 receptor. As antagonists or modulators for the CCR1 receptor, the compounds and compositions have utility in treating inflammatory and immune disorder conditions and diseases.

Human health depends on the body's ability to detect and destroy foreign pathogens that might otherwise take valuable resources from the individual and/or induce illness. The immune system, which comprises leukocytes (white blood cells (WBCs): T and B lymphocytes, monocytes, macrophages granulocytes, NK cell, mast cells, dendritic cell, and immune derived cells (for example, osteoclasts)), lymphoid tissues and lymphoid vessels, is the body's defense system. To combat infection, white blood cells circulate throughout the body to detect pathogens. Once a pathogen is detected, innate immune cells and cytotoxic T cells in particular are recruited to the infection site to destroy the pathogen. Chemokines act as molecular beacons for the recruitment and activation of immune cells, such as lymphocytes, monocytes and granulocytes, identifying sites where pathogens exist.

Despite the immune system's regulation of pathogens, certain inappropriate chemokine signaling can develop and has been attributed to triggering or sustaining inflammatory disorders, such as rheumatoid arthritis, multiple sclerosis and others. For example, in rheumatoid arthritis, unregulated chemokine accumulation in bone joints attracts and activates infiltrating macrophages and T-cells. The activities of these cells induce synovial cell proliferation that leads, at least in part, to inflammation and eventual bone and cartilage loss (see, DeVries, M. E., et al., Semin Immunol 11(2):95-104 (1999)). A hallmark of some demyelinating diseases such as multiple sclerosis is the chemokine-mediated monocyte/macrophage and T cell recruitment to the central nervous system (see, Kennedy, et al., J. Clin. Immunol. 19(5):273-279 (1999)). Chemokine recruitment of destructive WBCs to transplants has been implicated in their subsequent rejection. See, DeVries, M. E., et al., ibid. Because chemokines play pivotal roles in inflammation and lymphocyte development, the ability to specifically manipulate their activity has enormous impact on ameliorating and halting diseases that currently have no satisfactory treatment. In addition, transplant rejection may be minimized without the generalized and complicating effects of costly immunosuppressive pharmaceuticals.

Chemokines, a group of greater than 40 small peptides (7-10 kD), ligate receptors expressed primarily on WBCs or immune derived cells, and signal through G-protein-coupled signaling cascades to mediate their chemoattractant and chemostimulant functions. Receptors may bind more than one ligand; for example, the receptor CCR1 ligates RANTES (regulated on activation normal T cell expressed), MIP-1α (macrophage inflammatory protein), MPIF-1/CKβ8, and Leukotactin chemokines (among others with lesser affinities). To date, 24 chemokine receptors are known. The sheer number of chemokines, multiple ligand binding receptors, and different receptor profiles on immune cells allow for tightly controlled and specific immune responses. See, Rossi, et al., Ann. Rev. Immunol. 18(1):217-242 (2000). Chemokine activity can be controlled through the modulation of their corresponding receptors, treating related inflammatory and immunological diseases and enabling organ and tissue transplants.

The receptor CCR1 and its chemokine ligands, including, for example MIP-1α, MPIF-1/CKβ8, leukotactin and RANTES, represent significant therapeutic targets (see Saeki, et al., Current Pharmaceutical Design 9:1201-1208 (2003)) since they have been implicated in rheumatoid arthritis, transplant rejection (see, DeVries, M. E., et al., ibid.), and multiple sclerosis (see, Fischer, et al., J. Neuroimmunol. 110 (1-2):195-208 (2000); Izikson, et al., J. Exp. Med. 192(7): 1075-1080 (2000); and Rottman, et al., Eur. J. Immunol. 30(8):2372-2377 (2000). In fact, function-blocking antibodies, modified chemokine receptor ligands and small organic compounds have been discovered, some of which have been successfully demonstrated to prevent or treat some chemokine-mediated diseases (reviewed in Rossi, et al., ibid.). Notably, in an experimental model of rheumatoid arthritis, disease development is diminished when a signaling-blocking, modified-RANTES ligand is administered (see Plater-Zyberk, et al., Immunol Lett. 57(1-3):117-120 (1997)). While function-blocking antibody and small peptide therapies are promising, they suffer from the perils of degradation, extremely short half-lives once administered, and prohibitive expense to develop and manufacture, characteristic of most proteins. Small organic compounds are preferable since they often have longer half lives in vivo, require fewer doses to be effective, can often be administered orally, and are consequently less expensive. Some organic antagonists of CCR1 have been previously described (see, Hesselgesser, et al., J. Biol. Chem. 273(25): 15687-15692 (1998); Ng, et al., J. Med. Chem. 42(22):4680-4694 (1999); Liang, et al., J. Biol. Chem. 275(25):19000-19008 (2000); and Liang, et al., Eur. J. Pharmacol. 389(1):4149 (2000)). In view of the effectiveness demonstrated for treatment of disease in animal models (see, Liang, et al., J. Biol. Chem. 275(25):19000-19008 (2000)), the search has continued to identify additional compounds that can be used in the treatment of diseases mediated by CCR1 signaling.

BRIEF SUMMARY OF THE INVENTION

The present invention provides compounds having the formula:

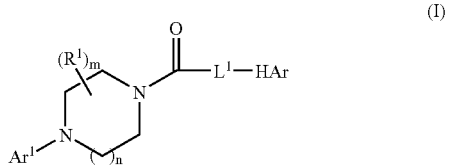
(I)

or a pharmaceutically acceptable salt thereof. In the formula above, the subscript n represents an integer of from 1 to 2, preferably 1. The subscript m represents an integer of from 0 to 10, limited by the number of available substituents positions on the piperazine or homopiperazine ring to which it is attached. For example, piperazine derivatives (n is 1) can have from 0 to 8 $R^1$ groups, preferably 0 to 4 $R^1$ groups, and more preferably 0, 1 or 2 $R^1$ groups. Each $R^1$ is a substituent independently selected from $C_{1-8}$ alkyl, $C_{1-8}$ haloalkyl, $C_{3-6}$ cycloalkyl, $C_{2-8}$ alkenyl and $C_{2-8}$ alkynyl, —$COR^a$, —$CO_2R^a$, —$CONR^aR^b$, —$NR^aCOR^b$, —$SO_2R^a$, —$X^1COR^a$, —$X^1CO_2R^a$, —$X^1CONR^aR^b$, —$X^1NR^aCOR^b$, —$X^1SO_2R^a$, —$X^1SO_2NR^aR^b$, —$X^1NR^aR^b$, —$X^1OR^a$, wherein $X^1$ is a member selected from the group consisting of $C_{1-4}$ alkylene, $C_{2-4}$ alkenylene and $C_{2-4}$ alkynylene and each $R^a$ and $R^b$ is independently selected from the group consisting of hydrogen, $C_{1-8}$ alkyl, $C_{1-8}$ haloalkyl and $C_{3-6}$ cycloalkyl, and wherein the aliphatic portions of each of said $R^1$ substituents is optionally substituted with from one to three members selected from the group consisting of OH, O($C_{1-8}$ alkyl), SH, S($C_{1-8}$ alkyl), CN, $NO_2$, $NH_2$, NH($C_{1-8}$ alkyl) and N($C_{1-8}$ alkyl)$_2$.

The symbol $Ar^1$ represents an optionally substituted aryl or heteroaryl group. Preferred aryl groups are phenyl and naphthyl. Preferred heteroaryl groups are those having from 5 to 10 ring vertices, at least one of which is a nitrogen atom (e.g., pyridyl, pyridazinyl, pyrazinyl, pyrimidinyl, triazinyl, quinolinyl, quinoxalinyl, purinyl and the like). Each of the $Ar^1$ rings is optionally substituted with from one to five $R^2$ substituents independently selected from halogen, —$OR^c$, —$OC(O)R^e$, —$NR^cR^d$, —$SR^c$, —$R^e$, —CN, —$NO_2$, —$CO_2R^c$, —$CONR^cR^d$, —$C(O)R^e$, —$OC(O)NR^cR^d$, —$NR^dC(O)R^e$, —$NR^dC(O)_2R^e$, —NR—C—$C(O)NR^cR^d$, —NH—$C(NH_2)$=NH, —$NR^eC(NH_2)$=NH, —NH—$C(NH_2)$=$NR^e$, —NH—C $(NHR^e)$=NH, —$S(O)R^e$, —$S(O)_2R^e$, —$NR^cS(O)_2R^e$, —$S(O)_2NR^cR^d$, —$N_3$, —$X^2OR^c$, —$X^2OC(O)R^c$, —$X^2NR^cR^d$, —$X^2SR^c$, —$X^2CN$, —$X^2NO_2$, —$X^2CO_2R^c$, —$X^2CONR^cR^d$, —$X^2C(O)R^c$, —$X^2OC(O)NR^cR^d$, —$X^2NR^dC(O)R^c$, —$X^2NR^dC(O)_2R^e$, —$X^2NR^cC(O)NR^c$ $R^d$, —$X^2NH$—$C(NH_2)$=NH, —$X^2NR^eC(NH_2)$=NH, —$X^2NH$—$C(NH_2)$=$NR^e$, —$X^2NH$—$C(NHR^e)$=NH, —$X^2S(O)R^e$, —$X^2S(O)_2R^e$, —$X^2NR^cS(O)_2R^e$, —$X^2S(O)_2$ $NR^cR^d$ and —$X^2N_3$, wherein $X^2$ is a member selected from the group consisting of $C_{1-4}$ alkylene, $C_{2-4}$ alkenylene and $C_{2-4}$ alkynylene and each $R^c$ and $R^d$ is independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, and each $R^e$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, and each of $R^c$, $R^d$ and $R^e$ is optionally further substituted with from one to three members selected from the group consisting of OH, O($C_{1-8}$ alkyl), SH, S($C_{1-8}$ alkyl), CN, $NO_2$, $NH_2$, NH($C_{1-8}$ alkyl) and N($C_{1-8}$ alkyl)$_2$.

The symbol HAr represents an optionally substituted heteroaryl group. The heteroaryl groups for HAr can be the same or different from any of the heteroaryl groups used for $Ar^1$. Generally, the HAr groups are monocyclic, but can also be fused bicyclic systems having from 5 to 10 ring atoms, at least one of which is a nitrogen atom. Certain preferred heteroaryl groups are 5 or 6-membered rings having at least one nitrogen atom as a ring vertex and fused ring systems having a 5-membered ring fused to a benzene ring, for example pyrazolyl, imidazolyl, triazolyl, tetrazolyl, oxazolyl, isoxazolyl, oxadiazolyl, oxathiadiazolyl, pyrrolyl, thiazolyl, isothiazolyl, benzimidazolyl, benzopyrazolyl and benzotriazolyl, each of which is substituted with from one to five $R^3$ substituents independently selected from the group consisting of halogen, phenyl, thienyl, furanyl, pyridyl, pyrimidinyl, pyrazinyl, pyridizinyl, pyrazolyl, imidazolyl, thiazolyl, oxazolyl, isoxazolyl, isothiazolyl, triazolyl, tetrazolyl, oxadiazolyl, —$OR^f$, —$OC(O)R^f$, —$NR^fR^g$, —$SR^f$, —$R^h$, —CN, —$NO_2$, —$CO_2R^f$, —$CONR^fR^g$, —$C(O)R^f$, —$OC(O)NR^fR^g$, —$NR^gC(O)R^f$, —$NR^gC(O)R^f$, —$NR^gC(O)_2R^h$, —$NR^f$—C $(O)NR^fR^g$, —NH—$C(NH_2)$=NH, —$NR^hC(NH_2)$=NH, —NH—$C(NH_2)$=$NR^h$, —NH—$C(NHR^h)$=NH, —$S(O)$ $R^h$, —$(O)_2R^h$, —$NR^fS(O)_2R^h$, —$S(O)_2NR^fR^g$, —$NR^fS(O)_2$ $R^h$, —$NR^fS(O)_2NR^fR^g$, —$N_3$, —$X^3OR^f$, —$X^3OC(O)R^f$, —$X^3NR^fR^g$, —$X^3SR^f$, —$X^3CN$, —$X^3NO_2$, —$X^3CO_2R^f$, —$X^3CONR^fR^g$, —$X^3C(O)R^f$, —$X^3OC(O)NR^fR^g$, —$X^3NR^gC(O)R^f$, —$X^3NR^gC(O)_2R^h$, —$X^3NR^f$—$C(O)NR^f$ $R^g$, —$X^3NH$—$C(NH_2)$=NH, —$X^3NR^hC(NH_2)$=NH, —$X^3NH$—$C(NH_2)$=$NR^h$, —$X^3NH$—$C(NHR^h)$=NH, —$X^3S(O)R^h$, —$X^3S(O)_2R^h$, —$X^3NR^fS(O)_2R^h$, —$X^3S(O)_2$ $NR^fR^g$ and —$X^3N_3$, wherein $X^3$ is selected from the group consisting of $C_{1-4}$ alkylene, $C_{2-4}$ alkenylene and $C_{2-4}$ alkynylene and each $R^f$ and $R^g$ is independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, and each $R^h$ is independently selected from the group consisting of $C_{1-8}$ alkyl, $C_{1-8}$ haloalkyl, $C_{3-4}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, and the aliphatic portions of $R^f$, $R^g$ and $R^h$ are optionally further substituted with from one to three members selected from the group consisting of OH, O($C_{1-8}$ alkyl), SH, S($C_{1-8}$ alkyl), CN, $NO_2$, $NH_2$, NH($C_{1-8}$ alkyl) and N($C_{1-8}$ alkyl)$_2$ and wherein any phenyl, thienyl, furanyl, pyridyl, pyrimidinyl, pyrazinyl, pyridizinyl, pyrazolyl, imidazolyl, thiazolyl, oxazolyl, isoxazolyl, isothiazolyl, triazolyl, tetrazolyl or oxadiazolyl $R^3$ groups present are optionally substituted with from one to three substitutents selected from the group consisting of halogen, —$OR^f$, —$NR^fR^g$, —$R^h$, —CN, —$NO_2$, —$CO_2R^f$, —$CONR^f$ $R^g$, —$C(O)R^f$, —$X^3OR^f$, —$X^3NR^fR^g$, —$X^3NR^fS(O)_2R^h$ and —$X^3S(O)_2NR^fR^g$. Among the most preferred HAr groups are substituted or unsubstituted pyrazoles and substituted or unsubstituted benzopyrazoles. Preferably, substituted or unsubstituted pyrazoles are attached to the remainder of the molecule via a nitrogen atom of the pyrazole ring. For those embodiments in which HAr is a benzopyrazole ring, attachment to the remainder of the molecule is preferably via a nitrogen on the pyrazole portion of the fused ring system.

The symbol $L^1$ represents a linking group having from one to three main chain atoms selected from the group consisting of C, N, O and S and being optionally substituted with from one to three substituents selected from the group consisting of halogen, phenyl, —$OR^i$, —$OC(O)R^i$, —$NR^iR^j$, —$SR^i$, —$R^k$, —CN, —$NO_2$, —$CO_2R^i$, —$CONR^iR^j$, —$C(O)R^i$, —OC(O)

NR$^i$R$^j$, —NR$^j$C(O)R$^i$, —NR$^j$C(O)$_2$R$^k$, —X$^4$OR$^i$, —X$^4$OC(O)R$^i$, —X$^4$NR$^i$R$^j$, —X$^4$SR$^i$, —X$^4$CN, —X$^4$NO$_2$, —X$^4$CO$_2$R$^i$, —X$^4$CONR$^i$R$^j$, —X$^4$C(O)R$^i$, —X$^4$OC(O)NR$^i$R$^j$, —X$^4$NR$^j$C(O)R$^i$ and —X$^4$NR$^j$C(O)$_2$R$^k$, wherein X$^4$ is selected from the group consisting of C$_{1-4}$ alkylene, C$_{2-4}$ alkenylene and C$_{2-4}$ alkynylene and each R$^i$ and R$^j$ is independently selected from hydrogen, C$_{1-8}$ alkyl, C$_{1-8}$ haloalkyl, C$_{3-6}$ cycloalkyl, C$_{2-8}$ alkenyl, C$_{2-8}$ alkynyl, aryl, heteroaryl, aryl-C$_{1-4}$ alkyl, and aryloxy-C$_{1-4}$ alkyl, and each R$^k$ is independently selected from the group consisting of C$_{1-8}$ alkyl, C$_{1-8}$ haloalkyl, C$_{3-6}$ cycloalkyl, C$_{2-8}$ alkenyl, C$_{2-8}$ alkynyl, aryl, heteroaryl, aryl-C$_{1-4}$ alkyl, and aryloxy-C$_{1-4}$ alkyl. In certain preferred embodiments, the linking groups are unsubstituted, while in other preferred embodiments, substituents are present that can increase partitioning into selected solvents or into selected tissues. For example, addition of a hydroxy group to a propylene linkage will generally provide compounds having more favorable solubility in water. Preferably, L$^1$ is selected from —CH$_2$—, —CH$_2$CH$_2$—, —CH$_2$CH$_2$CH$_2$—, —CH$_2$O—, —CH$_2$NH—, —CH$_2$OCH$_2$— and —CH$_2$NHCH$_2$—.

In addition to the compounds provided herein, the present invention further provides pharmaceutical compositions containing one or more of these compounds, as well as methods for the use of these compounds in therapeutic methods, primarily to treat diseases associated with CCR1 signalling activity.

DETAILED DESCRIPTION OF THE INVENTION

I. Abbreviation and Definitions

Figure 1:
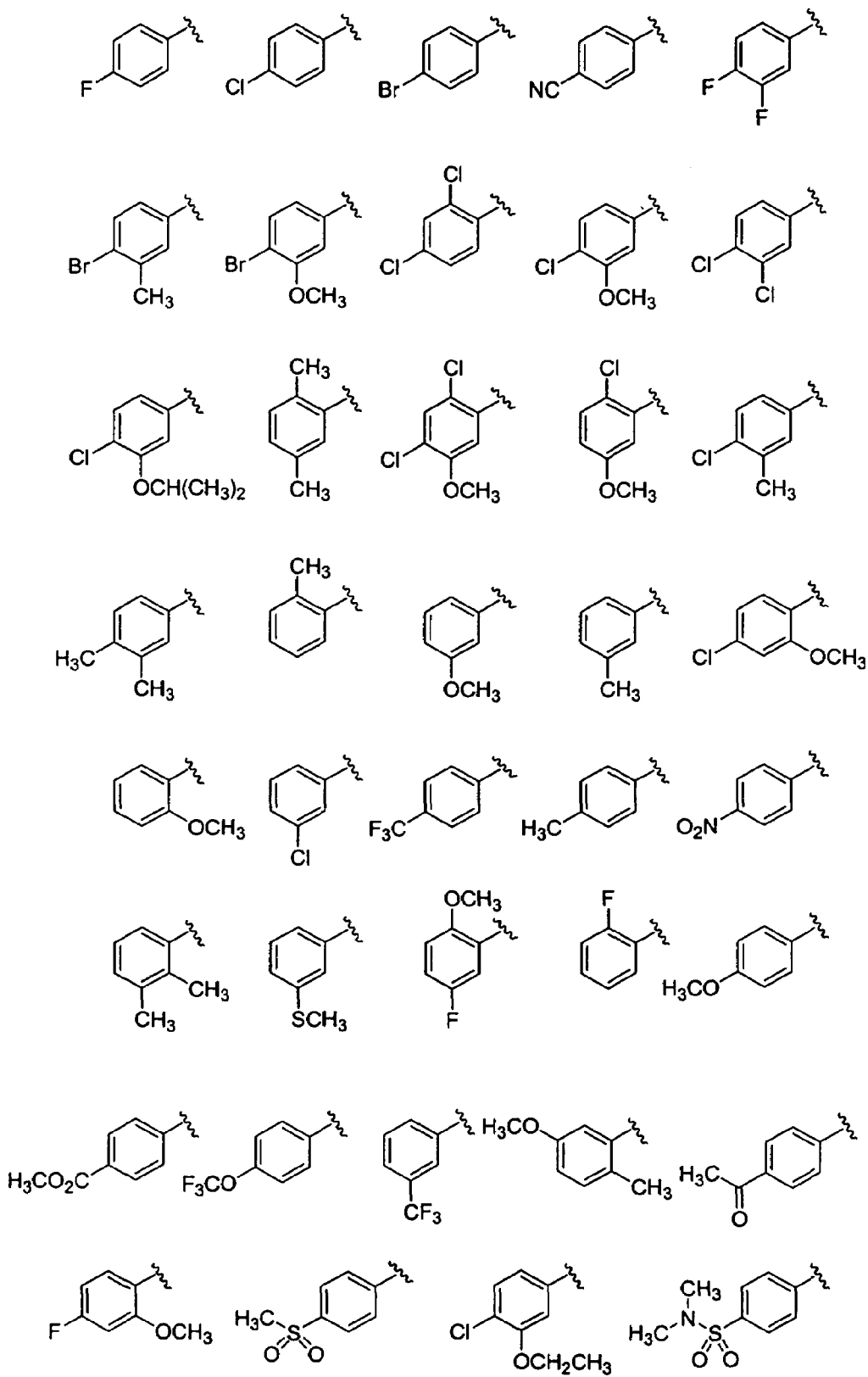
FIG. 1 provides selected and preferred Ar$^1$ groups for compounds of formulae I, II and III.

The term "alkyl", by itself or as part of another substituent, means, unless otherwise stated, a straight or branched chain hydrocarbon radical, having the number of carbon atoms designated (i.e. C$_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., C$_{3-6}$cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc.

The term "alkylene" by itself or as part of another substituent means a divalent radical derived from an alkane, as exemplified by —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —NR$^a$R$^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "C$_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include 1-pyrrolyl, 2-pyrrolyl, 3-pyrrolyl, 1-pyrazolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, benzopyrazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl includes both aryl and heteroaryl rings as defined above. Thus, the term "arylalkyl" is meant to include those radicals in which an aryl group is attached to an alkyl group (e.g., benzyl, phenethyl, pyridylmethyl and the like).

The above terms (e.g., "alkyl," "aryl" and "heteroaryl"), in some embodiments, will include both substituted and unsubstituted forms of the indicated radical. Preferred substituents for each type of radical are provided below. For brevity, the terms aryl and heteroaryl will refer to substituted or unsubstituted versions as provided below, while the term "alkyl" and related aliphatic radicals is meant to refer to unsubstituted version, unless indicated to be substituted.

Substituents for the alkyl radicals (including those groups often referred to as alkylene, alkenyl, alkynyl and cycloalkyl) can be a variety of groups selected from: -halogen, —OR', —NR'R", —SR', —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN and —NO$_2$ in a number ranging from zero to (2m'+1), where m' is the total number of carbon atoms in such radical. R', R" and R''' each independently refer to hydrogen, unsubstituted $C_{1-8}$ alkyl, unsubstituted heteroalkyl, unsubstituted aryl, aryl substituted with 1-3 halogens, unsubstituted $C_{1-8}$ alkyl, $C_{1-8}$ alkoxy or $C_{1-8}$ thioalkoxy groups, or unsubstituted aryl-$C_{1-4}$ alkyl groups. When R' and R'' are attached to the same nitrogen atom, they can be combined with the nitrogen atom to form a 3-, 4-, 5-, 6-, or 7-membered ring. For example, —NR'R'' is meant to include 1-pyrrolidinyl and 4-morpholinyl.

Similarly, substituents for the aryl and heteroaryl groups are varied and are generally selected from: -halogen, —OR', —OC(O)R', —NR'R'', —SR', —R', —CN, —NO$_2$, —CO$_2$R', —CONR'R'', —C(O)R', —OC(O)NR'R'', —NR''C(O)R', —NR''C(O)$_2$R', —NR'—C(O)NR''R''', —NH—C(NH$_2$)=NH, —NR'C(NH$_2$)=NH, —NH—C(NH$_2$)=NR', —S(O)R', —S(O)$_2$R', —S(O)$_2$NR'R'', —NR'S(O)$_2$R'', —N$_3$, perfluoro($C_1$-$C_4$)alkoxy, and perfluoro($C_1$-$C_4$)alkyl, in a number ranging from zero to the total number of open valences on the aromatic ring system; and where R', R'' and R''' are independently selected from hydrogen, $C_{1-8}$ alkyl, $C_{3-6}$ cycloalkyl, $C_{2-8}$ alkenyl, $C_{2-8}$ alkynyl, unsubstituted aryl and heteroaryl, (unsubstituted aryl)-$C_{1-4}$ alkyl, and unsubstituted aryloxy-$C_{1-4}$ alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula —T—C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula —A—(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted $C_{1-6}$ alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I, or carbon-14 ($^{14}$C). All isotopic variations of the compounds of the present invention, whether radioactive or not, are intended to be encompassed within the scope of the present invention.

II. General

The present invention derives from the discovery that compounds of formula I (as well as the subgeneric formulae II, III and IV) act as potent antagonists of the CCR1 receptor. This antagonist activity has been further confirmed in animal testing for inflammation, one of the hallmark disease states for CCR1. Accordingly, the compounds provided herein are useful in pharmaceutical compositions, methods for the treatment of CCR1-mediated diseases, and as controls in assays for the identification of competitive CCR1 antagonists.

III. Compounds

In one aspect, the present invention provides compounds having the formula:

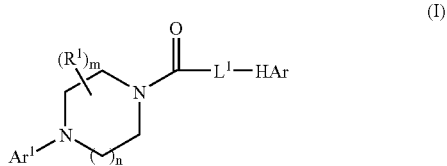

(I)

or a pharmaceutically acceptable salt thereof.

In the formula above, the subscript n represents an integer of from 1 to 2, preferably 1. The subscript m represents an integer of from 0 to 10, limited by the number of available substituents positions on the piperazine or homopiperazine ring to which it is attached. For example, piperazine derivatives (n is 1) can have from 0 to 8 $R^1$ groups, preferably 0 to 4 $R^1$ groups, and more preferably 0, 1 or 2 $R^1$ groups.

The symbol $Ar^1$ represents an optionally substituted aryl or heteroaryl group. Preferred aryl groups are phenyl and naphthyl. Preferred heteroaryl groups are those having from 5 to 10 ring vertices, at least one of which is a nitrogen atom (e.g., pyridyl, pyridazinyl, pyrazinyl, pyrimidinyl, triazinyl, quinolinyl, quinoxalinyl, purinyl and the like). Each of the $Ar^1$ rings is optionally substituted with from one to five $R^2$ substituents independently selected from halogen, —$OR^c$, —$OC(O)R^c$, —$NR^cR^d$, —$SR^c$, —$R^e$, —CN, —$NO_2$, —$CO_2R^c$, —$CONR^cR^d$, —$C(O)R^e$, —$OC(O)NR^cR^d$, —$NR^dC(O)R^c$, —$NR^dC(O)_2R^e$, —$NR^c$—$C(O)NR^cR^d$, —NH—$C(NH_2)$=NH, —$NR^eC(NH_2)$=NH, —NH—$C(NH_2)$=$NR^e$, —NH—C$(NHR^e)$=NH, —$S(O)R^e$, —$S(O)_2R^e$, —$NR^cS(O)_2R^e$, —$S(O)_2NR^cR^d$, —$N_3$, —$X^2OR^c$, —$X^2OC(O)R^c$, —$X^2NR^cR^d$, —$X^2SR^c$, —$X^2CN$, —$X^2NO_2$, —$X^2CO_2R^c$, —$X^2CONR^cR^d$, —$X^2C(O)R^e$, —$X^2OC(O)NR^cR^d$, —$X^2NR^dC(O)R^c$, —$X^2NR^dC(O)_2R^e$, —$X^2NR^cC(O)NR^c R^d$, —$X^2NH$—$C(NH_2)$=NH, —$X^2NR^eC(NH_2)$=NH, —$X^2NH$—$C(NH_2)$=$NR^e$, —$X^2NH$—$C(NHR^e)$=NH, —$X^2S(O)R^e$, —$X^2S(O)_2R^e$, —$X^2NR^cS(O)_2R^e$, —$X^2S(O)_2NR^cR^d$ and —$X^2N_3$, wherein $X^2$ is a member selected from the group consisting of $C_{1-4}$ alkylene, $C_{2-4}$ alkenylene and $C_{2-4}$ alkynylene and each $R^c$ and $R^d$ is independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, and each $R^e$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, and each of $R^c$, $R^d$ and $R^e$ is optionally further substituted with from one to three members selected from the group consisting of OH, O($C_{1-8}$ alkyl), SH, S($C_{1-8}$ alkyl), CN, $NO_2$, $NH_2$, NH($C_{1-8}$ alkyl) and N($C_{1-8}$ alkyl)$_2$.

HAr is an optionally substituted heteroaryl group. The heteroaryl groups for HAr can be the same or different from any of the heteroaryl groups used for $Ar^1$. Generally, the HAr groups are monocyclic, but can also be fused bicyclic ring systems having from 5 to 10 ring atoms, at least one of which is a nitrogen atom. Certain preferred heteroaryl groups are 5 or 6-membered rings having at least one nitrogen atom as a ring vertex and fused ring systems having a 5-membered ring fused to a benzene ring, for example pyrazolyl, imidazolyl, triazolyl, tetrazolyl, oxazolyl, isoxazolyl, oxadiazolyl, oxathiadiazolyl, pyrrolyl, thiazolyl, isothiazolyl, benzimidazolyl, benzopyrazolyl and benzotriazolyl. Preferably, the fused bicyclic HAr moiety, when present, is attached to the remainder of the molecule through the 5-member ring. Additionally, each of the HAr groups is substituted with from one to five $R^3$ substituents independently selected from the group consisting of halogen, phenyl, thienyl, furanyl, pyridyl, pyrimidinyl, pyrazinyl, pyridizinyl, pyrazolyl, imidazolyl, thiazolyl, oxazolyl, isoxazolyl, isothiazolyl, triazolyl, tetrazolyl, oxadiazolyl, —$OR^f$, —$OC(O)R^f$, —$NR^FR^g$, —$SR^f$, —$R^h$, —CN, —$NO_2$, —$CO_2R^f$, —$CONR^fR^g$, —$C(O)R^f$, —$OC(O)NR^fR^g$, —$NR^gC(O)R^f$, —$NR^gC(O)_2R^h$, —$NR^f$—$C(O)NR^f R^g$, —NH—$C(NH_2)$=NH, —$NR^hC(NH_2)$=NH, —NH—C$(NH_2)$=$NR^h$, —NH—C$(NHR^h)$=NH, —$S(O)R^h$, —$S(O)_2 R^h$, —$NR^fS(O)_2R^h$, —$S(O)_2NR^fR^g$, —$NR^fS(O)_2R^h$, —$NR^fS(O)NR^fR^g$, —$N_3$, —$X^3OR^f$, —$X^3OC(O)R^f$, —$X^3NR^fR^g$, —$X^3SR^f$, —$X^3CN$, —$X^3NO_2$, —$X^3CO_2R^f$, —$X^3CONR^fR^g$, —$X^3C(O)R^f$, —$X^3OC(O)NR^fR^g$, —$X^3NR^gC(O)R^f$, —$X^3NR^gC(O)_2R^h$, —$X^3NR^f$—$C(O)NR^fR^g$, —$X^3NH$—C$(NH_2)$=NH, —$X^3NR^hC(NH_2)$=NH, —$X^3NH$—$C(NH_2)$=$NR^h$, —$X^3NH$—$C(NHR^h)$=NH, —$X^3S(O)R^h$, —$X^3S(O)_2R^h$, —$X^3NR^fS(O)_2R^h$, —$X^3NR^fR^g$ and —$X^3N_3$ wherein $X^3$ is selected from the group consisting of $C_{1-4}$ alkylene, $C_{2-4}$ alkenylene and $C_{2-4}$ alkynylene and each $R^f$ and $R^g$ is independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, and each $R^h$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, and the aliphatic portions of $R^f$, $R^g$ and $R^h$ are optionally further substituted with from one to three members selected from the group consisting of OH, O($C_{1-8}$ alkyl), SH, S($C_{1-8}$ alkyl), CN, $NO_2$, $NH_2$, NH($C_{1-8}$ alkyl) and N($C_{1-8}$ alkyl)$_2$ and wherein any phenyl, thienyl, furanyl, pyridyl, pyrimidinyl, pyrazinyl, pyridizinyl, pyrazolyl, imidazolyl, thiazolyl, oxazolyl, isoxazolyl, isothiazolyl, triazolyl, tetrazolyl, or oxadiazolyl $R^3$ groups present are optionally substituted with from one to three substituents selected from the group consisting of halogen, —$OR^f$, —$NR^fR^g$, —$R^h$, —CN, —$NO_2$, —$CO_2R^f$, —$CONR^fR^g$, —$C(O)R^f$, —$X^3OR^f$, —$X^3NR^fR^g$, —$X^3NR^fS(O)_2R^h$ and —$X^3S(O)_2NR^fR^g$. Among the most preferred HAr groups are substituted or unsubstituted pyrazoles and substituted or unsubstituted benzopyrazoles. Preferably, substituted or unsubstituted pyrazoles are attached to the remainder of the molecule via a nitrogen atom of the pyrazole ring. For those embodiments in which HAr is a benzopyrazole ring, attachment to the remainder of the molecule is preferably via a nitrogen on the pyrazole portion of the fused ring system.

The symbol $L^1$ represents a linking group having from one to three main chain atoms selected from the group consisting of C, N, O and S and being optionally substituted with from one to three substituents selected from the group consisting of halogen, phenyl, —$OR^i$, —$OC(O)R^i$, —$NR^iR^j$, —$SR^i$, —$R^k$, —CN, —$NO_2$, —$CO_2R^i$, —$CONR^iR^j$, —$C(O)R^i$, —$OC(O)NR^iR^j$, —$NR^jC(O)R^i$, —$NR^jC(O)_2R^k$, —$X^4OR^i$, —$X^4OC$ (O)R$^i$, —X$^4$NR$^i$R$^j$, —X$^4$SR$^i$, —X$^4$CN, —X$^4$NO$_2$, —X$^4$CO$_2$R$^i$, —X$^4$CONR$^i$R$^j$, —X$^4$C(O)R$^i$, —X$^4$OC(O)NR$^i$R$^j$, —X$^4$NR$^j$C(O)R$^i$ and —X$^4$NR$^j$C(O)$_2$R$^k$, wherein X$^4$ is selected from the group consisting of C$_{1-4}$ alkylene, C$_{2-4}$ alkenylene and C$_{2-4}$ alkynylene and each R$^i$ and R$^j$ is independently selected from hydrogen, C$_{1-8}$ alkyl, C$_{1-8}$ haloalkyl, C$_{3-6}$ cycloalkyl, C$_{2-8}$ alkenyl, C$_{2-8}$ alkynyl, aryl, heteroaryl, aryl-C$_{1-4}$ alkyl, and aryloxy-C$_{1-4}$ alkyl, and each R$^k$ is independently selected from the group consisting of C$_{1-8}$ alkyl, C$_{1-8}$ haloalkyl, C$_{3-6}$ cycloalkyl, C$_{2-8}$ alkenyl, C$_{2-8}$ alkynyl, aryl, heteroaryl, aryl-C$_{1-4}$ alkyl, and aryloxy-C$_{1-4}$ alkyl. In certain preferred embodiments, the linking groups are unsubstituted, while in other preferred embodiments, substituents are present that can increase partitioning into selected solvents or into selected tissues. For example, addition of a hydroxy group to a propylene linkage will generally provide compounds having more favorable solubility in water. Preferably, L$^1$ is selected from —CH$_2$—, —CH$_2$CH$_2$—, —CH$_2$CH$_2$CH$_2$—, —CH$_2$O—, —CH$_2$NH—, —CH$_2$OCH$_2$— and —CH$_2$NHCH$_2$—.

Returning to the piperazine or homopiperazine portion of the compounds, each R$^1$ is a substituent independently selected from C$_{1-8}$ alkyl, C$_{1-8}$ haloalkyl, C$_{3-6}$ cycloalkyl, C$_{2-8}$ alkenyl and C$_{2-8}$ alkynyl, —COR$^a$, —CO$_2$R$^a$, —CONR$^a$R$^b$, —NR$^a$COR$^b$, —SO$_2$R$^a$, —X$^1$COR$^a$, —X$^1$CO$_2$R$^a$, —X$^1$CONR$^a$R$^b$, —X$^1$NR$^a$COR$^b$, —X$^1$SO$_2$R$^a$, —X$^1$SO$_2$NR$^a$R$^b$, —X$^1$NR$^a$R$^b$, —X$^1$OR$^a$,wherein X$^1$ is a member selected from the group consisting of C$_{1-4}$ alkylene, C$_{2-4}$ alkenylene and C$_{2-4}$ alkynylene and each R$^a$ and R$^b$ is independently selected from the group consisting of hydrogen, C$_{1-8}$ alkyl, C$_{1-8}$ haloalkyl and C$_{3-6}$ cycloalkyl, and wherein the aliphatic portions of each of said R$^1$ substituents is optionally substituted with from one to three members selected from the group consisting of OH, O(C$_{1-8}$ alkyl), SH, S(C$_{1-8}$ alkyl), CN, NO$_2$, NH$_2$, NH(C$_{1-8}$ alkyl) and N(C$_{1-8}$ alkyl)$_2$.

Excluded from the above generic formula, as well as each of the formulae below, are those compounds that are either commercially available or known in the literature, including: CAS Reg. No. 492422-98-7,1-[[4-bromo-5-methyl-3-(trifluoromethyl)-1H-pyrazol-1-yl]acetyl]-4-(5-chloro-2-methylphenyl)-piperazine; CAS Reg. No. 351986-92-0,1-[[4-chloro-5-methyl-3-(trifluoromethyl)-1H-pyrazol-1-yl]acetyl]-4-(4-fluorophenyl)-piperazine; CAS Reg. No. 356039-23-1,1-[(3,5-dimethyl-4-nitro-1H-pyrazol-1-yl) acetyl]-4-(4-fluorophenyl)-piperazine; 1-(2-{4-nitro-3,5-dimethyl-1H-pyrazol-1-yl}propanoyl)-4-phenylpiperazine; 2-(2,4-Dinitro-imidazol-1-yl)-1-[4-(4-fluorophenyl)-piperazin-1-yl]-ethanone; 2-(2,4-Dinitro-imidazol-1-yl)-1-(4-phenyl-piperazin-1-yl)-ethanone; 2-(4-Nitro-imidazol-1-yl)-1-(4-phenyl-piperazin-1-yl)-ethanone; and CAS Reg. No. 492992-15-1,3-[3-Fluoro-4-[4-[(1-pyrazolyl)acetyl]piperazine-1-yl]phenyl]-5-[[(isoxazol-3-yl)amino]methyl]isoxazole.

A number of preferred groups of embodiments can be outlined as follows.

In a first group of preferred embodiments, the compounds are represented by formula I in which Ar$^1$ is selected from (i) phenyl, substituted with from 1 to 5 R$^2$ groups;
(ii) pyridinyl, substituted with from 1 to 4 R$^2$ groups; and
(iii) pyrimidinyl, substituted with from 1 to 3 R$^2$ groups;
(iv) pyrazinyl, substituted with from 1 to 3 R$^2$ groups; and
(v) pyridazinyl, substituted with from 1 to 3 R$^2$ groups;

wherein each R$^2$ is a member independently selected from the group consisting of halogen, —OR$^c$, —OC(O)R$^c$, —NR$^c$R$^d$, —SR$^c$, —R$^e$, —CN, —NO$_2$, —CO$_2$R$^c$, —CONR$^c$R$^d$, —C(O)R$^c$, —OC(O)NR$^c$R$^d$, —NR$^d$C(O)R$^c$, —NR$^d$C(O)$_2$R$^e$, —NR$^c$—C(O)NR$^c$R$^d$, —S(O)R$^e$, —S(O)$_2$R$^e$, —NR$^c$S(O)$_2$R$^e$, —S(O)$_2$NR$^c$R$^d$ and —N$_3$, wherein each R$^c$ and R$^d$ is independently selected from hydrogen, C$_{1-8}$ alkyl, C$_{1-8}$ haloalkyl, C$_{3-6}$ cycloalkyl, C$_{2-8}$ alkenyl and C$_{2-8}$ alkynyl, and each R$^e$ is independently selected from the group consisting of C$_{1-8}$ alkyl, C$_{1-8}$ haloalkyl, C$_{3-6}$ cycloalkyl, C$_{2-8}$ alkenyl and C$_{2-8}$ alkynyl, wherein the aliphatic portions of R$^c$, R$^d$ and R$^e$ are optionally further substituted with from one to three members selected from the group consisting of OH, O(C$_{1-8}$ alkyl), SH, S(C$_{1-8}$ alkyl), CN, NO$_2$, NH$_2$, NH(C$_{1-8}$ alkyl) and N(C$_{1-8}$ alkyl)$_2$. More preferably, Ar$^1$ is phenyl substituted with from 1 to 3 R$^2$ groups. Among the most preferred Ar$^1$ groups are those represented by:

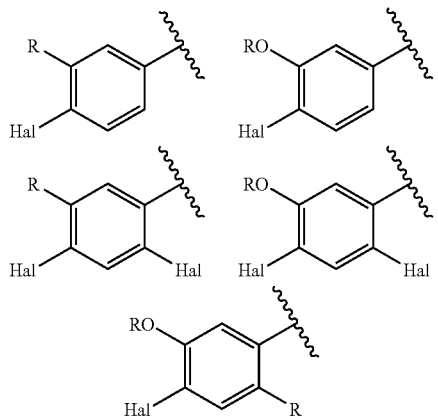

wherein Hal is F, Cl or Br and each R is independently C$_{1-6}$ alkyl or C$_{3-6}$ cycloalkyl.

Further preferred are those embodiments in which L$^1$ is —CH$_2$— and is optionally substituted with phenyl, —R$^k$, —X$^4$OR$^i$, —X$^4$OC(O)R$^i$, —X$^4$NR$^i$R$^j$, —X$^4$SR$^i$, —X$^4$CN or —X$^4$NO$_2$. In still further preferred embodiments, HAr is selected from pyrazolyl, triazolyl and tetrazolyl, each of which is optionally substituted with from one to three R$^3$ groups independently selected from halogen, phenyl, thienyl, —OR$^f$, —OC(O)R$^f$, —NR$^f$R$^g$, —SR$^f$, —R$^h$, —CN, —NO$_2$, —CO$_2$R$^f$, —CONR$^f$R$^g$, —C(O)R$^f$, —OC(O)NR$^f$R$^g$, —NR$^g$C(O)R$^f$, —NR$^g$C(O)$_2$R$^h$, —NR$^f$—C(O)NR$^f$R$^g$, —S(O)R$^h$, —S(O)$_2$R$^h$, —S(O)$_2$NR$^f$R$^g$, —NR$^f$S(O)$_2$R$^h$, —NR$^f$S(O)$_2$NR$^f$R$^g$, —N$_3$, —X$^3$OR$^f$, —X$^3$OC(O)R$^f$, —X$^3$NR$^f$R$^g$, —X$^3$SR$^f$, —X$^3$CN, —X$^3$NO$_2$, —X$^3$CO$_2$R$^f$, —X$^3$CONR$^f$R$^g$, —X$^3$C(O)R$^f$, —X$^3$OC(O)NR$^f$R$^g$, —X$^3$NR$^g$C(O)R$^f$, —X$^3$NR$^g$C(O)$_2$R$^h$, —X$^3$NR$^f$—C(O)NR$^f$R$^g$, —X$^3$S(O)R$^h$, —X$^3$S(O)$_2$R$^h$, —X$^3$NR$^f$S(O)$_2$R$^h$, —X$^3$S(O)$_2$NR$^f$R$^g$ and —X$^3$N$_3$ wherein R$^f$ and R$^g$ are each independently selected from the group consisting of H, C$_{1-8}$ alkyl and C$_{1-8}$ haloalkyl, and each R$^h$ is independently selected from the group consisting of C$_{1-8}$ alkyl and C$_{1-8}$ haloalkyl. In still further preferred embodiments, the subscript n is 1, m is 0, 1 or 2, Ar$^1$ is phenyl substituted with from one to three R$^2$ groups, HAr is pyrazolyl which is substituted with three R$^3$ groups and L$^1$ is —CH$_2$—. In the most preferred embodiments in this group, Ar$^1$ is selected from those substituted phenyl moieties provided in FIG. 1.

In a second group of preferred embodiments, the compounds are represented by formula I in which Ar$^1$ is selected from (i) phenyl, substituted with from 1 to 5 R$^2$ groups;
(ii) pyridinyl, substituted with from 1 to 4 R$^2$ groups; and (iii) pyrimidinyl, substituted with from 1 to 3 $R^2$ groups;
(iv) pyrazinyl, substituted with from 1 to 3 $R^2$ groups; and
(v) pyridazinyl, substituted with from 1 to 3 $R^2$ groups;

wherein each $R^2$ is a member independently selected from the group consisting of halogen, —$X^2OR^c$, —$X^2OC(O)R^c$, —$X^2NR^cR^d$, —$X^2SR^c$, —$X^2CN$, —$X^2NO_2$, —$X^2CO_2R^c$, —$X^2CONR^cR^d$, —$X^2C(O)R^c$, —$X^2OC(O)NR^cR^d$, —$X^2NR^dC(O)R^c$, —$X^2NR^dC(O)_2R^e$, —$X^2NR^cC(O)NR^cR^d$, —$X^2S(O)R^e$, —$X^2S(O)_2R^e$, —$X^2NR^cS(O)_2R^e$, —$X^2S(O)_2NR^cR^d$ and —$X^2N_3$, wherein each $R^c$ and $R^d$ is independently selected from hydrogen, $C_{1-8}$ alkyl, $C_{1-8}$ haloalkyl, $C_{3-6}$ cycloalkyl, $C_{2-8}$ alkenyl and $C_{2-8}$ alkynyl, and each $R^e$ is independently selected from the group consisting of $C_{3-6}$ alkyl, $C_{1-8}$ haloalkyl, $C_{3-4}$ cycloalkyl, $C_{2-8}$ alkenyl and $C_{2-8}$ alkynyl.

In a third group of preferred embodiments, the compounds are represented by formula I in which HAr is selected from pyrazolyl, triazolyl, tetrazolyl, benzimidazolyl, benzopyrazolyl and benzotriazolyl, each of which is optionally substituted with from one to five $R^3$ groups independently selected from the group consisting of halogen, phenyl, thienyl, —$OR^f$, —$COR^f$, —$CO_2R^f$, —$CONR^fR^g$, —$NO_2$, —$R^h$, —$CN$, —$SR^f$, —$S(O)R^h$, $S(O)_2R^h$ and —$NR^fR^g$, wherein $R^f$ and $R^g$ are each independently selected from the group consisting of H, $C_{1-8}$ alkyl, $C_{3-6}$ cycloalkyl and $C_{1-8}$ haloalkyl, and each $R^h$ is independently selected from the group consisting of $C_{1-8}$ alkyl, $C_{3-6}$ cycloalkyl and $C_{1-8}$ haloalkyl.

In another group of preferred embodiments, the compounds are represented by formula II:

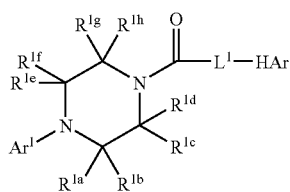

Figure 2:
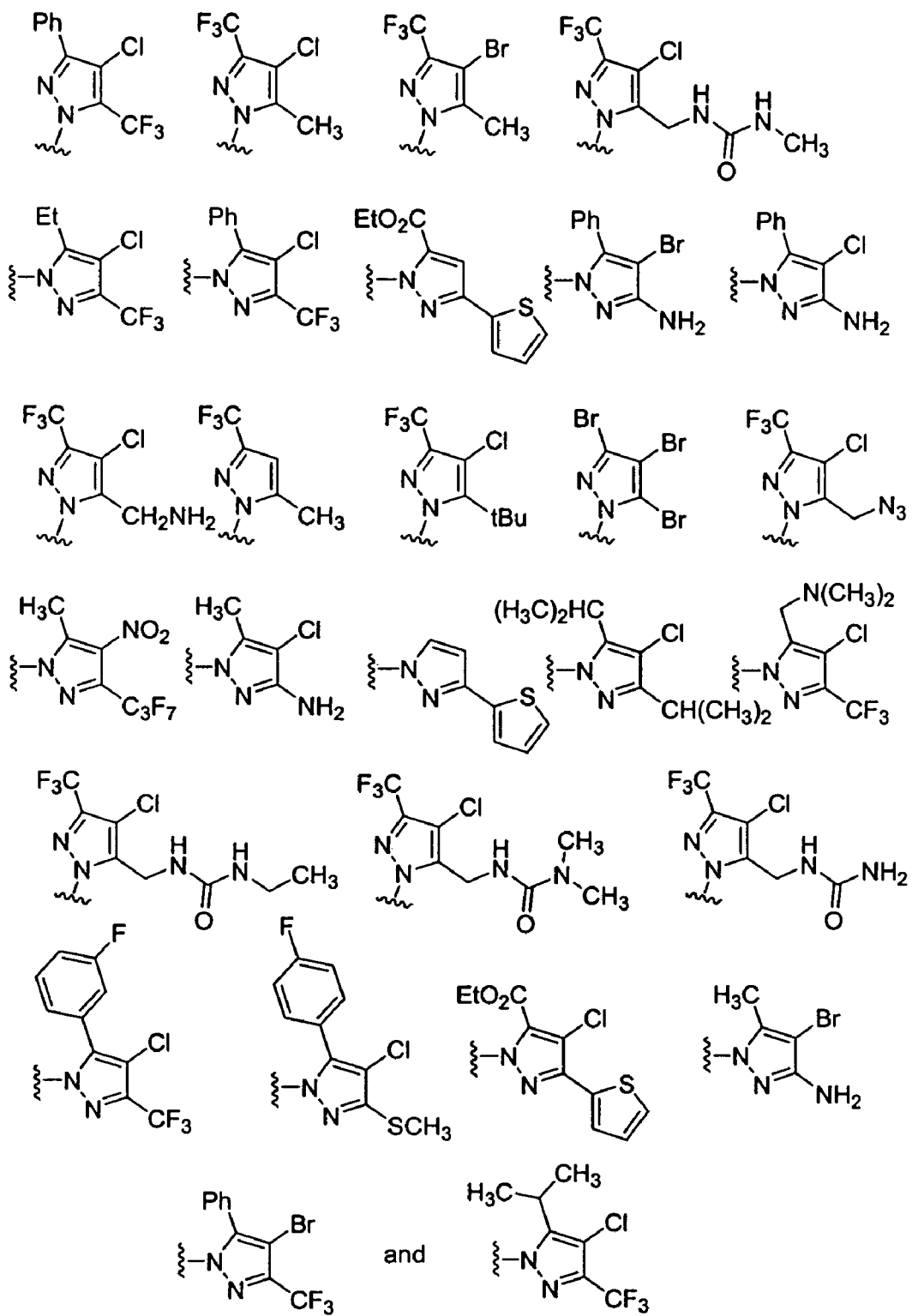
FIGS. 2 and 3 provide selected and preferred HAr groups for compounds of formulae I, II, III and IV.
Figure 3:
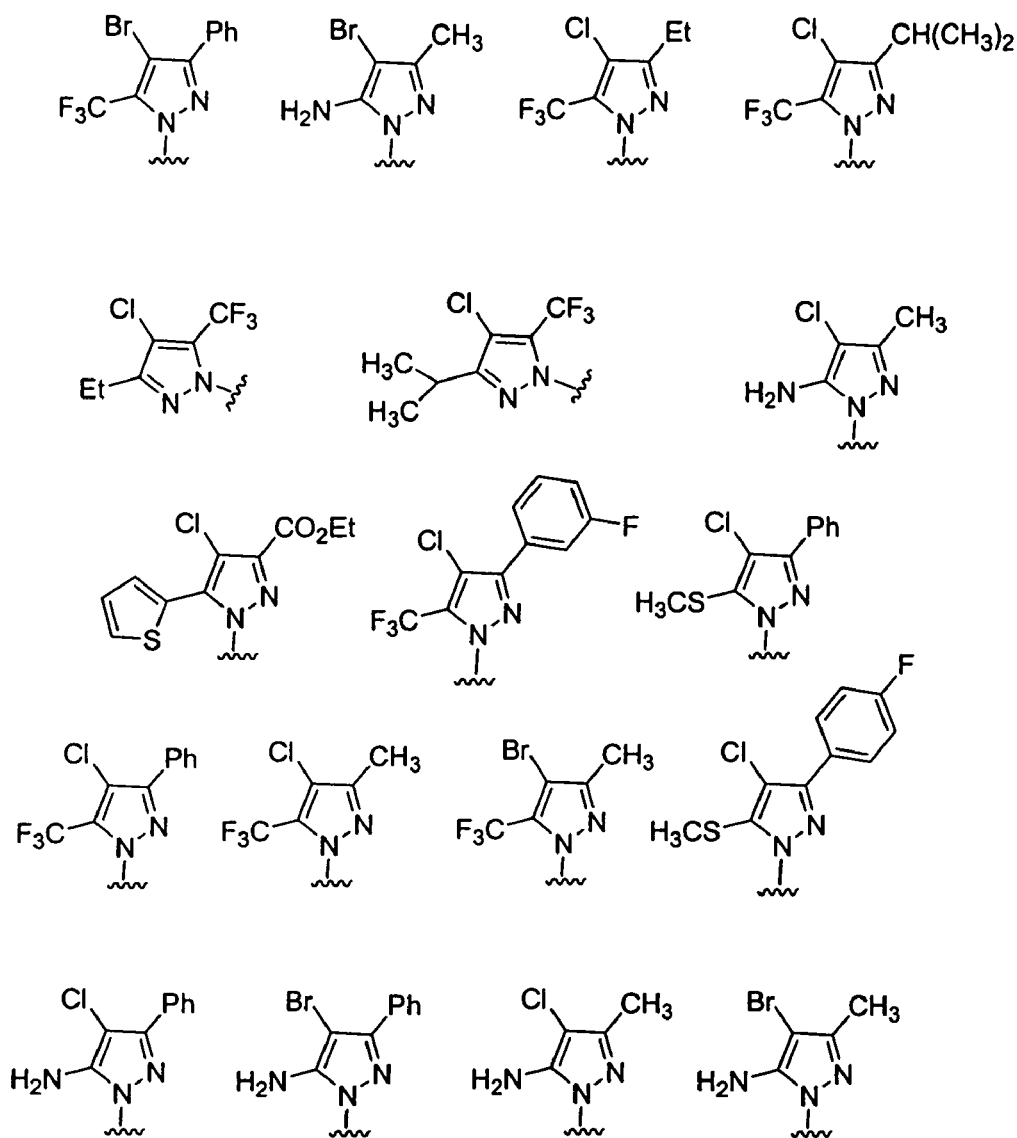

II or a pharmaceutically acceptable salt thereof, wherein each of $R^{1a}$, $R^{1b}$, $R^{1c}$, $R^{1d}$, $R^{1e}$, $R^{1f}$, $R^{1g}$ and $R^{1h}$ represents a member independently selected from the group consisting of H, C118 alkyl, $C_{1-8}$ haloalkyl, $C_{3-6}$ cycloalkyl, $C_{2-8}$ alkenyl and $C_{2-8}$ alkynyl. The remaining groups have the meanings provided above with reference to formula I in their most complete interpretation. Preferably, $Ar^1$ is selected from phenyl and naphthyl, each of which is optionally substituted with from one to five $R^2$ substitutents independently selected from halogen, —$OR^c$, —$OC(O)R^c$, —$NR^cR^d$, —$SR^c$, —$R^e$, —$CN$, —$NO_2$, —$CO_2R^c$, —$CONR^cR^d$, —$C(O)R^c$, —$OC(O)NR^cR^d$, —$NR^dC(O)R^c$, —$NR^dC(O)_2R^e$, —$NR^c$—$C(O)NR^cR^d$, —$S(O)R^e$, —$S(O)_2R^e$, —$NR^cS(O)_2R^e$, —$S(O)_2NR^cR^d$ and —$N_3$, wherein each $R^c$ and $R^d$ is independently selected from hydrogen, $C_{1-8}$ alkyl, $C_{1-8}$ haloalkyl, $C_{3-6}$ cycloalkyl, $C_{2-8}$ alkenyl and $C_{2-8}$ alkynyl, and each $R^e$ is independently selected from the group consisting of $C_{1-8}$ alkyl, $C_{1-8}$ haloalkyl, $C_{3-6}$ cycloalkyl, $C_{2-8}$ alkenyl and $C_{2-8}$ alkynyl. In related preferred embodiments, $Ar^1$ is selected from phenyl and naphthyl, each of which is optionally substituted with from one to five $R^2$ substitutents independently selected from halogen, —$X^2OR^c$, —$X^2OC(O)R^c$, —$X^2NR^cR^d$, —$X^2SR^c$, —$X^2CN$, —$X^2NO_2$, —$X^2CO_2R^c$, —$X^2CONR^cR^d$, —$X^2C(O)R^c$, —$X^2OC(O)NR^cR^d$, —$X^2NR^cC(O)R^c$, —$X^2NR^d C$ (O)$_2R^e$, —$X^2NR^cC(O)NR^cR^d$, —$X^2S(O)R^e$, —$X^2S(O)_2R^e$, —$X^2NR^cS(O)_2R^e$, —$X^2S(O)_2NR^cR^d$ and —$X^2N_3$, wherein each $R^c$ and $R^d$ is independently selected from hydrogen, $C_{1-8}$ alkyl, $C_{1-8}$ haloalkyl, $C_{3-6}$ cycloalkyl, $C_{2-8}$ alkenyl and $C_{2-8}$ alkynyl, and each $R^e$ is independently selected from the group consisting of $C_{1-8}$ alkyl, $C_{1-8}$ haloalkyl, $C_{3-6}$ cycloalkyl, $C_{2-8}$ alkenyl and $C_{2-8}$ alkynyl. Still more preferably, $L^1$ is a member selected from the group consisting of —$CH_2$—, —$CH_2CH_2$—, —$CH_2O$— and —$CH_2NH$—, each of which is optionally substituted with one or more substituents independently selected from the group consisting of $C_{1-4}$alkyl, $C_{1-4}$haloalkyl and phenyl. In still further preferred embodiments, HAr is selected from pyrazolyl, triazolyl, tetrazolyl and benzopyrazolyl, each of which is optionally substituted with from one to five $R^3$ groups independently selected from halogen, phenyl, thienyl, —$OR^f$, —$OC(O)R^f$, —$NR^fR^g$, —$SR^f$, —$R^h$, —$CN$, —$NO_2$, —$CO_2R^f$, —$CONR^fR^g$, —$C(O)R^f$, —$OC(O)NR^fR^g$, —$NR^gC(O)R^f$, —$NR^gC(O)_2R^h$, —$NR^f$—$C(O)NR^fR^g$, —$S(O)R^h$, —$S(O)_2R^h$, —$NR^fS(O)_2R^h$, —$S(O)_2NR^fR^g$, —$NR^fS(O)_2R^h$, —$NR^fS(O)_2NR^fR^g$, —$X^3OR^f$, —$X^3OC(O)R^f$, —$X^3NR^fR^g$, —$X^3SR^f$, —$X^3CN$, —$X^3NO_2$, —$X^3CO_2R^f$, —$X^3CONR^fR^g$, —$X^3C(O)R^f$, —$X^3OC(O)NR^fR^g$, —$X^3NR^gC(O)R^f$, —$X^3NR^gC(O)_2R^h$, —$X^3NR^f$—$C(O)NR^fR^g$, —$X^3S(O)R^h$, —$X^3S(O)_2R^h$, —$X^3NR^fS(O)_2R^h$ and —$X^3S(O)_2NR^fR^g$ wherein $X^3$ is selected from the group consisting of $C_{1-4}$ alkylene, $C_{2-4}$ alkenylene and $C_{2-4}$ alkynylene and each $R^f$ and $R^g$ is independently selected from hydrogen, $C_{1-8}$ alkyl, $C_{1-8}$ haloalkyl, $C_{3-6}$ cycloalkyl, $C_{2-8}$ alkenyl and $C_{2-8}$ alkynyl, and each $R^h$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, and wherein any phenyl or thienyl group present is optionally substituted with from one to three substitutents selected from the group consisting of halogen, —$OR^f$, —$NR^fR^g$, —$R^h$, —$CN$, —$NO_2$, —$CO_2R^f$, —$CONR^fR^g$, —$C(O)R^f$, —$X^3OR^f$, —$X^3NR^fR^g$, —$X^3NR^fS(O)_2R^h$ and —$X^3S(O)_2NR^fR^g$. Still more preferably, HAr is pyrazolyl or benzopyrazolyl, each of which is optionally substituted with from one to three $R^3$ groups independently selected from halogen, phenyl, thienyl, —$OR^f$, —$CO_2R^f$, —$COR^f$, —$CONR^fR^g$, —$NO_2$, —$R^h$, —$CN$, —$SR^f$, —$S(O)R^h$, —$S(O)_2R^h$ and —$NR^fR^g$, wherein each $R^f$ and $R^g$ is independently selected from H, $C_{1-8}$ alkyl and $C_{1-8}$ haloalkyl, and each $R^h$ is independently selected from $C_{1-8}$ alkyl and $C_{1-8}$ haloalkyl. Most preferably, HAr is selected from the substituted pyrazolyl moieties provided in FIGS. 2 and 3.

In a related group of preferred embodiments, the compound is represent by formula II, above, wherein $Ar^1$ is phenyl, optionally substituted with from one to five $R^2$ substitutents independently selected from the group consisting of halogen, —$OR^c$, —$OC(O)R^c$, —$NR^cR^d$, —$SR^c$, —$R^e$, —$CN$, —$NO_2$, —$CO_2R^c$, —$CONR^cR^d$, —$C(O)R^c$, —$OC(O)NR^cR^d$, —$NR^dC(O)R^c$, —$NR^dC(O)_2R^e$, —$NR^c$—$C(O)NR^cR^d$, —$S(O)R^e$, —$S(O)_2R^e$, —$S(O)_2NR^cR^d$ and —$N_3$, wherein each $R^c$ and $R^d$ is independently selected from hydrogen, $C_{1-8}$ alkyl, $C_{1-8}$ haloalkyl, $C_{3-6}$ cycloalkyl, $C_{2-8}$ alkenyl, and $C_{2-8}$ alkynyl, and each $R^e$ is independently selected from the group consisting of $C_{1-8}$ alkyl, $C_{1-8}$ haloalkyl, $C_{3-6}$ cycloalkyl, $C_{2-8}$ alkenyl and $C_{2-8}$ alkynyl, wherein the alkyl portions of the substituents are optionally substituted with one or two hydroxy or amino groups; $L^1$ is —$CH_2$—; HAr is pyrazolyl or benzopyrazolyl, each of which is optionally substituted with from one to three $R^3$ groups independently selected from the group consisting of halogen, phenyl, thienyl, $OR^f$, $CO_2R^f$, $CONR^fR^g$, $NO_2$, $R^h$, CN, $SR^f$, $S(O)R^h$, $S(O)_2R^h$ and $NR^fR^g$, wherein each $R^f$ and $R^g$ is independently selected from the group consisting of H, $C_{1-8}$ alkyl and $C_{1-8}$ haloalkyl, and each $R^h$ is independently selected from the group consisting of $C_{1-8}$ alkyl and $C_{1-8}$ haloalkyl; and each of $R^{1a}$, $R^{1b}$, $R^{1c}$, $R^{1d}$, $R^{1e}$, $R^{1f}$, $R^{1g}$ and $R^{1h}$ are members independently selected from the group consisting of H, $C_{1-4}$ alkyl and $C_{1-4}$ haloalkyl, wherein at least six of $R^{1a}$ through $R^{1h}$ are H.

In yet another group of preferred embodiments, compounds are provided having formula III:

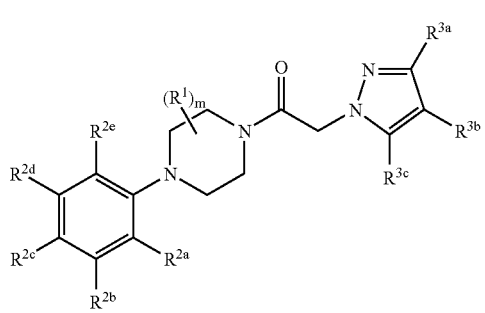

III or a pharmaceutically acceptable salt thereof, wherein the subscript m is an integer of from 0 to 2; each $R^1$ is selected from $C_{1-4}$ alkyl and $C_{1-4}$ haloalkyl; $R^{2a}$, $R^{2b}$, $R^{2c}$, $R^{2d}$ and $R^{2e}$ are each members independently selected from hydrogen, halogen, $-OR^c$, $-OC(O)R^c$, $-NR^cR^d$, $-SR^c$, $-R^e$, $-CN$, $-NO_2$, $-CO_2R^c$, $-CONR^cR^d$, $-C(O)R^c$, $-OC(O)NR^cR^d$, $-NR^dC(O)R^c$, $-NR^dC(O)_2R^e$, $-NR^c-C(O)NR^cR^d$, $-S(O)R^e$, $-S(O)_2R^e$, $-NR^cS(O)_2R^e$, $-S(O)_2NR^cR^d$, $-N_3$, $-X^2OR^c$, $-X^2OC(O)R^c$, $-X^2NR^cR^d$, $-X^2SR^c$, $-X^2CN$, $-X^2NO_2$, $-X^2C_2R^c$, $-X^2CONR^cR^d$, $-X^2C(O)R^c$, $-X^2OC(O)NR^cR^d$, $-X^2NR^dC(O)R^c$, $-X^2NR^dC(O)_2R^e$, $-X^2NR^cC(O)NR^cR^d$, $-X^2s(O)R^c$, $-X^2S(O)_2R^e$, $-X^2NR^cS(O)_2R^e$, $-X^2S(O)_2NR^cR^d$ and $-X^2N_3$, wherein $X^2$ is $C_{1-4}$ alkylene, and each $R^c$ and $R^d$ is independently selected from hydrogen, $C_{1-8}$ alkyl, $C_{1-8}$ haloalkyl, $C_{3-6}$ cycloalkyl, $C_{2-8}$ alkenyl and $C_{2-8}$ alkynyl, and each $R^e$ is independently selected from the group consisting of $C_{1-8}$ alkyl, $C_{1-8}$ haloalkyl, $C_{3-6}$ cycloalkyl, $C_{2-8}$ alkenyl and $C_{2-8}$ alkynyl, and each of $R^c$, $R^d$ and $R^e$ is optionally further substituted with from one to three members selected from the group consisting of OH, $O(C_{1-8}$ alkyl), SH, $S(C_{1-8}$ alkyl), CN, $NO_2$, $NH_2$, $NH(C_{1-8}$ alkyl) and $N(C_{1-8}$ alkyl$)_2$; $R^{3a}$, $R^{3b}$ and $R^{3c}$ are each members independently selected from hydrogen, halogen, phenyl, thienyl, furanyl, pyridyl, pyrimidinyl, pyrazinyl, pyridizinyl, pyrazolyl, imidazolyl, thiazolyl, oxazolyl, isoxazolyl, isothiazolyl, triazolyl, tetrazolyl, oxadiazolyl, $-OR^f$, $-OC(O)R^f$, $-NR^fR^g$, $-SR^f$, $-R^f$, $-CN$, $-NO_2$, $-CO_2R^f$, $-CONR^fR^g$, $-C(O)R^f$, $-OC(O)NR^fR^g$, $-NR^gC(O)R^f$, $-NR^gC(O)_2R^h$, $-NR^f-C(O)NR^fR^g$, $-S(O)R^h$, $-S(O)_2R^h$, $-NR^fS(O)_2R^h$, $-S(O)_2NR^fR^g$, $-NR^fS(O)_2R^h$, $-NR^fS(O)_2NR^fR^g$, $-X^3OR^f$, $-X^3OC(O)R^f$, $-X^3NR^fR^g$, $-X^3SR^f$, $-X^3CN$, $-X^3NO_2$, $-X^3CO_2R^f$, $-X^3CONR^fR^g$, $-X^3C(O)R^f$, $-X^3OC(O)NR^fR^g$, $-X^3NR^gC(O)R^f$, $-X^3NR^gC(O)_2R^h$, $-X^3NR^f-C(O)NR^fR^g$, $-X^3S(O)R^h$, $-X^3S(O)_2R^h$, $-X^3NR^fS(O)_2R^h$ and $-X^3S(O)_2NR^fR^g$ wherein $X^3$ is $C_{1-4}$ alkylene, each $R^f$ and $R^g$ is independently selected from hydrogen, $C_{1-8}$ alkyl, $C_{1-8}$ haloalkyl, $C_{3-6}$ cycloalkyl, $C_{2-8}$ alkenyl and $C_{2-8}$ alkynyl, and each $R^h$ is independently selected from the group consisting of $C_{1-8}$ alkyl, $C_{1-8}$ haloalkyl, $C_{3-6}$ cycloalkyl, $C_{2-8}$ alkenyl and $C_{2-8}$ alkynyl, and wherein any phenyl, thienyl, furanyl, pyridyl, pyrimidinyl, pyrazinyl, pyridizinyl, pyrazolyl, imidazolyl, thiazolyl, oxazolyl, isoxazolyl, isothiazolyl, triazolyl, tetrazolyl, or oxadiazolyl group present is optionally substituted with from one to three substitutents selected from the group consisting of halogen, $-OR^f$, $-NR^fR^g$, $-R^h$, $-CN$, $-NO_2$, $-CO_2R^f$, $-CONR^fR^g$, $-C(O)R^f$, $-X^3OR^f$, $-X^3NR^fR^g$, $-X^3NR^fS(O)_2R^h$ and $-X^3S(O)_2NR^fR^g$.

Within the preferred group of formula III above, certain groups of embodiments are particularly preferred. In one group of particularly preferred embodiments, the subscript m is 0 or 1 and at least one of $R^{2a}$ or $R^{2e}$ is hydrogen. More preferably, at least one of $R^{3a}$, $R^{3b}$ and $R^{3c}$ is selected from halogen and $C_{1-4}$ haloalkyl. Still more preferably, $R^{2d}$ is hydrogen and at least two of $R^{3a}$, $R^{3b}$ and $R^{3c}$ are selected from halogen and $C_{1-4}$ haloalkyl with the remaining member being other than hydrogen. In related, and preferred embodiments, m is 0 or 1 and at least one of $R^2$, or $R^{2e}$ is hydrogen, $R^{2d}$ is hydrogen, $R^{2c}$ is selected from F, Cl, Br, CN, $NO_2$, $CO_2CH_3$, $C(O)CH_3$ and $S(O)_2CH_3$, and at least two of $R^{3a}$, $R^{3b}$ and $R^{3c}$ are selected from halogen and $C_{1-4}$ haloalkyl with the remaining member being other than hydrogen. In another group of particularly preferred embodiments, the subscript m is 0 or 1; and $R^{2a}$ and $R^{2e}$ are both hydrogen. More preferably, at least one of $R^{3a}$, $R^{3b}$ and $R^{3c}$ is selected from halogen and $C_{1-4}$ haloalkyl. Still more preferably, at least one of $R^{3a}$, $R^{3b}$ and $R^{3c}$ is selected from halogen and $C_{1-4}$ haloalkyl, and the remaining members of $R^{3a}$, $R^{3b}$ and $R^{3c}$ are other than hydrogen. In yet another group of particularly preferred embodiments, the subscript m is 0 or 1; and $R^{2b}$ and $R^{2e}$ are both hydrogen. More preferably, at least one of $R^{3a}$, $R^{3b}$ and $R^e$ is selected from halogen and $C_{1-4}$ haloalkyl. Still more preferably, at least one of $R^{3a}$, $R^{3b}$ and $R^{3c}$ is selected from halogen and $C_{1-4}$ haloalkyl, and the remaining members of $R^{3a}$, $R^{3b}$ and $R^{3c}$ are other than hydrogen.

Still other preferred groups of formula III above, are:

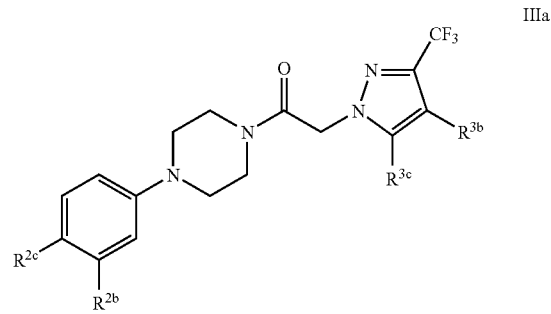

IIIa

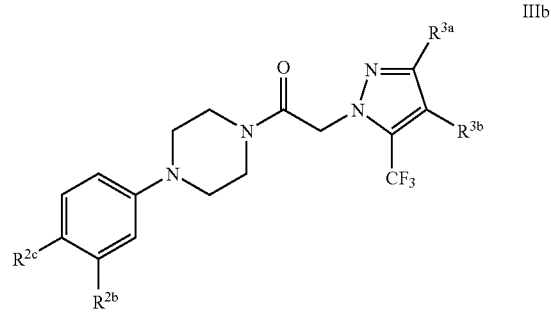

IIIb

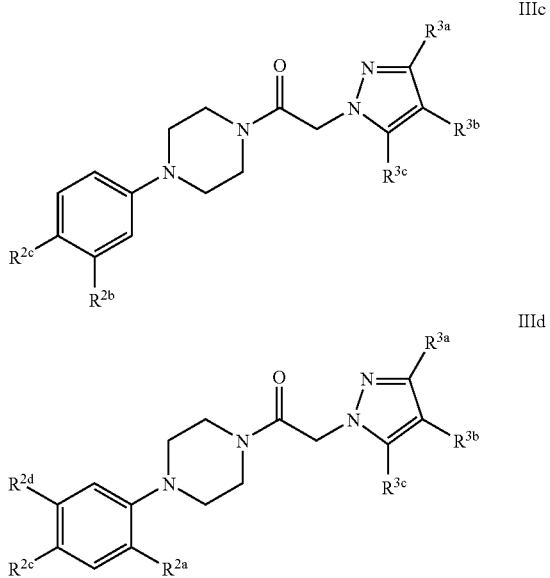

Turning first to the compounds of formula IIIa, $R^{3b}$ is preferably halogen, nitro or cyano, more preferably halogen and most preferably chloro or bromo; $R^{3c}$ is preferably $C_{1-6}$ alkyl, C haloalkyl or $C_{3-6}$ cycloalkyl; $R^{2c}$ is halogen and $R^{2b}$ is —$OR^c$ or $R^e$ wherein $R^c$ is selected from hydrogen, $C_{1-8}$ alkyl, $C_{1-8}$ haloalkyl, $C_{3-6}$ cycloalkyl, $C_{2-8}$ alkenyl and $C_{2-8}$ alkynyl, and $R^e$ is selected from the group consisting of $C_{1-8}$ alkyl, $C_{1-8}$ haloalkyl, $C_{3-6}$ cycloalkyl, $C_{2-8}$ alkenyl and $C_{2-8}$ alkynyl, and each of $R^cC$ and $R^e$ is optionally further substituted with from one to three members selected from the group consisting of OH, O($C_{1-8}$ alkyl), SH, S($C_{1-8}$ alkyl), CN, $NO_2$, $NH_2$, NH($C_{1-8}$ alkyl) and N($C_{1-8}$ alkyl)$_2$.

For the compounds of formula IIIb, $R^{3b}$ is preferably halogen, nitro or cyano, more preferably halogen and most preferably chloro or bromo; $R^{3a}$ is preferably $C_{1-6}$ alkyl, $C_{1-6}$ haloalkyl or $C_{3-6}$ cycloalkyl; $R^{2c}$ is preferably halogen and $R^{2b}$ is preferably $OR^c$ or $R^e$ wherein $R^c$ is selected from hydrogen, $C_{1-8}$ alkyl, $C_{1-8}$ haloalkyl, $C_{3-6}$ cycloalkyl, $C_{2-8}$ alkenyl and $C_{2-8}$ alkynyl, and $R^e$ is selected from the group consisting of $C_{1-8}$ alkyl, $C_{1-8}$ haloalkyl, $C_{3-6}$ cycloalkyl, $C_{2-8}$ alkenyl and $C_{2-8}$ alkynyl, and each of $R^cC$ and $R^e$ is optionally further substituted with from one to three members selected from the group consisting of OH, O($C_{1-8}$ alkyl), SH, S($C_{1-8}$ alkyl), CN, $NO_2$, $NH_2$, NH($C_{1-8}$ alkyl) and N($C_{1-8}$ alkyl)$_2$.

For the compounds of formula IIIc, $R^{3a}$ is selected from $NH_2$, $CF_3$, $SCH_3$, Ph and thienyl; $R^{3b}$ is chloro or bromo; $R^{3c}$ is preferably $C_{1-6}$ alkyl, $C_{1-6}$ haloalkyl or $C_{3-6}$ cycloalkyl; $R^{2c}$ is hydrogen, halogen, cyano or nitro; and $R^{2b}$ is selected from hydrogen, halogen, —$OR^c$, —$OC(O)R^c$, —$NR^cR^d$, —$SR^c$, —$R^e$, —$CO_2R^c$, —$CONR^cR^d$, —$C(O)R^c$, —$S(O)R^e$, —$S(O)_2R^e$, —$X^2OR^c$, —$X^2OC(O)R^c$, —$X^2NR^cR^d$, —$X^2SR^c$, —$X^2CO_2R^c$, —$X^2CONR^cR^d$, —$X^2C(O)R^c$, —$X^2OC(O)NR^cR^d$, —$X^2NR^dC(O)R^c$, —$X^2NR^dC(O)_2R^e$, —$X^2NR^cC(O)NR^cR^d$, —$X^2S(O)R^e$, —$X^2S(O)_2R^e$, —$X^2NR^cS(O)_2R^e$, —$X^2S(O)_2NR^cR^d$ and —$X^2N_3$, wherein $X^2$ is $C_{1-4}$ alkylene, and each $R^c$ and $R^d$ is independently selected from hydrogen, $C_{1-8}$ alkyl, $C_{1-8}$ haloalkyl, $C_{3-6}$ cycloalkyl, $C_{2-8}$ alkenyl and $C_{2-8}$ alkynyl, and each $R^e$ is independently selected from the group consisting of $C_{1-8}$ alkyl, $C_{1-8}$ haloalkyl, $C_{3-6}$ cycloalkyl, $C_{2-8}$ alkenyl and $C_{2-8}$ alkynyl, and each of $R^c$, $R^d$ and $R^e$ is optionally further substituted with from one to three members selected from the group consisting of OH, O($C_{1-8}$ alkyl), SH, S($C_{1-8}$ alkyl), CN, $NO_2$, $NH_2$, NH($C_{1-8}$ alkyl) and N($C_{1-8}$ alkyl)$_2$. In the most preferred embodiments, $R^{2c}$ is halogen, cyano or nitro; $R^{2b}$ is $R^e$ or —$OR^c$; $R^{3a}$ is selected from the group consisting of $NH_2$, $CF_3$, $SCH_3$, Ph and thienyl; $R^{3b}$ is chloro or bromo; and $R^{3c}$ is selected from the group consisting of $C_{1-6}$ alkyl and $C_{3-6}$ cycloalkyl.

In related, and preferred embodiments, compounds of formula IIIc are provided wherein $R^{3c}$ is selected from $NH_2$, $CF_3$, $SCH_3$, Ph and thienyl; $R^{3b}$ is chloro or bromo; $R^{3a}$ is preferably $C_{1-6}$ alkyl, $C_{1-6}$ haloalkyl or $C_{3-6}$ cycloalkyl; $R^{2c}$ is hydrogen, halogen, cyano or nitro, preferably halogen; and $R^{2b}$ is selected from hydrogen, halogen, —$OR^c$, —$OC(O)R^c$, —$NR^cR^d$, —$SR^c$, —$R^e$, —$CO_2R^c$, $CONR^cR^d$, —$C(O)R^c$, —$S(O)R^e$, —$S(O)_2R^e$, —$X^2OR^c$, —$X^2OC(O)R^c$, —$X^2NR^cR^d$, —$X^2SR^c$, —$X^2CO_2R^c$, —$X^2CONR^cR^d$, —$X^2C(O)R^c$, —$X^2NR^dC(O)R^c$, —$X^2NR^dC(O)_2R^e$, —$X^2S(O)R^e$, —$X^2NR^cC(O)NR^cR^d$, —$X^2S(O)R^e$, —$X^2S(O)_2R^e$, —$X^2NR^cS(O)_2R^e$, —$X^2S(O)_2NR^cR^d$ and —$X^2N_3$, wherein $X^2$ is $C_{1-4}$ alkylene, and each $R^cC$ and $R^d$ is independently selected from hydrogen, $C_{1-8}$ alkyl, $C_{1-8}$ haloalkyl, $C_{3-4}$ cycloalkyl, $C_{2-8}$ alkenyl and $C_{2-8}$ alkynyl, and each $R^e$ is independently selected from the group consisting of $C_{1-8}$ alkyl, $C_{1-8}$ haloalkyl, $C_{3-6}$ cycloalkyl, $C_{2-8}$ alkenyl and $C_{2-8}$ alkynyl, and each of $R^c$, $R^d$ and $R^e$ is optionally further substituted with from one to three members selected from the group consisting of OH, O($C_{1-8}$ alkyl), SH, S($C_{1-8}$ alkyl), CN, $NO_2$, $NH_2$, NH($C_{1-8}$ alkyl) and N($C_{1-8}$ alkyl)$_2$. In the most preferred embodiments, $R^{2c}$ is halogen, cyano or nitro; $R^{2b}$ is $R^e$ or —$OR^c$; $R^{3a}$ is selected from the group consisting of $C_{1-6}$ alkyl and $C_{3-6}$ cycloalkyl; $R^{3c}$ is selected from the group consisting of $NH_2$, $CF_3$, $SCH_3$, Ph and thienyl; and $R^{3b}$ is chloro or bromo.

For the compounds of formula IIId, $R^{3a}$ is selected from $NH_2$, $CF_3$, $SCH_3$, Ph and thienyl; $R^{3b}$ is chloro or bromo; $R^{3d}$ is preferably $C_{1-4}$ alkyl, $C_{3-6}$ haloalkyl or $C_{3-6}$ cycloalkyl; $R^{2a}$, is preferably other than hydrogen, and is selected from halogen, —$OR^c$, —$OC(O)R^c$, —$NR^cR^d$, —$SR^c$, —$R^e$, —$CO_2R^c$, —$CONR^cR^d$, —$C(O)R^c$, —$S(O)R^e$, —$S(O)_2R^e$, —$X^{20}R^c$, —$X^2OC(O)R^c$, —$X^2NR^cR^d$, —$X^2SR^c$, —$X^2CO_2R^c$, —$X^2CONR^cR^d$, —$X^2C(O)R^c$, —$X^2OC(O)NR^cR^d$, —$X^2NR^dC(O)R^c$, —$X^2NR^dC(O)_2R^e$, —$X^2NR^cC(O)NR^cR^d$, —$X^2S(O)R^e$, —$X^2S(O)_2R^e$, —$X^2NR^cS(O)_2R^e$, —$X^2S(O)_2NR^cR^d$ and —$X^2N_3$; $R^{2c}$ is hydrogen, halogen, cyano or nitro, preferably halogen; and $R^{2d}$ is selected from hydrogen, halogen, —$OR^c$, —$OC(O)R^c$, —$NR^cR^d$, —$SR^c$, —$R^e$, —$CO_2R^c$, —$CONR^cR^d$, —$C(O)R^c$, —$S(O)R^e$, —$S(O)_2R^e$, —$X^2OR^c$, —$X^2OC(O)R^c$, —$X^2NR^cR^d$, —$X^2SR^c$, —$X^2CO_2R^c$, —$X^2CONR^cR^d$, —$X^2C(O)R^c$, —$X^2OC(O)NR^cR^d$, —$X^2NR^dC(O)R^c$, —$X^2NR^dC(O)_2R^e$, —$X^2NR^cC(O)NR^cR^d$, —$X^2S(O)R^e$, —$X^2S(O)_2R^e$, —$X^2NR^cS(O)_2R^e$, —$X^2S(O)_2NR^cR^d$ and —$X^2N_3$, wherein each $X^2$ is $C_{1-4}$ alkylene, and each $R^c$ and $R^d$ is independently selected from hydrogen, $C_{1-8}$ alkyl, $C_{1-8}$ haloalkyl, $C_{3-6}$ cycloalkyl, $C_{2-8}$ alkenyl and $C_{2-8}$ alkynyl, and each $R^e$ is independently selected from the group consisting of $C_{1-8}$ alkyl, $C_{1-8}$ haloalkyl, $C_{3-6}$ cycloalkyl, $C_{2-8}$ alkenyl and $C_{2-8}$ alkynyl, and each of $R^c$, $R^d$ and $R^e$ is optionally further substituted with from one to three members selected from the group consisting of OH, O($C_{1-8}$ alkyl), SH, S($C_{1-8}$ alkyl), CN, $NO_2$, $NH_2$, NH($C_{1-8}$ alkyl) and N($C_{1-8}$ alkyl)$_2$; and no more than one of $R^{2a}$ and $R^{2d}$ is hydrogen. Preferably, each of $R^{2a}$ and $R^{2d}$ is other than hydrogen. In the most preferred embodiments, $R^{3c}$ is other than hydrogen; $R^{2c}$ is halogen cyano or nitro; $R^{2d}$ is $R^e$ or —$OR^c$; $R^{3a}$ is selected from the group consisting of $C_{1-4}$ alkyl and $C_{3-4}$ cycloalkyl; $R^{3b}$ is chloro or bromo; and $R^{3c}$ is selected from the group consisting of $NH_2$, $CF_3$, $SCH_3$, Ph and thienyl.

In related and preferred embodiments, compounds of formula Id are provided wherein $R^{3c}$ is selected from $NH_2$, $CF_3$, $SCH_3$, Ph and thienyl; $R^{3b}$ is chloro or bromo; $R^{3a}$ is preferably $C_{1-4}$ alkyl, $C_{1-4}$ haloalkyl or $C_{3-4}$ cycloalkyl; $R^{2a}$ is hydrogen, halogen, —$OR^c$, —$OC(O)R^c$, —$NR^cR^d$, —$SR^c$, —$R^e$, —$CO_2R^c$, —$CONR^cR^d$, —$C(O)R^c$, —$S(O)R^e$, —$S(O)_2R^e$, —$X^2OR^c$, —$X^2OC(O)R^c$, —$X^2NR^cR^d$, —$X^2SR^c$, —$X^2CO_2R^c$, —$X^2CONR^cR^d$, —$X^2C(O)R^c$, —$X^2OC(O)NR^cR^d$, —$X^2NR^dC(O)R^c$, —$X^2NR^dC(O)_2R^e$, —$X^2NR^cC(O)NR^cR^d$, —$X^2S(O)R^e$, —$X^2S(O)_2R^e$, —$X^2NR^cS(O)_2R^e$, —$X^2S(O)_2NR^cR^d$ and —$X^2N_3$; $R^{2c}$ is hydrogen, halogen, cyano or nitro; and $R^{2d}$ is selected from hydrogen, halogen, —$OR^c$, —$OC(O)R^c$, —$NR^cR^d$, —$SR^c$, —$R^e$, —$CO_2R^c$, —$CONR^cR^d$, —$C(O)R^c$, —$S(O)R^e$, —$S(O)_2R^e$, —$X^2OR^c$, —$X^2OC(O)R^c$, —$X^2NR^cR^d$, —$X^2SR^c$, —$X^2CO_2R^c$, $X^2CONR^cR^d$, —$X^2C(O)R^c$, —$X^2OC(O)NR^cR^d$, —$X^2NR^dC(O)R^c$, —$X^2NR^dC(O)_2R^e$, —$X^2NR^cC(O)NR^cR^d$, —$X^2S(O)R^e$, —$X^2S(O)_2R^e$, —$X^2NR^cS(O)_2R^e$, —$X^2S(O)_2NR^eR^d$ and —$X^2N_3$, wherein each $X^2$ is $C_{1-4}$ alkylene, and each $R^c$ and $R^d$ is independently selected from hydrogen, $C_{1-8}$ alkyl, $C_{1-8}$ haloalkyl, $C_{3-4}$ cycloalkyl, $C_{2-8}$ alkenyl and $C_{2-8}$ alkynyl, and each $R^e$ is independently selected from the group consisting of $C_{1-8}$ alkyl, $C_{1-8}$ haloalkyl, $C_{3-6}$ cycloalkyl, $C_{2-8}$ alkenyl and $C_{2-8}$ alkynyl, and each of $R^c$, $R^d$ and $R^e$ is optionally further substituted with from one to three members selected from the group consisting of OH, $O(C_{1-8}$ alkyl), SH, $S(C_{1-8}$ alkyl), CN, $NO_2$, $NH_2$, $NH(C_{1-8}$ alkyl) and $N(C_{1-8}$ alkyl)$_2$; and no more than one of $R^{2a}$ and $R^{2d}$ is hydrogen. Preferably, each of $R^{2a}$ and $R^{2d}$ is other than hydrogen. In the most preferred embodiments, $R^{2a}$ is other than hydrogen; $R^{2c}$ is halogen, cyano or nitro; $R^{2d}$ is $R^e$ or —$OR^c$; $R^{3a}$ is selected from the group consisting of $NH_2$, $CF_3$, $SCH_3$, Ph and thienyl; $R^{3b}$ is chloro or bromo; and $R^{3c}$ is selected from the group consisting of $C_{1-6}$ alkyl and $C_{3-6}$ cycloalkyl.

In yet another group of preferred embodiments, the compounds are selected from formulae IVa-IVe:

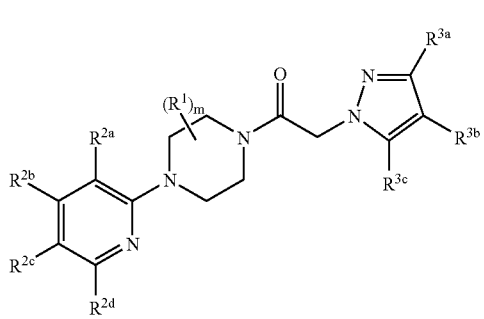

IVa

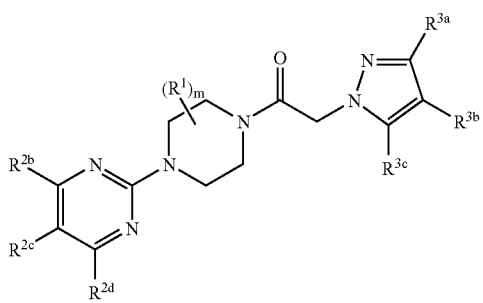

IVb

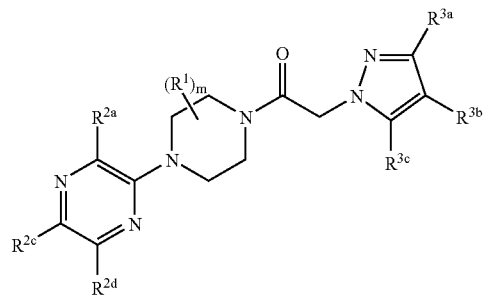

IVc

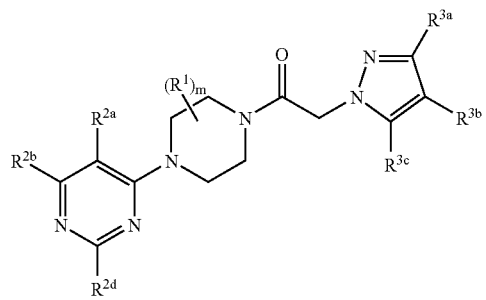

IVd

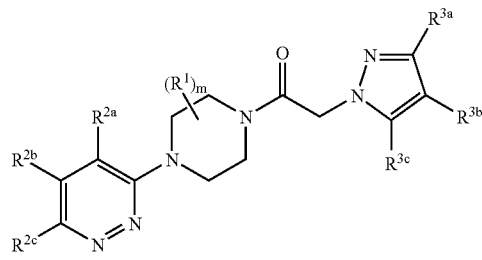

IVe wherein $R^1$ and the subscript m have the meaning provided above for formula III, and each of $R^{2a}$, $R^{2b}$, $R^{2c}$ and $R^{2d}$ are substituents independently selected from hydrogen, halogen, —$OR^c$, —$OC(O)R^c$, —$NR^cR^d$, —$SR^c$, —$R^e$, —CN, —$NO_2$, —$CO_2R^e$, —$CONR^cR^d$, —$C(O)R^c$, —$OC(O)NR^cR^d$, —$NR^dC(O)R^c$, —$NR^dC(O)_2R^e$, —$NR^c$—$C(O)NR^cR^d$, —NH—$C(NH_2)$=NH, —$NR^cC(NH_2)$=NH, —NH—$C(NH_2)$=$NR^e$, —NH—$C(NHR^e)$=NH, —$S(O)R^e$, —$S(O)_2R^e$, —$S(O)_2NR^cR^d$, —$NR^cS(O)_2R^c$, —$NR^cS(O)_2NR^cR^d$, —$N_3$, —$X^2OR^c$, —$X^2OC(O)R^c$, —$X^2NR^cR^d$, —$X^2SR^c$, —$X^2CN$, —$X^2NO_2$, —$X^2CO_2R^c$, —$X^2CONR^cR^d$, —$X^2C(O)R^c$, —$X^2OC(O)NR^cR^d$, —$X^2NR^dC(O)R^c$, —$X^2NR^dC(O)_2R^e$, —$X^2NR^cC(O)NR^cR^d$, —$X^2NH$—$C(NH_2)$=NH, —$X^2NR^eC(NH_2)$=NH, —$X^2NH$—$C(NH_2)$=$NR^e$, —$X^2NH$—$C(NHR^e)$=NH, —$X^2S(O)R^e$, —$X^2S(O)_2R^e$, —$X^2S(O)_2NR^cR^d$, —$X^2NR^cS(O)_2R^e$, —$X^1N_3$, aryl and heteroaryl, wherein $X^2$, $R^c$, $R^d$ and $R^e$ have the meanings provided above with respect to the compounds of formula I. Similarly, each of $R^{3a}$, $R^{3b}$ and $R^{3c}$ represents a substituent independently selected from hydrogen, halogen, phenyl, thienyl, furanyl, pyridyl, pyrimidinyl, pyrazinyl, pyridizinyl, pyrazolyl, imidazolyl, thiazolyl, oxazolyl, isoxazolyl, isothiazolyl, triazolyl, tetrazolyl, oxadiazolyl, —$OR^f$, —$OC(O)R^f$, —$NR^fR^g$, —$SR^f$, —$R^h$, —CN, —$NO_2$, —$CO_2R^f$, —$CONR^fR^g$, —$C(O)R^f$, —$OC(O)NR^fR^g$, —$NR^gC(O)R^f$, —$NR^gC(O)_2R^h$, —$NR^f$—$C(O)NR^fR^g$, —NH—$C(NH_2)$=NH, —$NR^hC(NH_2)$=NH, —NH—$C(NH_2)$=$NR^h$, —NH—$C(NHR^h)$=NH, —$S(O)R^h$, —$S(O)_2R^h$, —$S(O)_2NR^fR^g$, —$NR^fS(O)_2R^h$, —$NR^fS(O)_2NR^fR^g$, —$N_3$, —$X^3OR^f$, —X³OC(O)R^f, —X³NR^fR^g, —X³SR^f, —X³CN, —X³NO₂, —X³CO₂R^f, —X³CONR^fR^g, —X³C(O)R^f, —X³C(O)NR^fR^g, —X³NR^gC(O)R^f, —X³NR^gC(O)₂R^h, —X³NR^f—C(O)NR^fR^g, —X³NH—C(NH₂)=NH, —X³NR^hC(NH₂)=NH, —X³NH—C(NH₂)=NR^h, —X³NH—C(NHR^h)=NH, —X³S(O)R^h, —X³S(O)₂R^h, —X³S(O)₂NR^fR^g, —X³NR^fS(O)₂R^h and —X³N₃, wherein X³, R^f, R^g and R^h have the meaning provided above with respect to the compounds of formula I, and wherein no more than two of R³ᵃ, R³ᵇ and R³ᶜ are hydrogen, preferably, no more than one of R³ᵃ, R³ᵇ and R³ᶜ is hydrogen, and still more preferably, each of R³ᵃ, R³ᵇ and R³ᶜ is other than hydrogen.

Turning first to the compounds of formula IVa, in one group of particularly preferred embodiments, at least one of R³ᵃ, R³ᵇ and R³ᶜ is selected from halogen and $C_{1-4}$ haloalkyl. Still more preferably, at least one of R²ᵇ and R²ᵈ is hydrogen and at least two of R³ᵃ, R³ᵇ and R³ᶜ are selected from halogen and $C_{1-4}$ haloalkyl. In related, and preferred embodiments, R²ᶜ is selected from F, Cl, Br, CN, NO₂, CO₂CH₃, C(O)CH₃ and S(O)₂CH₃, and at least two of R³ᵃ, R³ᵇ and R³ᶜ are selected from halogen and $C_{1-4}$ haloalkyl with the remaining member being other than hydrogen.

Similarly, certain compounds of formula IVb are preferred. Particularly preferred are those compounds of formula IVb in which at least one of R³ᵃ, R³ᵇ and R³ᶜ is selected from halogen and $C_{1-4}$ haloalkyl. Still more preferably, at least one of R²ᵇ and R²ᵈ is hydrogen and at least two of R³ᵃ, R³ᵇ and R³ᶜ are selected from halogen and $C_{1-4}$ haloalkyl. In related, and preferred embodiments, R²ᶜ is selected from F, Cl, Br, CN, NO₂, CO₂CH₃, C(O)CH₃ and S(O)₂CH₃, and at least two of R³, R³ᵇ and R³ᶜ are selected from halogen and $C_{1-4}$ haloalkyl with the remaining member being other than hydrogen.

Turning next to the compounds of formula IVc, preferred embodiments are those in which at least one of R²ᵃ, R²ᶜ and R²ᵈ, preferably R²ᶜ is selected from F, Cl, Br, CN, NO₂, CO₂CH₃, C(O)CH₃ and S(O)₂CH₃; and at least two of R³ᵃ, R³ᵇ and R³ᶜ are selected from halogen and $C_{1-4}$ haloalkyl with the remaining member being other than hydrogen. In other preferred embodiments, one of R²ᶜ and R²ᵈ is selected from F, Cl, Br, CN, NO₂, CO₂CH₃, C(O)CH₃ and S(O)₂CH₃, and the other is an aryl or heteroaryl group, for example, phenyl, thienyl, furanyl, oxazolyl, isoxazolyl, thiazolyl and isothiazolyl, and at least two of R³ᵃ, R³ᵇ and R³ᶜ are selected from halogen and $C_{1-4}$ haloalkyl with the remaining member being other than hydrogen.

For the compounds of formula IVd, preferred embodiments are those in which at least one of R²ᵃ, R²ᵇ and R²ᵈ is selected from F, Cl, Br, CN, NO₂, CO₂CH₃, C(O)CH₃ and S(O)₂CH₃, and at least two of R³ᵃ, R³ᵇ and R³ᶜ are selected from halogen and $C_{1-4}$ haloalkyl with the remaining member being other than hydrogen. In other preferred embodiments, one of R²ᵇ and R²ᵈ is selected from F, Cl, Br, CN, NO₂, CO₂CH₃, C(O)CH₃ and S(O)₂CH₃, and the other is an aryl or heteroaryl group, for example, phenyl, thienyl, furanyl, oxazolyl, isoxazolyl, thiazolyl and isothiazolyl, and at least two of R³ᵃ, R³ᵇ and R³ᶜ are selected from halogen and $C_{1-4}$ haloalkyl with the remaining member being other than hydrogen.

For the compounds of formula IVe, preferred embodiments are those in which at least one of R²ᵃ, R²ᵇ and R²ᶜ is selected from F, Cl, Br, CN, NO₂, CO₂CH₃, C(O)CH₃ and S(O)₂CH₃, and at least two of R³ᵃ, R³ᵇ and R³ᶜ are selected from halogen and $C_{1-4}$ haloalkyl with the remaining member being other than hydrogen. In other preferred embodiments, one of R²ᵇ and R²ᶜ is selected from F, Cl, Br, CN, NO₂, CO₂CH₃, C(O)CH₃ and S(O)₂CH₃, and the other is an aryl or heteroaryl group, for example, phenyl, thienyl, furanyl, oxazolyl, isoxazolyl, thiazolyl and isothiazolyl, and at least two of R³ᵃ, R³ᵇ and R³ᶜ are selected from halogen and $C_{1-4}$ haloalkyl with the remaining member being other than hydrogen.

In yet another group of preferred embodiments, the compounds are selected from formulae IVf-IVi:

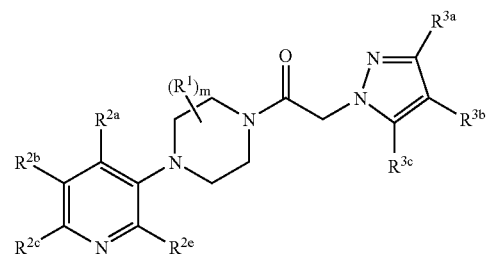

IVf

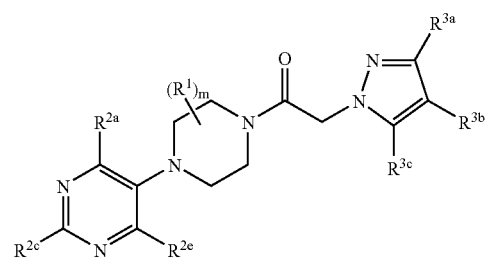

IVg

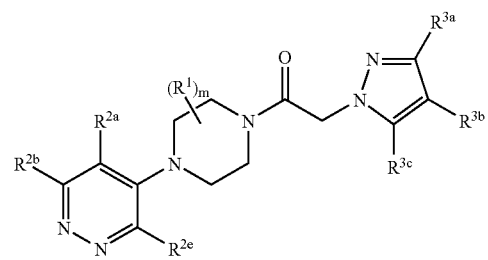

IVh

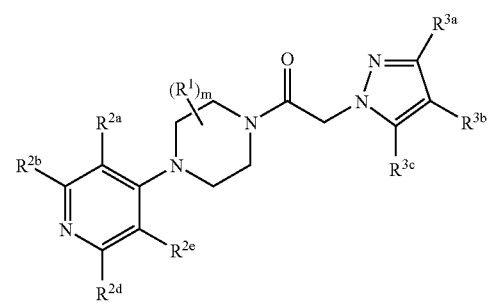

IVi wherein R¹ and the subscript m have the meaning provided above for formula III, and each of R²ᵃ, R²ᵇ, R²ᶜ, R²ᵈ, R³ᵃ, R³ᵇ and R³ᶜ have the meaning provided above for formulae IVa-IVe. Additionally, R²ᶜ represents a substituent selected from the groups provided for R²ᵃ in formulae IVa-IVe above.

In still other embodiments, compounds are provided having formulae Va and Vb:

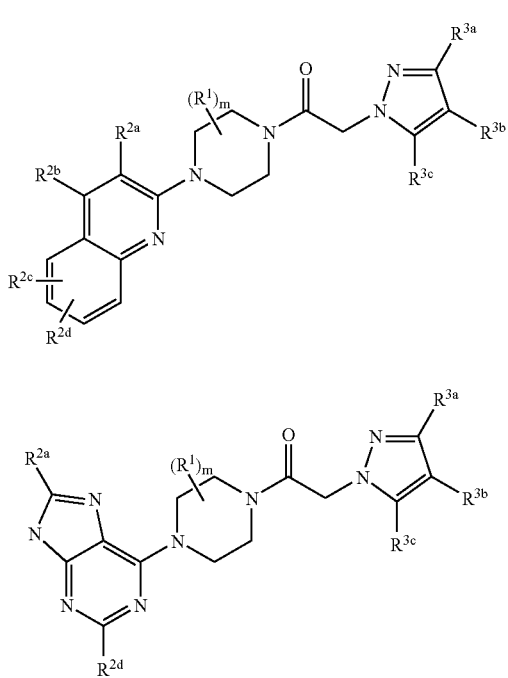

wherein each of $R^1$, the subscript m, $R^{2a}$, $R^{2b}$, $R^{2c}$, $R^{2d}$, $R^{3a}$, $R^{3b}$ and $R^{3c}$ have the meaning provided above for formulae IVa-IVe.

IV. Pharmaceutical Compositions

In addition to the compounds provided above, compositions for modulating CCR1 activity in humans and animals will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Patent Application 20020012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

V. Methods of Treating Diseases Modulated by CCR1

In yet another aspect, the present invention provides methods of treating CCR1-mediated conditions or diseases by administering to a subject having such a disease or condition, a therapeutically effective amount of a compound of formula I above. The "subject" is defined herein to include animals such as mammals, including, but not limited to, primates (e.g., humans), cows, sheep, goats, horses, dogs, cats, rabbits, rats, mice and the like.

CCR1 provides a target for interfering with or promoting specific aspects of immune cell functions, or more generally, with functions associated with CCR1 expression on a wide range of cell types in a mammal, such as a human. Compounds that inhibit CCR1, are particularly useful for modulating monocyte, macrophage, lymphocyte, granulocyte, NK cell, mast cells, dendritic cell, and certain immune derived cell (for example, osteoclasts) function for therapeutic purposes. Accordingly, the present invention is directed to compounds which are useful in the prevention and/or treatment of a wide variety of inflammatory and immunoregulatory disorders and diseases (see Saeki, et al., *Current Pharmaceutical Design* 9:1201-1208 (2003)).

For example, an instant compound that inhibits one or more functions of CCR1 may be administered to inhibit (i.e., reduce or prevent) inflammation or cellular infiltration associated with an immune disorder. As a result, one or more inflammatory processes, such as leukocyte emigration or infiltration, chemotaxis, exocytosis (e.g., of enzymes, histamine) or inflammatory mediator release, can be inhibited. For example, monocyte infiltration to an inflammatory site (e.g., an affected joint in arthritis, or into the CNS in MS) can be inhibited according to the present method.

Similarly, an instant compound that promotes one or more functions of CCR1 is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, monocytes can be recruited to combat bacterial infections.

Diseases and conditions associated with inflammation, immune disorders and infection can be treated using the method of the present invention. In a preferred embodiment, the disease or condition is one in which the actions of immune cells such monocyte, macrophage, lymphocyte, granulocyte, NK cell, mast cell, dendritic cell, or certain immune derived cell (for example, osteoclasts) are to be inhibited or promoted, in order to modulate the inflammatory or autoimmune response.

In one group of embodiments, diseases or conditions, including chronic diseases, of humans or other species can treated with modulators of CCR1 function. These diseases or conditions include: (1) allergic diseases such as systemic anaphylaxis or hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis, urticaria and pruritus, (5) vasculitis, (6) spondyloarthropathies, (7) scleroderma, (8) asthma and respiratory allergic diseases such as allergic asthma, allergic rhinitis, hypersensitivity lung diseases and the like, (9) autoimmune diseases, such as fibromyalagia, scleroderma, ankylosing spondylitis, juvenile RA, Still's disease, polyarticular juvenile RA, pauciarticular juvenile RA, polymyalgia rheumatica, rheumatoid arthritis, psoriatic arthritis, osteoarthritis, polyarticular arthritis, multiple sclerosis, systemic lupus erythematosus, type I diabetes, type II diabetes, glomerulonephritis, and the like, (10) graft rejection (including allograft rejection and graft-v-host disease), and (11) other diseases in which undesired inflammatory responses or immune disorders are to be inhibited, such as cardiovascular disease including atherosclerosis, myositis, neurodegenerative diseases (e.g., Alzheimer's disease), encephalitis, meningitis, hepatitis, nephritis, sepsis, sarcoidosis, allergic conjunctivitis, otitis, chronic obstructive pulmonary disease, sinusitis, Behcet's syndrome and gout and (12) immune mediated food allergies such as Celiac disease.

In another group of embodiments, diseases or conditions can be treated with modulators of CCR1 function. Examples of diseases to be treated with modulators of CCR1 function include cancers, cardiovascular diseases, diseases in which angiogenesis or neovascularization play a role (neoplastic diseases, retinopathy and macular degeneration), infectious diseases (viral infections, e.g., HIV infection, and bacterial infections) and immunosuppressive diseases such as organ transplant conditions and skin transplant conditions. The term "organ transplant conditions" is meant to include bone marrow transplant conditions and solid organ (e.g., kidney, liver, lung, heart, pancreas or combination thereof) transplant conditions.

The compounds of the present invention are accordingly useful in the prevention and treatment of a wide variety of inflammatory and immunoregulatory disorders and diseases.

Depending on the disease to be treated and the subject's condition, the compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex and diet of the subject, as well as the mode and time of administration, rate of excretion, drug combination, and the severity of the particular condition for the subject undergoing therapy.

Diseases and conditions associated with inflammation, immune disorder, infection and cancer can be treated or prevented with the present compounds, compositions, and methods.

The compounds and compositions of the present invention can be combined with other compounds and compositions having related utilities to prevent and treat the condition or disease of interest, such as inflammatory or autoimmune disorders, conditions and diseases, including inflammatory bowel disease, rheumatoid arthritis, osteoarthritis, psoriatic arthritis, polyarticular arthritis, multiple sclerosis, allergic diseases, psoriasis, atopic dermatitis and asthma, and those pathologies noted above.

For example, in the treatment or prevention of inflammation or autimmunity or for example arthritis associated bone loss, the present compounds and compositions may be used in conjunction with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non steroidal anti-inflammatory agent, or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds and compositions may be administered with an analgesic listed above; a potentiator such as caffeine, an H2 antagonist (e.g., ranitidine), simethicone, aluminum or magnesium hydroxide; a decongestant such as phenylephrine, phenylpropanolamine, pseudoephedrine, oxymetazoline, ephinephrine, naphazoline, xylometazoline, propylhexedrine, or levo desoxy ephedrine; an antitussive such as codeine, hydrocodone, caramiphen, carbetapentane, or dextromethorphan; a diuretic; and a sedating or non sedating antihistamine.

Likewise, compounds and compositions of the present invention may be used in combination with other drugs that are used in the treatment, prevention, suppression or amelioration of the diseases or conditions for which compounds and compositions of the present invention are useful. Such other drugs may be administered, by a route and in an amount commonly used therefor, contemporaneously or sequentially with a compound or composition of the present invention. When a compound or composition of the present invention is used contemporaneously with one or more other drugs, a pharmaceutical composition containing such other drugs in addition to the compound or composition of the present invention is preferred. Accordingly, the pharmaceutical compositions of the present invention include those that also contain one or more other active ingredients or therapeutic agents, in addition to a compound or composition of the present invention. Examples of other therapeutic agents that may be combined with a compound or composition of the present invention, either administered separately or in the same pharmaceutical compositions, include, but are not limited to: (a) VLA-4 antagonists, (b) corticosteroids, such as beclomethasone, methylprednisolone, betamethasone, prednisone, prenisolone, dexamethasone, fluticasone, hydrocortisone, budesonide, triamcinolone, salmeterol, salmeterol, salbutamol, formeterol; (c) immunosuppressants such as cyclosporine (cyclosporine A, Sandimmune®, Neoral®, tacrolimus (FK-506, Prograf®), rapamycin (sirolimus, Rapamune®) and other FK-506 type immunosuppressants, and mycophenolate, e.g., mycophenolate mofetil (CellCept®); (d) antihistamines (H1-histamine antagonists) such as bromopheniramine, chlorpheniramine, dexchloipheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non steroidal anti asthmatics (e.g. terbutaline, metaproterenol, fenoterol, isoetharine, albuterol, bitolterol and pirbuterol), theophylline, cromolyn sodium, atropine, ipratropium bromide, leukotriene antagonists (e.g., zafmlukast, montelukast, pranlukast, iralukast, pobilukast and SKB-106, 203), leukotriene biosynthesis inhibitors (zileuton, BAY-1005); (f) non steroidal anti-inflammatory agents (NSAIDs) such as propionic acid derivatives (e.g., alminoprofen, benoxaprofen, bucloxic acid, carprofen, fenbufen, fenoprofen, flu-profen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE IV); (i) gold compounds such as auranofin and aurothioglucose, (j) etanercept (Enbrel®), (k) antibody therapies such as orthoclone (OKT3), daclizumab (Zenapax®), basiliximab (Simulect®) and infliximab (Remicade®), (l) other antagonists of the chemokine receptors, especially CCR5, CXCR2, CXCR3, CCR2, CCR3, CCR4, CCR7, $CX_3CR1$ and CXCR6; (m) lubricants or emollients such as petrolatum and lanolin, (n) keratolytic agents (e.g., tazarotene), (O) vitamin $D_3$ derivatives, e.g., calcipotriene or calcipotriol (Dovonex®), (p) PUVA, (q) anthralin (Drithrocreme®), (r) etretinate (Tegison®) and isotretinoin and (s) multiple sclerosis therapeutic agents such as interferon β-1β (Betaseron®), interferon (β-1α (Avonex®), azathioprine (Imurek®, Imuran®), glatiramer acetate (Capoxone®), a glucocorticoid (e.g., prednisolone) and cyclophosphamide (t) DMARDS such as methotrexate (u) other compounds such as 5-aminosalicylic acid and prodrugs thereof; hydroxychloroquine; D-penicillamine; antimetabolites such as azathioprine, 6-mercaptopurine and methotrexate; DNA synthesis inhibitors such as hydroxyurea and microtubule disrupters such as colchicine. The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

VI. Examples

The following examples are offered to illustrate, but not to limit the claimed invention.

Reagents and solvents used below can be obtained from commercial sources such as Aldrich Chemical Co. (Milwaukee, Wis., USA). $^1$H-NMR were recorded on a Varian Mercury 400 MHz NMR spectrometer. Significant peaks are tabulated in the order: multiplicity (s, singlet; d, doublet; t, triplet; q, quartet; m, multiplet) and number of protons. Mass spectrometry results are reported as the ratio of mass over charge, followed by the relative abundance of each ion (in parenthesis). In tables, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC for sample delivery. Normally the analyte was dissolved in methanol at 0.1 mg/mL and 1 microlitre was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM $NH_4OAc$ in acetonitrile/water as delivery system.

Figure 4A:
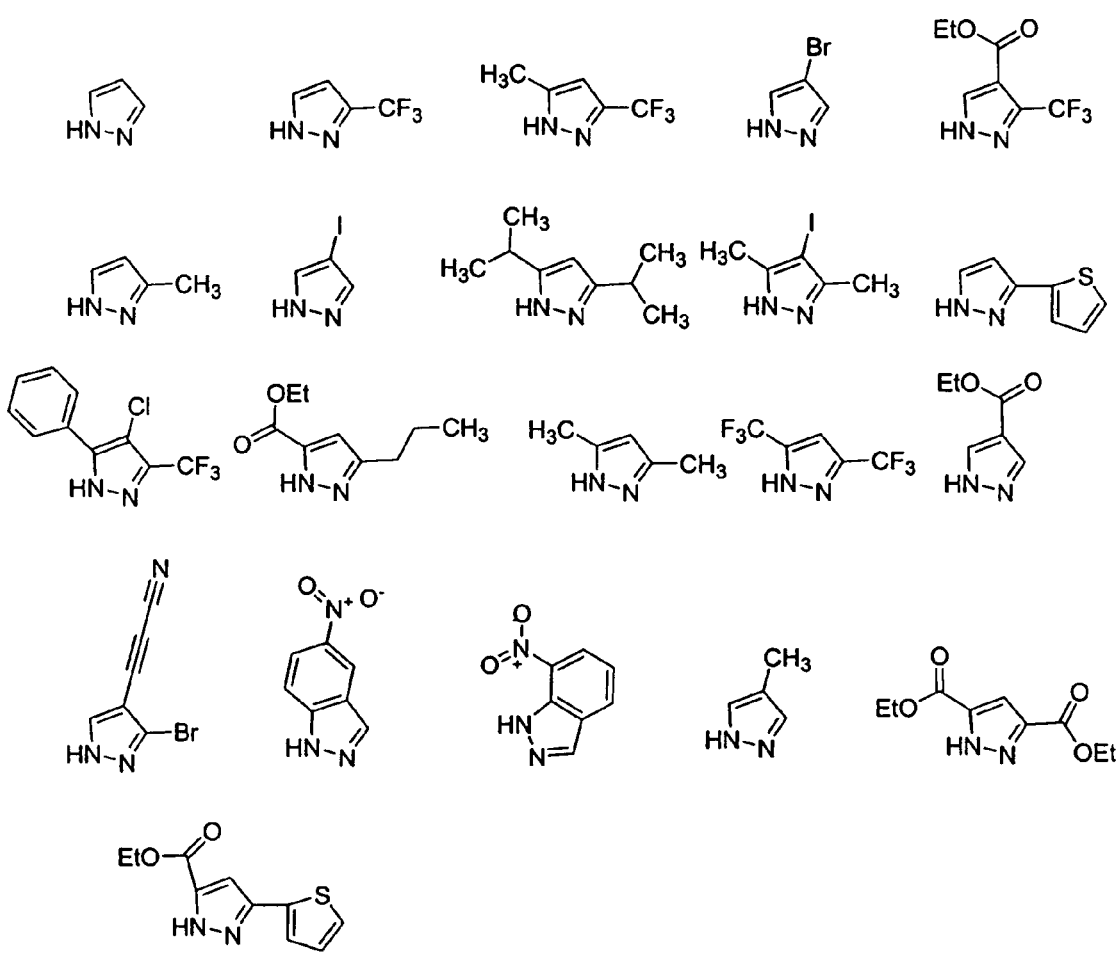
FIGS. 4A-4C provide structures of selected commercially available starting materials.
Figure 4B:
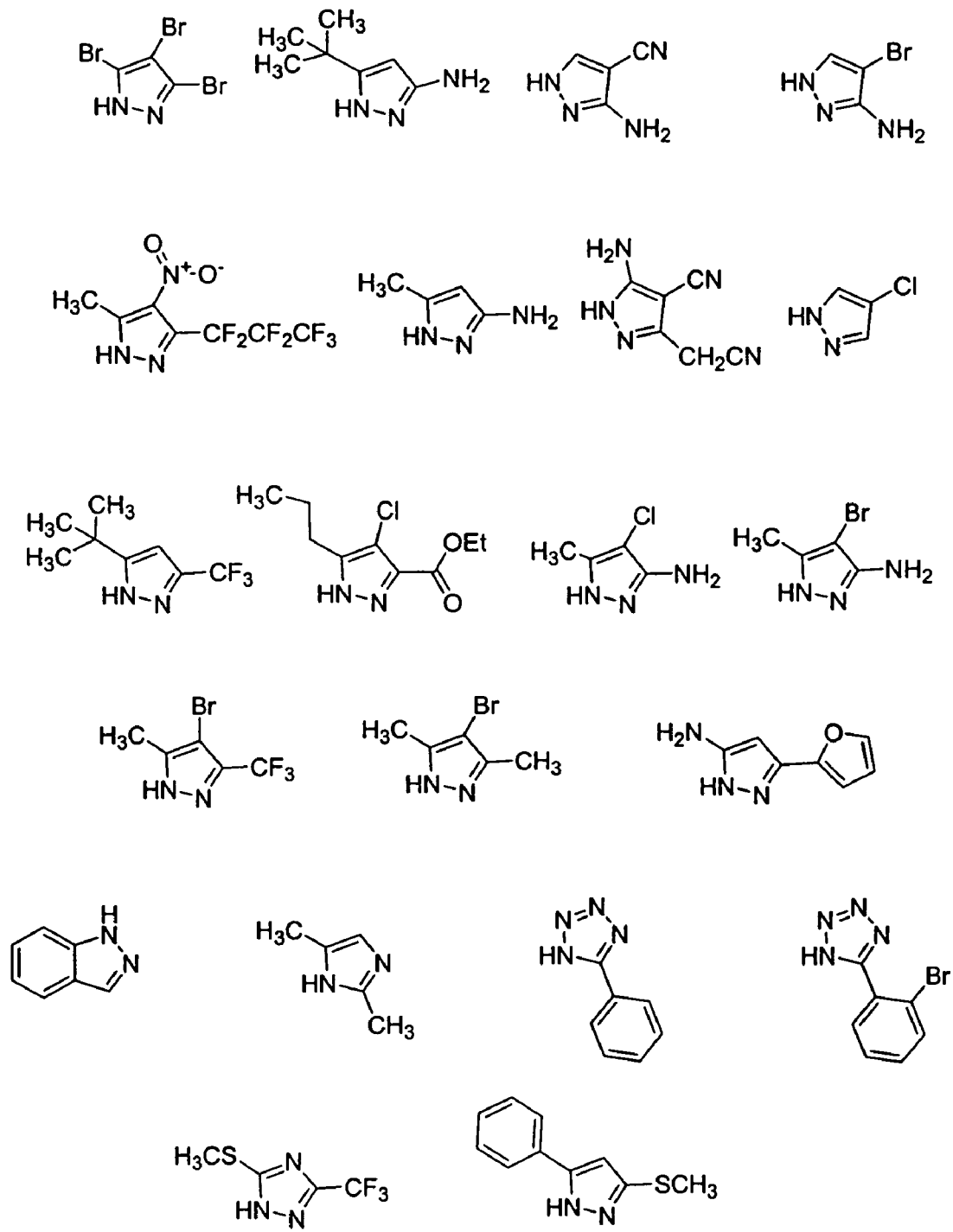
Figure 4C:
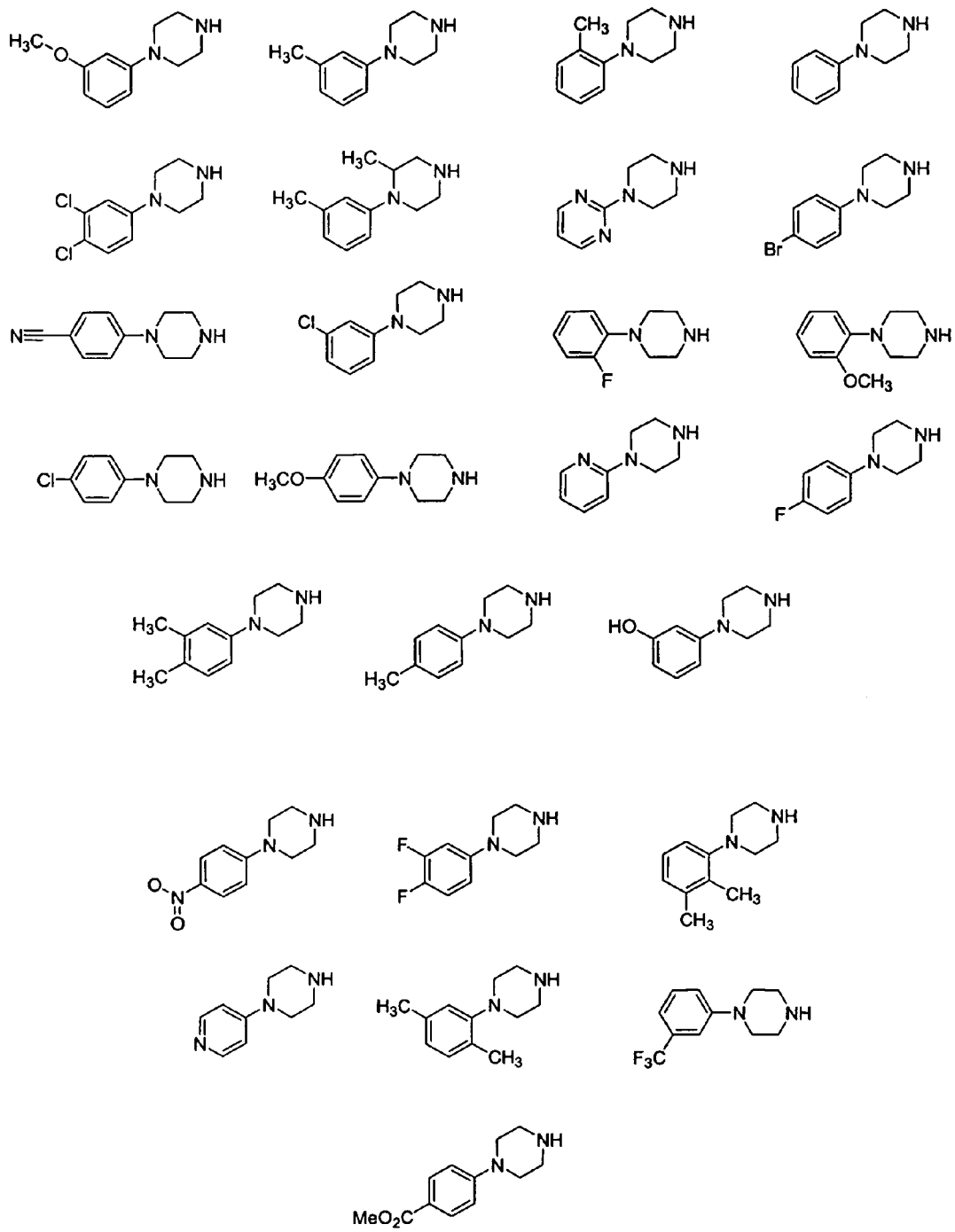
Figure 5A:
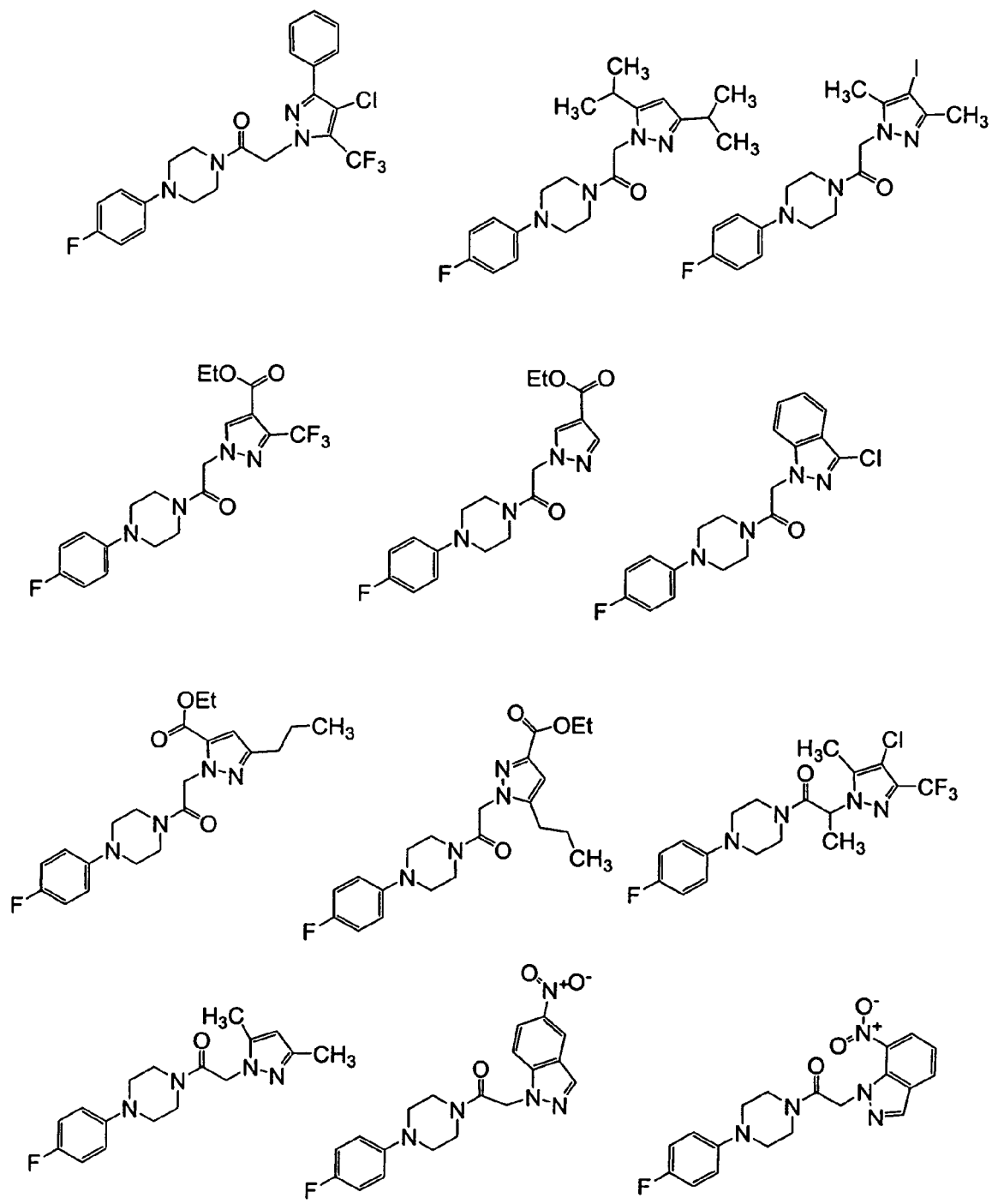
FIGS. 5A-5N provide structures of selected and preferred compounds of formula I.
Figure 5B:
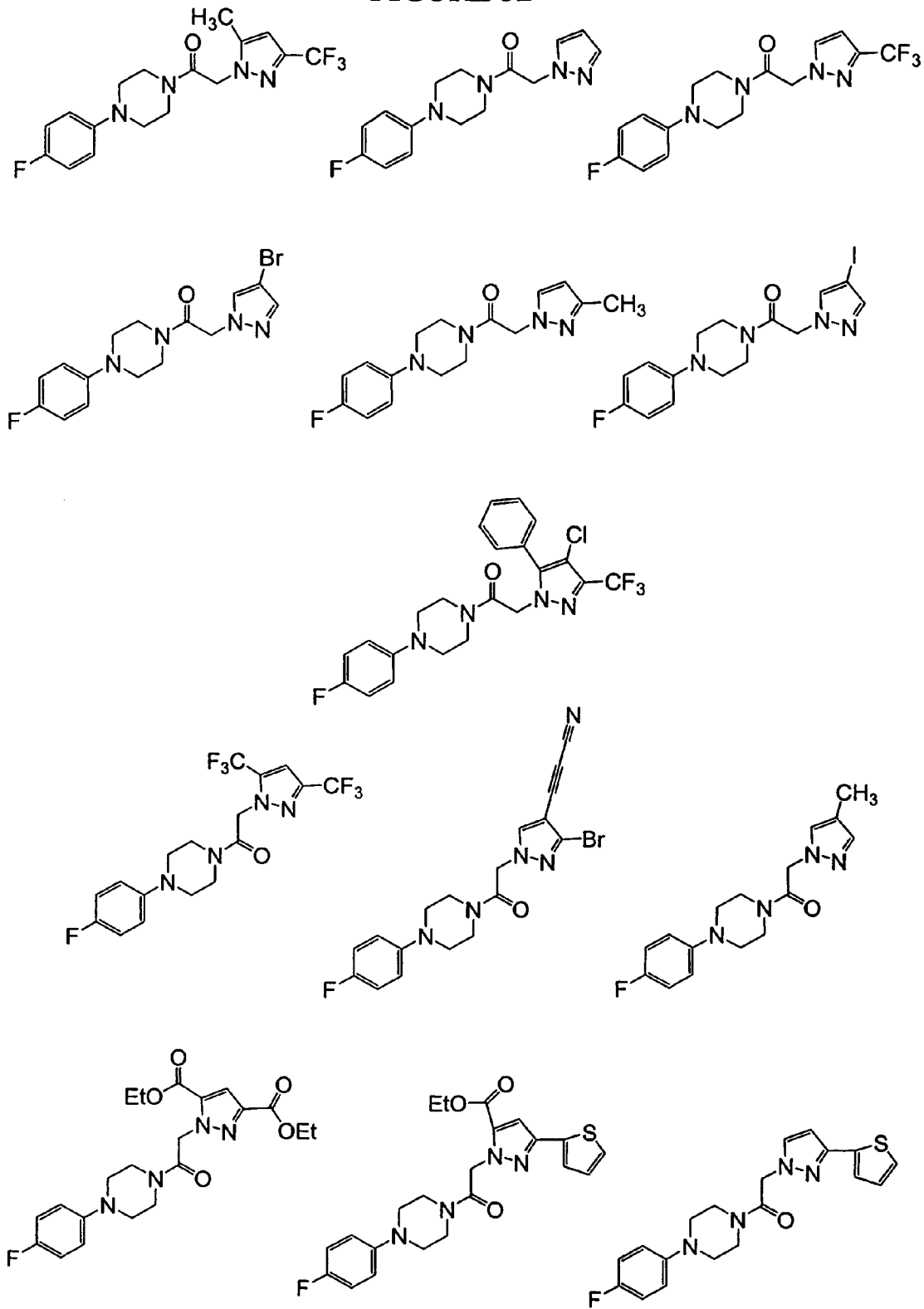
Figure 5C:
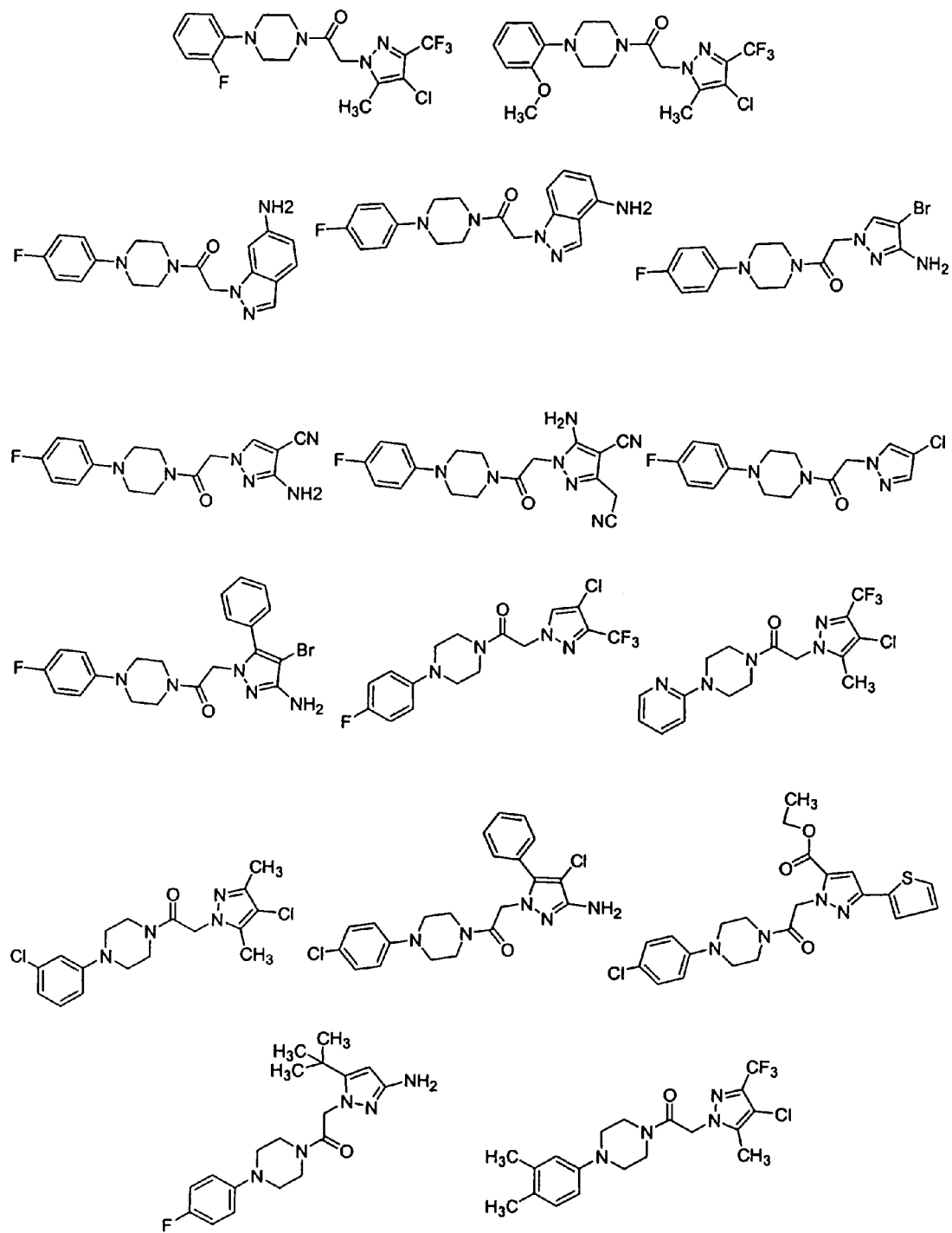
Figure 5D:
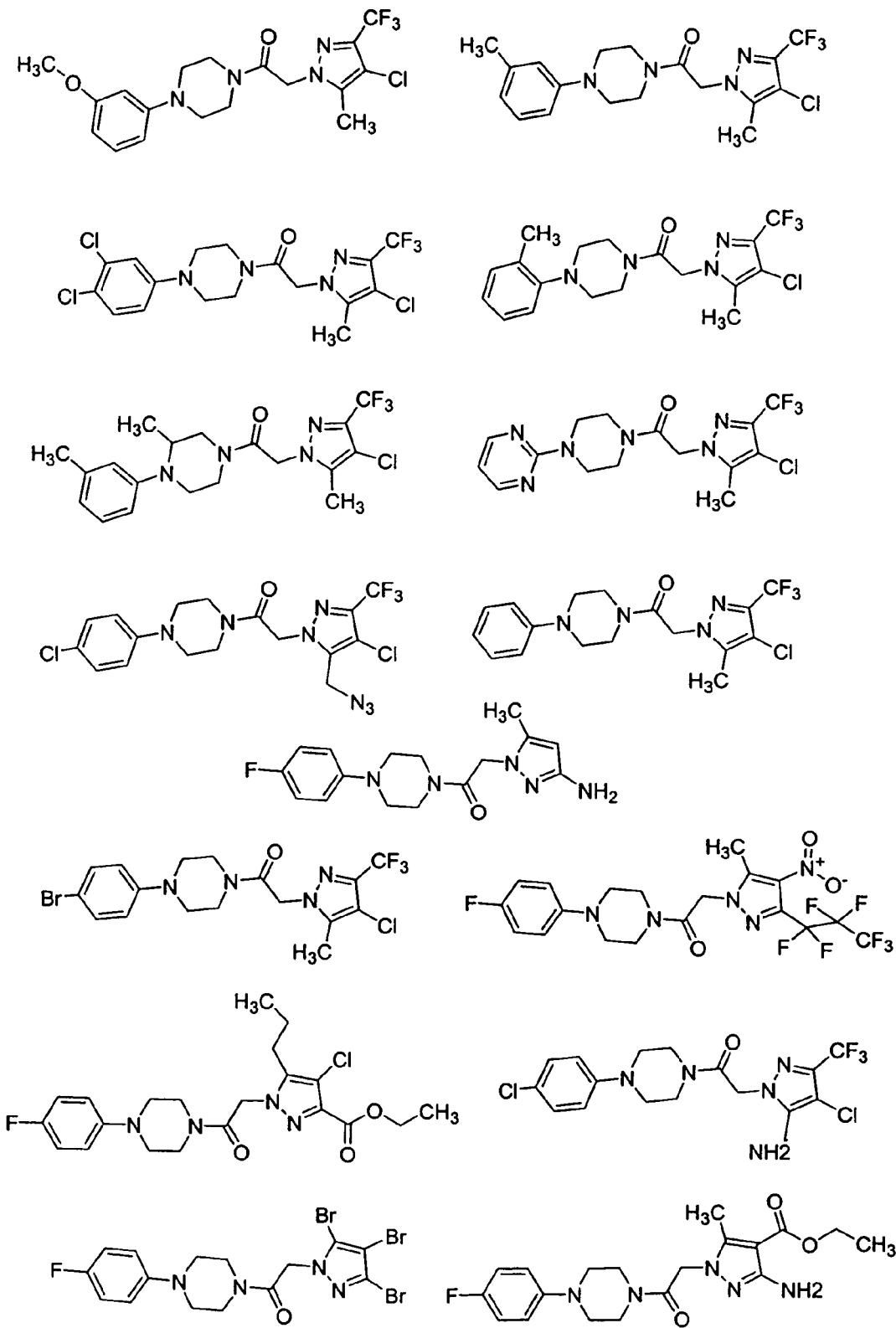
Figure 5E:
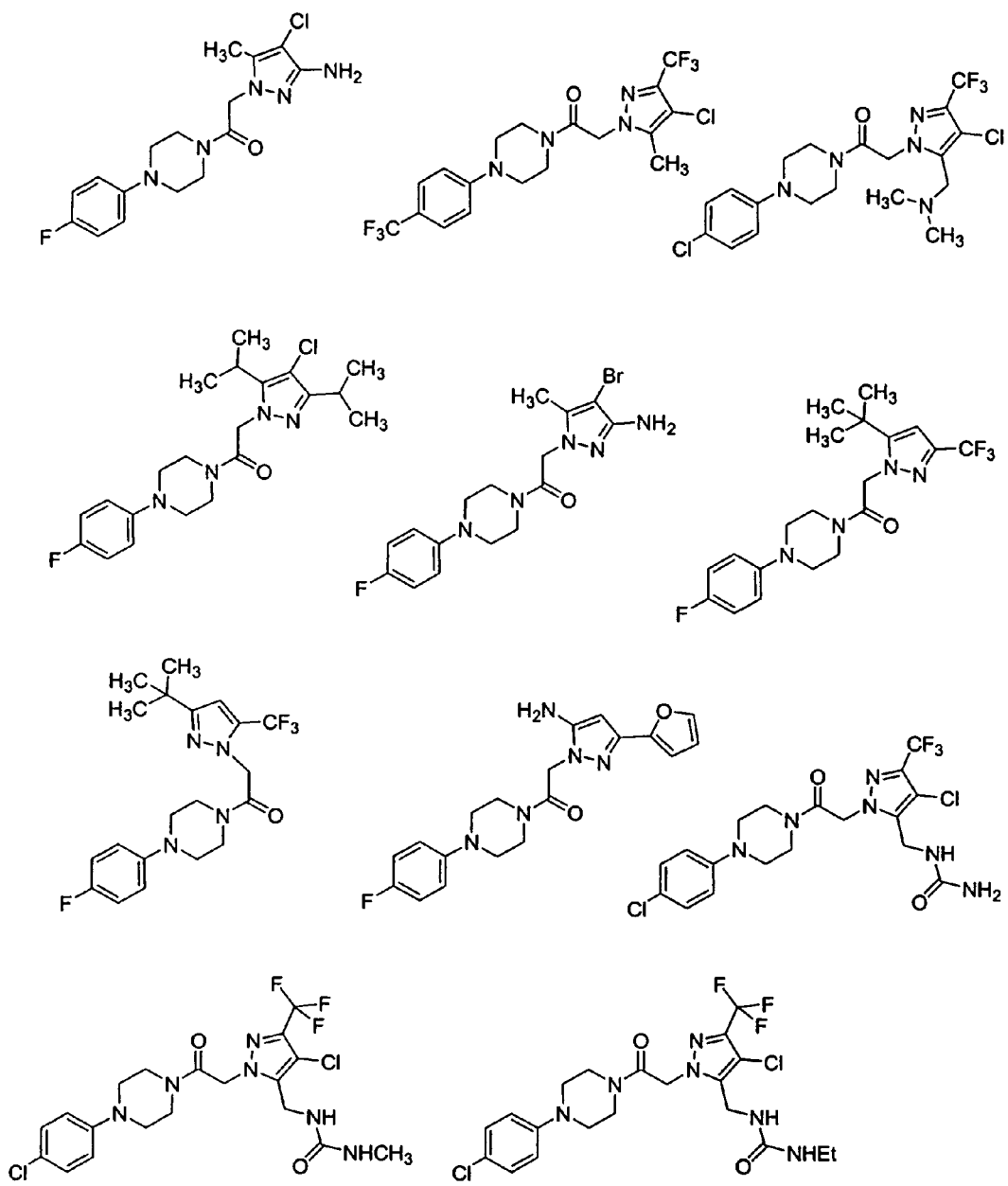
Figure 5F:
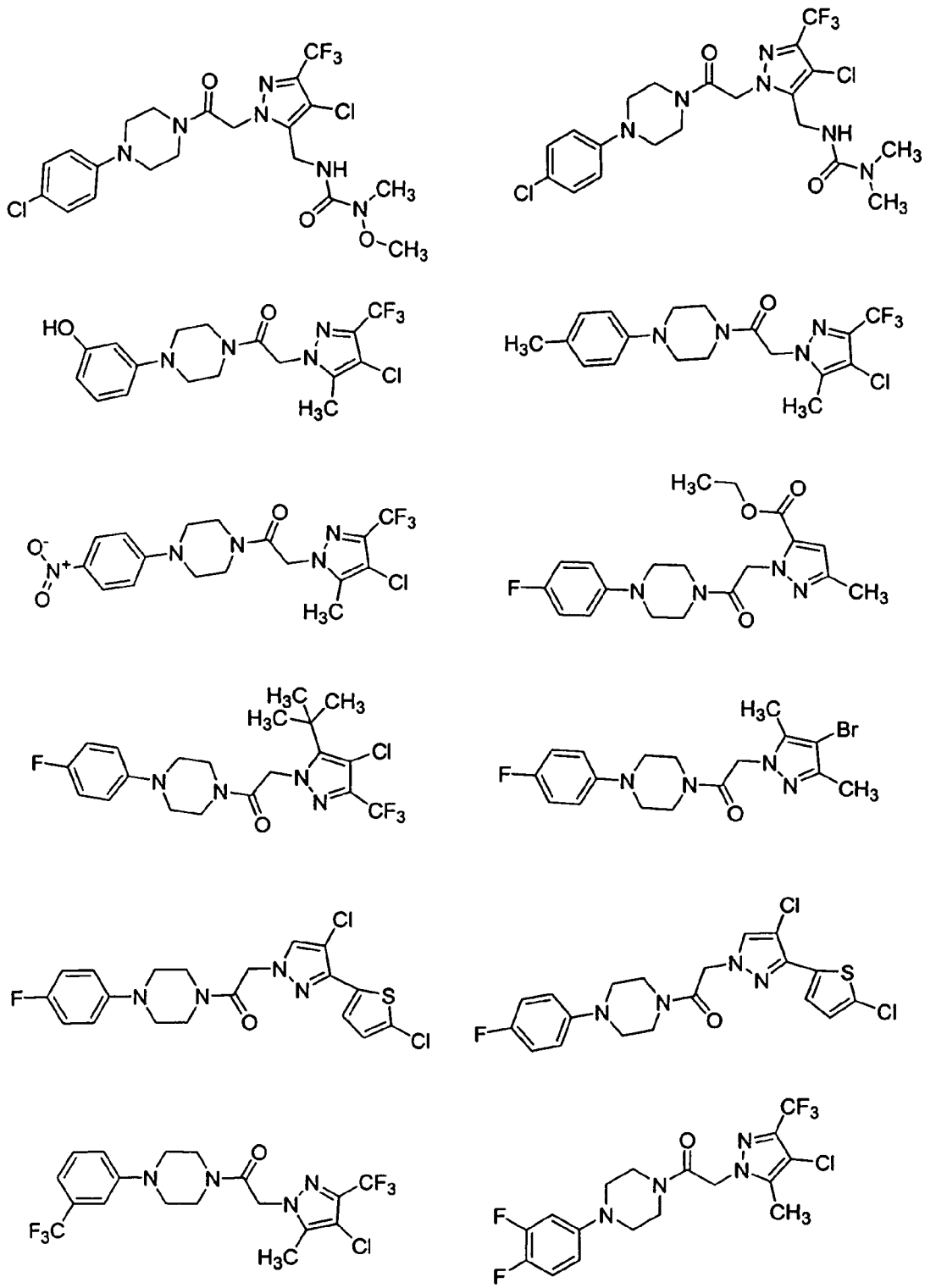
Figure 5G:
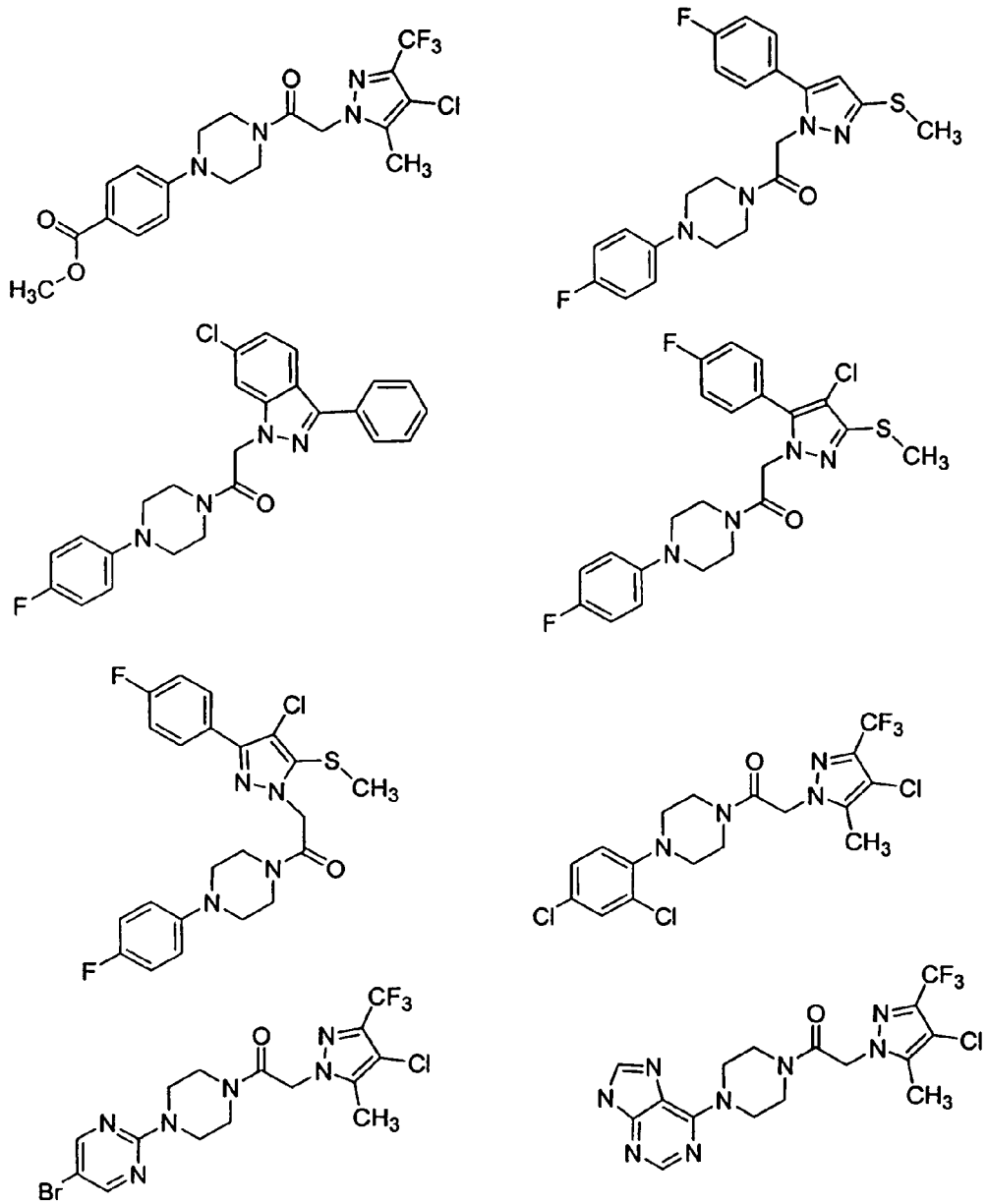
Figure 5H:
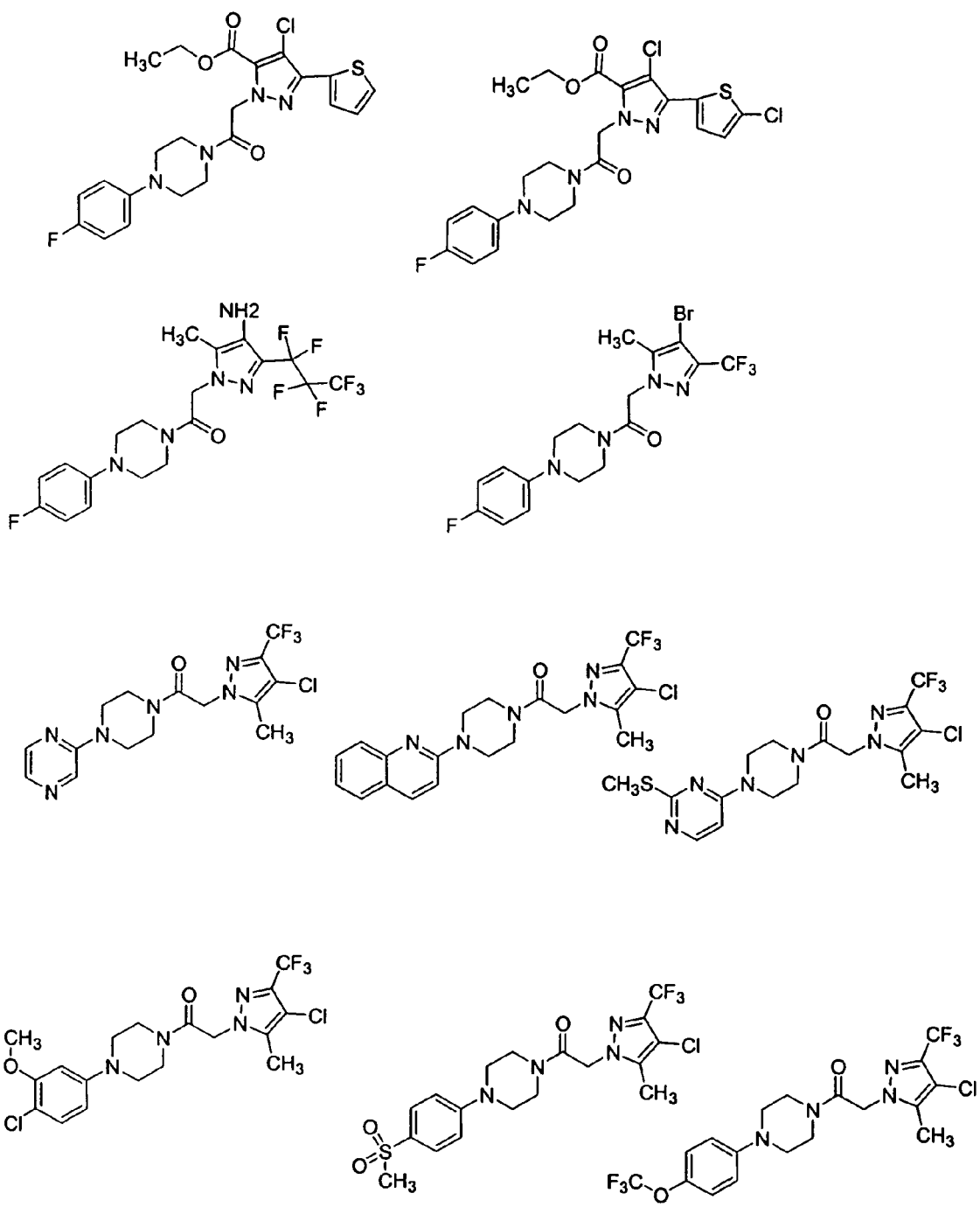
Figure 5I:
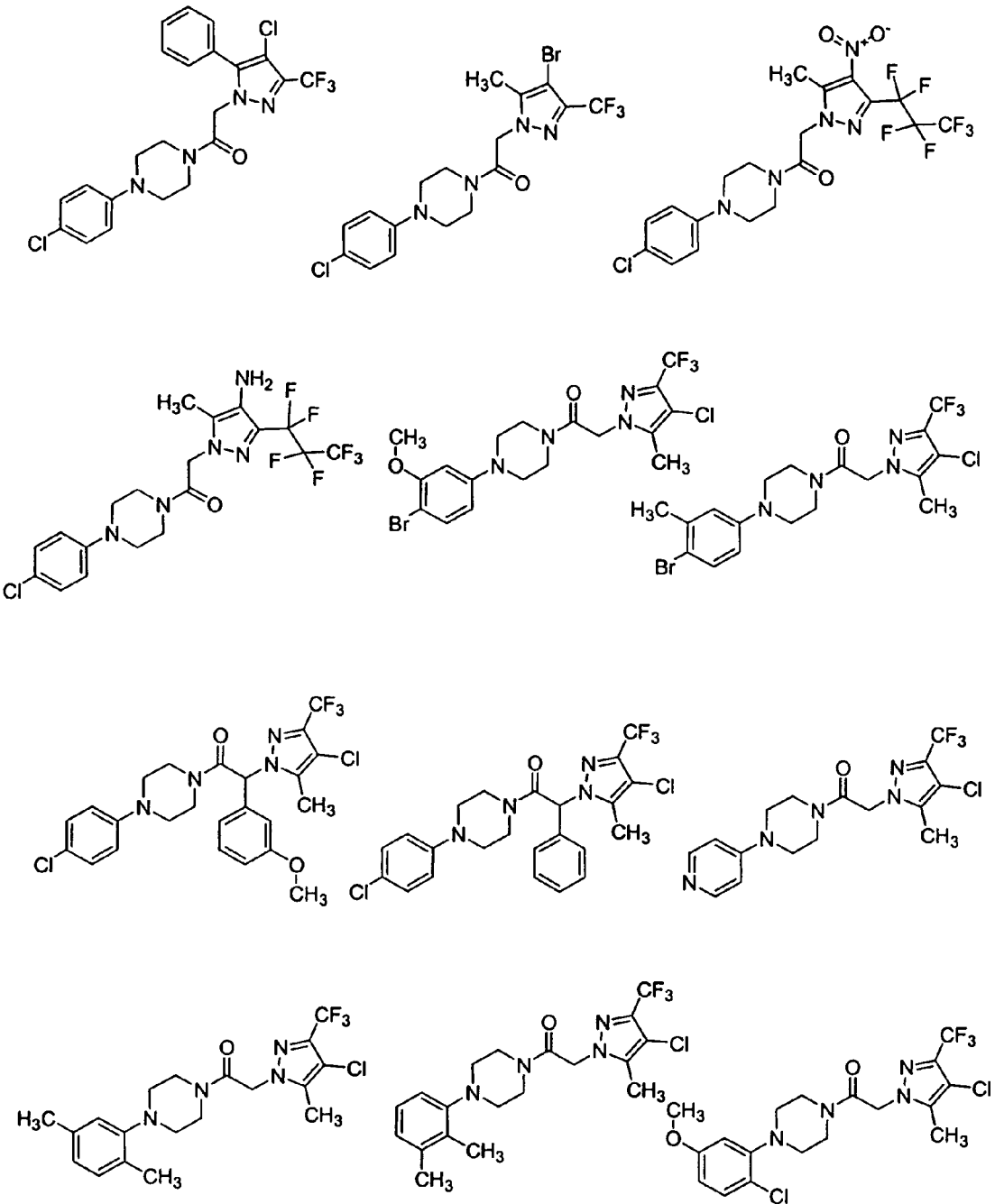
Figure 5J:
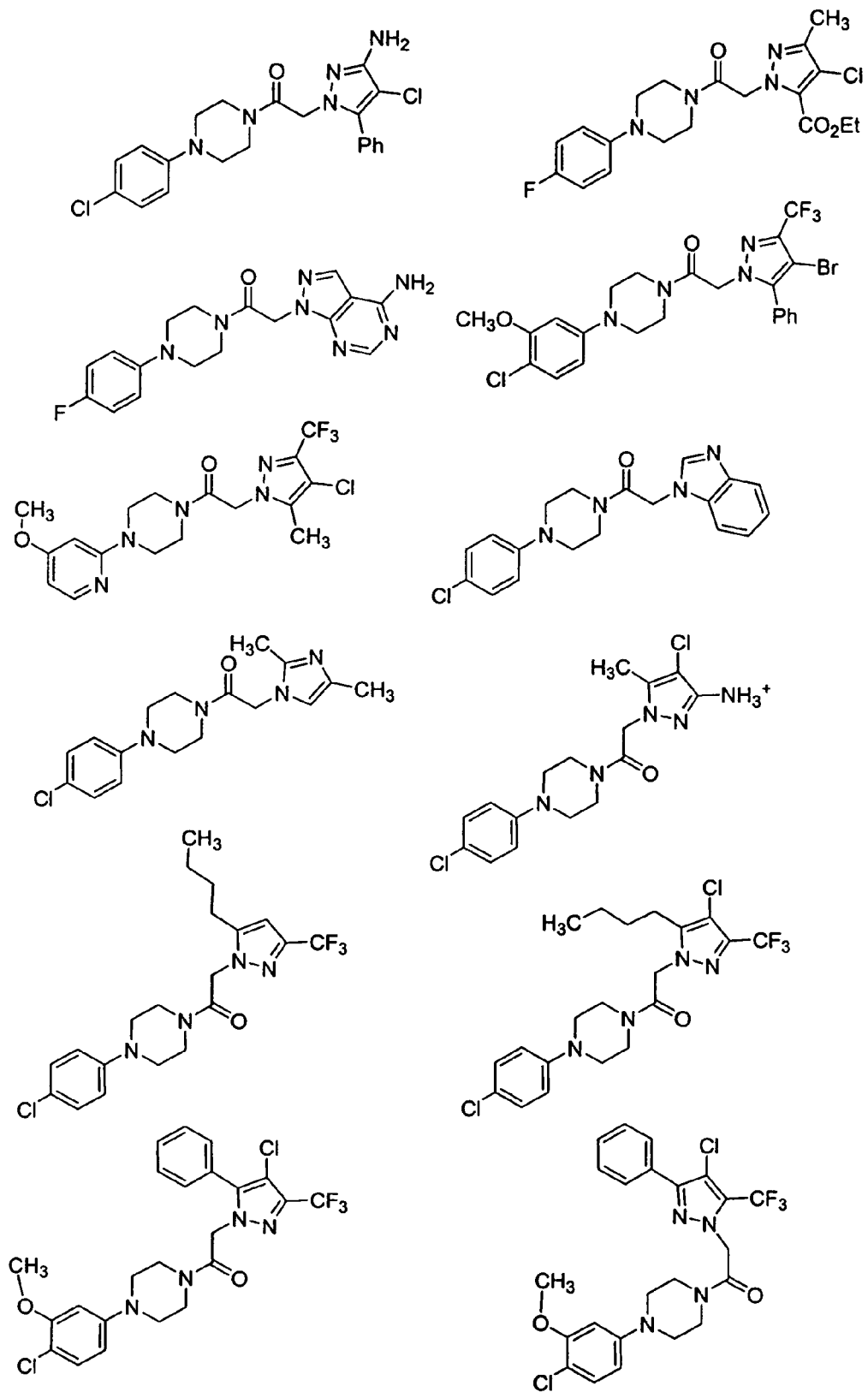
Figure 5K:
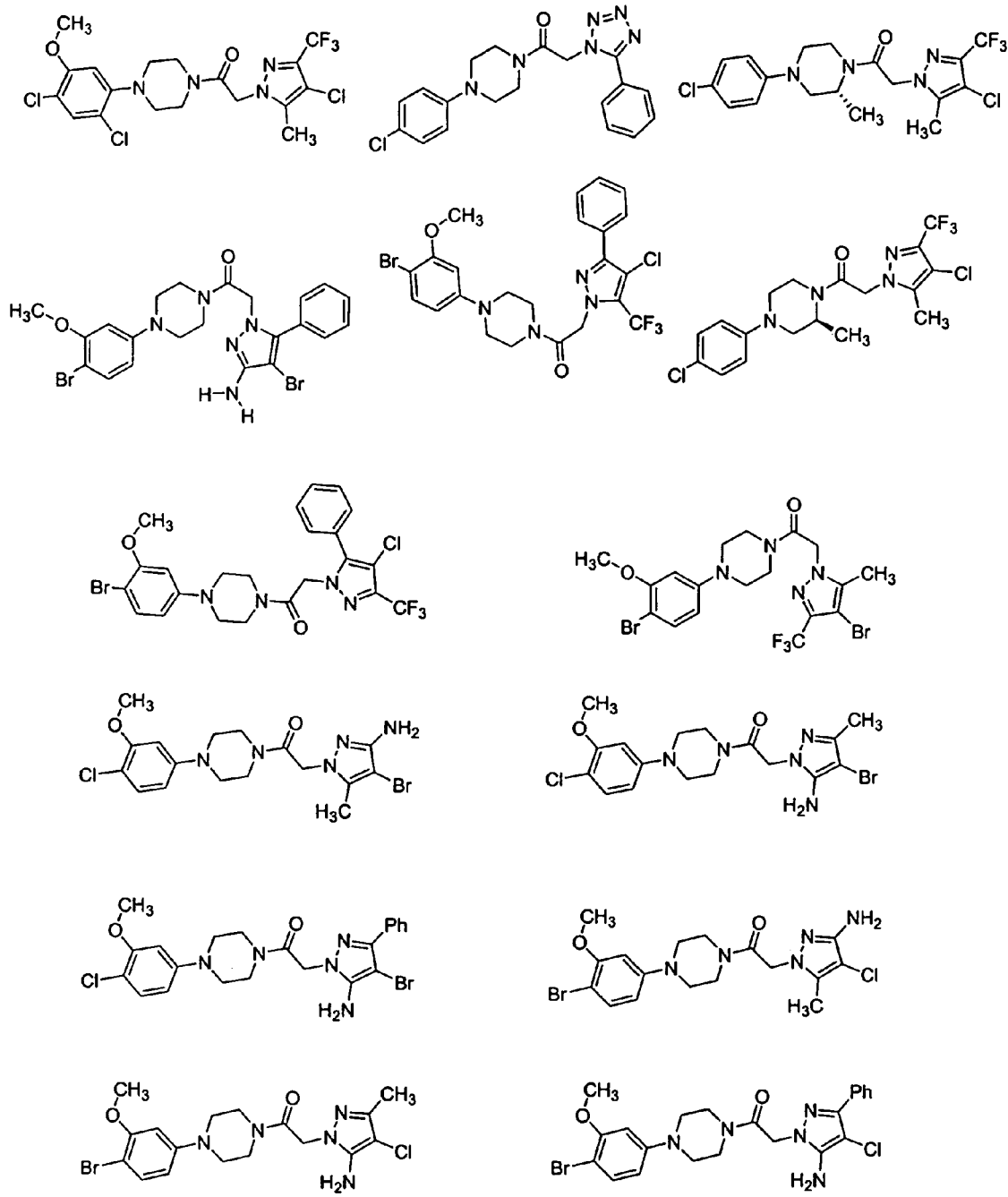
Figure 5L:
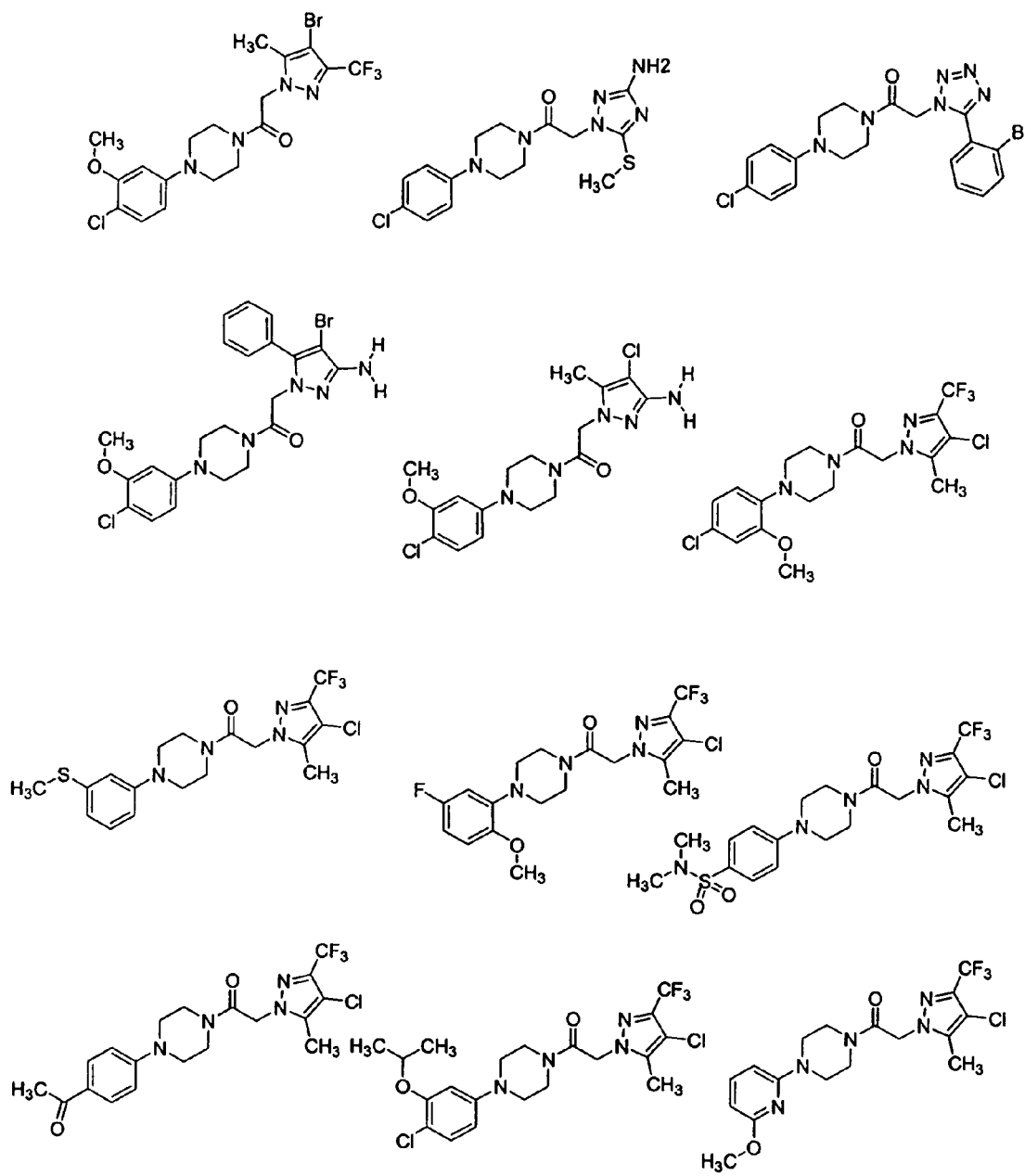
Figure 5M:
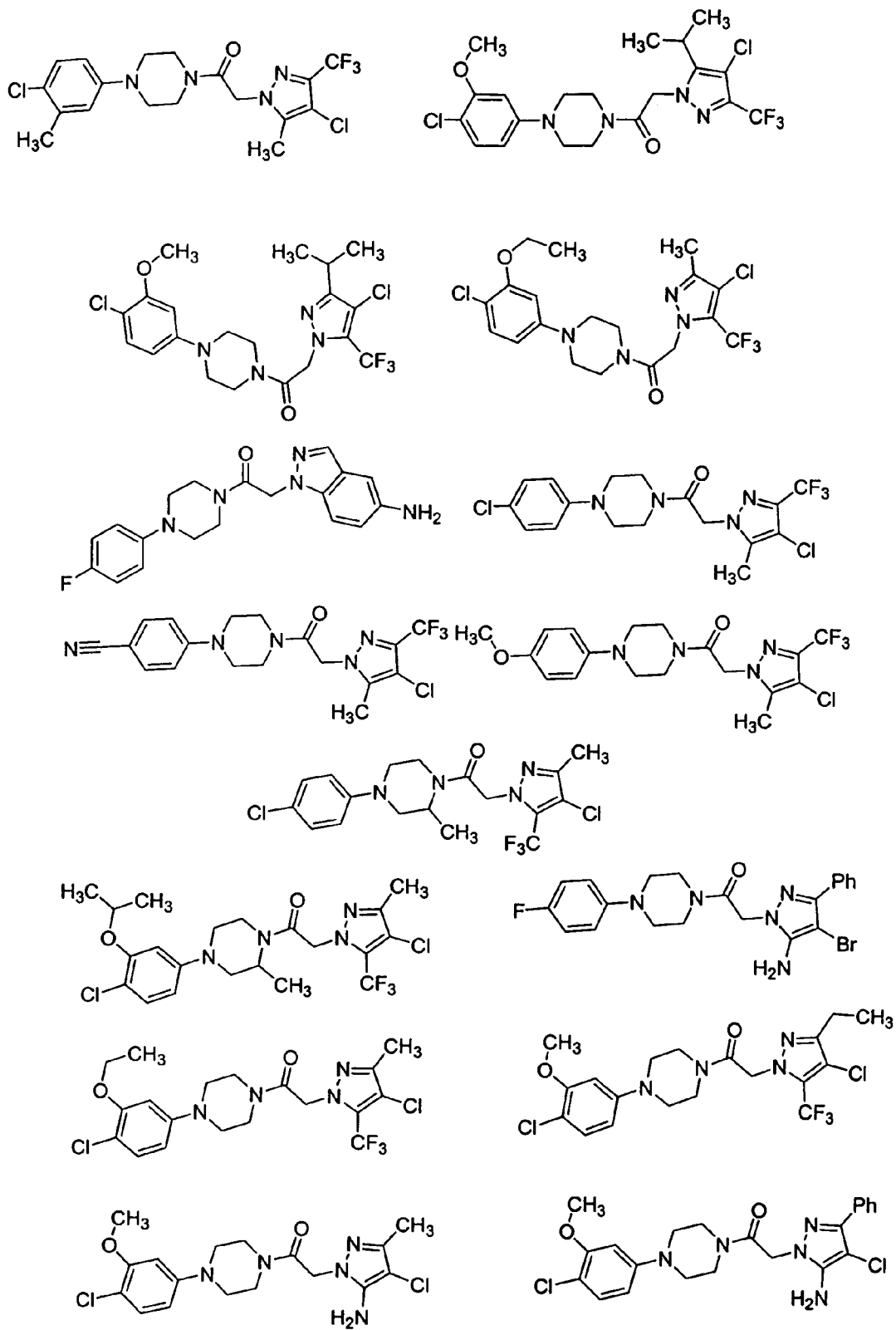
Figure 5N:
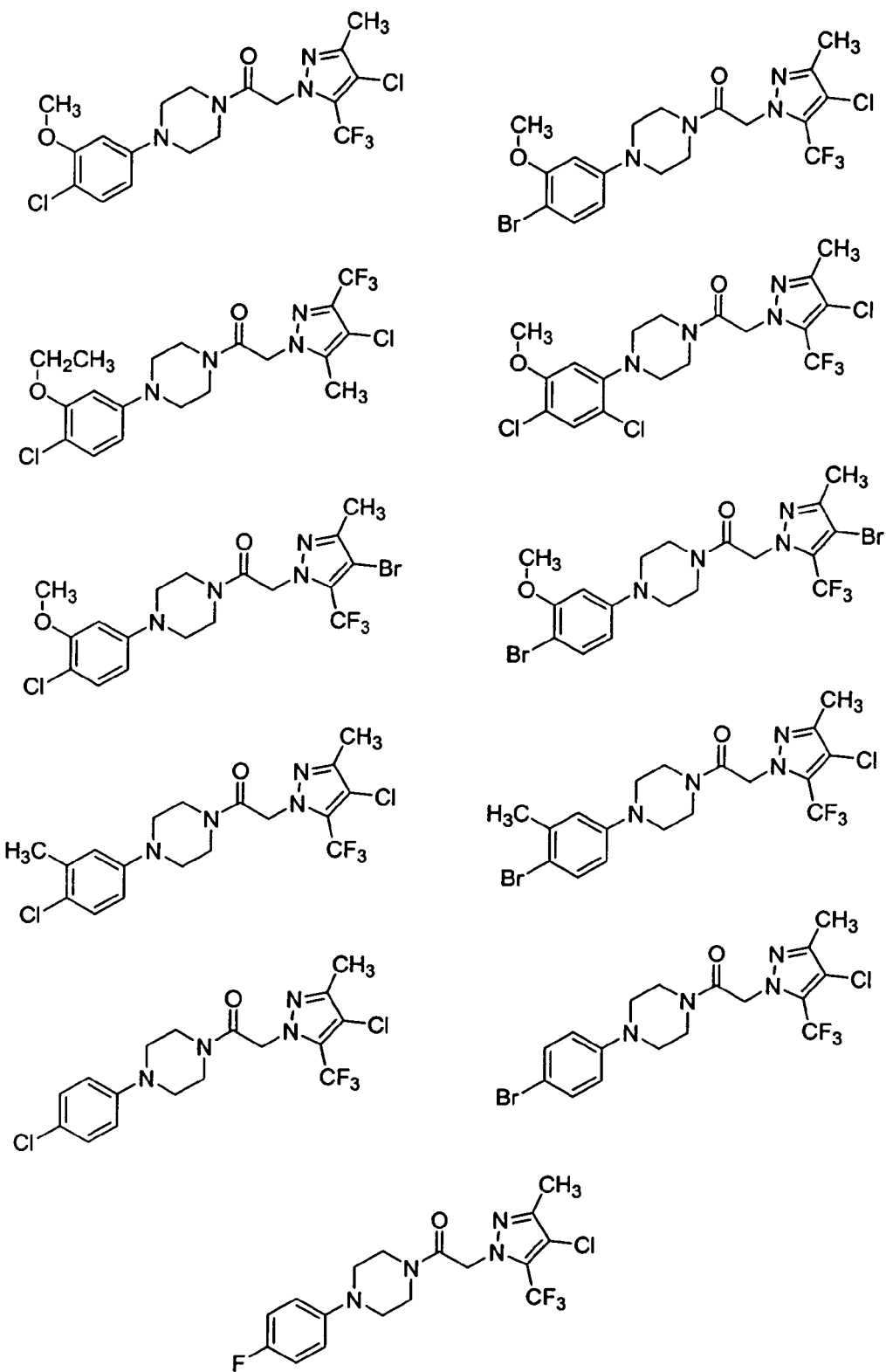

Compounds within the scope of this invention can be synthesized as described below, using a variety of reactions known to the skilled artisan. A sample of useful routes to both the arylpiperazine subunits and to the heteroaromatic subunit are provided below. In the descriptions of the syntheses that follow, some of the arylpiperazine and pyrazole precursors were obtained from commercial sources. These commercial sources include Aldrich Chemical Co., Acros Organics, Ryan Scientific Incorporated, Oakwood Products Incorporated, Lancaster Chemicals, Sigma Chemical Co., Lancaster Chemical Co., TCI-America, Alfa Aesar, Davos Chemicals, and GFS Chemicals. Some examples of these commercially available compounds are shown in the FIGS. 4A-4C. Also, standard chemistries have been employed to link the arylpiperazine and heteroaromatic subunits (whether commercially obtained or prepared by the methods below) using a suitably optimized linker, such as the acetyl unit described in the body of this invention.

One skilled in the art will also recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are claimed.

Regioisomerism is a common property in organic chemistry, and is especially common with regards to certain structural types provided herein. Those skilled in the art will recognize, with respect to the compounds described herein, that the coupling reactions with the heteroaromatic ring systems can lead to either one of or a mixture of detectable regioisomers.

The detailed description of the experimental procedures used to synthesize key compounds in this text lead to molecules that are described by the physical data identifying them as well as by the structural depictions associated with them.

Two regioisomers can sometimes exist for certain compounds of the invention. For example, compounds such as those of formula III can be prepared wherein the pyrazole moiety is linked to the remainder of the molecule via either of the nitrogen atoms in the pyrazole ring. In these cases, both regioisomeric types have demonstrated biological properties and are meant to be within the scope of all the appended claims, whether explicitly drawn or not.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example 1

The piperazine ring can be formally attached to the terminal aryl unit in a number of ways: by aromatic nuclephilic displacement reactions, metal catalyzed coupling reactions (arylation reactions of secondary amines), ring expansion, rearrangement and cyclization reactions and the like. Also, different protection/deprotection strategies can be utilized. Hence, either all or only part of the final molecular architecture can be present during the key aryl coupling step. Examples for a variety of such aryl coupling strategies are listed below.

Protocol A: Metal Catalysed Arylation Reactions of Secondary Amines

Synthesis of (5-Chloro-2-piperazin-1-yl-phenyl)-phenyl-methanone

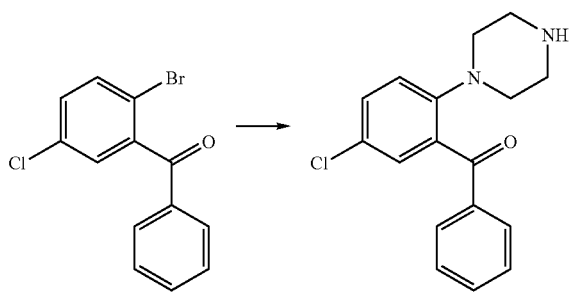

Piperazine (3.6 g, 42.5 mmol), Pd(II)acetate (0.007 g, 0.043 mmol), sodium t-butoxide (0.22 g, 2.4 mmol) and BINAP (0.042 g, 0.068 mmol) were stirred at room temperature in 10 mL dry toluene for 15 min. (2-Bromo-5-chloro-phenyl)-phenyl-methanone (0.5 g, 1.7 mmol) in 10 mL dry toluene was then added into the reaction mixture. The reaction mixture was refluxed at 110° C. for 20 hrs, filtered through a celite bed, washed with toluene, concentrated, taken in ethyl acetate and extracted with 1.5 (N)HCl solution three times. The combined aqueous layers were washed with diethyl ether. The aqueous layer was neutralized with 10% aqueous sodium hydroxide solution and then extracted with ethyl acetate three times. The combined ethyl acetate layers were washed with water and saturated brine solution, dried over anhydrous sodium sulfate and concentrated. Purification by flash chromatography (eluted with CHCl3-MeOH) afforded the title compound as product.

Synthesis of 1-(4-Trifluoromethoxy-phenyl)-piperazine

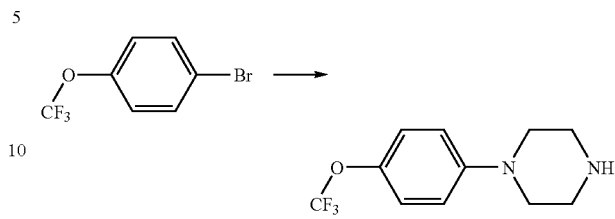

Piperazine (0.588 g, 6.84 mmol), Pd(II)acetate (0.027 g, 0.123 mmol), sodium t-butoxide (0.837 g, 10.06 mmol) and BINAP (0.154 g, 0.286 mmol) were stirred at room temperature in 10 mL dry toluene for 15 min. 4-trifluoromethoxy bromo benzene (1.5 g, 6.22 mmol) in 10 mL dry toluene was added into the reaction mixture. Then the reaction mixture was refluxed at 110° C. for 20 hrs. The reaction mixture was filtered through a celite bed, washed with toluene, concentrated, ethyl acetate added and then extracted with 1.5 (N) aqueous HCl solution three times. The combined aqueous layers were washed with diethyl ether. The aqueous layer was neutralized with 10% aqueous sodium hydroxide solution and then extracted with ethyl acetate three times. The combined ethyl acetate layers were washed with water and saturated brine solution, dried over anhydrous sodium sulfate and concentrated to afford the product.

Synthesis of 1-(4-Methanesulfonyl-phenyl)-piperazine

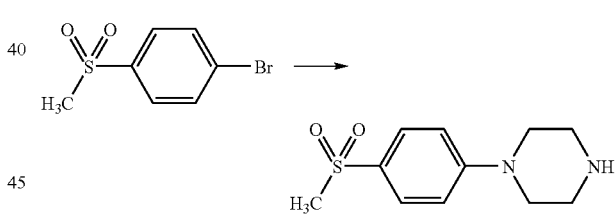

Piperazine (0.98 g, 11.5 mmol), Pd(II) acetate (0.017 g), sodium t-butoxide (0.37 g, 4.2 mmol) and BINAP (0.049 g) were stirred at room temperature in 10 mL dry toluene for 15 min. 1-Bromo-4-methanesulfonyl-benzene (0.9 g, 3.8 mmol) in 10 mL dry toluene was added into the reaction mixture. Then the reaction mixture was refluxed at 110° C. for 20 hrs. The reaction mixture was filtered through a celite bed and washed with toluene. The toluene was concentrated and the reaction mixture was taken in ethyl acetate and extracted with 1.5 (N) HCl solution three times. The combined aqueous layers were washed with diethyl ether. The aqueous layer was neutralized with 10% aqueous sodium hydroxide solution and then extracted with ethyl acetate three times. The combined ethyl acetate layers were washed with water and saturated brine solution, dried over anhydrous sodium sulfate, concentrated and chromatographed (9/1-CHCl3/MeOH) to afford the product.

Synthesis of 1-(4-Chloro-3-methoxy-phenyl)-piperazine

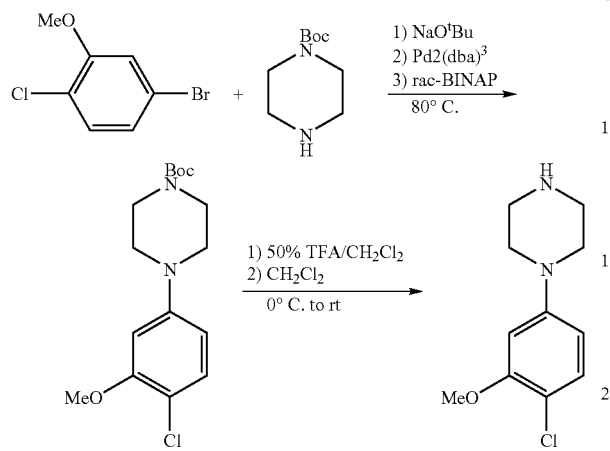

An oven dried glass vial was charged with 5-Bromo-2-chloroanisole (1.0 mmol), N-Bocpiperazine (1.2 mmol), NaOtBu (1.4 mmol), tris(dibenzylideneacetone)-dipalladium (0) {$Pd_2 dba_3$} (0.0025 mmol, 0.5 mol %) and BINAP (0.0075 mmol), and the vial was then flushed with nitrogen and capped tightly. The mixture was heated to 80° C. overnight and then cooled to room temperature, taken up in ether, filtered and concentrated. The crude product was purified by flash column chromatography on silica gel with ethyl acetate to yield 4-(4-Chloro-3-methoxy-phenyl)-piperazine-1-carboxylic acid tert-butyl ester.

This product (ca. 1 mmol) was dissolved in a methylene chloride (10mL) and the reaction mixture was cooled to 0° C. To the reaction mixture was added $TFA:CH_2Cl_2$ (2:1)(50% overall) slowly and the reaction was allowed to warm to room temperature. When TLC (1:1 Ethyl acetate:hexane) suggested total consumption of starting material, solvent was removed and the oil residue was taken in ethyl acetate (2×25 mL) and washed with saturated aqueous $NaHCO_3$. The organic layer was dried by $MgSO_4$ and solvent was removed to yield the title compound as a yellow oil, which solidified on standing. $^1$H NMR (400 MHz, $CDCl_3$): 7.18-7.22 (d, 1H), 6.44-6.48 (d, 1H), 6.36-6.42 (dd, 1H), 4.8 (s, 2H), 6.62-3.8 (m, 4H), 3.46-3.6 (m, 4H). $^{13}$C NMR (400 MHz, $CDCl_3$): 164, 158.2, 156.4, 148, 119.2, 117, 52.8, 52.2, 48.5, 46.2, 42, 40.4.

Similar approaches, using a key Buckwald coupling, were taken for the preparation of related phenylpiperazines, some examples of which are listed below.

Synthesis of 1-(4-Chloro-3-isopropoxy-phenyl)-piperazine

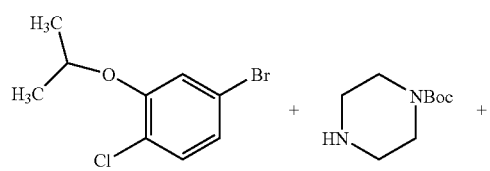

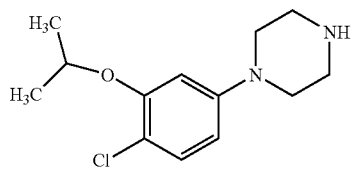

1-Bromo-3-isopropoxy-4-chlorobenzene (preparation described elsewhere) was combined with 1.11 g (6 mmol) of 1-Bocpiperazine, 672 mg (7.0 mmol) of sodium tert-butoxide, 93 mg (0.15 mmol) of rac-2,2'-Bis(diphenylphosphine)-1,1'-binaphthyl, and 45 mg (0.05 mmol) Tris(dibenzylideneacetone)dipalladium (0) in a flask under an N2 atmosphere, and the mixture was heated at 85° C. for 3.5 hours. The resulting residue was partitioned between a 1/1 mixture of ether and ethyl acetate and water, and the phases were separated. The ether/ethyl acetate phase was diluted with one volume of hexanes, washed twice with 0.5M pH=7 phosphate buffer, and once each with 1M NaOH and brine. The final organic phase was dried over Na2SO4, filtered, and concentrated in vacuo to an oil. The oil was dissolved in ethyl acetate, 10 mL each of 2M HCl in ether and methanol were added, and the product was isolated by filtration after crystallization. $^1$H NMR ($D_2O$, 400 MHz): 7.23 (d, 1H), 6.69 (s, 1H), 6.59 (d, 1H), 4.53 (m, 1H), 3.28 (m, 8H), 1.20 (d, 6H) ppm.

Synthesis of 1-(4-Chloro-3-ethoxy-phenyl)-piperazine

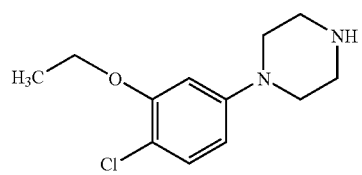

Title compound was obtained following the same procedure as that used to obtain 1-(4-Chloro-3-isopropoxy-phenyl)-piperazine hydrochloride, with the single modification of adding ethanol in place of isopropanol during the ether-forming reaction. $^1$H NMR ($D_2O$, 400 MHz) 7.22 (d, 1H), 6.64 (s, 1H), 6.54 (d, 1H), 4.03 (q, 2H), 3.29 (m, 8H), 1.25 (t, 3H) ppm.

Synthesis of 4-Piperazin-1-yl-benzoic acid methyl ester

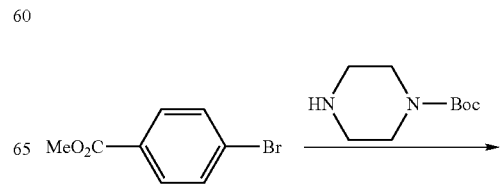

36

Synthesis of 1-(4-Chloro-phenyl)-3-(R)-methyl-piperazine

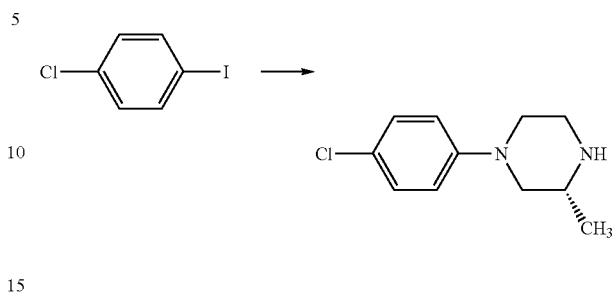

A single neck round bottom flask was charged with 1-chloro-4-iodo benzene (1.0 g, 0.0041 mol) and R(−)-2-methylpiperazine (0.5 g, 0.005 mol), potassium t-butoxide (0.705 g, 0.0062 mol), tris(benzylideneacetone)dipalladium (0) (0.095 g, 0.0002 mol) and 1,3 bis(2,6-diisopropylphenyl) imidazole-2-ylidene) (0.073 g, 0.0001 mol). The flask was evacuated and filled with nitrogen. Dry dioxane (20 mL) was added and stirred at 70° C. overnight. The reaction mixture was diluted with dichloromethane and filtered. Crude compound was purified by column chromatography. The compound was dissolved in ether and purged with HCl gas to yield 1-(4-Chloro-phenyl)-3-methyl-piperazine.

Synthesis of 1-(4-Chloro-2-Fluorophenyl)-piperazine

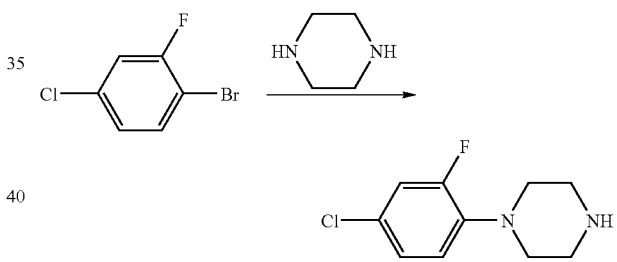

Piperazine (1.5 g, 17.8 mmol), Pd(II)acetate (0.032 g, 0.143 mmol), sodium t-butoxide (0.688 g, 10.06 mmol) and BINAP (0.18 g, 0.286 mmol) were stirred at room temperature in 10 mL dry toluene for 15 min. 1-bromo-4-chloro-2-fluorobenzene (1.5 g, 7.15 mmol) in 10 mL dry toluene was added into the reaction mixture. Then the reaction mixture was refluxed at 110° C. for 20 hrs. The reaction mixture was filtered through a celite bed and washed with toluene, then concentrated and the reaction mixture was taken into ethyl acetate and extracted with 1.5 (N)HCl solution three times. The combined aqueous layer was washed with diethyl ether. The aqueous layer was neutralized with 10% aqueous sodium hydroxide solution and then extracted with ethyl acetate three times. The combined ethyl acetate layers were washed with water and saturated brine solution, dried over anhydrous sodium sulfate, and concentrated to afford the product as a white solid.

Further Examples of Arylpiperazines Synthesized by Metal Catalysed Arylation Methods (Protocol A).

Many other arylpiperazine derivatives were prepared in addition to the specific experimental examples listed above using similar Palladium mediated coupling methodologies. Examples are listed below.

35

-continued

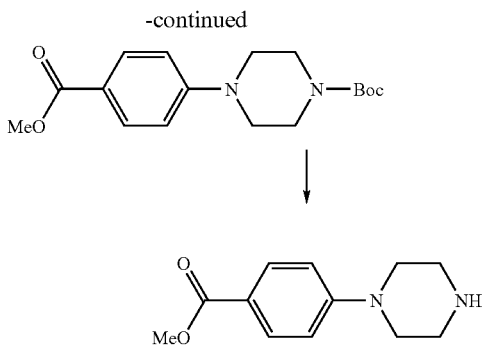

BINAP (230 mg, 0.37 mmol), Pd(II) acetate (417 mg, 0.186 mmol), tBuONa (1.25 g, 13 mmol), N-boc piperazine (1.9 g, 10.2 mmol) and THF (40 mL) were mixed together and stirred at room temperature for 30 min under a nitrogen atmosphere. 4-bromomethyl benzoate (2 g, 9.3 mmol) in THF (10 mL) was added to the mixture drop wise and heated at 70° C. for 14 h. Excess THF was then evaporated and extracted with ethyl acetate. The crude product was obtained on concentration of the ethyl acetate layer after washing with brine and drying. Flash chromatography on silica gel done eluting with 8% ethyl acetate in petroleum ether yielded pure N—BOC protected product. This intermediate (650 mg, 2.0 mmol) was dissolved in methanol (20 mL) and then HCl saturated ether (7 mL) was added. The mixture was stirred at room temperature for 14 hours and concentrated. The concentrate was washed with petroleum ether to obtain white solid compound, 4-Piperazin-1-yl-benzoic acid methyl ester.

Synthesis of 1-(2,4-Dichloro-phenyl)-piperazine

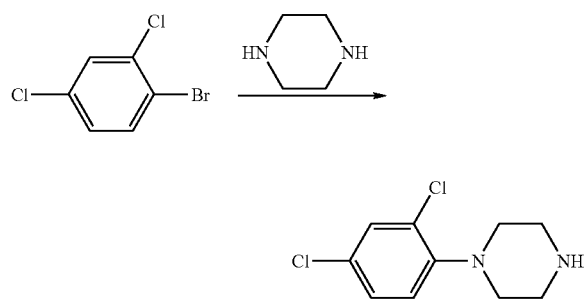

BINAP (219 mg), Pd(II) acetate (397 mg, 0.176 mmol), tBuONa (1.19 g, 12.3 mmol), piperazine (837 mg, 9.73 mmol) and THF (40 mL) were mixed together and stirred at room temperature for 30 min under nitrogen atmosphere. 2,4-dichlorobromobenzene (2 g, 8.84 mmol) in THF (10 mL) was added to the mixture drop wise and heated at 70° C. for 14 h. Excess THF was then evaporated and extracted with ethyl acetate. The crude product was obtained on concentration of the ethyl acetate layer after washing with brine and drying. Flash chromatography on silica gel eluting with 2% MeOH in CHCl3 gave 1-(2,4-Dichloro-phenyl)-piperazine.

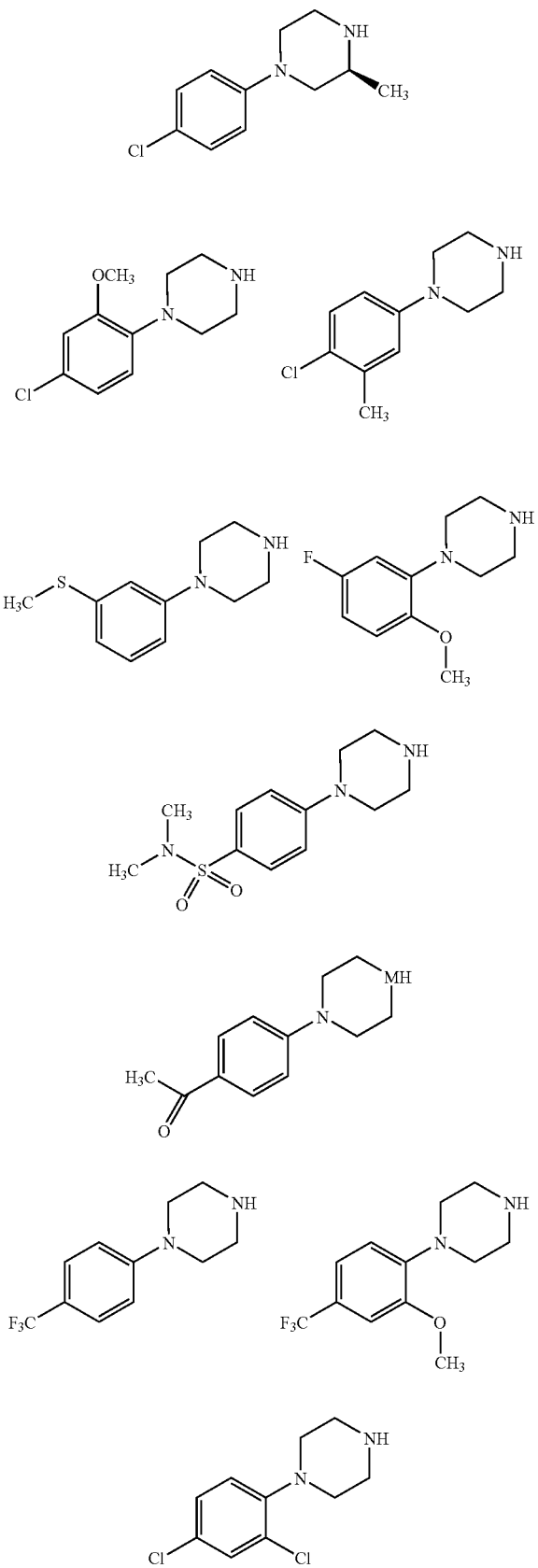

Protocol B: Piperidine Ring Formation Via Cyclization Reactions

Synthesis of 1-(3,4-Difluoro-phenyl)-piperazine 3,4-Difluoro-aniline (1 g, 7.7 mmol) was dissolved in dry n-butanol (10 mL) and dry sodium carbonate (3.2 g, 30 mmol) was added to it and the reaction mixture stirred for 1 hour under nitrogen. Bis(2-chloroethyl) amine hydrochloride (1.38 g, 7.7 mmol) in nBuOH (10 mL) were then added to the mixture via a syringe. The reaction was then heated at 120° C. for 48 h. The nBuOH was evaporated in vacuo and the residue was extracted with ethyl acetate. Drying of the organic layer with $Na_2SO_4$ followed by concentration afforded the crude product. Purification using flash column chromatography (chloroform/methanol) afforded 1-(3,4-Difluoro-phenyl)-piperazine as an off white solid.

Synthesis of 1-(4-bromo-phenyl)-piperazine

4-Bromo-aniline (2 g, 1.162 mmol) was taken in dry nBuOH (25 mL) and dry potassium carbonate (4.8 g, 34.8 mmol) was added to it and stirred at rt for 1 h under nitrogen. Bis-(2-chloroethyl) amine hydrochloride 2 (2.49 g, 13.9 mmol) in nBuOH (10 mL) was then added to the mixture through a syringe. The reaction mass was then heated at 100° C. for 12 h. nBuOH was evaporated in vacuo and the residue was extracted with ethyl acetate. Drying of the organic layer with $Na_2SO_4$ followed by concentration afforded the crude product that on purification silica gel column (chloroform/methanol) afforded the title compound.

Protocol C: Piperidine Ring Formation Via a Ring Opening/ Ring Cyclization Strategy Synthesis of 3-[2-(5-Methoxy-2-methyl-phenylamino)-ethyl]-oxazolidin-2-one

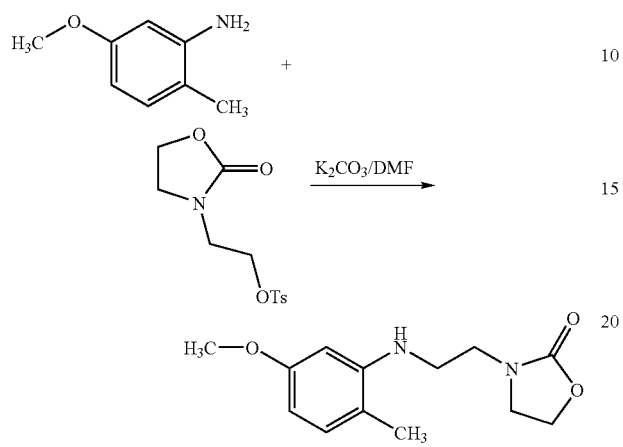

To a flask was added 2.95 g (10.3 mmol) of Toluene-4-sulfonic acid, 2-(2-oxo-oxazolidin-3-yl)-ethyl ester, 1.56 g (11.4 mmol) of 2-methyl-5-methoxyaniline, 2.58 g (18.7 mmol) of potassium carbonate, and 22 mL of anhydrous dimethylformamide, and the mixture was heated at 100° C. for seven hours. The reaction was allowed to cool to room temperature, and was partitioned between ethyl acetate and water. The phases were separated, and the ethyl acetate phase was washed with brine, dried over Na2SO4, filtered, and concentrated to an oil. The oil was purified by chromatography (120 mL silica, 60 ethyl acetate/40 hexanes) to give the corresponding product as a clear oil that solidified upon drying: $^1$H NMR (DMSO-d6, 400 MHz) 6.81 (d, 1H), 6.11 (s, 1H), 6.04 (d, 1H), 4.92 (t, 1H), 4.21 (t, 2H), 3.65 (s, 3H), 3.59 (m, 2H), 3.31 (m, 2H), 3.23 (m, 2H), 1.95 (s, 3H) ppm.

Synthesis of 1-(5-Methoxy-2-methyl-phenyl)-piperazine

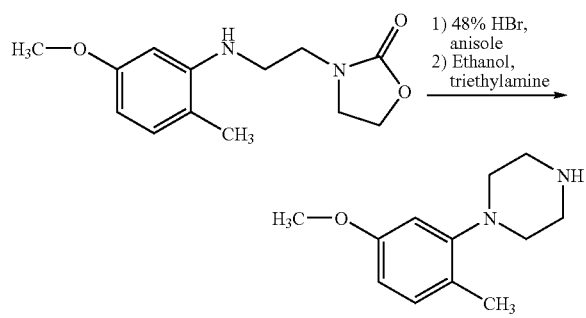

To 505 mg (2.0 mmol) of 3-[2-(5-Methoxy-2-methyl-phenylamino)-ethyl]-oxazolidin-2-one in a flask was added 2 mL of 48% HBr in acetic acid, 1 mL of acetic acid, and 1 mL of anisole, and the mixture was heated at 90° C. for six hours. The solution was allowed to cool to room temperature, and 5 mL of CH2Cl2 was added. The product crystallized and was isolated by filtration. The solids were dissolved in 55 mL of ethanol, 201 mg (2 mmol) of triethylamine were added, and the solution was heated at reflux for 3 hours. The solution was then concentrated in vacuo to give a residue that was partitioned between ether and water. The phases were separated, and the aqueous phase as basified with 1M NaOH. The aqueous phase was then extracted twice with ethyl acetate. The combined ethyl acetate phases were washed once with brine, dried over Na2SO4, filtered, and acidified with 2M HCl in ether. The product was isolated via filtration.

Addition of Various Piperazines to Aryl Halides and Heteroaryl Halides Via Aryl-Halogen Displacement Methodologies A direct halogen displacement strategy, with thermal assistance if necessary, can be complimentary to the metal mediated approaches, discussed above, for the construction of the ring systems provided herein.

Synthesis of 4-Piperazin-1-yl-benzoic acid ethyl ester

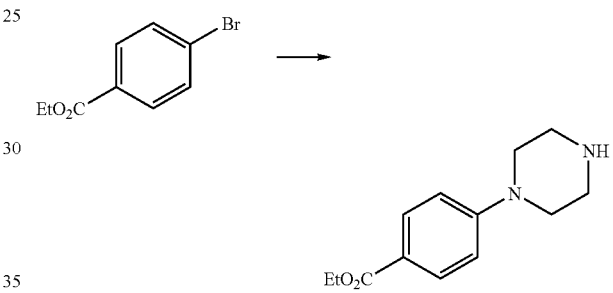

To 4-bromobenzoic acid (25 g) and ethanol (1000 mL) was added conc.sulfuric acid (20 g) drop wise. The reaction mixture was heated at 85° C. overnight. The reaction was cooled and ethanol was removed by distillation and the reaction mixture quenched with water and extracted with ethyl acetate. The extract was washed with 10% sodium bicarbonate, water, brine and then concentrated to yield the crude ester. 4-bromoethyl benzoate (10.0 g, 0.0437 mol) was taken into 250 mL of dry DMF, piperazine (37 g, 0.437 mol) was added, followed by 30 g (0.2185 mol) of dry potassium carbonate, 1.0 g of TBAI and 1.5 g of potassium iodide. The reaction mixture was heated at 135° C. for over night. The reaction mixture was quenched with water and extracted with ethyl acetate. The extracts were washed with water, then brine and then concentrated to yield 4-Piperazin-1-yl-benzoic acid ethyl ester as an off-white solid.

Synthesis of 1-(4-Methoxy-pyridin-2-yl)-piperazine

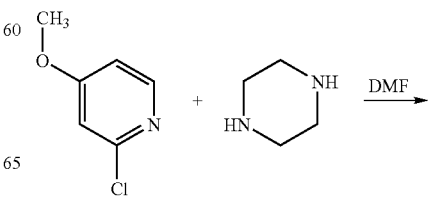

Protocol D: Synthesis and Addition of Elaborated Piperazines to Aryl and Heteroaryl Halides Via Aryl-Halogen Displacement Methodologies Synthesis of 2-(4-Chloro-5-methyl-3-trifluoromethyl-pyrazol-1-yl)-1-piperazin-1-yl-ethanone

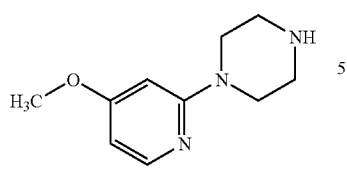

To 756 mg (5.29 mmol) of 2-Chloro-4-methoxypyridine and 2.27 g (26 mmol) of piperazine in a pressure flask was added 2.7 mL dimethylformamide, and the mixture was heated at 115° C. for 5 hours. The solution was allowed to cool before opening the flask, and the resulting slurry was partitioned between ethyl acetate and water. The phases were separated, and the aqueous phase was back-extracted once with ethyl acetate. The combined ethyl acetate phases were washed once with brine, dried over Na2SO4, filtered, and the filtrate was acidified with 2M HCl in ether. The product crystallized over night, and the solids were isolated by filtration to yield product as a white solid: $^1$H NMR (D$_2$O, 400 MHz) 7.72 (d, 1H), 6.61 (d, 1H), 6.48 (s, 1H), 3.88 (s, 3H), 3.79 (m, 4H), 3.36 (m, 4H) ppm.

Synthesis of 1-(3-Methoxy-pyridin-2-yl)-piperazine

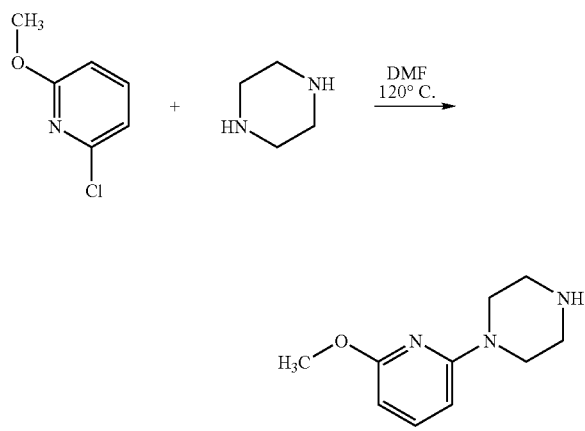

To 966 mg (6.7 mmol) of 2-Chloro-6-methoxypyridine and 2.90 g (34 mmol) of piperazine in a pressure flask was added 3.3 mL dimethylformamide, and the mixture was heated at 115° C. for 5 hours. The solution was allowed to cool before opening the flask, and the resulting slurry was partitioned between ethyl acetate and water. The phases were separated, and the aqueous phase was back-extracted once with ethyl acetate. The combined ethyl acetate phases were washed once with brine, dried over Na2SO4, filtered, and the filtrate was acidified with 2M HCl in ether. The product crystallized overnight, and was isolated by filtration to give a white solid: $^1$H NMR (D$_2$O, 400 MHz) 7.73 (t, 1H), 6.52 (d, 1H), 6.31 (d, 1H), 3.81 (s, 3H), 3.68 (m, 4H), 3.26 (m, 4H) ppm.

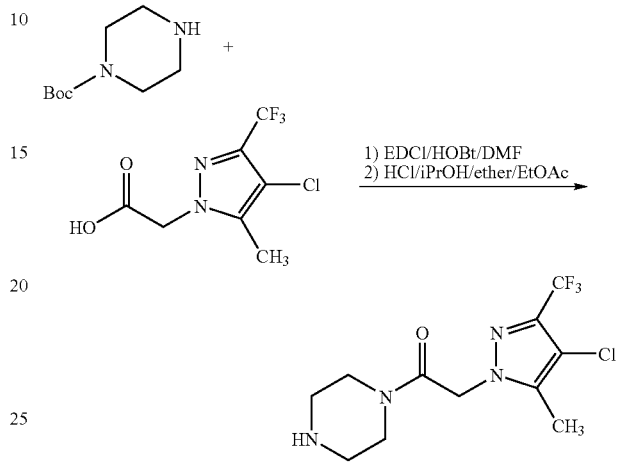

To a solution of 1.69 g (9.1 mmol) Boc-piperazine, 2.0 g (8.3 mmol) of (4-Chloro-5-methyl-3-trifluoromethyl-pyrazol-1-yl)-acetic acid, and 1.12 g (8.3 mmol) of 1-Hydroxybenzotriazole in 20 mL of dimethylformamide at 0° C. was added 1.73 g (9.1 mmol) of 1-(3-Dimethylaminopropyl)-3-ethylcarbodiimide hydrochloride. The reaction was allowed to stir and warm to room temperature over night, then was partitioned between ether and water. The phases were separated, and the ether phase was washed once each with 1M HCl, water, 1M NaOH, and brine. The ether phase was then dried over Na2SO4, filtered, and concentrated to a residue.

This crude residue was dissolved in 20 mL ether and 8 mL ethyl acetate, and 20 mL of 5M HCl in isopropanol was added. After 1 hour the mixture was placed in the freezer over night. The product was isolated by filtration to give a white solid. $^1$H NMR (DMSO-d6, 400 MHz) 9.21 (br s, 2H), 5.38 (s, 2H), 3.69 (m, 4H), 3.32 (m, 4H), 2.20 (s, 3H) ppm.

Alternative synthesis of 2-(4-Chloro-5-methyl-3-trifluoromethyl-pyrazol-1-yl)-1-piperazin-1-yl-ethanone

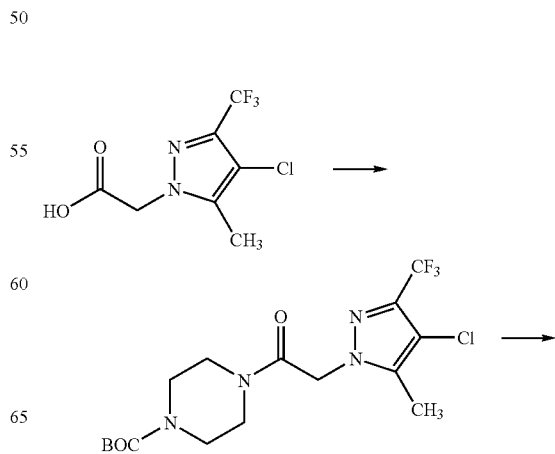

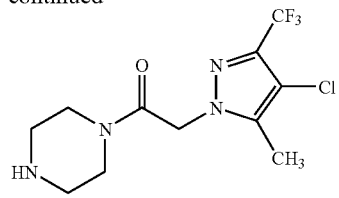

(4-Chloro-5-methyl-3-trifluoromethyl-pyrazol-1-yl)-acetic acid (1.5 g, 6.18 mmol) was taken in dry DCM (20 mL) and cooled to 0° C. To this cold mixture was added N-boc piperazine (1.15 g, 6.18 mmol) followed by addition of T3P (8 g, 12.4 mmol, 50% solution in EtOAc). The reaction was left overnight at rt. The mixture was diluted with CH2Cl2, washed with NaHCO3 soln, brine, dried (Na2SO4) and concentrated to afford the crude product that was washed thoroughly with ether-pet ether to afford 4-[2-(4-Chloro-5 methyl-3-trifluoromethyl-pyrazol-1-yl)-acetyl]-piperazine-1-carboxylic acid tert-butyl ester (1.2 g, 2.9 mmol). This was dissolved in methanol (25 mL) cooled to 0° C. and HCl saturated ether (3 mL) was added to it. The mixture was stirred at room temperature for 4 h and concentrated. Crystallization from MeOH/Petroleum ether yielded product.

Synthesis of 1-[4-(5-Bromo-pyrimidin-2-yl)-piperazin-1-yl]-2-(4-chloro-5-methyl-3-trifluoromethyl-pyrazol-1-yl)-ethanone (PROTOCOL D)

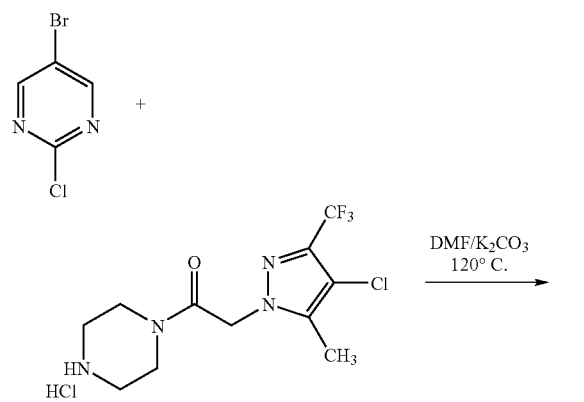

To 86 mg (0.25 mmol) of 2-(4-Chloro-5-methyl-3-trifluoromethyl-pyrazol-1-yl)-1-piperazin-1-yl-ethanone hydrochloride, 76 mg (0.6 mmol) potassium carbonate, and 48 mg (0.3 mmol) of 5-Bromo-2-chloropyrimidine in a vial was added 0.7 mL anhydrous dimethylformamide, and the mixture was heated at 120° C. for 12 hours. The reaction was allowed to cool to room temperature, and was partitioned between ethyl acetate and water. The phases were separated, and the aqueous phase was back-extracted once with ethyl acetate. The combined ethyl acetate phases were washed once each with water, 0.5M pH=7 phosphate buffer, water, 1M NaOH, and brine. The ethyl acetate phase was dried over 'Na2SO4, filtered, and acidified with 2M HCl in ether to precipitate the product as a powder: $^1$H NMR (DMSO-d6, 400 MHz) 8.48 (s, 2H), 5.37 (s, 2H), 3.81 (m, 2H), 3.72 (m, 2H), 3.57 (m, 4H), 2.18 (s, 3H) ppm; MS (ES) M+H expected=467.0, found 466.9.

Additional Compounds of the Invention Prepared by the Aryl-Halogen Displacement Method Synthesis of 2-(4-Chloro-5-methyl-3-trifluoromethyl-pyrazol-1-yl)-1-[4-(7H-purin-6-yl)piperazin1-yl]-ethanone

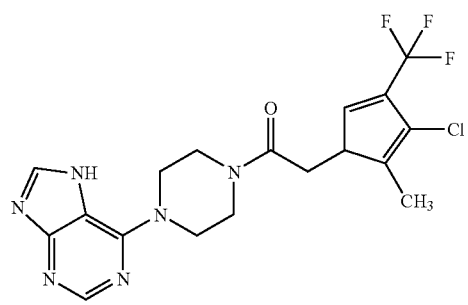

Title compound was prepared following protocol D, wherein 6-Chloropurine was used as the heteroaryl halide component: $^1$H NMR (DMSO-d6, 400 MHz) 8.23 (s, 1H), 8.14 (s, 1H), 5.39 (s, 2H), 4.32 (br, 2H), 4.22 (br, 2H), 3.60 (m, 4H), 2.19 (s, 3H) ppm; MS (ES) expect M+H=429.1, found 429.0.

Synthesis of 2-(4-Chloro-5-methyl-3-trifluoromethyl-pyrazol-1-yl)-1-(4-quinolin-2-yl-piperazin-1-yl)ethanone

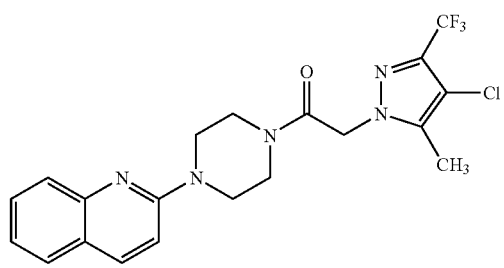

Title Compound was prepared following protocol D, wherein 2-Chloroquinoline was used as the heteroaryl halide component: $^1$H NMR (DMSO-d6, 400 MHz) 8.44 (d, 1H), 8.29 (br, 1H), 7.91 (d, 1H), 7.77 (t, 1H), 7.57 (d, 1H), 7.48 (t, 1H), 5.44 (s, 2H), 4.14 (br, 2H), 4.01 (br, 2H), 3.78 (br, 2H), 3.70 (br, 2H), 2.20 (s, 3H) ppm; MS (ES) expect M+H=438.1, found 438.0.

Synthesis of 2-(4-Chloro-5-methyl-3-trifluoromethyl-pyrazol-1-yl)-1-[4-(5-chloro-pyridin-2-yl)-piperazin-1-yl]-ethanone

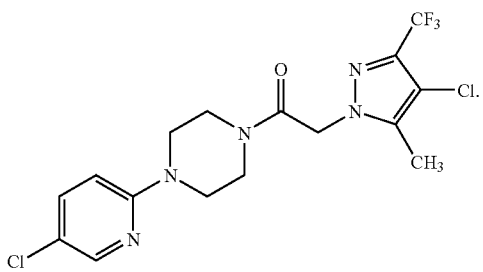

Title compound was prepared following protocol D, wherein 2,5-Dichloropyridine was used as the heteroaryl halide component: MS (ES) expect M+H=422.1, found=422.0; HPLC retention time=4.75 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 2-(4-Chloro-5-methyl-3-trifluoromethyl-pyrazol-1-yl)-1-(2,3,5,6-tetrahydro-[1,2']bipyrazinyl-4-yl)-ethanone

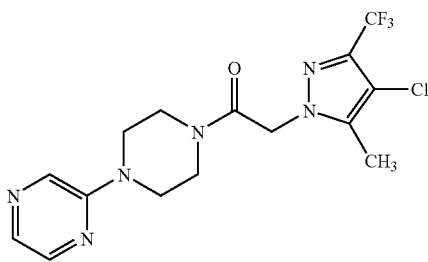

Title compound was prepared following protocol D, wherein 2-Chloropyrazine was used as the heteroaryl halide component: $^1$H NMR (DMSO-d6, 400 MHz) 8.34 (s, 1H), 8.09 (d, 1H), 7.85 (d, 1H), 5.38 (s, 2H), 3.68 (m, 2H), 3.58 (m, 4H), 3.44 (m, 2H), 2.19 (s, 3H) ppm; MS (ES) expect M+H=389.1, found 389.0.

Synthesis of 2-(4-Chloro-5-methyl-3-trifluoromethyl-pyrazol-1-yl)-1-[4-(6-methyl-pyridazin-3-yl)-piperazin-1-yl]-ethanone

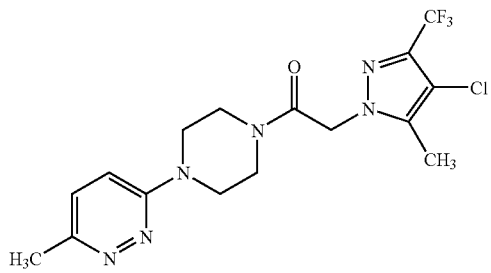

Title compound was prepared following protocol D, wherein 3-Chloro-6-methylpyridazine was used as the heteroaryl halide component: MS (ES) expect M+H=403.1, found=403.0; HPLC retention time=1.68 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 2-(4-Chloro-5-methyl-3-trifluoromethyl-pyrazol-1-yl)-1-[4-(4,6-dimethoxy-[1,3,5]triazin-2-yl)-piperazin-1-yl]-ethanone

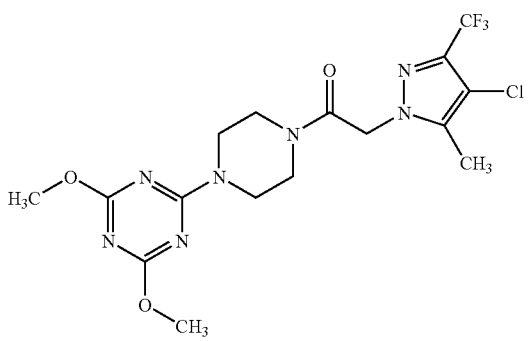

Title compound was prepared following protocol D, wherein 2-Chloro-4,6-dimethoxytriazine was used as the heteroaryl halide component: MS (ES) expect M+H=450.1, found=450.0; HPLC retention time=4.24 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 2-(4-Chloro-5-methyl-3-trifluoromethyl-pyrazol-1-yl)-1-[4-(2-methylsulfanyl-pyrimidin-4-yl)-piperazin-1-yl]-ethanone

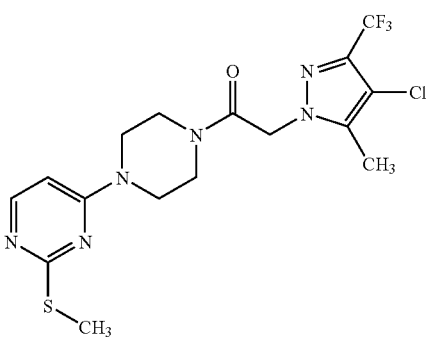

Title compound was prepared following protocol D, wherein 4-Chloro-2-methylthiopyrrimidine was used as the heteroaryl halide component: $^1$H NMR (DMSO-d6, 400 MHz) 8.16 (d, 1H), 6.87 (d, 1H), 5.41 (s, 2H), 3.90 (br m, 4H), 3.62 (m, 4H), 2.57 (s, 3H), 2.19 (s, 3H) ppm; MS (ES) expect M+Na=435.1, found 435.0.

Synthesis of 2-(4-Chloro-5-methyl-3-trifluoromethyl-pyrazol-1-yl)-1-[4-(4,6-dimethoxy-pyrimidin-2-yl)-piperazin-1-yl]-ethanone

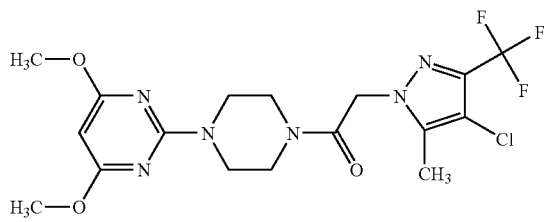

Title compound was prepared following protocol D, wherein 2-Chloro-4,6-dimethoxypyrrimidine was used as the heteroaryl halide component: MS (ES) expect M+H=449.1, found=449.0; HPLC retention time=4.92 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 1-[4-(6-Chloro-5-methyl-pyridazin-3-yl)-piperazin-1-yl]-2-(4-chloro-5-methyl-3-trifluoromethyl-pyrazol-1-yl)-ethanone

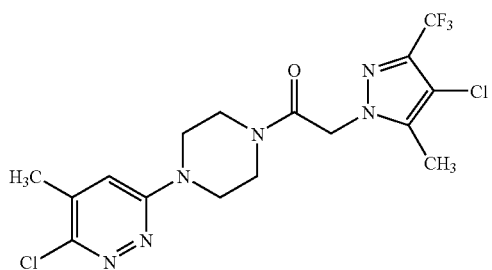

Title compound was prepared following protocol D, wherein 3,6-Dichloro-4-methylpyridazine was used as the heteroaryl halide component: MS (ES) expect M+H=437.1, found=437.0; HPLC retention time=4.17 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 2-(4-Chloro-5-methyl-3-trifluoromethyl-pyrazol-1-yl)-1-[4-(5-methoxy-1-H-benzoimidazol-2-yl)-piperazin-1-yl]-ethanone

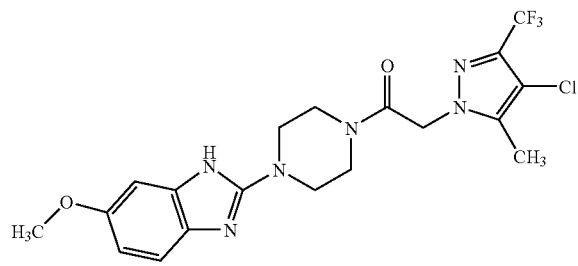

Title compound was prepared following protocol D, wherein 2-Chloro-5-methoxybenzimidazole was used as the heteroaryl halide component: MS (ES) expect M+H=457.1, found=457.0; HPLC retention time=2.85 minutes (Agilent Zorbax SB-C18, 2×50 mm, 51, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Further Functionalization of Arylpiperazine Ring System After its Formal Construction Key compounds of the current invention have, in addition to other selected substituents, a halogen atom at the 2- or 4-position. Approaches to install this are described in the following section.

Functionalization of the aryl ring within the arylpiperazine ring system can, in general, take place either before or after introduction of the piperazine ring, as illustrated in the examples below.

Protocol E: Selected Examples of Halogenation of Aromatic Systems after Attachment of the Piperazine Ring System Synthesis of 1-(4-Bromo-3-methoxy-phenyl)-piperazine hydrochloride

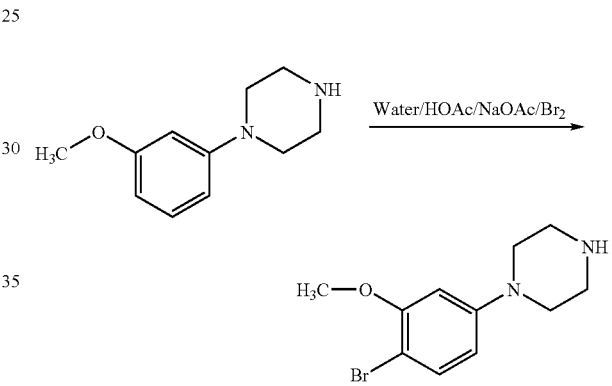

To a solution of 2.33 g (8.8 mmol) of 1-(3-Methoxyphenyl) piperazine dihydrochloride and 756 mg (9.7 mmol) sodium acetate in 70 mL of acetic acid and 15 mL of water at 0° C. was added 1.55 g (9.7 mmol) bromine. After 1 hour, the reaction was concentrated to an oil in vacuo, and the oil was partitioned between ethyl acetate and 1M NaOH. The phases were separated, and the ethyl acetate phase was washed once each with water and brine, dried over Na2SO4, filtered, and the filtrate was concentrated to an oil in vacuo. The oil was dissolved in a minimum volume of methanol, and the solution was acidified with 2M HCl in ether. The product was isolated by filtration. $^1$H NMR (D$_2$O, 400 MHz) 7.36 (d, 1H), 6.73 (s, 1H), 6.50 (d, 1H), 3.75 (s, 3H), 3.32 (m, 8H) ppm.

Synthesis of 1-(4-Bromo-3-methyl-phenyl)-piperazine hydrochloride

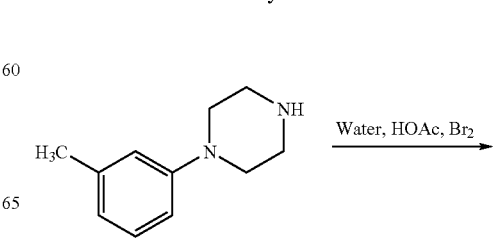

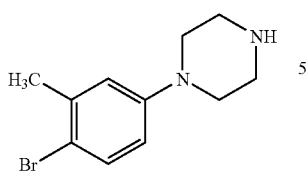

To a solution of 966 mg (4.0 mmol) of 1-(3-Methylphenyl) piperazine dihydrochloride in 9 mL of acetic acid and 1 mL of water at 0° C. was added 640 mg (4.0 mmol) of bromine. After 1 hour, the reaction was concentrated to an oil in vacuo, and the oil was partitioned between ethyl acetate and 1M NaOH. The phases were separated, and the ethyl acetate phase was washed once each with water and brine, dried over Na2SO4, filtered, and the filtrate was concentrated to an oil in vacuo. The oil was dissolved in a minimum volume of methanol, and the solution was acidified with 2M HCl in ether. The product was isolated by filtration. $^1$H NMR (D$_2$O, 400 MHz) 7.37 (d, 1H), 6.85 (s, 1H), 6.76 (d, 1H), 3.37 (m, 8H), 2.17 (s, 3H) ppm.

Synthesis of
1-(2-Chloro-5-methoxy-phenyl)-piperazine
hydrochloride

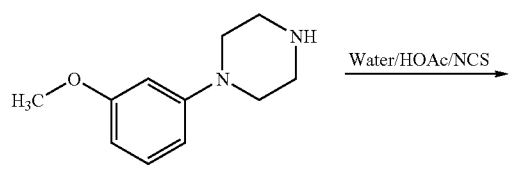

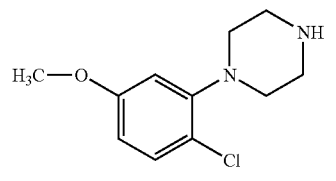

To a solution of 5.3 g (20 mmol) of 1-(3-Methoxyphenyl) piperazine dihydrochloride in 120 mL of acetic acid and 30 mL of water at 0° C. was added 3.3 g (20 mmol) of N-chlorosuccinimide. After 5 hours, the reaction was concentrated to an oil in vacuo, and the oil was partitioned between ethyl acetate and 1M NaOH. The phases were separated, and the ethyl acetate phase was washed once each with water and brine, dried over Na2SO4, filtered, and the filtrate was concentrated to an oil in vacuo. The oil was dissolved in a minimum volume of methanol, and the solution was acidified with 2M HCl in ether. The product was isolated by filtration. $^1$H NMR (D$_2$O, 400 MHz) 7.28 (d, 1H), 6.66 (m, 3H), 3.70 (s, 3H), 3.32 (m, 4H), 3.20 (m, 4H) ppm.

Synthesis of
1-(2,4-Dichloro-5-methoxy-phenyl)-piperazine
hydrochloride

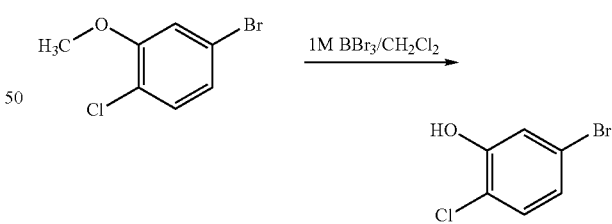

To a solution of 530 mg (2.0 mmol) of 1-(3-Methoxyphenyl)piperazine dihydrochloride in 7 mL of acetic acid and 4 mL of water at 0° C. was added 700 mg (4.4 mmol) of N-chlorosuccinimide. The reaction was taken out of the ice/water bath after 2 hours, and allowed to stir overnight. After 12 hours, the reaction was concentrated to an oil in vacuo, and the oil was partitioned between ether and water. The phases were separated, the aqueous was basified with 1M NaOH, and was extracted with ethyl acetate. The ethyl acetate phase was washed once each with water and brine, dried over Na2SO4, filtered, and the filtrate was concentrated to an oil in vacuo. The oil was dissolved in a minimum volume of methanol, the solution was acidified with 5M HCl in isopropanol and was diluted with ethyl acetate to effect crystallization. The product was isolated by filtration. $^1$H NMR (D$_2$O, 400 MHz) 7.38 (s, 1H), 6.72 (s, 1H), 3.78 (s, 3H), 3.32 (m, 4H), 3.19 (m, 4H) ppm.

Protocol F: Selected Examples of Demethylation/Etherification of Aromatic Precursors for Attachment of the Piperazine Ring System to Access Key Arylpiperazine Moieties Synthesis of 3-Bromo-6-chlorophenol To 50 mL of a 1M solution of boron tribromide in CH2Cl2 at 0° C. was added 5.71 g (25.8 mmol) of 5-Bromo-2-chloroanisole. After 2 hours, the reaction was allowed to warm to room temperature. After 5 hours, the solution was cooled to 0° C., and quenched with methanol. The resulting solution was partitioned between water and ethyl acetate, and the phases were separated. The aqueous phase was back-extracted once with ethyl acetate. The combined ethyl acetate phases were diluted with one volume of ether, and were extracted twice with 1M NaOH. The combined basic aqueous phases were acidified with 12M HCl, and were extracted once with ethyl acetate. The final ethyl acetate phase was washed once with brine, dried over MgSO$_4$, filtered, and concentrated to give the phenol as a tan solid. $^1$H NMR (DMSO-d6, 400 MHz) 10.66 (s, 1H), 7.27 (d, 1H), 7.08 (s, 1H), 6.95 (d, 1H) ppm.

Synthesis of
1-Bromo-3-isopropoxy-4-chlorobenzene

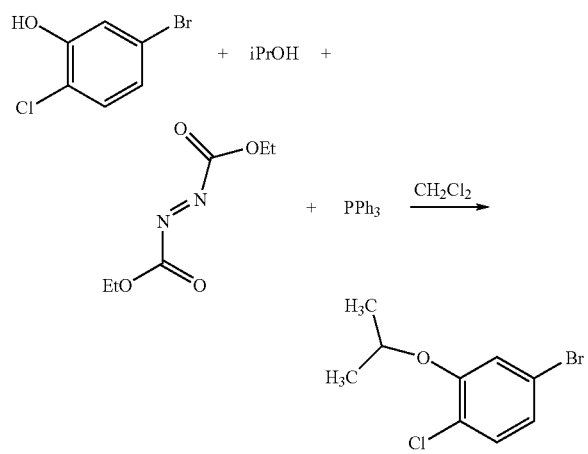

To 1.70 g (6.5 mmol) of triphenylphosphine in 25 mL of CH2Cl2 at 0° C. was added 1.14 g (6.5 mmol) of diethylazodicarboxylate. After 10 minutes, 390 mg (6.5 mmol) of isopropanol was added, followed rapidly by 1.03 g (5.0 mmol) of 3-Bromo-6-chlorophenol. The reaction was complete within three hours, and was partitioned between ether and water. The phases were separated, and the ether phase was diluted with hexanes and washed twice with 10% aqueous methanol and once with brine. The ether/hexanes phase was dried over Na2SO4, filtered, and concentrated in vacuo to yield product as a clear oil.

Protocol F: Additional Examples of Analogous Ring Systems Constructed Using Similar Demethylation/Etherification Strategies.

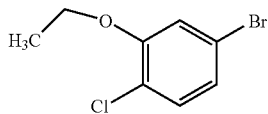

Protocol G: General Procedure for the Synthesis of Elaborated Aryl Bromides from Anilines Synthesis of 4-Chloro-2-fluoro-1-bromobenzene

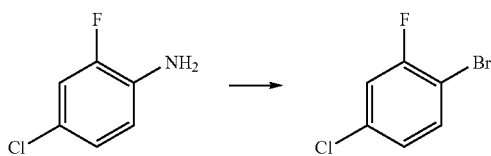

Sodium nitrite (2.35 g, 34.13 mmol) solution (40 mL) was added dropwise to 4-Chloro-2-fluoro aniline (4.5 g, 31 mmol) in 170 mL HBr at −10° C. bath temperature, then the mixture was stirred for 30 min at −10° C. bath temperature. In parallel, copper sulfate (10.22 g, 24.29 mmol) and sodium bromide (3.79 g, 36.8 mmol) were mixed and the reaction mixture was heated at 60° C. for 30 min. Then sodium sulfite (2.66 g, 21.2 mmol) was added into this copper sulfate reaction mixture and heated for 95° C. for 30 min. The reaction mixture was cooled to room temperature and solid formed was washed with water to afford white solid cuprous bromide. The diazonium salt was portion wise added into the freshly prepared cuprous bromide in 40 mL HBr at −10° C. bath temperature and the reaction mixture was then warmed to room temperature. The reaction mixture was heated at 55° C. for 20 min, cooled and then extracted with ethyl acetate three times. The combined organic layer was washed with water and saturated brine solution, dried over sodium sulfate and concentrated. The crude material was purified by column chromatography (5:95 ethyl acetate: pet ether) to afford solid product.

Synthesis of
(2-Bromo-5-chloro-phenyl)-phenyl-methanone

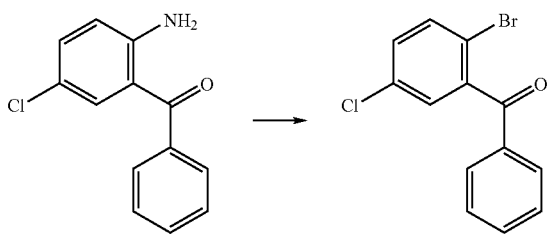

Sodium nitrite (2.5 g, 36.28 mmol) solution (40 mL) was dropwise added to the aniline (7 g, 30.2 mmol) in 100 mL HBr at −10° C. bath temperature, then the mixture was stirred for 30 min at −10° C. bath temperature to make diazonium salt.

Copper sulfate (10.22 g, 24.29 mmol) and sodium bromide (3.79 g, 36.8 mmol) was heated at 60° C. for 30 min. Then sodium sulfite (2.66 g, 21.2 mmol) was added into copper sulfate reaction mixture and heated for 95° C. for 30 min. Then the reaction mixture was cooled to rt and solid formed was washed with water to afford white solid cuprous bromide.

Diazonium salt was portion wise added into the freshly prepared cuprous bromide in 40 mL HBr at −10° C. bath temperature and the reaction mixture warmed to room temperature. Then the reaction mixture was heated at 55° C. for 20 min, cooled to room temperature and extracted with ethyl acetate three times. The combined organic layer was washed with water and saturated brine solution, dried over sodium sulfate and concentrated. The product was purified by crystallization from DCM/Pet ether.

Protocol G: Additional Examples of Analogous Ring Systems Constructed Using Similar Sandmeyer Type Strategies

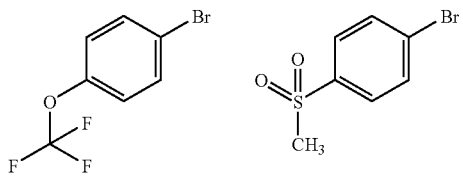

These preceding aryl bromides and similar substrates were used in a variety of chemistries, already described, to access arylpiperazines such as those listed below.

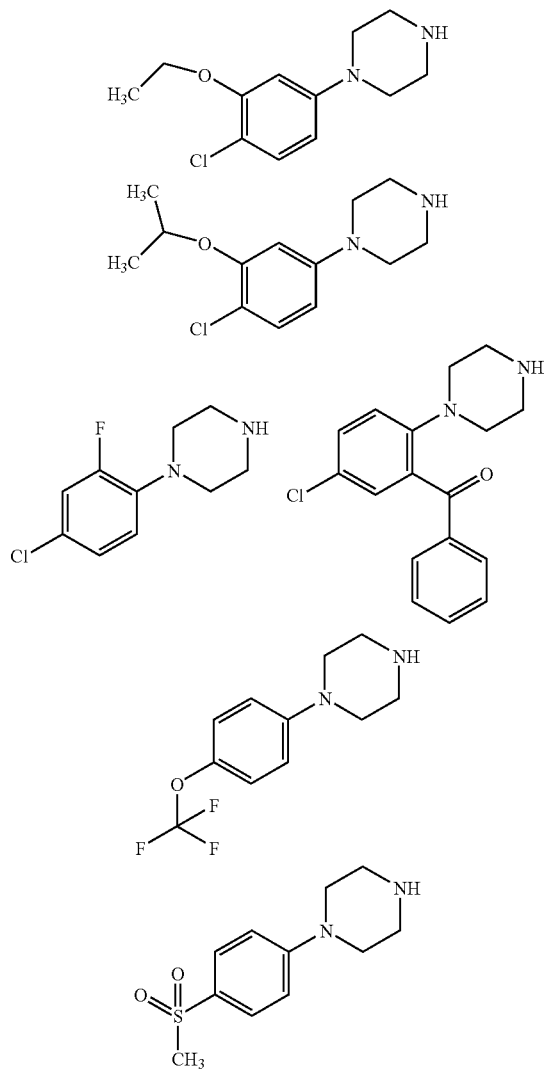

Synthesis of Heteroaromatic Ring Systems: Core Ring Structure Formation

The types of chemistries which can be applied to synthesize the key heteroaryl ring structures are listed below. They are separated into examples of ring formation and ring functionalization reactions.

Protocol H: Pyrazole Synthesis Via Addition of Hydrazines to α,β-Acetylenic Ketones Synthesis of 5-Butyl-3-trifluoromethyl-1H-pyrazole

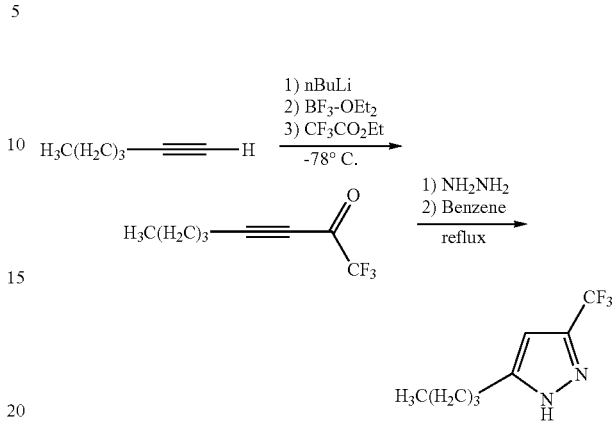

To a solution of 1-Hexyne (3.37 mL, 29.4 mmol) in THF (30 mL) was added n-BuLi (2.78 M, 10.2 mL, 29.4 mmol). The solution was stirred at −78° C. for 30 minutes then $CF_3CO_2Et$ (3.5 mL, 29.35 mL) and $BF_3$—$OEt_2$ were added successively. The reaction was further stirred at −78° C. for 2 h and was quenched with satd. $NH_4Cl$. It was then warmed up to the room temperature. The THF was removed, the residue taken into ether, washed with saturated brine solution, dried over $Na_2SO_4$ and reduced. The crude product was then dissolved in benzene (25 mL) and hydrazine (29.4 mmol) was added. The reaction mixture was refluxed overnight, then cooled, the solvent evaporated, and the residue taken into $CH_2Cl_2$ (30 mL), washed with brine, dried over $Na_2SO_4$ and concentrated to give the title compound as colorless oil.

Synthesis of 5-isopropyl-3-trifluoromethyl-1H-pyrazole

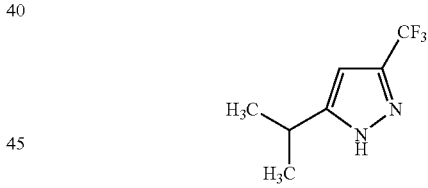

Following protocol H, 3-methylbutyne was treated with n-BuLi, $CF_3CO_2Et$ and $BF_3$—$OEt_2$ in THF. Reaction with hydrazine in benzene under similar reaction conditions yielded title compound.

Synthesis of 5-propyl-3-trifluoromethyl-1H-pyrazole

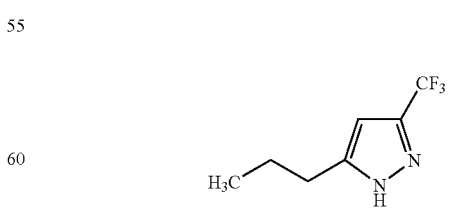

Following protocol H, 1-pentyne was treated with n-BuLi, $CF_3CO_2Et$ and $BF_3$—$OEt_2$ in THF. Reaction with hydrazine in benzene under similar reaction conditions yielded title compound.

Synthesis of 5-(3-Fluorophenyl)-3-trifluoromethyl-1H-pyrazole

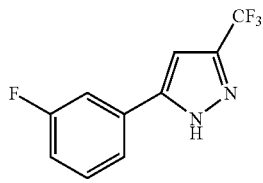

Following protocol H, 1-Ethynyl-3-fluoro-benzene was treated with n-BuLi, $CF_3CO_2Et$ and $BF_3$—$OEt_2$ in THF. Reaction with hydrazine in benzene under similar reaction conditions yielded title compound.

Protocol I: General Procedure for the Synthesis of Pyrazoles Via Condensation of Hydrazines with β-Diketones:

Synthesis of 5-ethyl-3-trifluoromethyl-1H-pyrazole

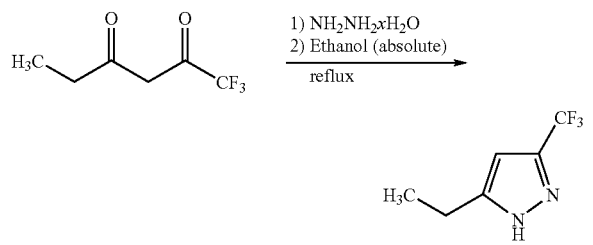

To a solution of 1,1,1-Trifluoro-hexane-2,4-dione (1 g, 5.95 mmol) in absolute ethanol (10 mL) was added $NH_2NH_2 \cdot xH_2O$ drop-wise at 0° C. The reaction mixture warmed to the room temperature during 1 hour and refluxed overnight. Ethanol was then evaporated, residue dissolved in ethyl acetate (20 mL), washed consecutively with saturated brine solution and water, dried with $Na_2SO_4$ and concentrated to give the title compound as colorless oil.

Protocol J: Pyrazole Synthesis Via Condensation of Hydrazines with β-Cyanoketones

Synthesis of 5-Phenyl-1-pyrazol-3-amine

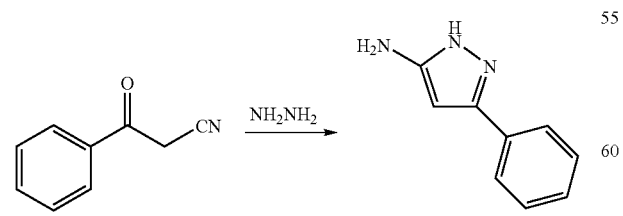

2.0 g (0.0138 mol, 1 eq) of benzoylacetonitrile in 40 mL of absolute ethanol was added 2.0 g (0.0399 mol, 3 eq) of anhydrous hydrazine and the reaction mixture stirred at 85° C. for 2 h. Ethanol was removed at 50° C. under vacuum. 5-Phenyl-1-pyrazol-3-amine, obtained as a yellow solid, was washed with pet ether (100 mL) and dried under vacuum.

Synthesis of Functionalized Heteroaryl Ring Systems

Chlorination or Bromination of Pyrazoles

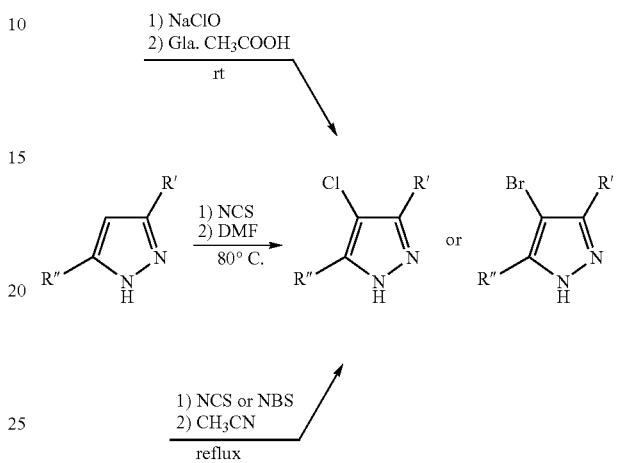

Protocol K: Chlorination of Pyrazoles with NaOCl in Glacial Acetic Acid

Synthesis of 4-Chloro-1H-pyrazole

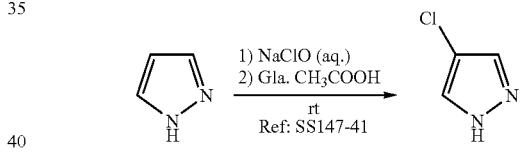

To a solution of pyrazole (0.5 g, 7.34 mmol) in glacial acetic acid (4 mL) was added NaOCl (0.55 g, 7.34 mmol). The reaction mixture was left at room temperature for 18 h, then neutralized with saturated $Na_2CO_3$ solution, extracted with $CH_2Cl_2$ (2×25 mL), the combined organic layers evaporated, then diluted with NaOH, and further extracted with $CH_2Cl_2$ (3×20 mL). The organic extracts were combined, dried over $Na_2SO_4$ and evaporated to give the title compound as a white solid.

Synthesis of 4-Chloro-3-trifluoromethyl-1H-pyrazole

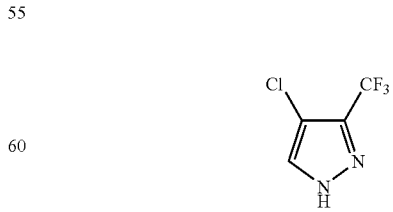

Following protocol K, 3-trifluoromethylpyrazole was treated with glacial acetic acid and NaOCl, yielding title compound.

Synthesis of 4-Chloro-3-methyl-1H-pyrazole

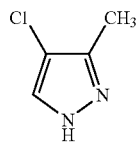

Following protocol K, 3-methylpyrazole was treated with glacial acetic acid and NaOCl, yielding title compound.

Synthesis of 4-Chloro-5-propyl-1H-pyrazole-3-carboxylic acid ethyl ester

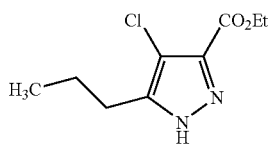

Following protocol K, 5-propyl-1H-pyrazole-3-carboxylic acid ethyl ester was treated with glacial acetic acid and NaOCl under similar reaction conditions, yielding the title compound.

Protocol L: Chlorination or Bromination of Pyrazoles with N-Chlorosuccinimide (NCS) or N-bromosuccinimide (NBS):

Synthesis of 4-Chloro-3-methyl-5-trifluoromethyl-1H-pyrazole

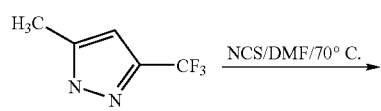

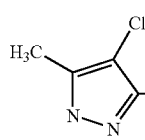

3-methyl-5-trifluoromethylpyrazole was taken into dry DMF (20 mL) and N-chloro succinimide (1.78 g) was added in portions. The mixture was then heated at 70° C. for 22 h, cooled to room temperature, and then water (100 mL) was added and the mixture extracted with ethyl acetate (4×25 mL). The organic layer was washed with water and brine and dried with $Na_2SO_4$. Evaporation of the solvent afforded the title compound.

Syntheses of 4-Chloro-5-thiophen-2-yl-2H-pyrazole-3-carboxylic acid ethyl ester

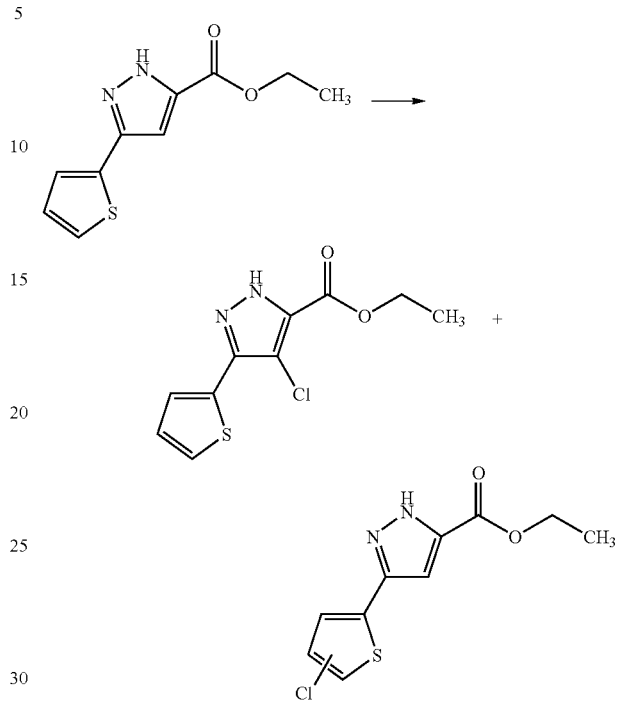

Pyrazole(1 eq) in DMF (0.14M Solution) was treated with NCS (1.5 eq.) in portions, and when all the NCS was dissolved in the reaction mixture, it was then heated at 70° C. overnight. The reaction mixture was then cooled to rt and quenched with water, extracted with ethyl acetate and dried in $MgSO_4$. Two products were isolated, including the title compound

Synthesis of 4-Chloro-3,5-diisopropyl-pyrazole

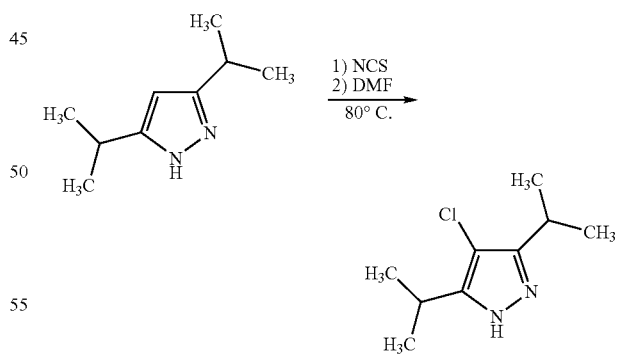

Following protocol L, a the solution of 3,5-diisopropyl-pyrazole (0.5 g, 3.57 mmol) in DMF (10 mL) was added NCS (0.72 g, 5.3 mmol) in portions under vigorous stirring. The reaction mixture was then heated at 80° C. for 14 h and then the reaction was quenched with water. It was then extracted with ethyl acetate (2×30 mL). The combined organics were washed with brine. The organic extracts were combined and dried with $Na_2SO_4$ and finally evaporated to give the title compound as colorless oil.

Synthesis of 4-Chloro-3-thiophen-2-yl-1H-pyrazole

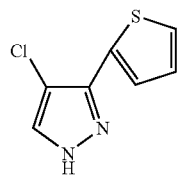

Following protocol L, 3-thiophen-2-yl-1H-pyrazole was treated with NCS in DMF, to yield title compound.

Synthesis of 5-tert-Butyl-4-chloro-3-trifluoromethyl-1H-pyrazole

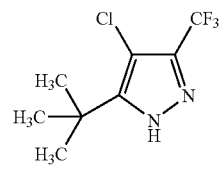

Following protocol L, 5-tert-butyl-3-trifluoromethyl-1H-pyrazole was treated with NCS in DMF to yield title compound.

Synthesis of 4-Chloro-3-methyl-1H-pyrazole-5-carboxylic acid ethyl ester

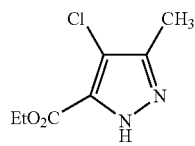

Following protocol L, 3-methyl-2H-pyrazole-5-carboxylic acid ethyl ester was treated with NCS in DMF to yield the title compound.

Synthesis of 4-Chloro-3-thiophen-2-yl-1H-pyrazole-5-carboxylic acid ethyl ester

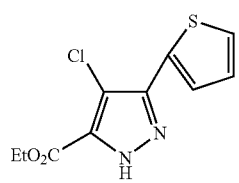

Following protocol L, 3-Thiophen-2-yl-1H-pyrazole-5-carboxylic acid ethyl ester was treated with NCS in DMF to yield the title compound.

Synthesis of 4-Chloro-5-(5-chloro-thiophen-2-yl)-2H-pyrazole-3-carboxylic acid ethyl ester

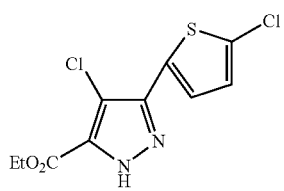

Following protocol L, 3-Thiophen-2-yl-1H-pyrazole-5-carboxylic acid ethyl ester was treated with NCS in DMF under to yield the title compound.

Synthesis of 4-Chloro-3-(4-fluoro-phenyl)-5-methyl-sulfanyl-1H-pyrazole

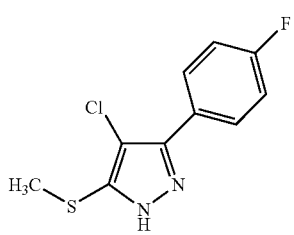

Following protocol L, 3-(4-fluoro-phenyl)-5-methylsulfanyl-1H-pyrazole was treated with NCS in to yield the title compound.

Synthesis of 5-Butyl-4-chloro-3-trifluoromethyl-1H-pyrazole

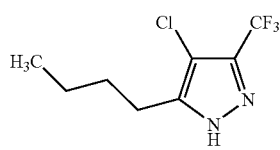

Following protocol L, 5-butyl-3-trifluoromethyl-1H-pyrazole was treated with NCS in DMF to yield the title compound.

Synthesis of 4-Chloro-5-phenyl-1-pyrazol-3-amine

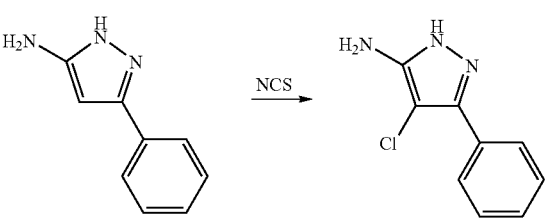

Following protocol L, to 0.5 g (0.0031 mol, 1 eq) of 5-phenyl-1-pyrazol-3-amine in 25 mL of dry acetonitrile was added 0.4 g (0.0031 mol, 1 eq) of N-chlorosuccinimide portion wise and the reaction mixture stirred at room temperature for 30 min. The reaction mixture was quenched with water and extracted with ethyl acetate. The organic layer was washed with water, brine and concentrated. The product was purified by 60-120 silica gel column (1% of methanol in chloroform).

Synthesis of 4-Bromo-5-phenyl-1-pyrazol-3-amine

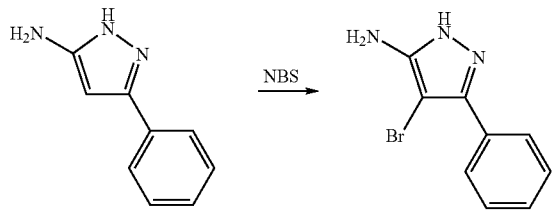

Following protocol L, to 0.5 g (0.003 μmol, 1 eq) of 5-phenyl-1-pyrazol-3-amine in 25 mL of dry acetonitrile was added 0.55 g (0.0031 mol, 1 eq) of N-bromosuccinimide portion wise and the reaction mixture stirred at room temperature for 30 min. The reaction mixture was quenched with water and extracted with ethyl acetate. The organic layer was washed with water, brine and concentrated. The product was purified by 60-120 silica gel column (1% of methanol in chloroform).

Synthesis of 4-Chloro-5-isopropyl-3-trifluoromethylpyrazole

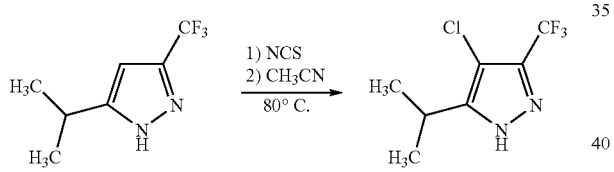

Following protocol L, to the solution of 3-trifluoromethyl-5-isopropyl-pyrazole (0.22 g, 1.23 mmol) in CH$_3$CN (10 mL) was added NCS (0.19 g, 1.43 mmol) in portions with vigorous stirring. The reaction mixture was then heated under reflux for 14 h, cooled and the reaction quenched with saturated NaHCO$_3$, extracted with methylene chloride (2×30 mL) and the combined organic extracts was washed with brine, dried with Na$_2$SO$_4$ and evaporated to give the title compound as a white solid.

Synthesis of 4-chloro-5-Ethyl-3-trifluoromethyl-1H-pyrazole

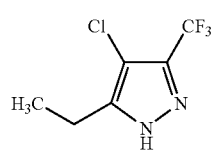

Following protocol L, 5-ethyl-3-trifluoromethyl-1H-pyrazole was treated with NCS in CH$_3$CN to yield title compound Synthesis of 4-chloro-5-propyl-3-trifluoromethyl-1H-pyrazole

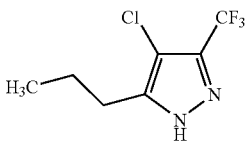

Following protocol L, 5-propyl-3-trifluoromethyl-1H-pyrazole was treated with NCS in CH$_3$CN to yield the title compound.

Synthesis of 4-chloro-5-(3-fluorophenyl)-3-trifluoromethyl-1H-pyrazole

Following protocol L, 5-(3-fluorophenyl)-3-trifluoromethyl-1H-pyrazole was treated with NCS in CH$_3$CN to yield the title compound.

Synthesis of 4-chloro-3,5-bistrifluoromethyl-1H-pyrazole

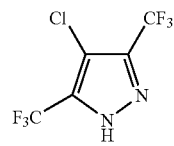

Following protocol L, 3,5-bistrifluoromethyl-1H-pyrazole was treated with NCS in CH$_3$CN to yield the title compound.

Synthesis of N-(4-Chloro-5-methyl-1H-pyrazol-3-yl)-2,2,2-trifluoro-acetamide

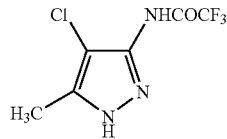

Following protocol L, 2,2,2-Trifluoro-N-(5-methyl-1H-pyrazol-3-yl)-acetamide was treated with NCS in CH$_3$CN to yield the title compound.

Protocol M: General Procedure for Reduction of Nitropyrazoles

Synthesis of 3-Heptafluoropropyl-5-methyl-1H-pyrazol-4-ylamine

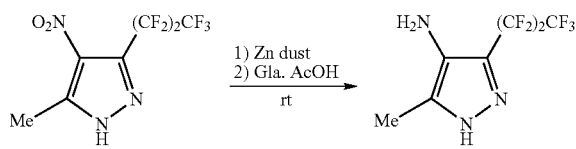

To a suspension of zinc dust (1.5 g) in glacial acetic acid (10 mL) was added drop-wise, a solution of 3-Heptafluoropropyl-5-methyl-4-nitro-1H-pyrazole (0.295 g, 1.0 mmol) in glacial acetic acid (5 mL). The reaction mixture was then allowed to stir at room temperature for 14 h. The zinc salts were then removed by filtration and the residue washed with ethyl acetate. The combined organic extract was concentrated in vacuum, re-dissolved in CHCl$_3$, washed with NaHCO$_3$, water and brine. Finally the organic layer was dried with Na$_2$SO4 and solvent evaporated to give the title compound as white solid.

Synthesis of Bromo-Pyrazoles for Aryl-Aryl Cross Coupling Reactions and for Metal Mediated Aminations

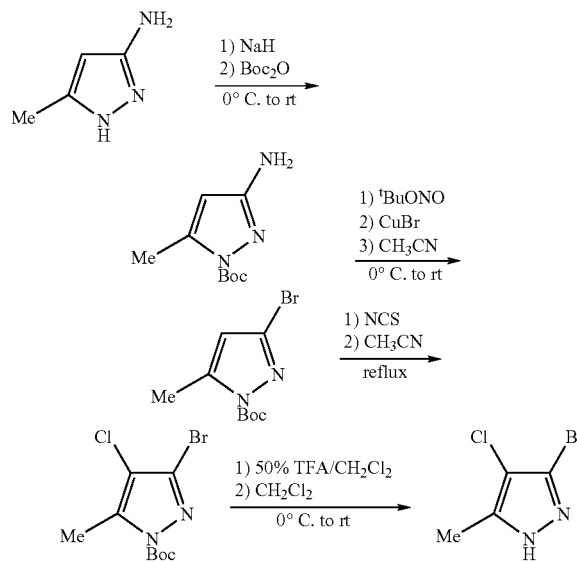

General Procedure for Trifluoroacetylation of Aminopyrazoles:

Synthesis of 2,2,2-Trifluoro-N-(5-methyl-1H-pyrazol-3-yl)-acetamide

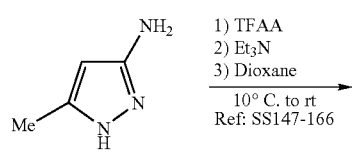

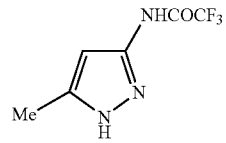

To a solution of 3-amino-5-methylpyrazole (0.97 g, 10 mmol) and Et$_3$N (1.39 mL, 10 mmol) in dioxane (25 mL) was added Trifluoroacetic anhydride (TFAA) (1.39 mL, 10 mmol) drop-wise at 10° C. The reaction mixture was stirred at that temperature for 1 h then slowly warmed to room temperature through next 1 h. Once the reaction is over dioxane was evaporated, residue resolved in water (20 mL), washed with methylene chloride (30 mL). Organic layer was then dried with Na$_2$SO$_4$ and concentrated to give the title compound as white solid.

Protocol N: Functionalization of Alkyl Substituted Heteroaryl Ring Systems: Aminomethylation Synthesis of (5-Bromomethyl-4-chloro-3-methyl-pyrazol-1-yl)-acetic acid ethyl ester

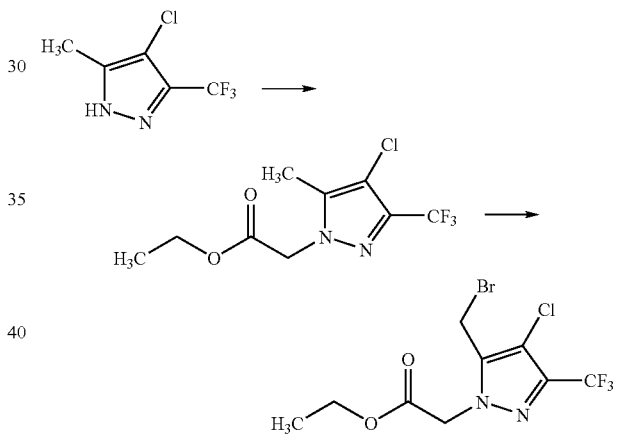

Reagents and Conditions: i) BrCH$_2$CO$_2$Et/K$_2$CO$_3$/CH$_3$CN; ii) NBS/AIBN/CCl$_4$ 4-Chloro-3-methyl-5-trifluoromethyl-1H-pyrazole, (10 g, 54 mmol) was dissolved in acetonitrile (100 mL) and potassium carbonate (30 g, 0.215 mol) added. After stirring at room temperature for 1 hour, ethyl bromoacetate (11 g, 65 mmol) was added. After 14 h at 70° C., the mixture was filtered and the filtrate was concentrated to obtain the crude product, which was re-crystallized from petroleum ether.

This intermediate ester (5 g, 0.019 mol) was taken in CCl$_4$ (100 mL) and AIBN (0.053 g, 0.33 mmol) was added to it under nitrogen. The mixture was irradiated with a regular light bulb. The mixture was brought to reflux and then NBS (3.42 g, 0.019 mol), in four portions in 15 min intervals, was added to the mixture. After complete addition the mixture was left refluxing under the influence of light for 3 h. The reaction mixture was then filtered and the filtrate was washed with water and brine. Drying the organic layer (Na$_2$SO$_4$) followed by evaporation of the solvent afforded (5-Bromomethyl-4-chloro-3-trifluoromethyl-pyrazol-1-yl)-acetic acid ethyl ester.

Protocol O: Synthesis of (5-Azidomethyl-4-chloro-3-trifluoromethyl-pyrazol-1-yl)-acetic acid:

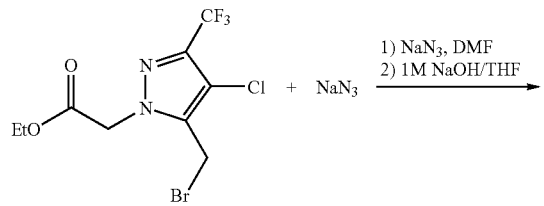

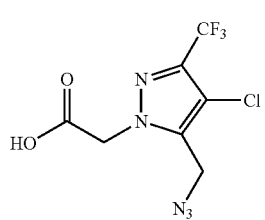

To 4.6 g (13.2 mmol) of (5-Bromomethyl-4-chloro-3-trifluoromethyl-pyrazol-1-yl)-acetic acid ethyl ester dissolved in 40 mL of anhydrous dimethylformamide was added 1.03 g (15.8 mmol) of sodium azide. After stirring for 12 hours, the solution was partitioned between ethyl acetate and water. The phases were separated, the aqueous phase was back-extracted with ethyl acetate and the combined ethyl acetate phases were washed with water and brine, dried over Na2SO4, filtered, and concentrated in vacuo to yield an orange oil.

The oil was dissolved in 25 mL of tetrahydrofuran, 25 mL of 1M NaOH was added, and the mixture was stirred vigorously for three hours. The tetrahydrofuran was then removed in vacuo, and the aqueous solution was washed once with ether. The aquous phase was then acidified with 1M HCl, and extracted twice with ethyl acetate. The combined ethyl acetate phases were washed with brine, dried over Na2SO4, filtered, and concentrated to yield the title compounds as an orange solid.

Protocol P (vide infra): Synthesis of 2-(5-Azidomethyl-4-chloro-3-trifluoromethyl-pyrazol-1-yl)-1-[4-(4-chlorophenyl)-piperazin-1-yl]-ethanone:

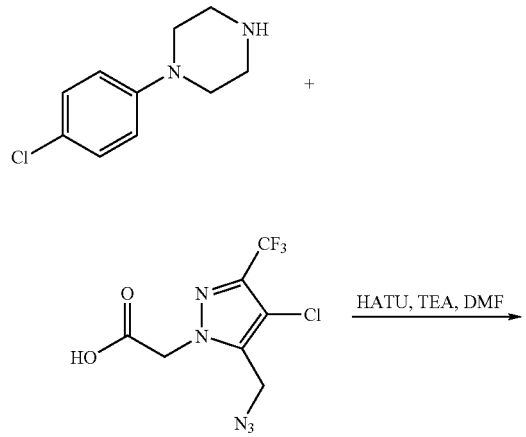

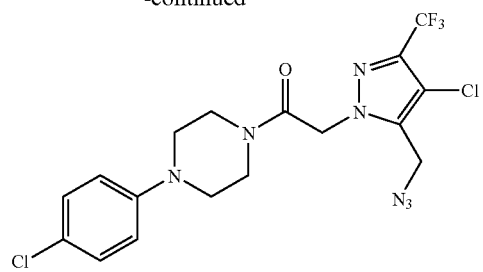

To 2.71 g (13.7 mmol) of 1-(4-Chlorophenyl)piperazine and 3.58 g (12.5 mmol) of (5-Azidomethyl-4-chloro-3-trifluoromethyl-pyrazol-1-yl)-acetic acid in 40 mL of anhydrous dimethylformamide was added 4.36 mL (31.2 mmol) of triethylamine. The solution was cooled to 0° C., and 5.21 g (13.7 mmol) of O-(7-Azabenzotriazol-1-yl)-N,N,N',N'-tetramethyluronium hexafluorophosphate (HATU) was added. After 2 hours the reaction was diluted with two volumes of water, and the solvent was decanted away from the resulting oil. The oil was crystallized by dissolving in methanol and adding water in small portions. The product was isolated as a white solid by filtration: $^1$H NMR (DMSO-d6, 400 MHz) 7.23 (d, 2H), 6.97 (d, 2H), 5.48 (s, 2H), 4.62 (s, 2H), 3.60 (m, 4H), 3.24 (m, 2H), 3.12 (m, 2H) ppm; MS (ES) M+H expected=462.1, found=462.0.

Protocol Q: Synthesis of 2-(5-Aminomethyl-4-chloro-3-trifluoromethyl-pyrazol-1-yl)-1-[4-(4-chlorophenyl)-piperazin-1-yl]-ethanone

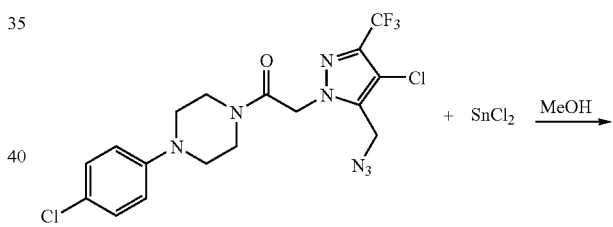

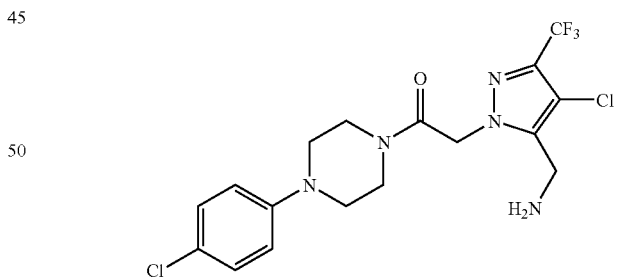

2.85 g (6.2 mmol) of 2-(5-Azidomethyl-4-chloro-3-trifluoromethyl-pyrazol-1-yl)-1-[4-(4-chlorophenyl)-piperazin-1-yl]-ethanone was dissolved in 80 mL methanol, and 3.61 g (16.0 mmol) of SnCl2 hydrate was added. After two hours, the reaction was concentrated in vacuo to remove the methanol. The residue was partitioned between 0.5M NaOH and ethyl acetate, and the phases were separated. The aqueous phase was back-extracted once with ethyl acetate. The combined ethyl acetate phases were extracted twice with 1M HCl. The acidic aqueous phase was basified with 1M NaOH, and was extracted once with ethyl acetate. The final ethyl acetate phase was washed once with brine, dried over Na2SO4, filtered, and concentrated to an oil. The oil was dissolved in methanol, acidified with 2M HCl in ether, and the product was isolated by filtration after precipitation: ¹H NMR (DMSO-d6, 400 MHz) 8.58 (s, 3H), 7.27 (d, 2H), 7.03 (d, 2H), 5.71 (s, 2H), 4.10 (d, 2H), 3.64 (m, 4H), 3.32 (m, 2H), 3.19 (m, 2H) ppm; MS (ES) M+H expected=436.1, found=436.0.

Synthesis of 2-(5-N,N-Dimethylaminomethyl-4-chloro-3-trifluoromethyl-pyrazol-1-yl)-1-[4-(4-chlorophenyl)-piperazin-1-yl]-ethanone

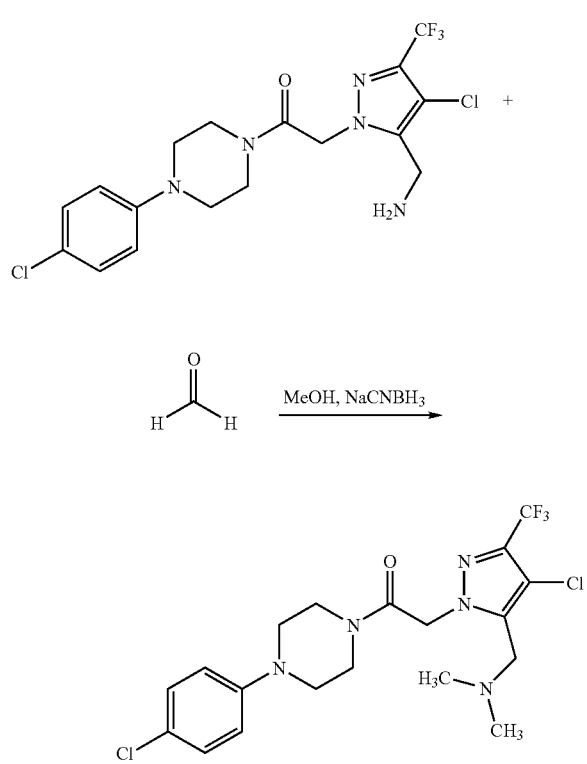

To a solution of 50 mg (0.1 mmol) of 2-(5-Aminomethyl-4-chloro-3-trifluoromethyl-pyrazol-1-yl)-1-[4-(4-chlorophenyl)-piperazin-1-yl]-ethanone hydrochloride and 13 mg (0.20 mmol) sodium cyanoborohydride in 0.7 mL methanol was added 0.025 mL (0.3 mmol) of 37% aqueous formaldehyde. After stirring for four hours, the reaction was quenched with 0.1 mL 12M HCl. One hour later, the solution was concentrated in vacuo. The residue was partitioned between water and ether, and the phases were separated. The ether phase was back-extracted once with water. The combined aqueous phases were basified with 1M NaOH, and was extracted once with ethyl acetate. The ethyl acetate phase was washed once with brine, dried over Na2SO4, filtered, and concentrated to an oil. The oil was dissolved in methanol, acidified with 2M HCl in ether, and the product was isolated as a white solid by filtatration: ¹H NMR (DMSO-d6, 400 MHz) 11.07 (br, 1H), 7.26 (d, 2H), 7.02 (d, 2H), 5.76 (s, 2H), 4.43 (s, 2H), 3.62 (m, 4H), 3.31 (m, 2H), 3.18 (m, 2H), 2.81 (s, 6H) ppm; MS (ES) M+H expected=464.1, found=464.0.

Protocol R: Urea Derivatization of Aminomethyl Functionality on Pyrazole Ring System Synthesis of 1-(4-Chloro-2-{2-[4-(4-chloro-phenyl)-piperazin-1-yl]-2-oxo-ethyl}-5-trifluoromethyl-2H-pyrazol-3-ylmethyl)-urea

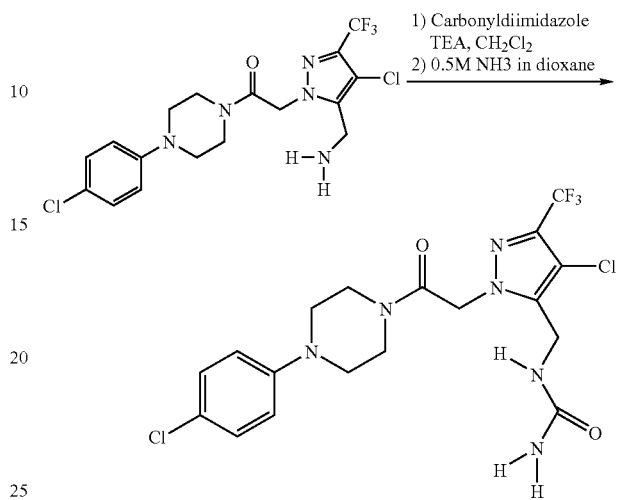

To a slurry of 12 mg (0.07 mmol) carbonyldiimidazole and 25 mg (0.05 mmol) of 2-(5-Aminomethyl-4-chloro-3-trifluoromethyl-pyrazol-1-yl)-1-[4-(4-chlorophenyl)-piperazin-1-yl]-ethanone hydrochloride in 1.0 mL CH2Cl2 at 0° C. was added 23 mg (0.22 mmol) of triethylamine dissolved in 0.2 mL CH2Cl2 over five minutes. The mixture was allowed to warm to room temperature after one hour, and was stirred for an additional hour.

1.0 mL (0.5 mmol) of 0.5M ammonia in dioxane was added, and the resulting solution was stirred for 12 hours. The solution was concentrated in vacuo, and the resulting residue was partitioned between ethyl acetate and water. The phases were separated, and the aqueous phase was back-extracted once with ethyl acetate. The combined ethyl acetate phases were washed once each with water, 1M NaOH, brine, dried over Na2SO4, filtered, and concentrated to a residue. The residue was triturated with ethyl acetate, and the product was isolated as a white solid by filtration: ¹H NMR (DMSO-d6, 400 MHz) 7.23 (d, 2H), 6.96 (d, 2H), 6.48 (t, 1H), 5.62 (s, 2H), 5.48 (s, 2H), 4.16 (d, 2H), 3.57 (m, 4H), 3.25 (m, 2H), 3.14 (m, 2H) ppm; MS (ES) M+H expected=479.1, found=479.0.

Synthesis of 3-(4-Chloro-2-{2-[4-(4-chloro-phenyl)-piperazin-1-yl]-2-oxo-ethyl}-5-trifluoromethyl-2H-pyrazol-3-ylmethyl)-1,1-dimethyl-urea

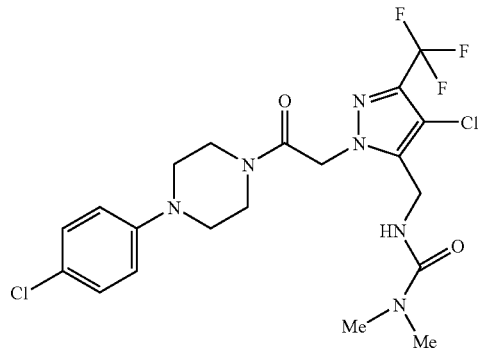

Title compound was prepared following protocol R, using 2M dimethylamine in tetrahydrofuran as the amine component in the second step, to give the desired product as a solid: $^1$H NMR (DMSO-d6, 400 MHz): 7.23 (d, 2H), 6.96 (d, 2H), 6.81 (t, 1H), 5.43 (s, 2H), 4.21 (d, 2H), 3.56 (m, 4H), 3.22 (m, 2H), 3.13 (m, 2H), 2.73 (s, 3H) ppm; MS (ES) M+H expected=507.1, found=507.1.

Synthesis of 1-(4-Chloro-2-{2-[4-(4-chloro-phenyl)-piperazin-1-yl]-2-oxo-ethyl}-5-trifluoromethyl-2H-pyrazol-3-ylmethyl)-3-methyl-urea

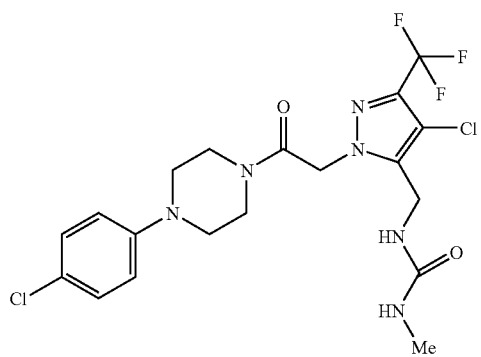

Title compound was prepared following the protocol R, using 2M methylamine in tetrahydrofuran as the amine component in the second step, to give the desired product as a solid: $^1$H NMR (DMSO-d6, 400 MHz) 7.23 (d, 2H), 6.96 (d, 2H), 6.45 (t, 1H), 5.86 (m, 1H), 5.48 (s, 2H), 4.18 (d, 2H), 3.58 (m, 4H), 3.31 (s, 3H), 3.25 (m, 2H), 3.13 (m, 2H) ppm; MS (ES) M+H expected=493.1, found=493.0.

Synthesis of 3-(4-Chloro-2-{2-[4-(4-chloro-phenyl)-piperazin-1-yl]-2-oxo-ethyl}-5-trifluoromethyl-2H-pyrazol-3-ylmethyl)-1-methoxy-1-methyl-urea

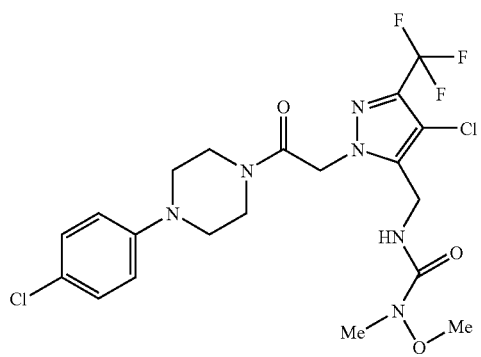

Title compound was prepared following protocol R, using 1M N,O-dimethylhydroxylamine in tetrahydrofuran as the amine component in the second step, to give the desired product as a solid: $^1$H NMR (DMSO-d6, 400 MHz) 7.63 (t, 1H), 7.23 (d, 2H), 6.96 (d, 2H), 5.42 (s, 2H), 4.25 (d, 2H), 3.57 (m, 4H), 3.52 (s, 3H), 3.25 (m, 2H), 3.13 (m, 2H), 2.89 (s, 3H) ppm; MS (ES) M+H expected=523.1, found 523.0.

Synthesis of 1-(4-Chloro-2-{2-[4-(4-chloro-phenyl)-piperazin-1-yl]-2-oxo-ethyl}-5-trifluoromethyl-2H-pyrazol-3-ylmethyl)-3-ethyl-urea

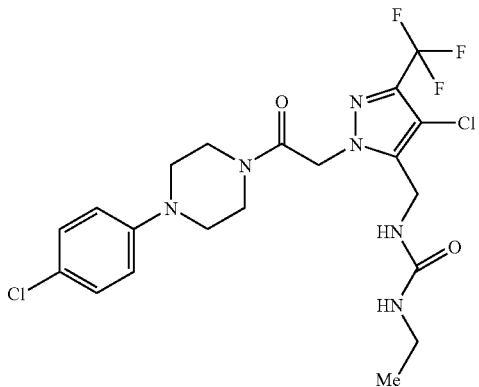

Title compound was prepared following protocol R, using 2M ethylamine in tetrahydrofuran as the amine component in the second step, to give the desired product as a solid: $^1$H NMR (DMSO-d6, 400 MHz) 7.26 (d, 2H), 7.03 (d, 2H), 6.95 (br, 1H), 6.47 (br, 1H), 5.49 (s, 2H), 4.17 (s, 1H), 3.61 (m, 4H), 3.28 (m, 2H), 3.17 (m, 2H), 2.95 (q, 2H), 0.93 (t, 3H) ppm; MS (ES) M+H expected=507.1, found=507.0

Coupling of Pyrazolyl Systems with Carboxylic Acid Equivalents

The following synthesis is an example of this type of chemistry: additional examples (procedure N) have been described elsewhere in this patent.

Synthesis of 4-Chloro-3-methyl-5-trifluoromethylpyrazol-1-yl)-acetic acid

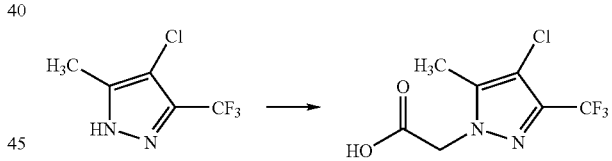

Reagents and conditions: BrCH$_2$CO$_2$Et/K$_2$CO$_3$/CH$_3$CN, then LiOH/THF

4-Chloro-3-methyl-5-trifluoromethylpyrazole (10 g, 0.0539 mol) was taken in acetonitrile (100 mL) and K$_2$CO$_3$ (30 g, 0.213 mol) was added to it. The mixture was stirred at rt for 1 h and ethyl bromoacetate (11 g, 0.065 mol) was added slowly to it. The mixture was then stirred for 12 h at 70° C. The mixture was filtered and the filtrate was concentrated to get a crude mixture. This crude product was re-crystallized from pet ether to obtain the corresponding ester The ester (14.8 g, 0.0565 mol) was dissolved in THF (100 mL) and a solution of LiOH (6.9 g) in water (50 mL) was added to it. The mixture was stirred for 10 h at room temperature. Excess THF was evaporated under reduced pressure and the aqueous layer was washed with ethyl acetate to remove any unhydrolysed material. The aqueous layer was then acidified with 1.5N HCl and extracted with ethyl acetate. The ethyl acetate layer was dried and concentrated to obtain the crude acid. On re-crystallization from ether/pet, product was obtained as white crystals.

Couplings of Arylpiperazines with Pyrazolyl-Acetic Acid derivatives

Protocol P: Compounds Prepared by HATU Mediated Coupling:

Synthesis of 2-(4-Chloro-5-methyl-3-trifluoromethyl-pyrazol-1-yl)-1-[4-(2,5-dimethyl-phenyl)-piperazin-1-yl]-ethanone

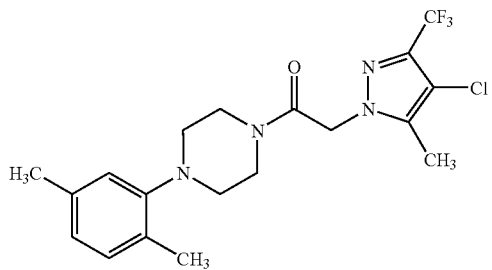

To 38 mg (0.20 mmol) of 1-(2,5-Dimethylphenyl)piperazine and 53 mg (0.22 mmol) of (4-Chloro-5-methyl-3-trifluoromethyl-pyrazol-1-yl)-acetic acid in 1.6 mL of anhydrous dimethylformamide was added 62 mg (0.6 mmol) of triethylamine, followed by 84 mg (0.22 mmol) of O-(7-Azabenzotriazol-1-yl)-N,N,N',N'-tetramethyluronium hexafluorophosphate (HATU). After 6 hours, the reaction was partitioned between ethyl acetate and water, and the phases were separated. The aqueous phase was back-extracted once with ethyl acetate, and the combined ethyl acetate phases were washed once each with 0.5M pH=7 phosphate buffer, water, 1M NaOH, water, brine. The ethyl acetate phase was then dried over Na2SO4, filtered, and concentrated to a residue in vacuo. The residue was dissolved in a minimum volume of 5M HCl in isopropanol, and was precipitated by diluting the solution with ethyl acetate. The product was isolated by filtration to give a white solid: $^1$H NMR (DMSO-d6, 400 MHz) 7.07 (d 1H), 6.90 (s, 1H), 6.82 (d, 1H), 5.39 (s, 2H), 3.66 (m, 4H), 2.98 (m, 2H), 2.89 (m, 2H), 2.26 (s, 3H), 2.24 (s, 3H), 2.20 (s, 3H) ppm; MS (ES) M+H expected=415.1, found 415.1.

Examples of Additional Compounds Prepared by HATU Mediated Coupling:

Synthesis of 2-(4-Chloro-5-methyl-3-trifluoromethyl-pyrazol-1-yl)-1-[4-(3-methoxy-phenyl)-piperazin-1-yl]-ethanone

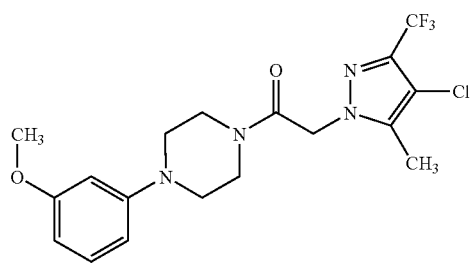

Title compound was prepared following protocol P, wherein 1-(3-methoxyphenyl)piperazine and (4-Chloro-5-methyl-3-trifluoromethyl-pyrazol-1-yl)-acetic acid were used as the coupling components, to give the product as a white solid: $^1$H NMR (DMSO-d6, 400 MHz) 7.15 (t, 1H), 6.65 (d, 1H), 6.60 (s, 1H), 6.47 (d, 1H), 5.38 (s, 2H), 3.72 (s, 3H), 3.65 (m, 4H), 3.28 (m, 2H), 3.19 (m, 2H), 2.18 (s, 3H) ppm; MS (ES) M+H expect=417.1, found=417.1.

Synthesis of 2-(4-Chloro-5-methyl-3-trifluoromethyl-pyrazol-1-yl)-1-[4-(4-chloro-phenyl)-2-(R)-methyl-piperazin-1-yl]-ethanone

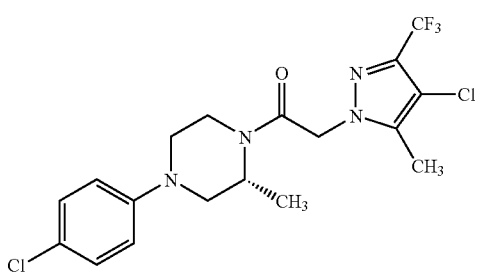

Title compound was prepared following the HATU mediated coupling protocol P, wherein 1-(4-Chlorophenyl)-3-(R)-methylpiperazine and (4-Chloro-5-methyl-3-trifluoromethyl-pyrazol-1-yl)-acetic acid were used as the coupling components, to give the product as a white solid: $^1$H NMR (CDCl$_3$, 300 MHz) 7.25 (d 2H), 6.83 (d, 2H), 4.91 (m, 3H), 4.28 (m, 1H), 3.80-3.10 (m, 4H), 2.86 (m, 1H), 2.71 (m, 1H), 2.29 (s, 3H), 1.40 (m, 3H) ppm; MS (ES) expect M+H=435.1, found 435.0.

Synthesis of 2-(4-Chloro-5-methyl-3-trifluoromethyl-pyrazol-1-yl)-1-(4-o-tolyl-piperazin-1-yl)-ethanone

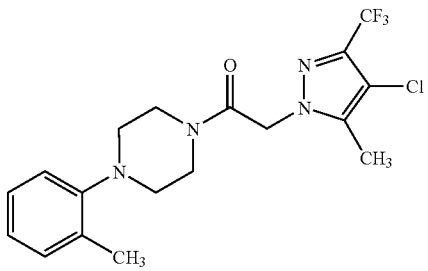

Title compound was prepared following the HATU mediated coupling protocol P, wherein 1-(2-Methylphenyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.14 (m, 2H), 6.98 (m, 2H), 5.37 (s, 2H), 3.60 (m, 4H), 2.89 (m, 2H), 2.81 (m, 2H), 2.27 (s, 3H), 2.20 (s, 3H) ppm; MS (ES) M+H expect=401.1, found=401.1.

Synthesis of 2-(4-Chloro-5-methyl-3-trifluoromethyl-pyrazol-1-yl)-1-[4-(4-chloro-phenyl)-2-(S)-methyl-piperazin-1-yl]-ethanone

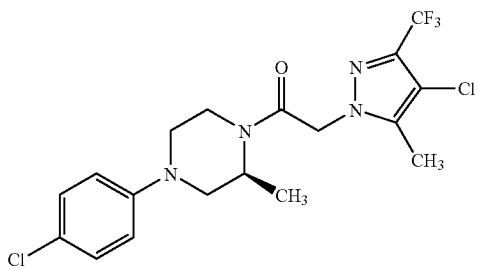

Title compound was prepared following the HATU mediated coupling protocol P, wherein 1-(4-Chlorophenyl)-3-(S)-methylpiperazine and (4-Chloro-5-methyl-3-trifluoromethyl-pyrazol-1-yl)-acetic acid were used as the coupling components, to give the product as a solid: $^1$H NMR (CDCl$_3$, 300 MHz) 7.25 (d 2H), 6.83 (d, 2H), 4.91 (m, 3H), 4.28 (m, 1H), 3.80-3.10 (m, 4H), 2.86 (m, 1H), 2.71 (m, 1H), 2.29 (s, 3H), 1.40 (m, 3H) ppm; MS (ES) M+H expected=435.1, found=435.0.

Synthesis of 2-(4-Chloro-3-trifluoromethyl-5-methyl-pyrazol-1-yl)-1-[4-(5-fluoro-2-methoxy-phenyl)-piperazin-1-yl]-ethanone

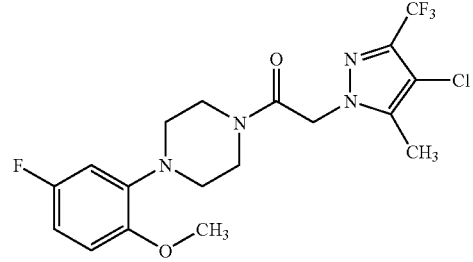

Title compound was prepared following the HATU mediated coupling protocol P, wherein 1-(2-Methoxy-5-fluorophenyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 6.93 (m, 1H), 6.77 (m, 3H), 5.36 (s, 2H), 3.77 (s, 3H), 3.59 (m, 4H), 3.07 (m, 2H), 2.98 (m, 2H), 2.19 (s, 3H) ppm; MS (ES) M+H expect 435.1, found 435.0.

Synthesis of 2-{4-chloro-3-methyl-5-trifluoromethyl-pyrazol-1-yl}-1-[4-(3-Methylsulfanyl-phenyl)-piperazin-1-yl]-ethanone

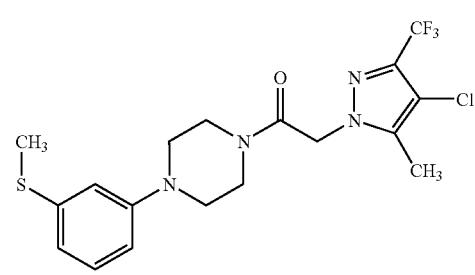

Title compound was prepared following the HATU mediated coupling protocol P, wherein 1-(3-Methylthiophenyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.21 (t, 1H), 6.98 (s, 1H), 6.91 (d, 1H), 6.81 (d, 1H), 5.39 (s, 2H), 3.68 (m, 4H), 3.34 (m, 2H), 3.24 (m, 2H), 2.44 (s, 3H), 2.19 (s, 3H) ppm; MS (ES) M+H expect 433.1, found 433.0.

Synthesis of 1-[4-(4-Bromo-phenyl)-piperazin-1-yl]-2-(4-chloro-5-methyl-3-trifluoromethyl-pyrazol-1yl)-ethanone

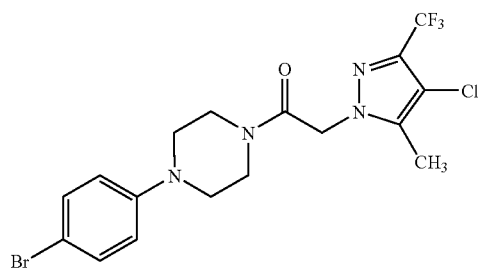

Title compound was prepared following the HATU mediated coupling protocol P, wherein 1-(4-Bromophenyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.36 (d, 2H), 6.92 (d, 2H), 5.37 (s, 2H), 3.60 (m, 4H), 3.24 (m, 2H), 3.14 (m, 2H), 2.18 (s, 3H) ppm; MS (ES) M+H expect=465.0, found=465.0.

Synthesis of 2-(4-Chloro-3-trifluoromethyl-5-methyl-pyrazol-1-yl)-1-[4-(2,3-dimethyl-phenyl)piperazin-1-yl]-ethanone

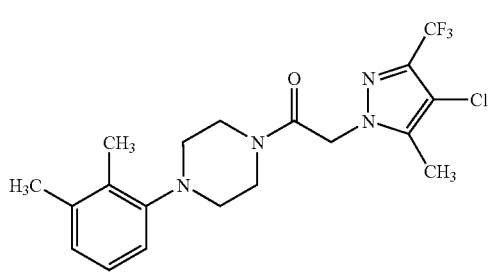

Title compound was prepared following the HATU mediated coupling protocol P, wherein 1-(2,3-Dimethylphenyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.04 (t, 1H), 6.99 (m, 2H), 5.38 (s, 2H), 3.64 (m, 4H), 2.89 (m, 2H), 2.81 (m, 2H), 2.21 (m, 9H) ppm; MS (ES) M+H expect 415.1, found 415.1.

Synthesis of 2-(4-Chloro-3-trifluoromethyl-5-methyl-pyrazol-1-yl)-1-[4-(2-chloro-5-methoxy-phenyl)-piperazin-1-yl]-ethanone

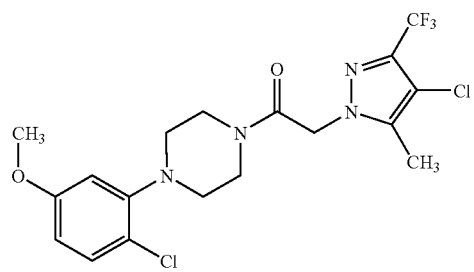

Title compound was prepared following the HATU mediated coupling protocol P, wherein 1-(2-Chloro-5-methoxyphenyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.31 (d, 1H), 6.65 (m, 2H), 5.37 (s, 2H), 3.73 (s, 3H), 3.62 (m, 4H), 3.02 (m, 2H), 2.96 (m, 2H), 2.19 (s, 3H) ppm; MS (ES) M+H expect=451.1, found=451.0.

Synthesis of 1-[4-(4-Bromo-3-methoxy-phenyl)-piperazin-1-yl]-2-(4-chloro-5-methyl-3-trifluoromethyl-pyrazol-1-yl)-ethanone

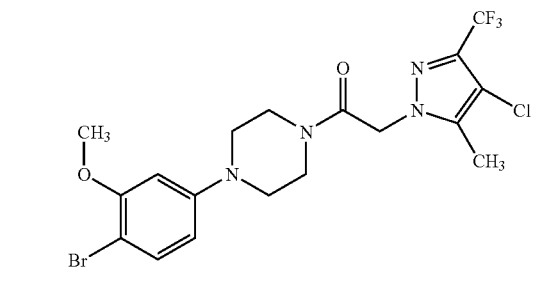

Title compound was prepared following the HATU mediated coupling protocol P, wherein 1-(4-Bromo-3-methoxyphenyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.34 (d, 1H), 6.71 (s, 1H), 6.52 (d, 1H), 5.39 (s, 2H), 3.82 (s, 3H), 3.62 (m, 4H), 3.30 (m, 2H), 3.20 (m, 2H), 2.19 (s, 3H) ppm; MS (ES) M+H expected=495.0, found=495.0.

Synthesis of 2-(4-Chloro-5-methyl-3-trifluoromethyl-pyrazol-1-yl)-1-[4-(2,4-dichloro-phenyl)-piperazin-1-yl]-ethanone

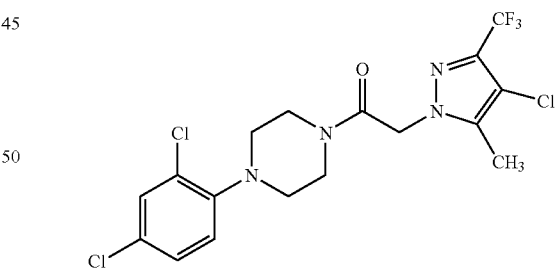

Title compound was prepared following the HATU mediated coupling protocol P, wherein 1-(2,4-Dichlorophenyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.56 (s, 1H), 7.36 (d, 1H), 7.15 (d, 1H), 5.37 (s, 2H), 3.61 (m, 4H), 3.01 (m, 2H), 2.94 (m, 2H), 2.19 (s, 3H) ppm; MS (ES) M+H expect 455.0, found=454.9.

Synthesis of 2-(4-Chloro-5-methyl-3-trifluoromethyl-pyrazol-1-yl)-1-[4-(4-methoxy-pyridin-2-yl)-piperazin-1-yl]-ethanone

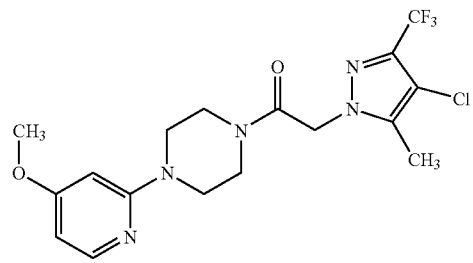

Title compound was prepared following the HATU mediated coupling protocol P, wherein 1-(4-Methoxy-pyridin-2-yl)-piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.92 (d, 1H), 6.67 (s 1H), 6.63 (d, 1H), 5.42 (s, 2H), 3.96 (s, 3H), 3.88 (m, 2H), 3.73 (m, 4H), 3.62 (m, 2H), 2.19 (s, 3H) ppm; MS (ES) M+H expected=418.1, found=418.0.

Synthesis of 2-(4-Chloro-5-methyl-3-trifluoromethyl-pyrazol-1-yl)-1-[4-(3,4-dimethyl-phenyl)-piperazin1-yl]-ethanone

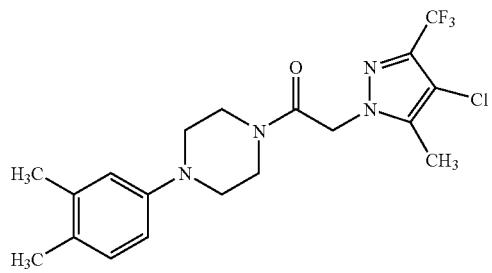

Title compound was prepared following the HATU mediated coupling protocol P, wherein 1-(3,4-Dimethylphenyl)-piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.03 (d, 1H), 6.94 (br s, 1H), 6.84 (br s, 1H), 5.38 (s, 2H), 3.68 (m, 4H), 3.25 (m, 2H), 3.15 (m, 2H), 2.18 (s, 6H), 2.14 (s, 3H) ppm; MS (ES) M+H expected=415.1, found=415.1.

Synthesis of 2-(4-Chloro-3-trifluoromethyl-5-methyl-pyrazol-1-yl)-1-[4-(4-trifluoromethoxy-phenyl)-piperazin-1-yl]-ethanone

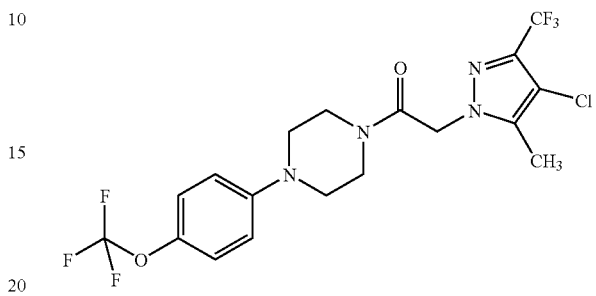

Title compound was prepared following the HATU mediated coupling protocol P, wherein 1-(4-Trifluoromethoxyphenyl)-piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.20 (d, 2H), 7.04 (d, 2H), 5.38 (s, 2H), 3.60 (m, 4H), 3.27 (m, 2H), 3.17 (m, 2H), 2.18 (s, 3H) ppm; MS (ES) M+H expected=471.1, found=471.0.

Synthesis of 2-(4-Chloro-3-trifluoromethyl-5-methyl-pyrazol-1-yl)-1-[4-(2,4-dichloro-5-methoxyphenyl)-piperazin-1-yl]-ethanone

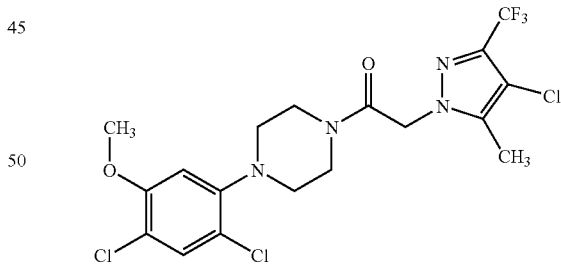

Title compound was prepared following the HATU mediated coupling protocol P, wherein 1-(2,4-Dichloro-5-methoxyphenyl)-piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.50 (s, 1H), 6.84 (s, 1H), 5.37 (s, 2H), 3.85 (s, 3H), 3.62 (m, 4H), 3.07 (m, 2H), 3.00 (m, 2H), 2.19 (s, 3H) ppm; MS (ES) M+H expected=485.1, found=485.0.

Synthesis of 2-(4-Chloro-5-methyl-3-trifluoromethyl-pyrazol-1-yl)-1-[4-(4-nitro-phenyl)-piperazin-1-yl]ethanone

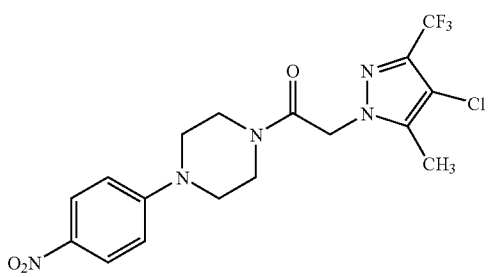

Title compound was prepared following the HATU mediated coupling protocol P, wherein 1-(4-Nitrophenyl)-piperazine and (4-Chloro-5-methyl-3-trifluoromethyl-pyrazol-1-yl)-acetic acid were used as the coupling components, to give the product as a yellow solid: $^1$H NMR (DMSO-d6, 400 MHz) 8.05 (d, 2H), 7.01 (d, 2H), 5.38 (s, 2H), 3.62 (m, 6H), 3.52 (m, 2H), 2.19 (s, 3H) ppm; MS (ES) expect M+H=432.1, found=432.0.

Synthesis of 2-(4-Chloro-5-methyl-3-trifluoromethyl-pyrazol-1-yl)-1-[4-(4-chloro-2-methoxy-phenyl)-piperazin-1-yl]-ethanone

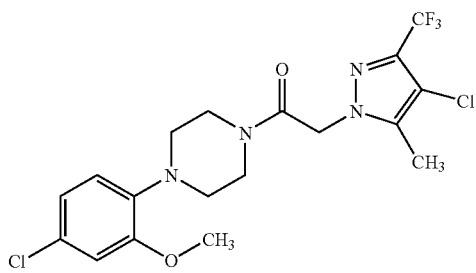

Title compound was prepared following the HATU mediated coupling protocol P, wherein 1-(4-Chloro-2-methoxyphenyl)-piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.02 (s, 1H), 6.93 (m, 2H), 5.36 (s, 2H), 3.82 (s, 3H), 3.60 (m, 4H), 3.03 (m, 2H), 2.95 (m, 2H), 2.19 (s, 3H) ppm; MS (ES) M+H expected=451.1, found=451.0.

Synthesis of 1-[4-(4-Bromo-3-methyl-phenyl)-piperazin-1-yl]-2-(4-chloro-5-methyl-3-trifluoromethyl-pyrazol-1-yl)-ethanone

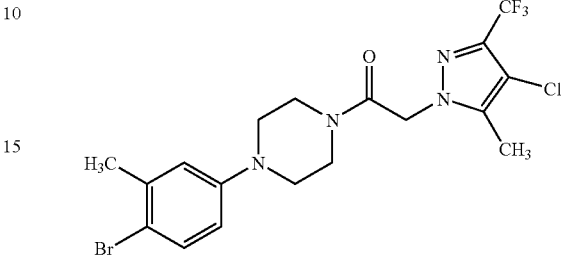

Title compound was prepared following the HATU mediated coupling protocol P, wherein 1-(4-Bromo-3-methylphenyl)-piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.38 (d, 1H), 7.01 (s, 1H), 6.78 (d, 1H), 5.38 (s, 2H), 3.60 (m, 4H), 3.26 (m, 2H), 3.16 (m, 2H), 2.28 (s, 3H), 2.19 (s, 3H) ppm; MS (ES) M+H expected=479.0, found=478.9.

Synthesis of 1-[4-(4-Acetyl-phenyl)-piperazin-1-yl]-2-(4-chloro-5-methyl-3-trifluoromethyl-pyrazol-1-yl)-ethanone

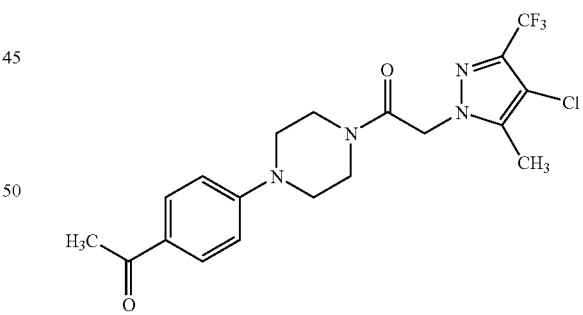

Title compound was prepared following the HATU mediated coupling protocol P, wherein 1-(4-Acetyl-phenyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.80 (d, 1H), 6.98 (d, 2H), 5.38 (s, 2H), 3.61 (m, 4H), 3.48 (m, 2H), 3.39 (m, 2H), 2.46 (s, 3H), 2.19 (s, 3H) ppm; MS (ES) M+H expected=429.1, found=429.0.

81

Synthesis of 2-(4-Chloro-5-methyl-3-trifluoromethyl-pyrazol-1-yl)-1-[4-(3,4-dichloro-phenyl)-piperazin-1-yl]-ethanone

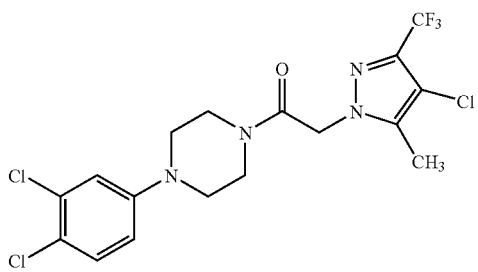

Title compound was prepared following the HATU mediated coupling protocol P, wherein 1-(3,4-Dichlorophenyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.40 (d, 1H), 7.16 (s, 1H), 6.95 (d, 1H), 5.37 (s, 2H), 3.59 (m, 4H), 3.31 (m, 2H), 3.21 (m, 2H), 2.18 (s, 3H) ppm; MS (ES) M+H expected=455.0, found=455.0.

Synthesis of 2-(4-Chloro-5-methyl-3-trifluoromethyl-pyrazol-1-yl)-1-[4-(3-chloro-phenyl)-piperazin-1yl]-ethanone

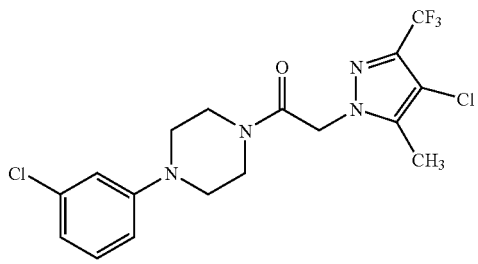

Title compound was prepared following the HATU mediated coupling protocol P, wherein 1-(3-Chlorophenyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.23 (t, 1H), 7.19 (s, 1H), 6.90 (d, 1H), 6.79 (d, 1H), 5.37 (s, 2H), 3.58 (m, 4H), 3.29 (m, 2H), 3.19 (m, 2H), 2.18 (s, 3H) ppm; MS (ES) M+H expected=421.1, found=421.0.

82

Synthesis of 2-(4-Chloro-5-methyl-3-trifluoromethyl-pyrazol-1-yl)-1-(4-m-tolyl-piperazin-1-yl)-ethanone

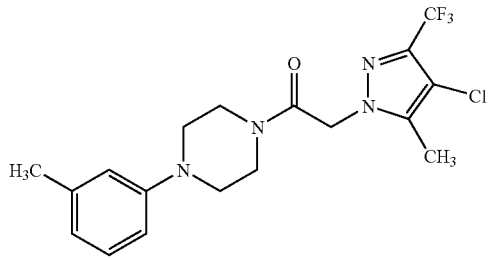

Title compound was prepared following the HATU mediated coupling protocol P, wherein 1-(3-Methylphenyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.17 (t, 1H), 6.97 (br, 2H), 6.77 (d, 1H), 5.39 (s, 2H), 3.68 (m, 4H), 3.31 (m, 2H), 3.22 (m, 2H), 2.27 (s, 3H), 2.19 (s, 3H) ppm; MS (ES) M+H expected=401.1, found=401.1.

Synthesis of 1-[4-(4-Chloro-3-methoxy-phenyl)-piperazin-1-yl]-2-(4-chloro-5-methyl-3-trifluoromethyl-pyrazol-1-yl)-ethanone

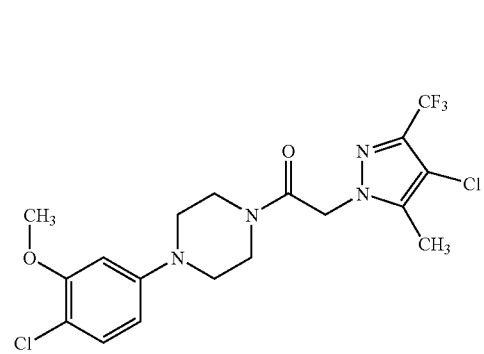

Title compound was prepared following the HATU mediated coupling protocol P, wherein 1-(4-Chloro-3-methoxyphenyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.21 (d, 1H), 6.74 (s, 1H), 6.56 (d, 1H), 5.39 (s, 2H), 3.82 (s, 3H), 3.63 (m, 4H), 3.30 (m, 2H), 3.19 (m, 2H), 2.19 (s, 3H) ppm; MS (ES) M+H expected=451.1, found 451.0.

Synthesis of 4-{4-[2-(4-Chloro-5-methyl-3-trifluoromethyl-pyrazol-1-yl)-acetyl]-piperazin-1-yl}-benzoic acid methyl ester

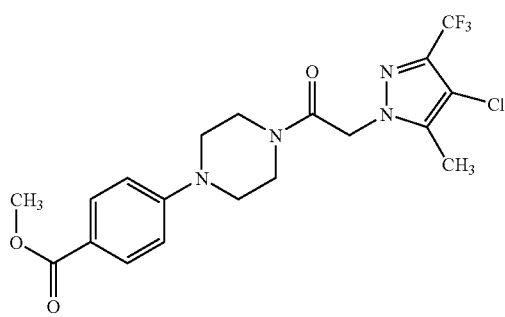

Title compound was prepared following the HATU mediated coupling protocol P, wherein 4-Piperazin-1-yl-benzoic acid methyl ester and (4-Chloro-5-methyl-3-trifluoromethyl-pyrazol-1-yl)-acetic acid were used as the coupling components, to give the product as a solid: $^1$H NMR (DMSO-d6, 400 MHz) 7.78 (d, 2H), 6.98 (d, 2H), 5.38 (s, 2H), 3.71 (s, 3H), 3.60 (m, 4H), 3.46 (m, 2H), 3.37 (m, 2H), 2.19 (s, 3H) ppm; MS (ES) expect M+H=445.1, found 445.0.

Synthesis of 2-(4-Chloro-3,5-dimethyl-pyrazol-1-yl)-1-(4-pyridin-4-yl-piperazin-1-yl)-ethanone

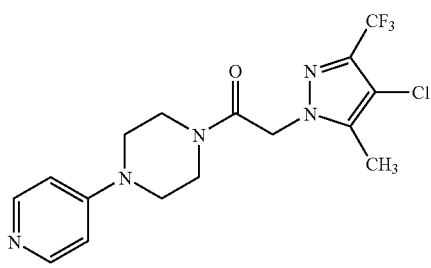

Title compound was prepared following the HATU mediated coupling protocol P, wherein 1-(4-pyridyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 8.28 (d, 2H), 7.18 (d, 2H), 5.41 (s, 2H), 3.83 (m, 2H), 3.72 (m, 4H), 3.63 (m, 2H), 2.18 (s, 3H) ppm; MS (ES) M+H expected=388.1, found=388.0.

Synthesis of 2-(4-Chloro-5-methyl-3-trifluoromethyl-pyrazol-1-yl)-1-[4-(5-methoxy-2-methyl-phenyl)-piperazin-1-yl]-ethanone

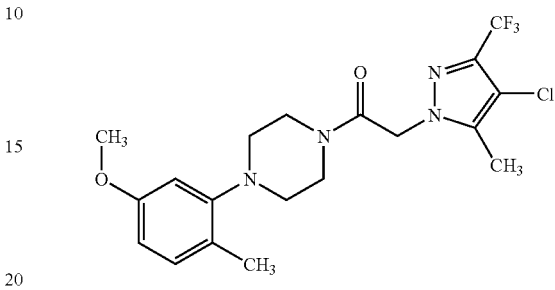

Title compound was prepared following the HATU mediated coupling protocol P, wherein 1-(3-Methoxy-5-methylphenyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.06 (d, 1H), 6.56 (m, 2H), 5.38 (s, 2H), 3.69 (s, 3H), 3.62 (m, 4H), 2.92 (m, 2H), 2.84 (m, 2H), 2.20 (s, 3H) ppm; MS (ES) M+H expected=431.1, found=431.1.

Synthesis of 2-(4-Chloro-3-trifluoromethyl-5-methyl-pyrazol-1-yl)-1-(4-phenyl-piperazin-1-yl)-ethanone

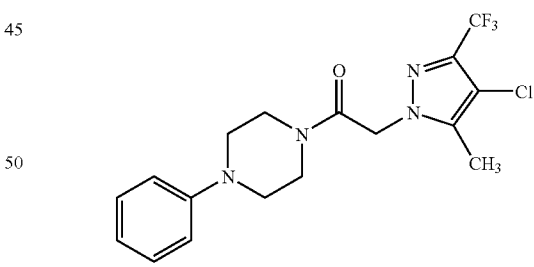

Title compound was prepared following the HATU mediated coupling protocol P, wherein 1-Phenylpiperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.32 (m 4H), 7.02 (m, 1H), 5.40 (s, 2H), 3.74 (m, 4H), 3.39 (m, 2H), 3.29 (m, 2H), 2.19 (s, 3H) ppm; MS (ES) expect M+H=387.1, found 387.1.

Synthesis of 1-[4-(4-Chloro-3-ethoxy-phenyl)-piperazin-1-yl]-2-(4-chloro-5-methyl-3-trifluoromethyl-pyrazol-1-yl)-ethanone

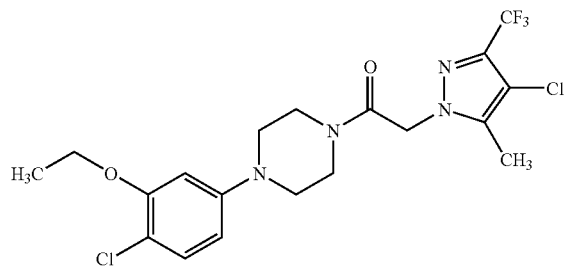

Title compound was prepared following the HATU mediated coupling protocol P, wherein 1-(4-Chloro-3-ethoxyphenyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.20 (d, 1H), 6.66 (s, 1H), 6.48 (d, 1H), 5.38 (s, 2H), 4.08 (q, 2H), 3.61 (m, 4H), 3.25 (m, 2H), 3.16 (m, 2H), 2.18 (s, 3H), 1.33 (t, 3H) ppm; MS (ES) M+H expected=465.1, found 465.0.

Synthesis of 2-(4-Chloro-5-methyl-3-trifluoromethyl-pyrazol-1-yl)-1-(4-pyridin-2-yl-piperazin-1-yl)-ethanone

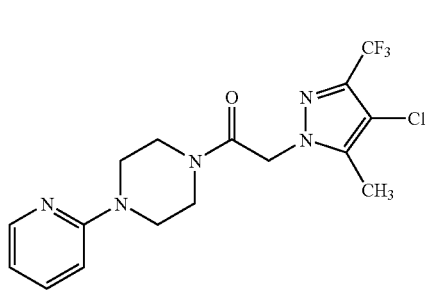

Title compound was prepared following the HATU mediated coupling protocol P, wherein 1-(2-Pyridyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 8.11 (d, 1H), 7.53 (t, 1H), 6.85 (d, 1H), 6.65 (t, 1H), 5.37 (s, 2H), 3.59-3.50 (m, 8H), 2.18 (s, 3H) ppm; MS (ES) M+H expected=388.1, found=388.0.

Synthesis of 2-(4-Chloro-5-methyl-3-trifluoromethyl-pyrazol-1-yl)-1-(4-p-tolyl-piperazin-1-yl)-ethanone

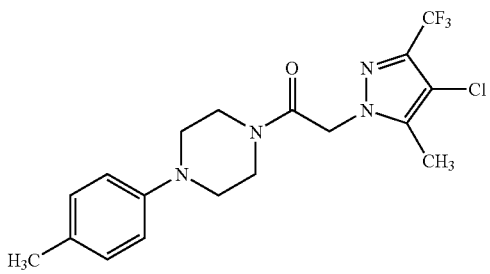

Title compound was prepared following the HATU mediated coupling protocol P, wherein 1-(4-Methylphenyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.20 (m, 4H), 5.40 (s, 2H), 3.79 (m, 4H), 3.37 (m, 2H), 3.28 (m, 2H), 2.49 (s, 3H), 2.19 (s, 3H) ppm; MS (ES) M+H expected=401.1, found 401.0.

Synthesis of 1-[(4-Methanesulfonyl-phenyl)-piperazine-1-yl]-2-(4-chloro-5-methyl-3-trifluoromethyl-pyrazol-1-yl)-ethanone

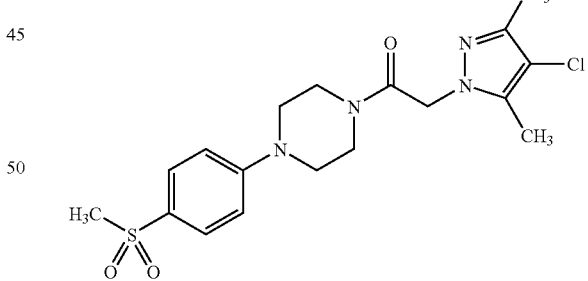

Title compound was prepared following the HATU mediated coupling protocol P, wherein 1-(4-Methanesulfonyl-phenyl)-piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.69 (d, 2H), 7.08 (d, 2H), 5.38 (s, 2H), 3.59 (m, 4H), 3.49 (m, 2H), 3.38 (m, 2H), 3.09 (s, 3H), 2.19 (s, 3H) ppm; MS (ES) M+H expected=465.1, found=465.0.

Synthesis of 2-(4-Chloro-5-methyl-3-trifluoromethyl-pyrazol-1-yl)-1-[4-(4-chloro-phenyl)-piperazin-1-yl]-ethanone

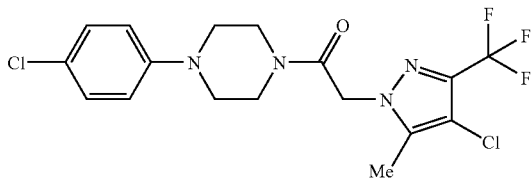

Title compound was prepared following the HATU mediated coupling protocol P, wherein 1-(4-Chlorophenyl)-piperazine and (4-Chloro-5-methyl-3-trifluoromethyl-pyrazol-1-yl)-acetic acid were used as the coupling components, to give the product as a solid: $^1$H NMR (CDCl$_3$, 400 MHz) 7.22 (d, 2H), 6.83 (d, 2H), 4.99 (s, 2H), 3.77 (m, 2H), 3.72 (m, 2H), 3.19 (m, 2H), 3.16 (m, 2H), 2.28 (s, 3H) ppm; MS (ES) M+Na expected=443.0, found 443.0.

Synthesis of 2-(4-Chloro-5-methyl-3-trifluoromethyl-pyrazol-1-yl)-1-[4-(4-methoxy-phenyl)-piperazin-1-yl]-ethanone

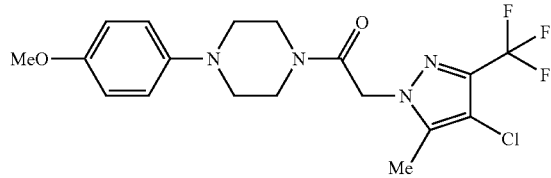

Title compound was prepared following the HATU mediated coupling protocol P, wherein 1-(4-Methoxyphenyl)-piperazine and (4-Chloro-5-methyl-3-trifluoromethyl-pyrazol-1-yl)-acetic acid were used as the coupling components, to give the product as a solid: $^1$H NMR (CDCl$_3$, 400 MHz) 6.88 (m, 4H), 5.00 (s, 2H), 3.78 (m, 3H), 3.76 (m, 2H), 3.70 (m, 2H), 3.08 (m, 4H), 2.30 (s, 3H) ppm; MS (ES) M+Na expected=439.0, found 439.0.

Synthesis of 4-{4-[2-(4-Chloro-5-methyl-3-trifluoromethyl-pyrazol-1-yl)-acetyl]-piperazin-1-yl}-benzonitrile

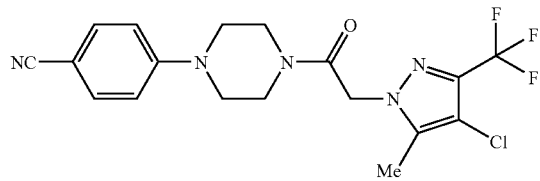

Title compound was prepared following the HATU mediated coupling protocol P, wherein 1-(4-Cyanophenyl)-piperazine and (4-Chloro-5-methyl-3-trifluoromethyl-pyrazol-1-yl)-acetic acid were used as the coupling components, to give the product as a solid: $^1$H NMR (CDCl$_3$, 400 MHz) 7.44 (d, 2H), 6.77 (d, 2H), 4.90 (s, 2H), 3.67 (m, 4H), 3.29 (m, 4H), 2.22 (s, 3H) ppm; MS (ES) M+Na expected=434.0, found 434.0.

Synthesis of 2-(4-Chloro-5-methyl-3-trifluoromethyl-pyrazol-1-yl)-1-[4-(2-fluoro-phenyl)-piperazin-1-yl]-ethanone

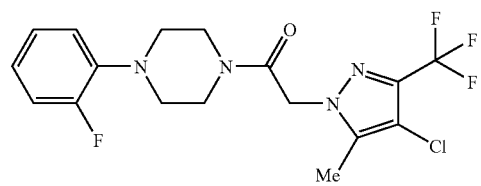

Title compound was prepared following the HATU mediated coupling protocol P, wherein 1-(2-Fluorophenyl)-piperazine and (4-Chloro-5-methyl-3-trifluoromethyl-pyrazol-1-yl)-acetic acid were used as the coupling components, to give the product as a solid: $^1$H NMR (CDCl$_3$, 400 MHz) 7.02 (m, 4H), 5.00 (s, 2H), 3.80 (m, 2H), 3.70 (m, 2H), 3.53 (m, 2H), 3.25 (m, 2H), 2.30 (s, 3H) ppm; MS (ES) M+Na expected=427.0, found 427.0.

Synthesis of 2-(4-Chloro-5-methyl-3-trifluoromethyl-pyrazol-1-yl)-1-[4-(2-methoxy-phenyl)-piperazin-1-yl]-ethanone

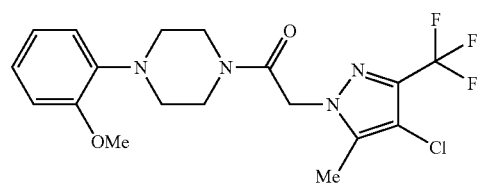

Title compound was prepared following the HATU mediated coupling protocol P, wherein 1-(2-Methoxyphenyl)-piperazine and (4-Chloro-5-methyl-3-trifluoromethyl-pyrazol-1-yl)-acetic acid were used as the coupling components, to give the product as a solid: $^1$H NMR (CDCl$_3$, 400 MHz) 6.62 (m, 1H), 6.48 (m, 3H), 5.01 (s, 2H), 3.73 (s, 3H), 3.61 (m, 4H), 3.43 (m, 2H), 2.31 (s, 3H) ppm; MS (ES) M+H expected=439.0, found 439.1.

Synthesis of 2-(4-Chloro-5-methyl-3-trifluoromethyl-pyrazol-1-yl)-1-[4-(3-trifluoromethyl-phenyl)-piperazin-1-yl]-ethanone

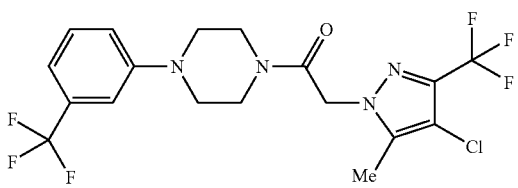

Title compound was prepared following the HATU mediated coupling protocol P, wherein 1-(3-Trifluoromethylphenyl)-piperazine and (4-Chloro-5-methyl-3-trifluoromethyl-pyrazol-1-yl)-acetic acid were used as the coupling components, to give the product as a solid: $^1$H NMR (CDCl$_3$, 400 MHz) 7.38 (m, 1H), 7.11 (m, 3H), 5.00 (s, 2H), 3.79 (m, 2H), 3.73 (m, 2H), 3.27 (m, 2H), 3.23 (m, 2H), 2.30 (s, 3H) ppm; MS (ES) M+H expected 455.0, found 455.0.

Synthesis of 2-(4-Chloro-5-methyl-3-trifluoromethyl-pyrazol-1-yl)-1-(4-pyrimidin-2-yl-piperazin-1-yl)-ethanone

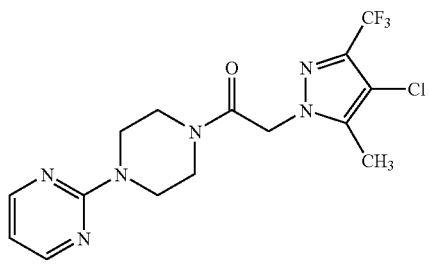

Title compound was prepared following the HATU mediated coupling protocol P, wherein 1-(2-Pyrimidinyl)-piperazine and (4-Chloro-5-methyl-3-trifluoromethyl-pyrazol-1-yl)-acetic acid were used as the coupling components, to give the product as a solid: MS (ES) M+H expected=389.1, found=389.0; HPLC retention time=3.99 minutes (Agilent Zorbax SB-C18, 2.1×50 mm, 5μ, 35° C.) using a 4.5 minute gradient of 20% to 95% B (A=0.1% formic acid/5% acetonitrile/94.9% water, B=0.08% formic acid/99.9% acetonitrile).

Synthesis of 1-[4-(4-Chloro-3-isopropoxy-phenyl)-piperazin-1-yl]-2-(4-chloro-5-methyl-3-trifluoromethyl-pyrazol-1-yl)-ethanone

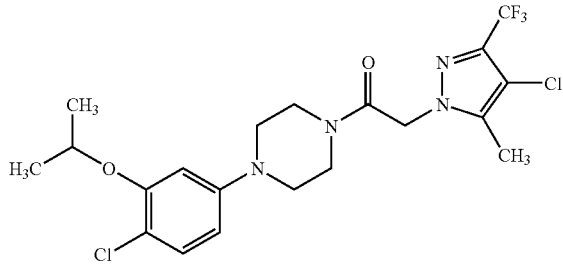

Title compound was prepared following the HATU mediated coupling protocol P, wherein 1-(4-Chloro-3-isopropoxy-phenyl)-piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.21 (d, 1H), 6.71 (s, 1H), 6.53 (d, 1H), 5.38 (s, 2H), 4.66 (m, 1H), 3.58 (m, 4H), 3.25 (m, 2H), 3.15 (m, 2H), 2.18 (s, 3H), 1.26 (d, 6H) ppm; MS (ES) M+H expected=479.1, found=479.0.

Synthesis of 2-(4-Chloro-5-methyl-3-trifluoromethyl-pyrazol-1-yl)-1-[4-(3,4-difluoro-phenyl)piperazin-1-yl]-ethanone

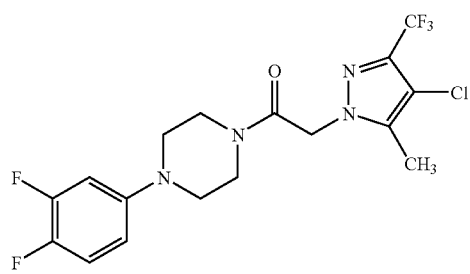

Title compound was prepared following the HATU mediated coupling protocol P, wherein 1-(3,4-Difluorophenyl)-piperazine and (4-Chloro-5-methyl-3-trifluoromethyl-pyrazol-1-yl)-acetic acid were used as the coupling components, to give the product as a solid: $^1$H NMR (DMSO-d6, 400 MHz, not F-decoupled) 7.25 (q, 1H), 7.04 (m, 1H), 6.74 (d, 1H), 5.37 (s, 2H), 3.57 (m, 4H), 3.24 (m, 2H), 3.12 (m, 2H), 2.18 (s, 3H) ppm; MS (ES) M+H expected=423.1, found=423.0.

Synthesis of 2-(4-Chloro-5-methyl-3-trifluoromethyl-pyrazol-1-yl)-1-[4-(6-methoxy-pyridin-2-yl)-piperazin-1-yl]-ethanone

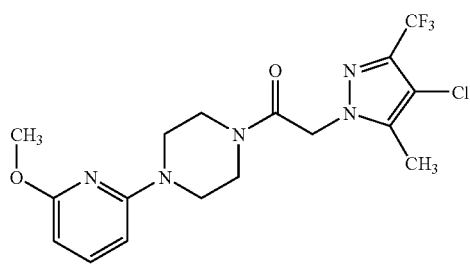

Title compound was prepared following the HATU mediated coupling protocol P, wherein 1-(6-Methoxy-pyridin-2-yl)-piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.45 (t, 1H), 6.34 (d, 1H), 6.05 (d, 1H), 5.37 (s, 2H), 3.77 (s, 3H), 3.50 (m, 6H), 3.34 (m, 2H), 2.18 (s, 3H) ppm; MS (ES) M+H expected=418.1, found=418.0.

Synthesis of 4-{4-[2-(4-Chloro-5-methyl-3-trifluoromethyl-pyrazol-1-yl)-acetyl]-piperazin-1-yl}-N,N-dimethyl-benzenesulfonamide

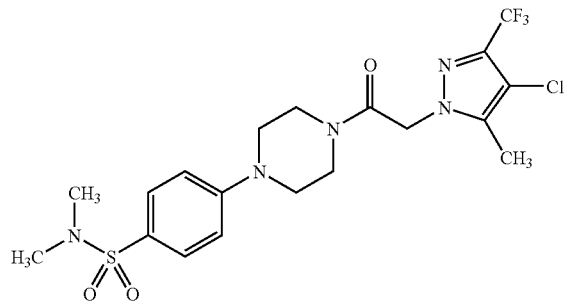

Title compound was prepared following the HATU mediated coupling protocol P, wherein N,N-Dimethyl-4-piperazin-1-yl-benzenesulfonamide and (4-Chloro-5-methyl-3-trifluoromethyl-pyrazol-1-yl)-acetic acid were used as the coupling components, to give the product as a solid: $^1$H NMR (DMSO-d6, 400 MHz) 7.54 (d, 2H), 7.08 (d, 2H), 5.38 (s, 2H), 3.62 (m, 4H), 3.48 (m, 2H), 3.37 (m, 2H), 2.19 (s, 3H) ppm; MS (ES) M+H expected=494.1, found=494.0.

Synthesis of 1-[4-(4-Chloro-3-methyl-phenyl)-piperazin-1-yl]-2-(4-chloro-5-methyl-3-trifluoromethyl-pyrazol-1-yl)-ethanone

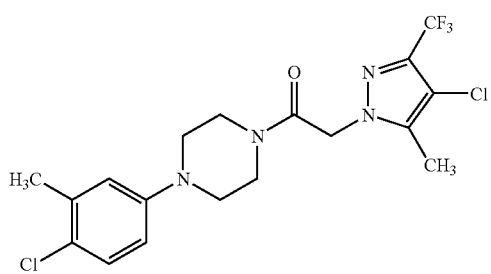

Title compound was prepared following the HATU mediated coupling protocol P, wherein 1-(4-Chloro-3-methylphenyl)-piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.25 (d, 1H), 7.05 (s, 1H), 6.90 (d, 1H), 5.38 (s, 2H), 3.64 (m, 4H), 3.27 (m, 2H), 3.17 (m, 2H), 2.26 (s, 3H), 2.19 (s, 3H) ppm; MS (ES) M+H expected=435.1, found=435.0.

Synthesis of 2-(4-Chloro-5-methyl-3-trifluoromethyl-pyrazol-1-yl)-1-[4-(3-hydroxy-phenyl)-piperazin-1-yl]-ethanone

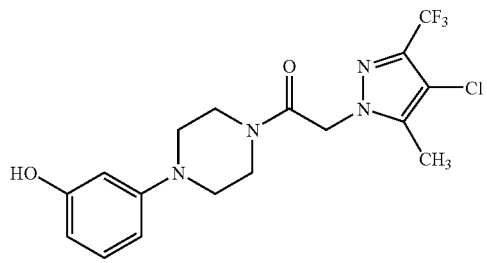

Title compound was prepared following the HATU mediated coupling protocol P, wherein 1-(3-Hydroxyphenyl)-piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.10 (t, 1H), 6.66 (m, 2H), 6.45 (d, 1H), 5.39 (s, 2H), 3.74 (m, 4H), 3.33 (br, 2H), 3.24 (br, 2H), 2.19 (s, 3H) ppm; MS (ES) M+H expected=403.1, found 403.0.

Synthesis of 2-(4-Chloro-5-methyl-3-trifluoromethyl-pyrazol-1-yl)-1-[4-(4-trifluoromethyl-phenyl)-piperazin-1-yl]-ethanone

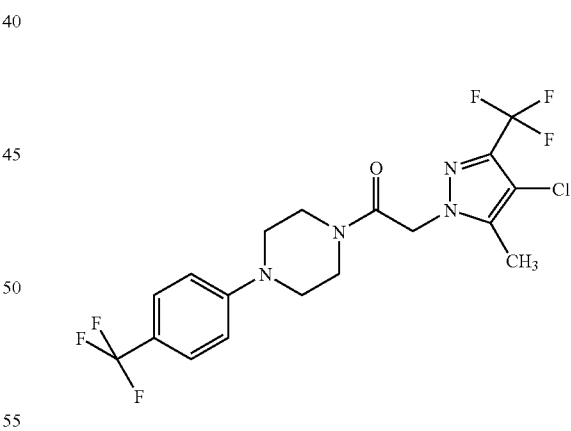

Title compound was prepared following the HATU mediated coupling protocol P, wherein 1-(4-Trifluoromethylphenyl)-piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.50 (d, 2H), 7.07 (d, 2H), 5.38 (s, 2H), 3.60 (m, 4H), 3.41 (m, 2H), 3.31 (m, 2H), 2.19 (s, 3H) ppm; MS (ES) M+H expected=455.1, found=455.0.

Synthesis of 2-(4-Chloro-5-methyl-3-trifluoromethyl-pyrazol-1-yl)-1-(3-methyl-4-m-tolyl-piperazin-1-yl)-ethanone

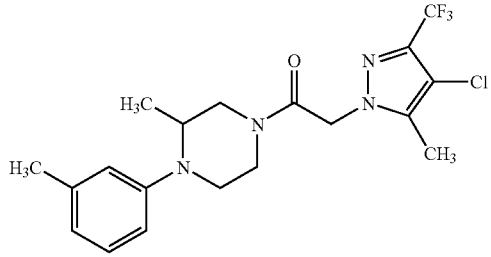

Title compound was prepared following the HATU mediated coupling protocol P, wherein 1-(3-Methylphenyl)-2-methyl-piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.68 (br, 1H), 7.17 (br, 1H), 6.71 (br, 2H), 5.41 (m, 2H), 4.08 (m, 4H), 3.70 (m, 2H), 3.50 (br m, 2H), 2.30 (s, 3H), 2.18 (s, 3H), 1.01 (m, 3H) ppm; MS (ES) M+H expected=415.1, found=415.1.

Protocol S: Preparation of Chloroacetyl Arylpiperazines

Synthesis of 2-Chloro-1-[4-(4-fluoro-phenyl)-piperazin-1-yl]-ethanone

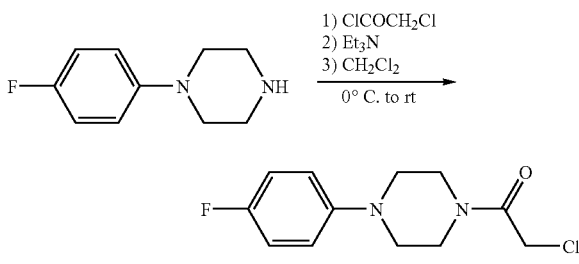

1-(4-Fluorophenyl) piperazine (2.8 mmol) was dissolved in 10 mL of CH$_2$Cl$_2$. Triethylamine (5.5 mmol) was added to it and the reaction was cooled to 0° C. Chloroacetylchloride (4.2 mmol) was added to it slowly, and the reaction was warmed to room temperature overnight. After completion, the reaction was quenched with brine solution and reaction mixture was extracted with methylene chloride. The combined organic phases were washed with brine and water and dried over magnesium sulfate. The solvent was evaporated and the compound purified by column-chromatography (hexane/ethyl acetate=1.5/1) to afford the title compound as a white solid. $^1$H NMR (400 MHz, CDCl$_3$): δ 8 6.9-7.2 (m, 2H), 6.82-6.92 (m, 2H), 4.1 (s, 2H), 6.62-3.8 (m, 4H), 3.46-3.6 (m, 4H). $^{13}$C NMR (400 MHz, CDCl$_3$): 164, 158, 156.2, 148.5, 118.2, 116.8, 52.6, 52.2, 48, 46, 42.1, 40.6.

Synthesis of 2-Chloro-1-[4-(4-chloro-phenyl)-piperazin-1-yl]-ethanone

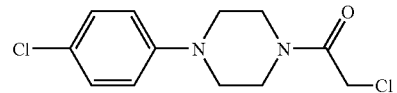

Protocol S was followed using 1-(4-chloro-phenyl) piperazine, Et$_3$N, chloroacetyl chloride and methylene chloride. Column chromatography using a solvent mixture (hexane/ethyl acetate=1.5/1) afforded the title compound as a white solid.

Synthesis of 2-Chloro-1-[4-(4-chloro-3-methoxyphenyl)-piperazin-1-yl]-ethanone

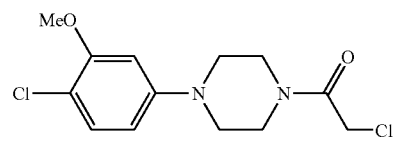

Protocol S was followed using 1-(4-chloro-3-methoxyphenyl) piperazine, Et$_3$N, chloroacetyl chloride and methylene chloride. Column chromatography using a solvent mixture (hexane/ethyl acetate=1.5/1) afforded the title compounds as a white solid

Synthesis of 2-Chloro-1-[4-(4-bromo-3-methoxyphenyl)-piperazin-1-yl]-ethanone

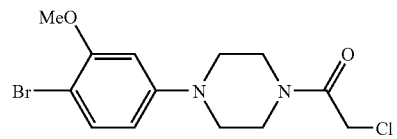

Protocol S was followed using 1-(4-bromo-3-methoxyphenyl) piperazine, Et$_3$N, chloroacetyl chloride and methylene chloride. Column chromatography using a solvent mixture (hexane/ethyl acetate=1.5/1) afforded the title compounds as a white solid

Synthesis of 2-Chloro-1-[4-(4-chloro-phenyl)-2-methyl-(R)-piperazin-1-yl]-ethanone

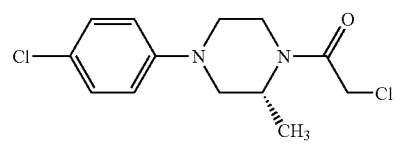

Protocol S was followed using 1-(4-Chloro-phenyl)-3-(R)-methyl-piperazine, Et$_3$N, chloroacetyl chloride and methylene chloride. Column chromatography afforded the title compound

Synthesis of 2-Chloro-1-[4-(4-chloro-phenyl)-2-methyl-(S)-piperazin-1-yl]-ethanone

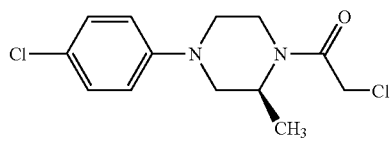

Protocol S was followed using 1-(4-Chloro-phenyl)-3-(S)-methyl-piperazine, Et$_3$N, chloroacetyl chloride and methylene chloride. Column chromatography afforded the title compound.

Protocol T: K$_2$CO$_3$ Mediated Coupling Reaction of Chloroacetyl Arylpiperazines with Pyrazoles

Synthesis of 1-[4-(4-Fluoro-phenyl)-piperazin-1-yl]-2-pyrazol-1-yl-ethanone

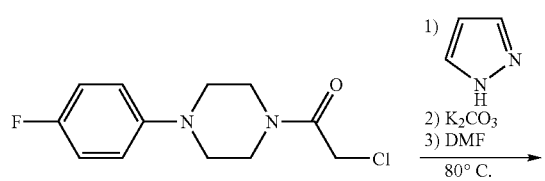

Pyrazole (112.33 mg, 1.65 mmol) was dissolved in DMF (10 mL). K$_2$CO$_3$ (228.05 mg, 1.65 mmol) and 2-Chloro-1-[4-(4-fluoro-phenyl)-piperazin-1-yl]-ethanone (300 mg, 1.67 mmol) were added to it. The reaction was heated to 80° C. for 14 h. After completion, the reaction was cooled to room temperature, quenched with brine and then extracted with ethyl acetate. The organic layer was further washed with water (2×25 mL) and brine (2×25 mL) and dried over magnesium sulfate. The solvent was removed by rotary evaporation to give the crude product which was purified by column chromatography on silica gel using a solvent mixture (hexane/ethyl acetate=1/1) to afford the title compound as white solid. $^1$H NMR (400 MHz, CDCl$_3$): 7.2-7.58 (d, 2H), 6.94-7.2 (t, 2H), 6.84-6.9 (dd, 2H), 6.32-6.36 (t, 1H), 5.6 (s, 2H), 3.76-3.82 (m, 2H), 3.68-3.74 (m, 2H), 3.04-3.1 (m, 2H), 3.0-3.04 (m, 2H). $^{13}$C NMR (400 MHz, CDCl$_3$):165, 158, 146.5, 140, 130, 118.4, 118.2, 116, 115.8, 107, 54, 51, 50.8 45.8, 42.8.

Synthesis of 2-(4-Chloro-5-phenyl-3-trifluoromethyl-pyrazol-1-yl)-1-[4-(4-fluoro phenyl)-piperazin-1-yl]-ethanone and 2-(4-Chloro-3-phenyl-5-trifluoromethyl-pyrazol-1-yl)-1-[4-(4-fluoro-phenyl)-piperazin-1-yl]-ethanone

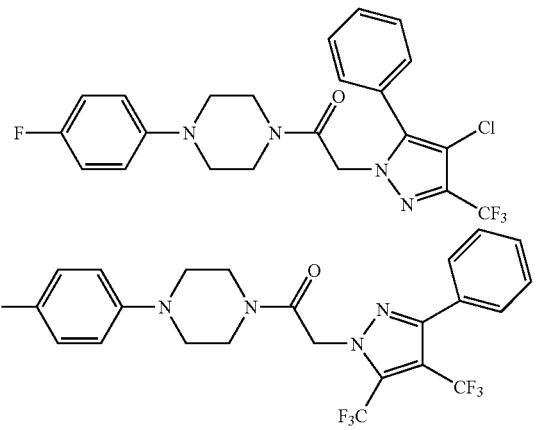

Protocol T was followed using 4-Chloro-5-phenyl-3-trifluoromethyl-1H-pyrazole, K$_2$CO$_3$, 2-Chloro-1-[4-(4-fluoro-phenyl)-piperazin-1-yl]-ethanone and DMF. Column chromatography using a solvent mixture (hexane/ethyl acetate=1.5/1) afforded a mixture of the title compounds, both as white solids

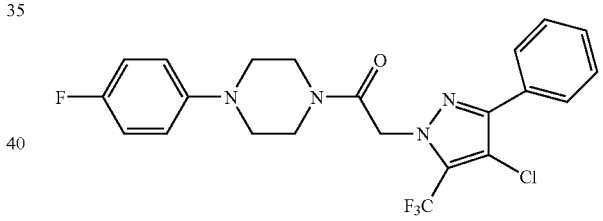

$^1$H NMR (400 MHz, CDCl$_3$): 7.44-7.54 (m, 5H), 6.94-7.2 (t, 2H), 6.84-6.9 (dd, 2H), 4.94 (s, 1H), 3.72-3.8 (m, 2H), 3.5-3.6 (m, 2H), 3.0-3.1 (m, 4H). $^{13}$C NMR (400 MHz, CDCl$_3$) δ163.8, 158, 146.5, 130, 128.6, 128.2, 118.2, 114.5, 52, 50, 44.5, 42.

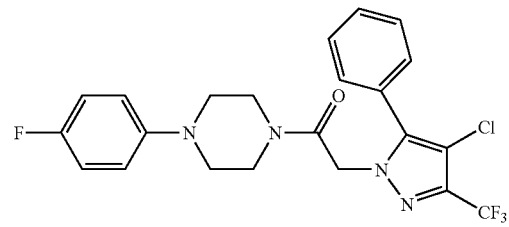

$^1$H NMR (400 MHz, CDCl$_3$): 7.82-7.88 (m, 2H), 7.38-7.48 (m, 3H), 6.96-7.04 (m, 2H), 6.86-6.94 (m, 2H), 5.2 (s, 1H), 3.76-3.86 (m, 2H), 3.62-3.68 (m, 2H), 3.06-3.22 (m, 4H). $^{13}$C NMR (400 MHz, CDCl$_3$): 164, 130, 128.4, 126, 118, 116.4, 52, 50, 43.8, 41.6.

Synthesis of 2-{2-[4-(4-Fluoro-phenyl)-piperazin-1-yl]-2-oxo-ethyl}-5-thiophen-2-yl-2H-pyrazole-3-carboxylic acid ethyl ester

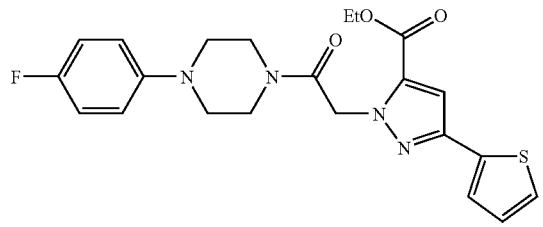

Protocol T was followed using 5-Thiophen-2-yl-2H-pyrazole-3-carboxylic acid ethyl ester, $K_2CO_3$, 2-Chloro-1-[4-(4-fluoro-phenyl)-piperazin-1-yl]-ethanone and DMF. Column chromatography using a solvent mixture (hexane/ethyl acetate=1.5/1) afforded the title compound. $^1$H NMR (400 MHz, CDCl$_3$): 7.32-7.36 (m, 1H), 7.22-7.26 (m, 1H), 7.08 (s, 1H), 7.02-7.08 (dd, 1H), 6.96-7.2 (m, 2H), 6.86-6.92 (m, 2H), 4.3-4.4 (q, 2H), 3.52-3.58 (m, 4H), 3.05-3.25 (m, 4H), 1.3-1.42 (m, 3H). $^{13}$C NMR (400 MHz, CDCl$_3$): 164, 130, 126.8, 126.4, 120, 118.2, 115.4, 62.3, 54, 50.5, 42, 44.5, 14.6.

Synthesis of 2-(3-Amino-4-bromo-5-phenyl-pyrazol-1-yl)-1-[4-(4-fluoro-phenyl)-piperazin-1-yl]-ethanone

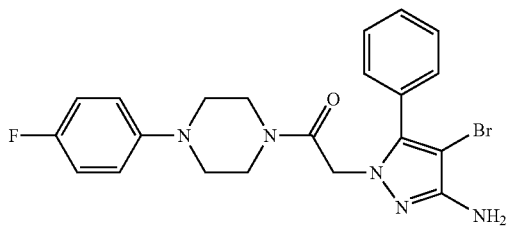

Protocol T was followed using 4-Bromo-5-phenyl-1H-pyrazol-3-ylamine, $K_2CO_3$, 2-Chloro-1-[4-(4-fluoro-phenyl)-piperazin-1-yl]-ethanone and DMF. Column chromatography using a solvent mixture (hexane/ethyl acetate=3/7) afforded the title compound as yellow solid. $^1$H NMR (400 MHz, CDCl$_3$): 7.74-7.78 (m, 2H), 7.24-7.36 (m, 3H), 6.86-6.92 (m, 2H), 6.74-6.78 (m, 2H), 4.9 (s, 2H), 4.22 (s, 2H), 3.64-3.74 (m, 4H), 2.86-3.04 (m, 4H). $^{13}$C NMR (400 MHz, CDCl$_3$): 164, 146.2, 144.8, 128, 126.8, 118, 114.8, 60, 50.2, 50, 48.8, 46, 42, 20.

Synthesis of 2-(3-Amino-4-bromo-5-phenyl-pyrazol-1-yl)-1-[4-(4-chloro-phenyl)-piperazin-1-yl]-ethanone

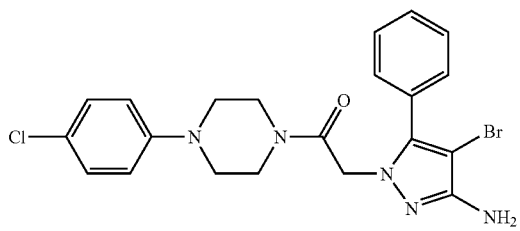

Protocol T was followed using 4-Bromo-5-phenyl-1H-pyrazol-3-ylamine, $K_2CO_3$, 2-Chloro-1-[4-(4-chloro-phenyl)-piperazin-1-yl]-ethanone and DMF. Column chromatography using a solvent mixture (hexane/ethyl acetate=1/4) afforded the title compound as white solid. $^1$H NMR (400 MHz, CDCl$_3$); 7.7-7.8 (m, 2H), 7.24-7.3 (m, 3H), 6.8-6.92 (m, 2H), 6.74-6.78 (m, 2H), 4.9 (s, 2H), 4.2 (s, 2H), 3.6-3.7 (m, 4H), 2.86-3.04 (m, 4H). $^{13}$C NMR (400 MHz, CDCl$_3$): 164, 146, 145, 128, 127, 118, 114.8, 60.2, 50.4, 50, 48.8, 46, 42, 22.

Synthesis of 1-[4-(4-Fluoro-phenyl)-piperazin-1-yl]-2-(3-heptafluoropropyl-5-methyl-4-nitro-pyrazol-1-yl)-ethanone

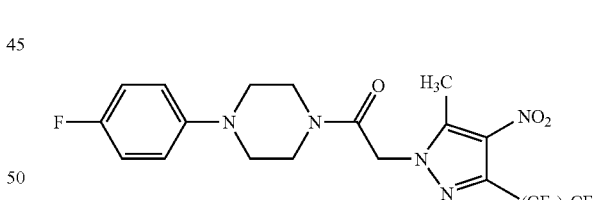

Protocol T was followed using 3-Heptafluoropropyl-5-methyl-4-nitro-1H-pyrazole, $K_2CO_3$, 2-Chloro-1-[4-(4-fluoro-phenyl)-piperazin-1-yl]-ethanone and DMF. Column chromatography using a solvent mixture (hexane/ethyl acetate=3/7) afforded the title compound as oil. $^1$H NMR (400 MHz, CDCl$_3$): 6.9-7.0 (m, 2H), 6.8-6.9 (m, 2H), 5.06-5.14 (d, 2H), 3.6-3.8 (m, 4H), 3.06-3.18 (m, 4H), 2.56-2.66 (d, 3H). $^{13}$C NMR (400 MHz, CDCl$_3$): 160, 146.2, 144, 119.2, 118, 52.2, 50.8, 50.4, 46, 42.2, 12.

Synthesis of 1-[4-(4-Chloro-phenyl)-piperazin-1-yl]-2-(4-chloro-5-phenyl-3-trifluoromethyl-pyrazol-1-yl)-ethanone

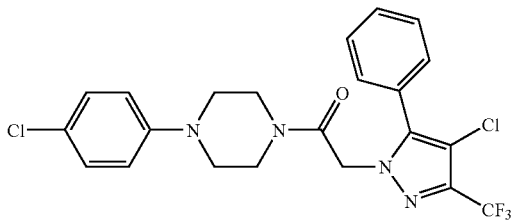

Protocol T was followed using 4-Chloro-5-phenyl-3-trifluoromethyl-1H-pyrazole, K₂CO₃, 2-Chloro-1-[4-(4-chlorophenyl)-piperazin-1-yl]-ethanone and DMF. Column chromatography using a solvent mixture (hexane/ethyl acetate=2/3) afforded the title compound as white solid. $^1$H NMR (400 MHz, CDCl$_3$); 7.82-7.84 (m, 2H), 7.4-7.48 (m, 3H), 6.9-7.04 (m, 2H), 6.88-6.94 (m, 2H), 5.22 (s, 1H), 3.76-3.88 (m, 2H), 3.6-3.68 (m, 2H), 3.1-3.22 (m, 4H). $^{13}$C NMR (400 MHz, CDCl$_3$): 164.2, 130.4, 128, 126, 118.2, 116.4, 52.2, 50, 44, 41.8.

Synthesis of 1-[4-(4-Fluoro-phenyl)-piperazin-1-yl]-2-(4-bromo-5-methyl-3-trifluoromethyl-pyrazol-1-yl)-ethanone

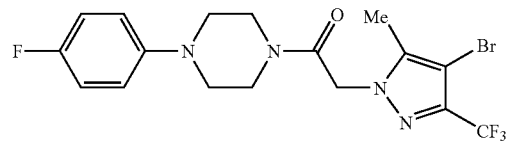

Protocol T was followed using 4-Bromo-5-methyl-3-trifluoromethyl-1H-pyrazole, K₂CO₃, 2-Chloro-1-[4-(4-fluorophenyl)-piperazin-1-yl]-ethanone and DMF. Column chromatography using a solvent mixture (hexane/ethyl acetate=2/3) afforded the title compound as white solid. $^1$H NMR (400 MHz, CDCl$_3$): 6.96-7 (m, 2H), 6.84-6.9 (m, 2H), 5 (s, 2H), 3.6-3.8 (m, 4H), 3.02-3.16 (m, 4H), 2.3 (s, 3H). $^{13}$C NMR (400 MHz, CDCl$_3$): 162.6, 146.5, 142, 118.5, 116, 52.2, 50.4, 46, 42.2, 15.

Synthesis of 1-[4-(4-Chloro-phenyl)-piperazin-1-yl]-2-(4-bromo-5-methyl-3-trifluoromethyl-pyrazol-1-yl)-ethanone

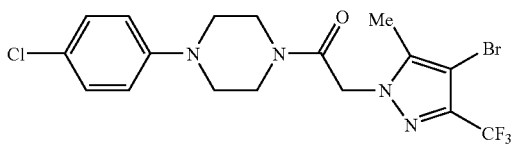

Protocol T was followed using 4-Bromo-5-methyl-3-trifluoromethyl-1H-pyrazole, K₂CO₃, 2-Chloro-1-[4-(4-chlorophenyl)-piperazin-1-yl]-ethanone and DMF. Column chromatography using a solvent mixture (hexane/ethyl acetate=2/3) afforded the title compound as white solid. $^1$H NMR (400 MHz, CDCl$_3$): 6.96-7.1 (m, 2H), 6.84-6.89 (m, 2H), 5.2 (s, 2H), 3.6.2-3.8 (m, 4H), 3.0-3.16 (m, 4H), 2.32 (s, 3H). $^{13}$C NMR (400 MHz, CDCl$_3$): 162, 146.4, 142.2, 118.5, 116.2, 52, 50.4, 46.2, 42.2, 15.2.

Synthesis of 1-[4-(4-Chloro-phenyl)-piperazin-1-yl]-2-(3-heptafluoropropyl-5-methyl-4-nitro-pyrazol-1-yl)-ethanone

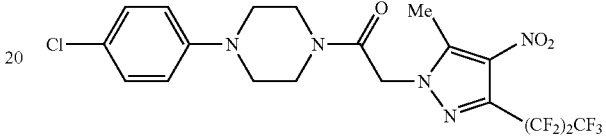

Protocol T was followed using 3-Heptafluoropropyl-5-methyl-4-nitro-1H-pyrazole, K₂CO₃, 2-Chloro-1-[4-(4-chlorophenyl)-piperazin-1-yl]-ethanone and DMF. Column chromatography using a solvent mixture (hexane/ethyl acetate=1/4, R$_f$=0.81) afforded the title compound as colorless oil. $^1$H NMR (400 MHz, CDCl$_3$): δ6.92-7.02 (m, 2H), 6.82-6.9 (m, 2H), 5.04-5.14 (m, 2H), 3.64-3.82 (m, 4H), 3.06-3.18 (m, 4H), 2.6-2.66 (d, 3H). $^{13}$C NMR (400 MHz, CDCl$_3$): 160.4, 146, 144.2, 119.2, 118.2, 52, 50.8, 50.6, 46, 42, 12.2.

Synthesis of 1-[4-(4-Chloro-3-methoxyphenyl)-piperazin-1-yl]-2-(4-chloro-5-phenyl-3-trifluoromethyl-pyrazol-1-yl)-ethanone

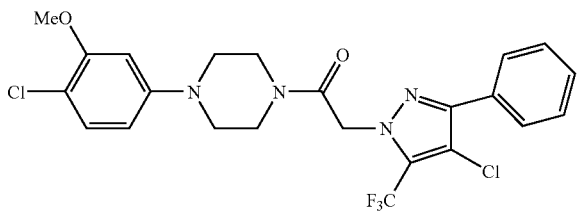

Protocol T was followed using 4-Chloro-5-phenyl-3-trifluoromethyl-1H-pyrazole, K₂CO₃, 2-Chloro-1-[4-(4-chloro-3-methoxy-phenyl)-piperazin-1-yl]-ethanone and DMF. Column chromatography using a solvent mixture (hexane/ethyl acetate=2/3) afforded the title compound as a white solid. $^1$H NMR (400 MHz, CDCl$_3$): 7.4-7.52 (m, 5H), 7.18-7.22 (d, 1H), 6.44-6.48 (d, 1H), 6.36-6.42 (dd, 1H), 4.72 (s, 2H), 3.86 (s, 3H), 3.5-3.78 (m, 4H), 3.1 (s, 4H). $^{13}$C NMR (400 MHz, CDCl$_3$) 164, 156.2, 150.4, 130.5, 130, 128.5, 110, 102.2, 56, 52, 50, 44.8, 42.

Synthesis of 1-[4-(4-Bromo-3-methoxyphenyl)-piperazin-1-yl]-2-(4-chloro-3-phenyl-5-trifluoromethyl-pyrazol-1-yl)-ethanone

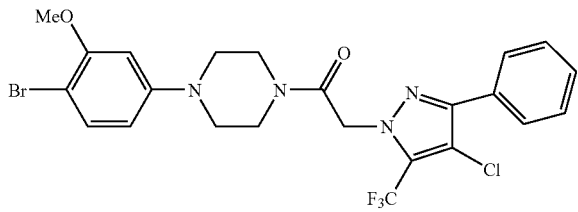

Protocol T was followed using 4-Chloro-5-phenyl-3-trifluoromethyl-1H-pyrazole, $K_2CO_3$, 2-Chloro-1-[4-(4-bromo-3-methoxy-phenyl)-piperazin-1-yl]-ethanone and DMF. Column chromatography using a solvent mixture (hexane/ethyl acetate=2/3) afforded the title compound as a white solid. $^1$H NMR (400 MHz, CDCl$_3$): 7.42-7.52 (m, 4H), 7.36-7.38 (d, 1H), 6.42-6.46 (d, 1H), 6.34-6.38 (dd, 1H), 4.72 (s, 2H), 3.88 (s, 3H), 3.74-3.78 (m, 2H), 3.54-3.58 (m, 2H), 3.12-3.18 (m, 4H). $^{13}$C NMR (400 MHz, CDCl$_3$): 164, 156.2, 152, 132.6, 130.2, 130, 128.8, 110, 102.2, 56, 52, 50, 44.8, 42.

Synthesis of 1-[4-(4-Chloro-3-methoxy-piperazin-1-yl]-2-(4-bromo-5-methyl-3-trifluoromethyl-pyrazol-1-yl)-ethanone

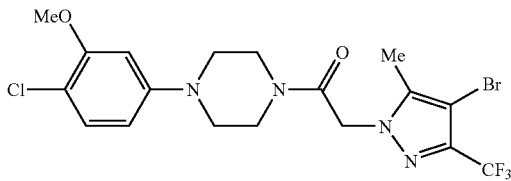

Protocol T was followed using 4-Bromo-5-methyl-3-trifluoromethyl-1H-pyrazole, $K_2CO_3$, 2-Chloro-1-[4-(4-chloro-3-methoxy-phenyl)-piperazin-1-yl]-ethanone and DMF. Column chromatography using a solvent mixture (hexane/ethyl acetate=1/4) afforded the title compound as white solid. $^1$H NMR (400 MHz, CDCl$_3$): 7.18-7.22 (d, 1H), 6.44-6.48 (d, 1H), 6.36-6.42 (dd, 1H), 5.0 (s, 2H), 3.6.2-3.8 (m, 4H), 3.1-3.2 (m, 4H), 2.3 (s, 3H). $^{13}$C NMR (400 MHz, CDCl$_3$): 162, 146.6, 142.2, 118.8, 116, 52.2, 50.4, 46.2, 42.2, 15.2.

Synthesis of 2-(3-Amino-4-bromo-5-phenyl-pyrazol-1-yl)-1-[4-(4-chloro-3-methoxyphenyl)-piperazin-1-yl]-ethanone

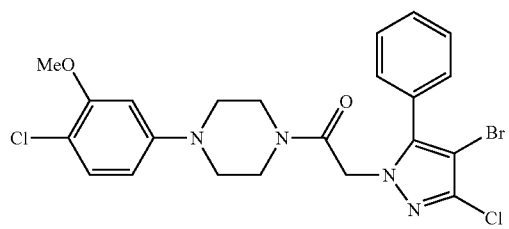

Protocol T was followed using 4-Bromo-5-phenyl-1H-pyrazol-3-ylamine, $K_2CO_3$, 2-Chloro-1-[4-(4-chloro-3-methoxy-phenyl)-piperazin-1-yl]-ethanone and DMF. Column chromatography using a solvent mixture (hexane/ethyl acetate=1/4) afforded the title compound as white solid. $^1$H NMR (400 MHz, CDCl$_3$): 7.78-7.84 (d, 2H), 7.32-7.42 (m, 3H), 7.18-7.22 (d, 1H), 6.44-6.48 (d, 1H), 6.36-6.42 (dd, 1H), 4.94 (s, 2H), 4.28 (s, 2H), 3.88 (s, 3H), 3.76-3.86 (m, 4H), 3.12-3.18 (m, 4H). $^{13}$C NMR (400 MHz, CDCl$_3$): 164.6, 154.8, 150.2, 144.6, 130, 128.2, 128, 126.4, 109.2, 102, 56, 51, 50, 49.6, 45.6, 42.

Synthesis of 2-(3-Amino-4-chloro-5-methyl-pyrazol-1-yl)-1-[4-(4-chloro-3-methoxyphenyl)-piperazin-1-yl]-ethanone

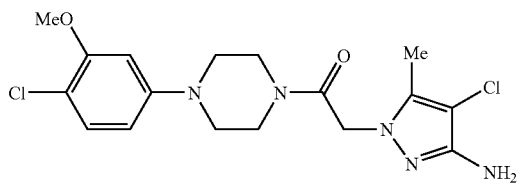

Protocol T was followed using 4-Chloro-5-methyl-1H-pyrazol-3-ylamine, $K_2CO_3$, 2-Chloro-1-[4-(4-chloro-3-methoxy-phenyl)-piperazin-1-yl]-ethanone and DMF. Column chromatography using a solvent mixture (hexane/ethyl acetate=1/4) afforded the title compound as colorless oil. $^1$H NMR (400 MHz, CDCl$_3$): 7.18-7.22 (d, 1H), 6.44-6.48 (d, 1H), 6.36-6.42 (dd, 1H), 5.0 (s, 2H), 4.24 (s, 2H), 2.4 (s, 3H), 3.76-3.86 (m, 4H), 3.12-3.18 (m, 4H). $^{13}$C NMR (400 MHz, CDCl$_3$): 164.6, 154.8, 144.6, 130.2, 130, 128.8, 109.2, 102, 56, 51, 49.6, 45.6, 42.

Synthesis of 1-[4-(4-Bromo-3-methoxy-piperazin-1-yl]-2-(4-bromo-5-methyl-3-trifluoromethyl-pyrazol-1-yl)-ethanone

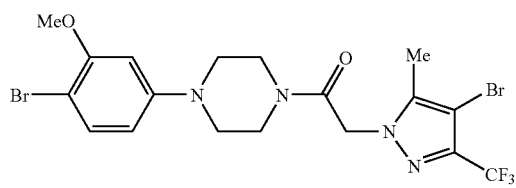

Protocol T was followed using 4-Bromo-5-methyl-3-trifluoromethyl-1H-pyrazole, $K_2CO_3$, 2-Chloro-1-[4-(4-bromo-3-methoxy-phenyl)-piperazin-1-yl]-ethanone and DMF. Column chromatography using a solvent mixture (hexane/ethyl acetate=1/4) afforded the title compound as white solid. $^1$H NMR (400 MHz, CDCl$_3$): 7.38-7.4 (d, 1H), 6.44-6.46 (d, 1H), 6.26-6.4 (dd, 2H), 5.0 (s, 2H), 3.88 (s, 3H), 3.68-3.8 (m, 4H), 3.14-3.22 (m, 4H), 2.3 (s, 3H). $^{13}$C NMR (400 MHz, CDCl$_3$): 164.4, 158, 152.2, 144, 134, 110, 102.2, 56.6, 54.2, 50, 48.8, 46, 42.2, 12.

Synthesis of 1-[4-(4-Fluoro-phenyl)-piperazin-1-yl]-2-(3-thiophen-2-yl-pyrazol-1-yl)-ethanone

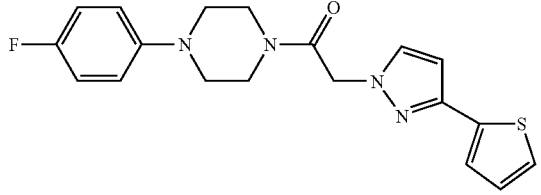

Protocol T was followed using 3-(2-thienyl)pyrazole, K$_2$CO$_3$, 2-Chloro-1-[4-(4-fluoro-phenyl)-piperazin-1-yl]-ethanone and DMF. Column chromatography using a solvent mixture (hexane/ethyl acetate=1/1) afforded the title compound as a white solid. $^1$H NMR (400 MHz, CDCl$_3$); 7.48-7.52 (d, 1H), 7.24-7.28 (dd, 1H), 7.14-7.2 (dd, 1H), 6.98-7.2 (m, 1H), 6.88-6.96 (m, 2H), 6.78-6.84 (m, 2H), 6.46-6.52 (d, 1H), 5.0 (s, 2H), 3.64-3.8 (m, 4H), 2.94-3.1 (m, 4H). $^{13}$C NMR (400 MHz, CDCl$_3$): 164.4, 158, 152.2, 144, 134, 132, 126, 124, 123.8, 118, 116, 115.8, 102.2, 54, 51.2, 50.8, 45.8, 42.2.

Synthesis of 2-(4-Chloro-3-trifluoromethyl-pyrazol-1-yl)-1-[4-(4-fluoro-phenyl)-piperazin-1-yl]-ethanone

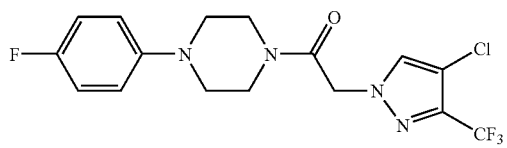

Protocol T was followed using 4-Chloro-3-trifluoromethyl-1H-pyrazole, K$_2$CO$_3$, 2-Chloro-1-[4-(4-fluoro-phenyl)-piperazin-1-yl]-ethanone and DMF. Column chromatography using a solvent mixture (hexane/ethyl acetate=1/1) afforded the title compound as colorless oil. $^1$H NMR (400 MHz, CDCl$_3$): 7.64-7.68 (d, 1H), 6.98-7.4 (m, 2H), 6.86-6.92 (m, 2H), 6.98-7.2 (m, 1H), 5.4 (s, 2H), 3.78-3.84 (m, 2H), 3.68-3.92 (m, 2H), 3-3.1 (m, 4H). $^{13}$C NMR (400 MHz, CDCl$_3$): 164.4, 158, 152.2, 144, 132, 118.2, 116, 54, 50.2, 50.0, 46.0, 42.2.

Synthesis of 1-[4-(4-Fluoro-phenyl)-piperazin-1-yl]-2-(3,4,5-tribromo-pyrazol-1-yl)-ethanone

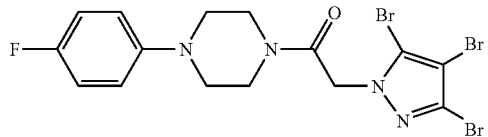

Protocol T was followed using 3,4,5-Tribromo-1H-pyrazole, K$_2$CO$_3$, 2-Chloro-1-[4-(4-fluoro-phenyl)-piperazin-1-yl]-ethanone and DMF. Column chromatography using a solvent mixture (hexane/ethyl acetate=1/4) afforded the title compound as white solid. $^1$H NMR (400 MHz, CDCl$_3$): 6.96-7.2 (m, 2H), 6.84-6.9 (m, 2H), 5.4 (s, 2H), 3.74-3.8 (m, 2H), 3.6-3.68 (m, 2H), 3.04-3.14 (m, 4H). $^{13}$C NMR (400 MHz, CDCl$_3$): 164.4, 158, 156, 144.2, 128, 118.4, 118.2, 116, 100, 52.8, 50.2, 50.0, 46.0, 42.2.

Synthesis of 2-(3-tert-Butyl-4-chloro-5-trifluoromethyl-pyrazol-1-yl)-1-[4-(4-fluoro-phenyl)-piperazin-1-yl]-ethanone

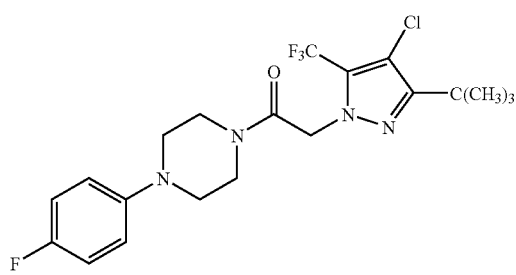

Protocol T was followed using 5-tert-Butyl-4-chloro-3-trifluoromethyl-1H-pyrazole, K$_2$CO$_3$, 2-Chloro-1-[4-(4-fluoro-phenyl)-piperazin-1-yl]-ethanone and DMF. Column chromatography using a solvent mixture (hexane/ethyl acetate=1/1) afforded the title compound as white solid. $^1$H NMR (400 MHz, CDCl$_3$): 6.94-7.22 (m, 2H), 6.84-6.92 (m, 2H), 5.3 (s, 2H), 3.68-3.8 (m, 2H), 3.6-3.68 (m, 2H), 3.04-3.2 (m, 4H), 1.4 (s, 9H). $^{13}$C NMR (400 MHz, CDCl$_3$): 164.8, 119, 118.4, 118.2, 116.2, 116, 54, 51, 50.8, 45.4, 42.2, 30, 29, 27.

Synthesis of 2-[3-(4-Fluoro-phenyl)-5-methylsulfanyl-pyrazol-1-yl]-1-[4-(4-fluoro-phenyl)-piperazin-1-yl]-ethanone

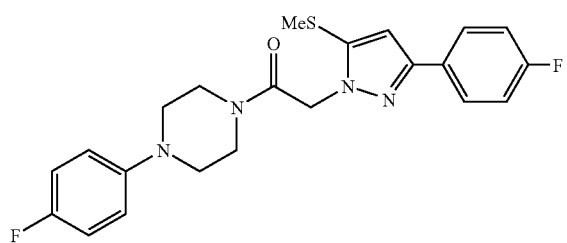

Protocol T was followed using 3-(4-Fluoro-phenyl)-5-methylsulfanyl-1H-pyrazole, K$_2$CO$_3$, 2-Chloro-1-[4-(4-fluoro-phenyl)-piperazin-1-yl]-ethanone and DMF. Column chromatography using a solvent mixture (hexane/ethyl acetate=2/3) afforded the title compound as white solid. $^1$H NMR (400 MHz, CDCl$_3$): 7.7-7.76 (m, 2H), 6.96-7.1 (m, 4H), 6.88-6.92 (m, 2H), 6.64 (s, 1H), 5.3 (s, 2H), 3.7-3.84 (m, 4H), 3.04-3.2 (m, 4H), 2.5 (s, 3H). $^{13}$C NMR (400 MHz, CDCl$_3$): 164.8, 152, 140, 127.4, 119, 118.4, 118.2, 116.2, 116, 108, 52.8, 52, 51.8, 45.4, 42.2, 20.

Synthesis of 2-[4-Chloro-5-(4-Fluoro-phenyl)-3-methylsulfanyl-pyrazol-1-yl]-1-[4-(4-fluoro-phenyl)-piperazin-1-yl]-ethanone

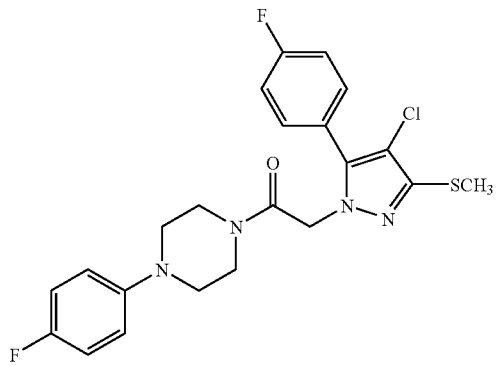

Protocol T was followed using 4-Chloro-3-(4-Fluoro-phenyl)-5-methylsulfanyl-1H-pyrazole, K$_2$CO$_3$, 2-Chloro-1-[4-(4-fluoro-phenyl)-piperazin-1-yl]-ethanone and DMF. Column chromatography using a solvent mixture (hexane/ethyl acetate=2/3) afforded the title compound as white solid. $^1$H NMR (400 MHz, CDCl$_3$): 7.82-7.88 (m, 2H), 7.06-7.12 (m, 2H), 6.96-7.1 (m, 2H), 6.88-6.92 (m, 2H), 5.2 (s, 2H), 3.68-3.84 (m, 4H), 3.06-3.18 (m, 4H), 2.4 (s, 3H). $^{13}$C NMR (400 MHz, CDCl$_3$): 164.8, 158, 147, 135, 127.4, 127, 119, 112.4, 112.2, 110, 108.8, 52.8, 52, 51.8, 45.4, 42.2, 18.6.

Synthesis of 2-[4-Chloro-3-(4-Fluoro-phenyl)-5-methylsulfanyl-pyrazol-1-yl]-1-[4-(4-fluoro-phenyl)-piperazin-1-yl]-ethanone

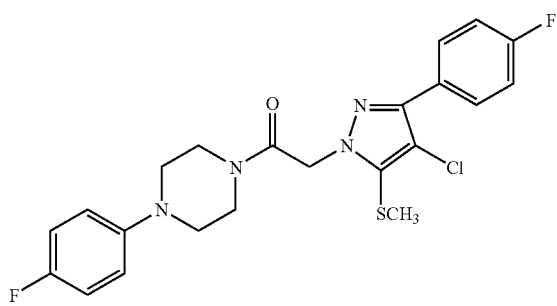

Protocol T was followed using 4-Chloro-3-(4-Fluoro-phenyl)-5-methylsulfanyl-1H-pyrazole, K$_2$CO$_3$, 2-Chloro-1-[4-(4-fluoro-phenyl)-piperazin-1-yl]-ethanone and DMF. Column chromatography using a solvent mixture (hexane/ethyl acetate=2/3) afforded the title compound as white solid. $^1$H NMR (400 MHz, CDCl$_3$): 7.46-7.5 (m, 2H), 7.12-7.18 (m, 2H), 6.96-7.1 (m, 2H), 6.88-6.92 (m, 2H), 4.86 (s, 2H), 3.72-3.78 (m, 2H), 3.56-3.62 (m, 2H), 3.06-3.18 (m, 4H), 2.54 (s, 3H).

Synthesis of 2-{2-[4-(4-Fluoro-phenyl)-piperazin-1-yl]-2-oxo-ethyl}-4-Chloro-3-thiophen-2-yl-2H-pyrazole-5-carboxylic acid ethyl ester

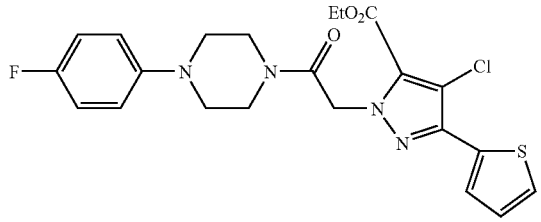

Protocol T was followed using 4-Chloro-3-Thiophen-2-yl-2H-pyrazole-5-carboxylic acid ethyl ester, K$_2$CO$_3$, 2-Chloro-1-[4-(4-fluoro-phenyl)-piperazin-1-yl]-ethanone and DMF. Column chromatography using a solvent mixture (hexane/ethyl acetate=1.5/1: R$_f$=0.62) afforded the title compound. $^1$H NMR (400 MHz, CDCl$_3$): 7.06-7.36 (m, 1H), 6.96-7.2 (m, 3H), 6.84-6.92 (m, 3H), 54.46 (s, 2H), 4.3-4.4 (q, 2H), 3.6-3.82 (m, 4H), 3.05-3.25 (m, 4H), 1.3-1.42 (m, 3H).

Synthesis of 2-(4-Amino-3-heptafluoropropyl-5-methyl-pyrazol-1-yl)-1-[4-(4-fluoro-phenyl)-piperazin-1-yl]-ethanone

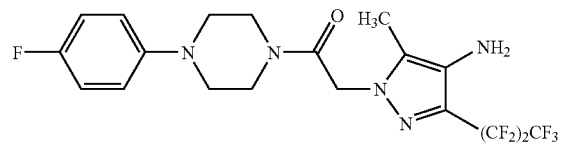

Protocol T was followed using 4-Amino-3-heptafluoropropyl-5-methyl-1H-pyrazole, K$_2$CO$_3$, 2-Chloro-1-[4-(4-fluoro-phenyl)-piperazin-1-yl]-ethanone and DMF. Column chromatography using a solvent mixture (hexane/ethyl acetate=1/4) afforded the title compound as colorless oil. $^1$H NMR (400 MHz, CDCl$_3$); 6.92-7.02 (m, 4H), 5.14 (s, 2H), 3.64-3.82 (m, 4H), 3.6 (s, 2H), 3.1-3.22 (m, 4H), 2.16 (s, 3H). $^{13}$C NMR (400 MHz, CD$_6$CO): 160.4, 158, 146, 144.2, 119.8, 118.2, 52, 50.8, 50.6, 46, 42, 12.2.

Synthesis of 2-(5-Butyl-3-trifluoromethyl-pyrazol-1-yl)-1-[4-(4-chloro-phenyl)-piperazin-1-yl]-ethanone

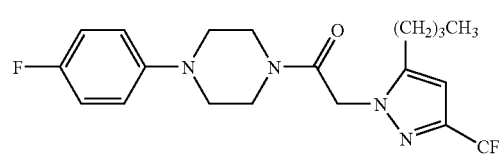

Protocol T was followed using 5-n-Butyl-3-trifluoromethyl-1H-pyrazole, K$_2$CO$_3$, 2-Chloro-1-[4-(4-fluoro-phenyl)-piperazin-1-yl]-ethanone and DMF. Column chromatography using a solvent mixture (hexane/ethyl acetate=1/4) afforded the title compound as colorless oil. $^1$H NMR (400 MHz, CDCl$_3$): 7.18-7.24 (m, 2H), 6.78-6.84 (m, 2H), 6.32 (s, 1H), 5.0 (s, 2H), 3.66-3.78 (m, 4H), 3.08-3.18 (m, 4H), 2.58-2.64 (t, 2H), 1.6-1.7 (m, 2H), 1.38-1.48 (m, 2H), 0.6-1.0 (t, 3H). $^{13}$C NMR (400 MHz, CDCl$_3$): 160.4, 150, 148, 142, 130, 126, 119.8, 103.2, 52, 50.8, 50.6, 46, 42, 30, 26, 22, 14.

Synthesis of 2-(4-Chloro-5-butyl-3-trifluoromethyl-pyrazol-1-yl)-1-[4-(4-chloro-phenyl)-piperazin-1-yl]-ethanone

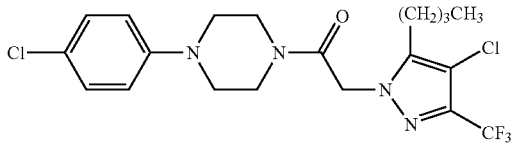

Protocol T was followed using 4-Chloro-5-n-butyl-3-trifluoromethyl-1H-pyrazole, $K_2CO_3$, 2-Chloro-1-[4-(4-fluoro-phenyl)-piperazin-1-yl]-ethanone and DMF. Column chromatography using a solvent mixture (hexane/ethyl acetate=1/4) afforded the title compound as colorless oil. $^1$H NMR (400 MHz, $CDCl_3$): 7.18-7.24 (m, 2H), 6.78-6.84 (m, 2H), 5.0 (s, 2H), 3.66-3.78 (m, 4H), 3.08-3.2 (m, 4H), 2.58-2.64 (t, 2H), 1.5-1.54 (m, 2H), 1.38-1.48 (m, 2H), 0.6-1.0 (t, 3H). $^{13}$C NMR (400 MHz, $CDCl_3$): 160.4, 148, 142, 130, 128, 119.8, 52, 50.8, 50.6, 46, 42, 30.4, 26, 23, 14.

Synthesis of 2-(3-Amino-4-bromo-5-phenyl-pyrazol-1-yl)-1-[4-(4-bromo-3-methoxyphenyl)-piperazin-1-yl]-ethanone

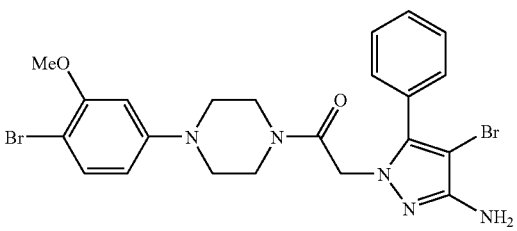

Protocol T was followed using 4-Bromo-5-phenyl-1H-pyrazol-3-ylamine, $K_2CO_3$, 2-Chloro-1-[4-(4-bromo-3-methoxy-phenyl)-piperazin-1-yl]-ethanone and DMF. Column chromatography using a solvent mixture (hexane/ethyl acetate=1/1.5) afforded the title compound as white solid. $^1$H NMR (400 MHz, $CDCl_3$): 7.78-7.84 (d, 2H), 7.32-7.42 (m, 3H), 7.18-7.22 (d, 1H), 6.44-6.52 (d, 1H), 6.36-6.42 (dd, 1H), 4.94 (s, 2H), 4.28 (s, 2H), 3.84 (s, 3H), 3.76-3.82 (m, 4H), 3.12-3.18 (m, 4H). $^{13}$C NMR (400 MHz, $CDCl_3$): 164.6, 154.8, 150.2, 144.6, 130, 128.8, 128.6, 126.4, 109.2, 102, 56, 51, 50, 49.6, 45.6, 42.

Synthesis of 2-(4-Bromopyrazol)-1-[4-(4-fluoro-phenyl)-piperazin-1-yl]-ethanone

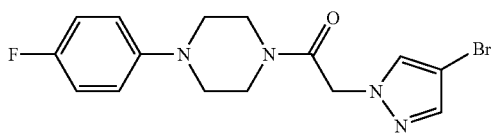

Protocol T was followed using 4-Bromo-1H-pyrazol, $K_2CO_3$, 2-Chloro-1-[4-(4-fluoro-phenyl)-piperazin-1-yl]-ethanone and DMF. Column chromatography using a solvent mixture (hexane/ethyl acetate=1/1) afforded the title compound as a white solid. $^1$H NMR (400 MHz, $CDCl_3$): 7.52-7.58 (d, 1H), 7.48-7.52 (d, 1H), 6.95-7.0 (m, 2H), 6.82-6.92 (dd, 2H), 5.00 (s, 2H), 3.72-3.80 (t, 2H), 3.64-3.72 (t, 2H), 3.02-3.12 (m, 4H). $^{13}$C NMR (400 MHz, $CDCl_3$): 164.6, 158.2, 156.2, 146.6, 141.6, 140.2, 130.5, 129.6, 118.2, 118.0, 115.2, 116.4, 94.2, 53.8, 50.8, 50.2, 45.4, 42.

Synthesis of 2-(4-Iodopyrazol)-1-[4-(4-fluoro-phenyl)-piperazin-1-yl]-ethanone

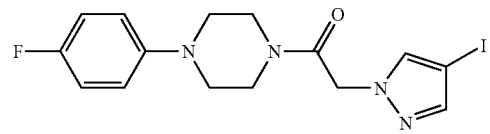

Protocol T was followed using 4-Iodo-1H-pyrazol, $K_2CO_3$, 2-Chloro-1-[4-(4-fluoro-phenyl)-piperazin-1-yl]-ethanone and DMF. Column chromatography using a solvent mixture (hexane/ethyl acetate=1/1) afforded the title compound as a white solid. $^1$H NMR (400 MHz, $CDCl_3$); 7.58-7.62 (d, 1H), 7.52 (s, 1H), 6.95-7.1 (m, 2H), 6.84-6.92 (dd, 2H), 5.00 (s, 2H), 3.72-3.80 (t, 2H), 3.64-3.72 (t, 2H), 3.02-3.12 (m, 4H). $^{13}$C NMR (400 MHz, $CDCl_3$): 164.6, 158.2, 156.2, 146.8, 140.8, 140.2, 130.5, 129.6, 118.2, 118.0, 115.4, 116.8, 96.0, 53.4, 51.2, 50.2, 45.2, 42.

Synthesis of 2-(3,5-Diisopropyl-pyrazol-1-yl)-1-[4-(4-fluoro-phenyl)-piperazin-1-yl]-ethanone

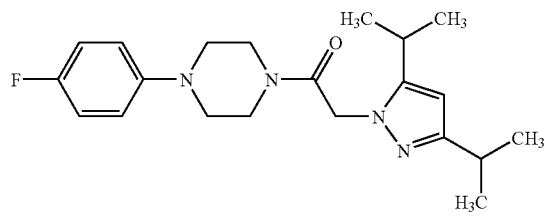

Protocol T was followed using 3,5-Diisopropyl-1H-pyrazole, $K_2CO_3$, 2-Chloro-1-[4-(4-fluoro-phenyl)-piperazin-1-yl]-ethanone and DMF. Column chromatography using a solvent mixture (hexane/ethyl acetate=1/1) afforded the title compound as white solid. $^1$H NMR (400 MHz, $CDCl_3$): 6.92-7.0 (m, 2H), 6.80-6.88 (dd, 2H), 5.88 (s, 1H), 4.92 (s, 2H), 3.70-3.80 (t, 4H), 2.90-3.10 (m, 4H), 1.40-1.60 (m, 12H). $^{13}$C NMR (400 MHz, $CDCl_3$): 160.6, 158.2, 150.2, 119.2, 118.0, 100.0, 50.8, 50.5, 50.2, 45.2, 42, 28.2, 26.0, 22.4.

Synthesis of 1-{2-[4-(4-Fluoro-phenyl)-piperazin-1-yl]-2-oxo-ethyl}-3-trifluoromethyl-1H-pyrazole-4-carboxylic acid ethyl ester

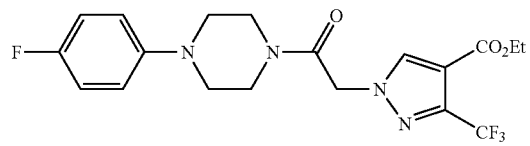

Protocol T was followed using 3-Trifluoromethyl-1H-pyrazole-4-carboxylic acid ethyl ester, K₂CO₃, 2-Chloro-1-[4-(4-fluoro-phenyl)-piperazin-1-yl]-ethanone and DMF. Column chromatography using a solvent mixture (hexane/ethyl acetate=1/1) afforded the title compound as colorless oil. ¹H NMR (400 MHz, CDCl₃); 8.15 (s, 1H), 6.98-7.04 (m, 2H), 6.86-6.92 (m, 2H), 5.1 (s, 2H), 4.28-4.38 (q, 2H), 3.78-3.84 (m, 2H), 3.62-3.74 (m, 2H), 3.04-3.2 (m, 4H), 1.3-1.4 (t, 3H). ¹³C NMR (400 MHz, CDCl₃): 163.4, 160.5, 159.2, 156.2, 147, 137.2, 119, 118.8, 116, 115.8, 61, 54, 50.8, 50.0, 45.0, 42.2, 14.2.

Synthesis of 1-[4-(4-Fluoro-phenyl)-piperazin-1-yl]-2-(4-iodo-3,5-dimethyl-pyrazol-1-yl)-ethanone

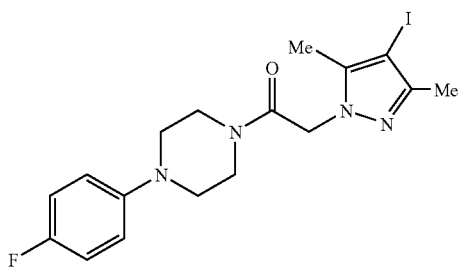

Protocol T was followed using 4-Iodo-3,5-dimethyl-pyrazole, K₂CO₃, 2-Chloro-1-[4-(4-fluoro-phenyl)-piperazin-1-yl]-ethanone and DMF. Column chromatography using a solvent mixture (hexane/ethyl acetate=1/1) afforded the title compound as a white solid. ¹H NMR (400 MHz, CDCl₃); 6.95-7.1 (m, 2H), 6.84-6.92 (dd, 2H), 5.00 (s, 2H), 3.62-3.82 (m, 4H), 3.02-3.12 (m, 4H), 2.22-2.32 (d, 6H). ¹³C NMR (400 MHz, CDCl₃): 165, 158.2, 156.2, 150.2, 146.8, 141.8, 118.8, 115.4, 115.2, 52.8, 51.6, 50.2, 45.2, 42, 14.8, 12.6.

Synthesis of 2-(3-Chloro-indazol-1-yl)-1-[4-(4-fluoro-phenyl)-piperazin-1-yl]-ethanone

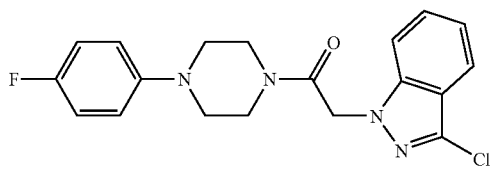

Protocol T was followed using 3-Chloro-1H-indazole, K₂CO₃, 2-Chloro-1-[4-(4-fluoro-phenyl)-piperazin-1-yl]-ethanone and DMF. Column chromatography using a solvent mixture (hexane/ethyl acetate=1/4) afforded the title compound as a white solid. ¹H NMR (400 MHz, CDCl₃); 7.64-7.70 (m, 1H), 7.38-7.48 (m, 2H), 7.18-7.26 (m, 2H), 6.94-7.0 (m, 2H), 6.82-6.88 (dd, 2H), 5.2 (s, 2H), 3.72-3.82 (m, 4H), 3.02-3.08 (m, 4H). ¹³C NMR (400 MHz, CDCl₃): 165, 158.2, 142.8, 134.8, 128.8, 128.4, 122, 121.6, 118.8, 118.6, 115.4, 115.2, 110.6, 110.0, 51.8, 50.6, 50.2, 45.2, 42.

Synthesis of 2-{2-[4-(4-Fluoro-phenyl)-piperazin-1-yl]-2-oxo-ethyl}-5-propyl-2H-pyrazole-3-carboxylic acid ethyl ester

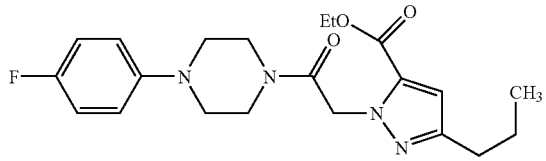

Protocol T was followed using 5-Propyl-2H-pyrazole-3-carboxylic acid ethyl ester, K₂CO₃, 2-Chloro-1-[4-(4-fluoro-phenyl)-piperazin-1-yl]-ethanone and DMF. Column chromatography using a solvent mixture (hexane/ethyl acetate=1/1) afforded the title compound as a white solid. ¹H NMR (400 MHz, CDCl₃): 6.94-7.0 (m, 2H), 6.82-6.90 (dd, 2H), 6.7 (s, 1H), 5.5 (s, 2H), 4.26-4.32 (q, 2H), 3.62-3.82 (m, 4H), 3.04-3.18 (m, 4H), 2.58-2.64 (t, 2H), 1.64-1.74 (m, 2H), 1.34-1.38 (t, 3H), 0.96-1.0 (t, 3H). ¹³C NMR (400 MHz, CDCl₃): 165, 160, 156.2, 152.4, 146.8, 132.8, 118.2, 118.1, 115.8, 115.4, 110.2, 61, 53, 50.6, 50.2, 45, 42, 30, 22.8, 14.2, 14.

Synthesis of 2-{2-[4-(4-Fluoro-phenyl)-piperazin-1-yl]-2-oxo-ethyl}-3-propyl-2H-pyrazole-5-carboxylic acid ethyl ester

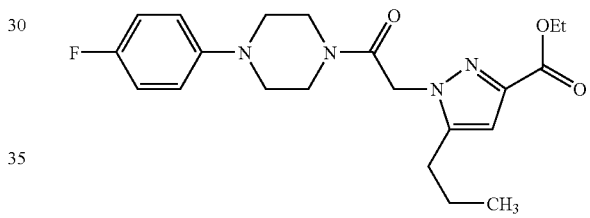

Protocol T was followed using 5-Propyl-2H-pyrazole-3-carboxylic acid ethyl ester, K₂CO₃, 2-Chloro-1-[4-(4-fluoro-phenyl)-piperazin-1-yl]-ethanone and DMF. Column chromatography using a solvent mixture (hexane/ethyl acetate=1/1) afforded the title compound as white solid. ¹H NMR (400 MHz, CDCl₃): 6.94-7.0 (m, 2H), 6.82-6.90 (dd, 2H), 6.2 (s, 1H), 5.06 (s, 2H), 4.34-4.40 (q, 2H), 3.62-3.8 (m, 4H), 3.02-3.12 (m, 4H), 2.54-2.60 (t, 2H), 1.64-1.78 (m, 2H), 1.34-1.38 (t, 3H), 0.98-1.4 (t, 3H). ¹³C NMR (400 MHz, CDCl₃): 165, 160, 156.4, 152.2, 146.6, 132.8, 118.4, 118.2, 115.8, 115.4, 113.2, 61, 53, 50.6, 50.2, 45.2, 42, 28, 21.8, 14.2, 14.

Synthesis of 2-(3,5-Bis-trifluoromethyl-pyrazol-1-yl)-1-[4-(4-fluoro-phenyl)-piperazin-1-yl]-ethanone

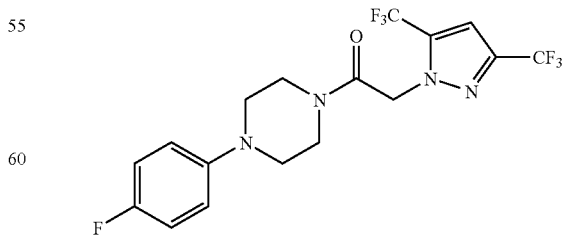

Protocol T was followed using 3,5-Bis-trifluoromethyl-1H-pyrazole, K₂CO₃, 2-Chloro-1-[4-(4-fluoro-phenyl)-piperazin-1-yl]-ethanone and DMF. Column chromatography using a solvent mixture (hexane/ethyl acetate=1/1) afforded the title compound as a white solid. ¹H NMR (400 MHz, CDCl₃): 6.94-7.0 (m, 2H), 6.92 (s, 1H), 6.82-7.90 (dd, 2H), 5.2 (s, 2H), 3.72-3.8 (t, 2H), 3.58-3.66 (t, 2H), 3.12-3.18 (t, 2H), 3.02-3.12 (t, 2H). ¹³C NMR (400 MHz, CDCl₃): 162.2, 158.2, 156.4, 146.5, 118.4, 116.2, 115.8, 113.2, 60.4, 53.2, 50.6, 50.2, 45.2, 42.2, 21.2, 14.2.

Synthesis of 1-{2-[4-(4-Fluoro-phenyl)-piperazin-1-yl]-2-oxo-ethyl}-1H-pyrazole-3,5-dicarboxylic acid diethyl ester

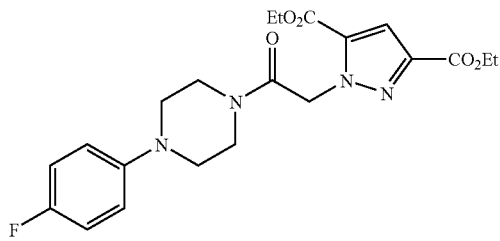

Protocol T was followed using 1H-Pyrazole-3,5-dicarboxylic acid diethyl ester, K₂CO₃, 2-Chloro-1-[4-(4-fluoro-phenyl)-piperazin-1-yl]-ethanone and DMF. Column chromatography using a solvent mixture (hexane/ethyl acetate=1/1) afforded the title compound as a white solid. ¹H NMR (400 MHz, CDCl₃): 7.38 (s, 1H), 6.94-7.0 (m, 2H), 6.82-7.90 (dd, 2H), 5.54 (s, 2H), 4.36-4.42 (q, 2H), 4.26-4.32 (q, 2H), 3.60-3.80 (m, 4H), 3.02-3.20 (m, 4H), 1.22-1.42 (m, 6H). ¹³C NMR (400 MHz, CDCl₃): 164.2, 162.2, 158.2, 157.4, 156.2, 148.5, 144.4, 134.2, 118.4, 116.2, 115.8, 114.2, 62, 61.8, 54.2, 50.6, 50.2, 45.2, 42.2, 14.6, 14.2.

Synthesis of 2-(3-Amino-4-t-butyl-pyrazol-1-yl)-1-[4-(4-fluorophenyl)-piperazin-1-yl]-ethanone

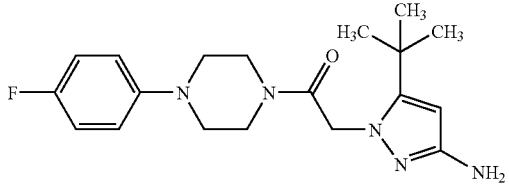

Protocol T was followed using 5-tert-Butyl-1H-pyrazol-3-ylamine, K₂CO₃, 2-Chloro-1-[4-(4-fluoro-phenyl)-piperazin-1-yl]-ethanone and DMF. Column chromatography using a solvent mixture (hexane/ethyl acetate=3/7: R_f=0.49) afforded the title compound as colorless oil. ¹H NMR (400 MHz, CDCl₃): 6.92-7.98 (t, 2H), 6.82-6.88 (dd, 2H), 4.84 (s, 2H), 3.95 (s, 2H), 3.70-3.90 (m, 4H), 2.95-3.10 (m, 4H), 1.25 (s, 9H).

Synthesis of 2-{2-[4-(4-Fluoro-phenyl)-piperazin-1-yl]-2-oxo-ethyl}-4-chloro-5-propyl-2H-pyrazole-3-carboxylic acid ethyl ester

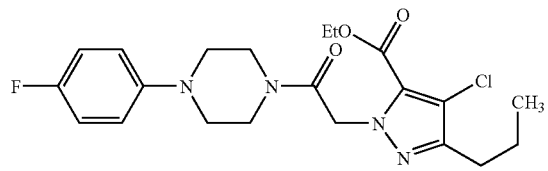

Protocol T was followed using 4-Chloro-5-Propyl-2H-pyrazole-3-carboxylic acid ethyl ester, K₂CO₃, 2-Chloro-1-[4-(4-fluoro-phenyl)-piperazin-1-yl]-ethanone and DMF. Column chromatography using a solvent mixture (hexane/ethyl acetate=3/7) afforded the title compound as a white solid. ¹H NMR (400 MHz, CDCl₃): 6.94-7.0 (m, 2H), 6.82-6.90 (dd, 2H), 5.0 (s, 2H), 4.36-4.40 (q, 2H), 3.62-3.82 (m, 4H), 3.04-3.18 (m, 4H), 2.58-2.66 (t, 2H), 1.64-1.76 (m, 2H), 1.34-1.38 (t, 3H), 0.94-1.0 (t, 3H). ¹³C NMR (400 MHz, CDCl₃): 165, 160.2, 156.2, 152.4, 147, 133, 118.4, 118.2, 115.8, 115.4, 112.2, 61, 53, 50.6, 50.2, 45, 42, 30, 22.8, 14.4, 14.2.

Synthesis of 2-(3-tert-Butyl-5-trifluoromethyl-pyrazol-1-yl)-1-[4-(4-fluoro-phenyl)-piperazin-1-yl]-ethanone

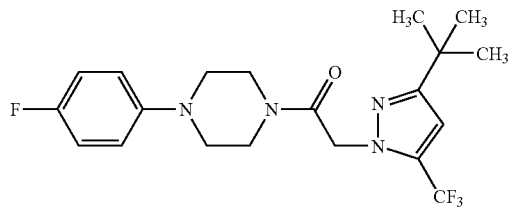

Protocol T was followed using 5-tert-Butyl-3-trifluoromethyl-1H-pyrazole, K₂CO₃, 2-Chloro-1-[4-(4-fluoro-phenyl)-piperazin-1-yl]-ethanone and DMF. Column chromatography using a solvent mixture (hexane/ethyl acetate=1/1) afforded the title compound as a colorless oil. ¹H NMR (400 MHz, CDCl₃); 6.92-7.08 (t, 2H), 6.82-6.88 (dd, 2H), 6.52 (s, 1H), 5.08 (s, 2H), 3.70-3.80 (m, 2H), 3.58-3.68 (m, 2H), 3.05-3.15 (m, 4H), 1.3 (s, 9H). ¹³C NMR (400 MHz, CDCl₃): 164, 161.2, 158.2, 156.4, 147.2, 118.4, 118.2, 115.8, 115.4, 108.2, 54, 50.6, 50.2, 45, 44, 30.

Synthesis of 2-(5-Amino-3-furan-2-yl-pyrazol-1-yl)-1-[4-(4-fluoro-phenyl)-piperazin-1-yl]-ethanone

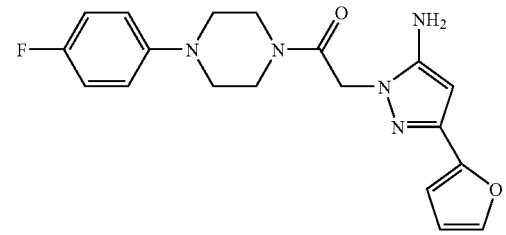

Protocol T was followed using 3-Furan-2-yl-2H-pyrazol-5-ylamine, K₂CO₃, 2-Chloro-1-[4-(4-fluoro-phenyl)-piperazin-1-yl]-ethanone and DMF. Column chromatography using 100% ethyl acetate afforded the title compound as a white solid. $^1$H NMR (400 MHz, CD$_6$CO); 7.48-7.52 (m, 1H), 6.98-7.06 (m, 2H), 6.52-6.56 (m, 2H), 6.44-6.48 (m, 2H), 5.74 (s, 1H), 4.98 (s, 2H), 3.68-3.88 (m, 4H), 3.12-3.24 (m, 4H). MS (ES) M+H) expected=369.4, found 370.1.

Synthesis of 1-[4-(4-Fluoro-phenyl)-piperazin-1-yl]-2-(4-bromo-3,5-dimethyl-pyrazol-1-yl)-ethanone

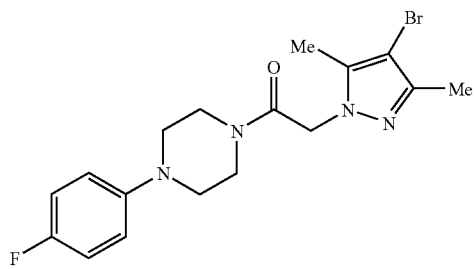

Protocol T was followed using 4-Bromo-3,5-dimethyl-pyrazole, K$_2$CO$_3$, 2-Chloro-1-[4-(4-fluoro-phenyl)-piperazin-1-yl]-ethanone and DMF. Column chromatography using a solvent mixture (hexane/ethyl acetate=1/1) afforded the title compound as a white solid. $^1$H NMR (400 MHz, CDCl$_3$): 6.95-7.1 (m, 2H), 6.84-6.92 (dd, 2H), 4.90 (s, 2H), 3.62-3.82 (m, 4H), 3.02-3.12 (m, 4H), 2.24-2.34 (d, 6H). $^{13}$C NMR (400 MHz, CDCl$_3$): 165, 158.4, 156.6, 150.6, 146.8, 141.4, 119, 115.6, 115.2, 52.6, 51.6, 50.4, 45.2, 42.2, 14.8, 12.6.

Synthesis of 2-[4-Chloro-3-(5-chloro-thiophen-2-yl)-pyrazol-1-yl]-1-[4-(4-fluoro-phenyl)-piperazin-1-yl]-ethanone

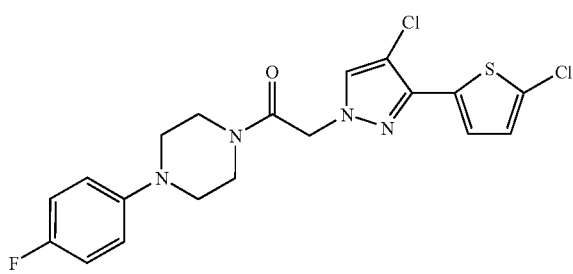

Protocol T was followed using 4-Chloro-3-(5-chloro-thiophen-2-yl)-1H-pyrazole, K$_2$CO$_3$, 2-Chloro-1-[4-(4-fluoro-phenyl)-piperazin-1-yl]-ethanone and DMF. Column chromatography using a solvent mixture (hexane/ethyl acetate=2/3) afforded the title compound as yellow solid. $^1$H NMR (400 MHz, CDCl$_3$): 7.58 (s, 1H), 7.38-7.42 (d, 1H), 6.94-7.1 (m, 2H), 6.84-6.88 (dd, 2H), 4.96 (s, 2H), 3.62-3.81 (m, 4H), 3.02-3.14 (m, 4H). $^{13}$C NMR (400 MHz, CDCl$_3$): 165, 158.8, 156.8, 142.4, 131, 126.8, 124.8, 119, 116, 115.6, 54, 52, 51.6, 46, 42.6.

Synthesis of 4-Chloro-2-{2-[4-(4-fluoro-phenyl)-piperazin-1-yl]-2-oxo-ethyl}-5-methyl-2H-pyrazole-3-carboxylic acid ethyl ester

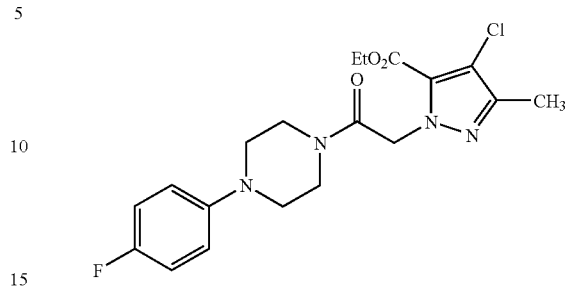

Protocol T was followed using 4-Chloro-5-methyl-2H-pyrazole-3-carboxylic acid ethyl ester, K$_2$CO$_3$, 2-Chloro-1-[4-(4-fluoro-phenyl)-piperazin-1-yl]-ethanone and DMF. Column chromatography using a solvent mixture (hexane/ethyl acetate=2/3) afforded the title compound as a white solid. $^1$H NMR (400 MHz, CDCl$_3$): 6.94-7.1 (m, 2H), 6.84-6.88 (dd, 2H), 5.04 (s, 2H), 4.38-4.44 (q, 2H), 3.62-3.80 (m, 4H), 3.02-3.14 (m, 4H), 2.3 (s, 3H), 1.36-1.42 (t, 3H). $^{13}$C NMR (400 MHz, CDCl$_3$): 182, 165, 119, 116.2, 116, 61.4, 52.3, 51, 50.8, 45.8, 42.6, 14.4, 10.

Synthesis of 4-Chloro-5-(5-chloro-thiophen-2-yl)-2-{2-[4-(4-fluoro-phenyl)-piperazin-1-yl]-2-oxo-ethyl}-2H-pyrazole-3-carboxylic acid ethyl ester

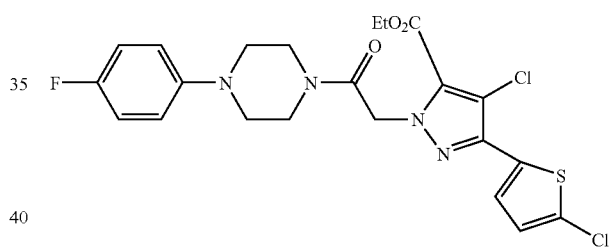

Protocol T was followed using 4-Chloro-5-(5-chloro-thiophen-2-yl)-2H-pyrazole-3-carboxylic acid ethyl ester, K$_2$CO$_3$, 2-Chloro-1-[4-(4-fluoro-phenyl)-piperazin-1-yl]-ethanone and DMF. Column chromatography using a solvent mixture (hexane/ethyl acetate=2/3) afforded the title compound as a yellow solid. $^1$H NMR (400 MHz, CDCl$_3$): 7.46-7.48 (m, 1H), 6.94-7.1 (m, 2H), 6.84-6.92 (m, 3H), 5.4 (s, 2H), 4.34-4.4 (q, 2H), 3.62-3.81 (m, 4H), 3.04-3.24 (m, 4H), 1.36-1.44 (m, 3H). MS (ES) M+H) expected=511.41, found 511.

Synthesis of 2-(3-Amino-4-chloro-5-methyl-pyrazol-1-yl)-1-[4-(4-chlorophenyl)-piperazin-1-yl]-ethanone

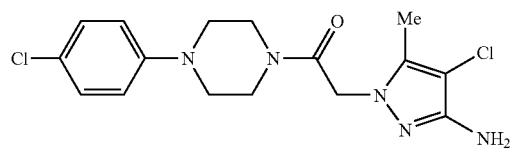

Protocol T was followed using 4-Chloro-5-methyl-1H-pyrazol-3-ylamine, K$_2$CO$_3$, 2-Chloro-1-[4-(4-chloro-phenyl)-piperazin-1-yl]-ethanone and DMF. Column chromatography using a solvent mixture (hexane/ethyl acetate=1/4) afforded the title compound as a colorless oil. ¹H NMR (400 MHz, CDCl₃): 7.18-7.22 (d, 1H), 6.78-6.84 (d, 2H), 4.8 (s, 2H), 4.4 (s, 2H), 3.72-3.82 (m, 4H), 3.08-3.18 (m, 4H), 2.14 (s, 3H).

Synthesis of 1-[4-(4-Bromo-3-methoxyphenyl)-piperazin-1-yl]-2-(4-chloro-5-phenyl-3-trifluoromethyl-pyrazol-1-yl)-ethanone

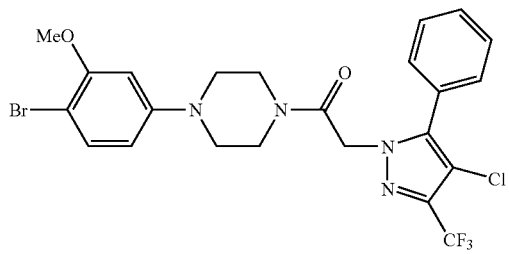

Protocol T was followed using 4-Chloro-5-phenyl-3-trifluoromethyl-1H-pyrazole, K₂CO₃, 2-Chloro-1-[4-(4-bromo-3-methoxy-phenyl)-piperazin-1-yl]-ethanone and DMF. Column chromatography using a solvent mixture (hexane/ethyl acetate=2/3: $R_f$=0.58) afforded the title compound as a white solid. ¹H NMR (400 MHz, CDCl₃): 7.81-7.86 (m, 1H), 7.36-7.44 (m, 4H), 6.42-6.48 (d, 1H), 6.34-6.38 (dd, 2H), 5.2 (s, 2H), 3.88 (s, 3H), 3.62-3.82 (m, 4H), 3.12-3.22 (m, 4H).

Synthesis of 1-[4-(4-Fluorophenyl)-piperazin-1-yl]-2-(3-trifluoromethyl-pyrazol)-ethanone

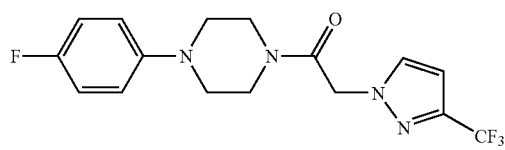

Protocol T was followed using 3-trifluoromethyl-1H-pyrazole, K₂CO₃, 2-Chloro-1-[4-(4-fluoro-phenyl)-piperazin-1-yl]-ethanone and DMF. Column chromatography using a solvent mixture (hexane/ethyl acetate=1/1) afforded the title compound as a white solid. ¹H NMR (400 MHz, CDCl₃): 7.54-7.60 (m, 1H), 6.94-7.0 (m, 2H), 6.80-6.88 (m, 2H), 6.52-6.58 (d, 1H), 5.2 (s, 2H), 3.72-3.80 (t, 2H), 3.62-3.72 (t, 2H), 3.02-3.12 (m, 4H). MS (ES) M+H expected 356.33, found 357.1.

Synthesis of 1-[4-(4-Fluorophenyl)-piperazin-1-yl]-2-(3-methyl-pyrazol)-ethanone

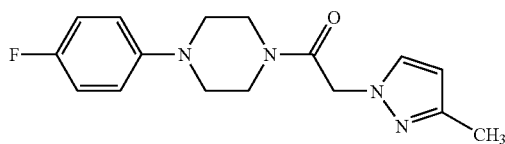

Protocol T was followed using 3-methyl-1H-pyrazole, K₂CO₃, 2-Chloro-1-[4-(4-fluoro-phenyl)-piperazin-1-yl]-ethanone and DMF. Column chromatography using a solvent mixture (hexane/ethyl acetate=1/1) afforded the title compound as a white solid. ¹H NMR (400 MHz, CDCl₃): 7.38-7.41 (m, 1H), 6.94-7.0 (m, 2H), 6.80-6.88 (m, 2H), 6.08-6.10 (d, 1H), 4.95 (s, 2H), 3.74-3.82 (t, 2H), 3.62-3.72 (t, 2H), 3.0-3.1 (m, 4H), 2.28 (s, 3H). MS (ES) M+H expected 302.05, found 303.1.

Synthesis of 1-{2-[4-(4-Fluoro-phenyl)-piperazin-1-yl]-2-oxo-ethyl}-1H-pyrazole-4-carboxylic acid ethyl ester

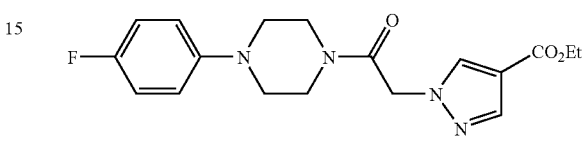

Protocol T was followed using 1H-Pyrazole-4-carboxylic acid ethyl ester, K₂CO₃, 2-Chloro-1-[4-(4-fluoro-phenyl)-piperazin-1-yl]-ethanone and DMF. Column chromatography using a solvent mixture (hexane/ethyl acetate=1/1) afforded the title compound as a white solid. ¹H NMR (400 MHz, CDCl₃): 8.2 (s, 1H), 7.92 (s, 1H), 6.94-7.0 (m, 2H), 6.82-6.88 (m, 2H), 5.0 (s, 2H), 4.1-4.2 (q, 2H), 3.74-3.82 (t, 2H), 3.62-3.72 (t, 2H), 3.0-3.12 (m, 4H), 1.28-1.42 (t, 3H). MS (ES) M+H expected 360.39, found 361.1.

Synthesis of 1-[4-(4-Fluorophenyl)-piperazin-1-yl]-2-(4-methyl-pyrazol)-ethanone

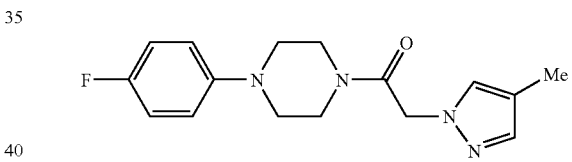

Protocol T was followed using 4-methyl-1H-pyrazole, K₂CO₃, 2-Chloro-1-[4-(4-fluoro-phenyl)-piperazin-1-yl]-ethanone and DMF. Column chromatography using a solvent mixture (hexane/ethyl acetate=1/1) afforded the title compound as a white solid. ¹H NMR (400 MHz, CDCl₃): 7.26-7.32 (m, 1H), 6.94-7.0 (m, 2H), 6.80-6.88 (m, 2H), 5.0 (s, 2H), 3.62-3.82 (m, 4H), 3.0-3.1 (m, 4H), 2.1 (s, 3H). MS (ES) M+H expected 302.35, found 303.1.

Synthesis of 1-[4-(4-Fluorophenyl)-piperazin-1-yl]-2-(3-amino-4-bromopyrazole)-ethanone

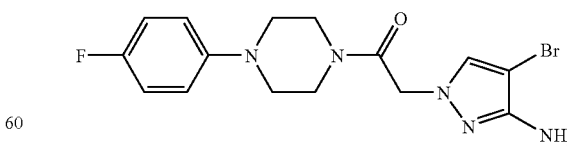

Protocol T was followed using 4-bromo-3-aminopyrazole, K₂CO₃, 2-Chloro-1-[4-(4-fluoro-phenyl)-piperazin-1-yl]-ethanone and DMF. Column chromatography using a solvent mixture (hexane/ethyl acetate=3/7) afforded the title compound as a white solid. ¹H NMR (400 MHz, CDCl₃): 7.23 (s, 1H), 6.94-7.0 (m, 2H), 6.80-6.88 (m, 2H), 4.9 (s, 2H), 4.2 (s, 2H), 3.72-3.82 (m, 4H), 3.0-3.14 (m, 4H). MS (ES) M+H expected 382.24, found 382.

Synthesis of 1-[4-(4-Fluorophenyl)-piperazin-1-yl]-2-(3-amino-4-cyanopyrazole)-ethanone

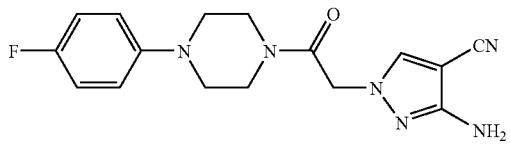

Protocol T was followed using 3-amino-4-cyano-pyrazole, $K_2CO_3$, 2-Chloro-1-[4-(4-fluoro-phenyl)-piperazin-1-yl]-ethanone and DMF. Column chromatography using a solvent mixture (hexane/ethyl acetate=3/7) afforded the title compound as a solid. $^1$H NMR (400 MHz, CDCl$_3$): 7.48 (s, 1H), 6.96-7.2 (m, 2H), 6.86-6.92 (m, 2H), 4.96 (s, 2H), 4.88 (s, 2H), 3.78-3.86 (m, 4H), 3.08-3.16 (m, 4H). MS (ES) M+H expected 328.25, found 329.1

Synthesis of 3-Amino-5-cyanomethyl-1-{2-[4-(4-fluoro-phenyl)-piperazin-1-yl]-2-oxo-ethyl}-1H-pyrazole-4-carbonitrile

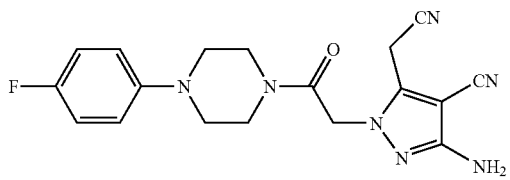

Protocol T was followed using 5-amino-3-cyanomethyl-1H-pyrazole-4-carbonitrile, $K_2CO_3$, 2-Chloro-1-[4-(4-fluoro-phenyl)-piperazin-1-yl]-ethanone and DMF. Column chromatography using a solvent mixture (hexane/ethyl acetate=3/2) afforded the title compound as white solid. $^1$H NMR (400 MHz, CDCl$_3$): 6.96-7.2 (m, 2H), 6.86-6.92 (m, 2H), 5.2 (s, 2H), 4.86 (s, 2H), 3.78-3.86 (m, 4H), 3.7 (s, 2H), 3.08-3.16 (m, 4H). MS (ES) M+H expected 367.39, found 368.1.

Synthesis of 1-[4-(4-Fluorophenyl)-piperazin-1-yl]-2-(4-chloro-pyrazol)-ethanone

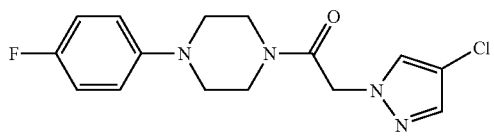

Protocol T was followed using 4-chloro-1H-pyrazole, $K_2CO_3$, 2-Chloro-1-[4-(4-fluoro-phenyl)-piperazin-1-yl]-ethanone and DMF. Column chromatography using a solvent mixture (hexane/ethyl acetate=3/2) afforded the title compound as a white solid. $^1$H NMR (400 MHz, CDCl$_3$): 7.54-7.56 (d, 2H), 7.46 (s, 1H), 6.94-7.2 (m, 2H), 6.84-6.88 (m, 2H), 4.98 (s, 2H), 3.62-3.82 (m, 4H), 3.0-3.1 (m, 4H). MS (ES) M+H expected 322.77, found 323.1

Synthesis of 2-(3-Amino-5-methyl-pyrazol-1-yl)-1-[4-(4-fluorophenyl)-piperazin-1-yl]-ethanone

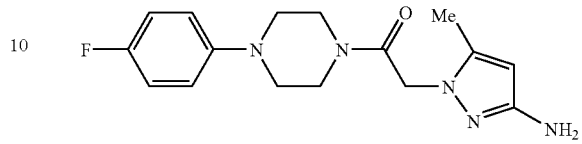

Protocol T was followed using 5-methyl-1H-pyrazol-3-ylamine, $K_2CO_3$, 2-Chloro-1-[4-(4-fluoro-phenyl)-piperazin-1-yl]-ethanone and DMF. Column chromatography using a solvent mixture (hexane/ethyl acetate=1/4) afforded the title compound as a colorless oil. $^1$H NMR (400 MHz, CDCl$_3$): 7.12-7.18 (m, 3H), 7.0-7.08 (t, 2H), 4.8 (s, 2H), 5.1 (s, 2H), 3.78-3.88 (m, 4H), 3.18-3.38 (m, 4H), 2.28 (s, 3H). MS (ES) M+H expected 317.37, found 318.1

Synthesis of 3-Amino-1-{2-[4-(4-fluoro-phenyl)-piperazin-1-yl]-2-oxo-ethyl}-5-methyl-1H-pyrazole-4-carboxylic acid ethyl ester

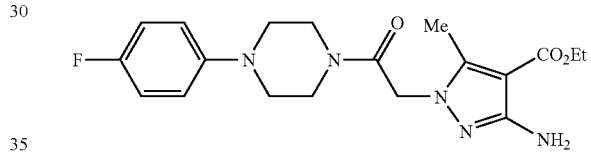

Protocol T was followed using 3-Amino-5-methyl-1H-pyrazole-4-carboxylic acid ethyl ester, $K_2CO_3$, 2-Chloro-1-[4-(4-fluoro-phenyl)-piperazin-1-yl]-ethanone and DMF. Column chromatography using a solvent mixture (hexane/ethyl acetate=1/4) afforded the title compound as a colorless oil. $^1$H NMR (400 MHz, CDCl$_3$): 6.94-7.1 (m, 2H), 6.84-6.88 (m, 2H), 5.52 (s, 2H), 4.78 (s, 2H), 4.24-4.32 (q, 2H), 3.74-3.82 (m, 4H), 3.0-3.1 (m, 4H), 2.3 (s, 3H), 1.31-1.38 (t, 3H). MS (ES) M+H expected 389.43, found 390.1.

Synthesis of 2-(3-Amino-4-chloro-5-methyl-pyrazol-1-yl)-1-[4-(4-fluorophenyl)-piperazin-1-yl]-ethanone

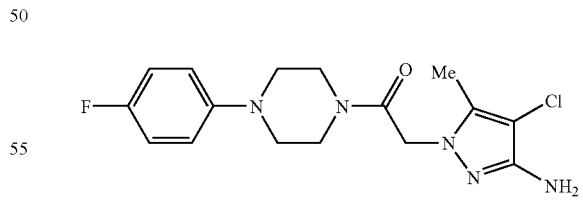

Protocol T was followed using 4-Chloro-5-methyl-1H-pyrazol-3-ylamine, $K_2CO_3$, 2-Chloro-1-[4-(4-fluoro-phenyl)-piperazin-1-yl]-ethanone and DMF. Column chromatography using a solvent mixture (hexane/ethyl acetate=1/4) afforded the title compound as colorless oil. $^1$H NMR (400 MHz, CDCl$_3$): 7.02-7.08 (m, 2H), 6.94-7.0 (t, 2H), 4.85 (s, 2H), 4.2 (s, 2H), 3.80-3.88 (m, 4H), 3.14-3.34 (m, 4H), 2.34 (s, 3H). MS (ES) M+H expected 317.37, found 318.1. MS (ES) M+H expected 351.81, found 352.1.

Synthesis of 2-(3-Amino-4-bromo-5-methyl-pyrazol-1-yl)-1-[4-(4-fluorophenyl)-piperazin-1-yl]-ethanone

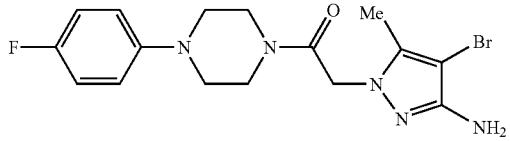

Protocol T was followed using 4-Bromo-5-methyl-1H-pyrazol-3-ylamine, K$_2$CO$_3$, 2-Chloro-1-[4-(4-fluoro-phenyl)-piperazin-1-yl]-ethanone and DMF. Column chromatography ethyl acetate afforded the title compound as a colorless oil. $^1$H NMR (400 MHz, CDCl$_3$): 6.94-7.02 (m, 2H), 6.82-6.88 (t, 2H), 4.84 (s, 2H), 4.1 (s, 2H), 3.72-3.78 (m, 4H), 3.04-3.08 (m, 4H), 2.16 (s, 3H). MS (ES) M+H expected 317.37, found 318.1. MS (ES) M+H expected 396.27, found 396.

Synthesis of 2-(5-tert-Butyl-3-trifluoromethyl-pyrazol-1-yl)-1-[4-(4-fluoro-phenyl)-piperazin-1-yl]-ethanone

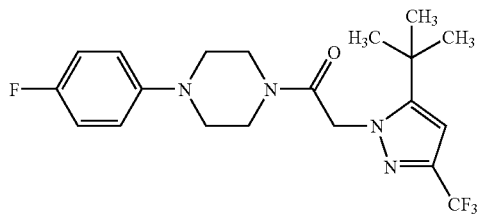

Protocol T was followed using 5-tert-Butyl-3-trifluoromethyl-1H-pyrazole, K$_2$CO$_3$, 2-Chloro-1-[4-(4-fluoro-phenyl)-piperazin-1-yl]-ethanone and DMF. Column chromatography using a solvent mixture (hexane/ethyl acetate=1/1) afforded the title compound as a colorless oil. $^1$H NMR (400 MHz, CDCl$_3$); 6.94-7.08 (t, 2H), 6.82-6.88 (dd, 2H), 6.32 (s, 1H), 5.14 (s, 2H), 3.62-3.80 (m, 4H), 3.05-3.18 (m, 4H), 1.35 (s, 9H). MS (ES) M+H expected 412.43, found 413.1

Synthesis of 2-{2-[4-(4-Fluoro-phenyl)-piperazin-1-yl]-2-oxo-ethyl}-5-methyl-2H-pyrazole-3-carboxylic acid ethyl ester

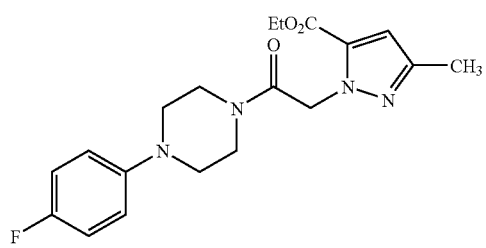

Protocol T was followed using 5-methyl-2H-pyrazole-3-carboxylic acid ethyl ester, K$_2$CO$_3$, 2-Chloro-1-[4-(4-fluoro-phenyl)-piperazin-1-yl]-ethanone and DMF. Column chromatography using a solvent mixture (hexane/ethyl acetate=1/1) afforded the title compound as a white solid. $^1$H NMR (400 MHz, CDCl$_3$): 6.94-7.0 (m, 2H), 6.84-6.88 (dd, 2H), 6.58 (s, 1H), 5.04 (s, 2H), 4.3-4.38 (q, 2H), 3.62-3.80 (m, 4H), 3.02-3.14 (m, 4H), 2.3 (s, 3H), 1.32-1.38 (t, 3H). $^{13}$C NMR (400 MHz, CDCl$_3$): 180, 165, 119, 116.2, 116, 109, 61.8, 52, 51.5, 50.8, 45.8, 42.6, 14.4, 10.2.

Synthesis of 2-(3,5-Diisopropyl-4-chloro-pyrazol-1-yl)-1-[4-(4-fluoro-phenyl)-piperazin-1-yl]-ethanone

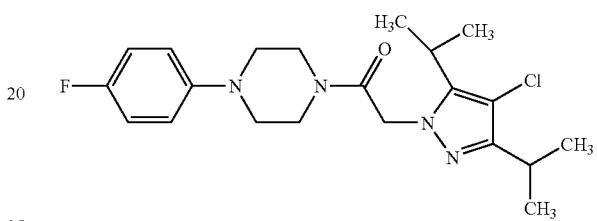

Protocol T was followed using 3,5-Diisopropyl-4-chloro-1H-pyrazole, K$_2$CO$_3$, 2-Chloro-1-[4-(4-fluoro-phenyl)-piperazin-1-yl]-ethanone and DMF. Column chromatography using a solvent mixture (hexane/ethyl acetate=1/1, R$_f$=0.76) afforded the title compound as white solid. MS (ES) M+H expected=406.9, found 407.1.

Synthesis of 2-{2-[4-(4-Chloro-phenyl)-piperazin-1-yl]-2-oxo-ethyl}-5-thiophen-2-yl-2H-pyrazole-3-carboxylic acid ethyl ester

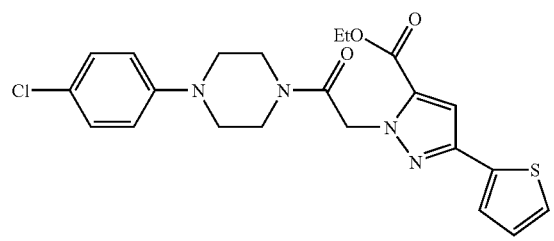

Protocol T was followed using 5-Thiophen-2-yl-2H-pyrazole-3-carboxylic acid ethyl ester, K$_2$CO$_3$, 2-Chloro-1-[4-(4-Chloro-phenyl)-piperazin-1-yl]-ethanone and DMF. Column chromatography using a solvent mixture (hexane/ethyl acetate=1.5/1) afforded the title compound. $^1$H NMR (400 MHz, CDCl$_3$): 7.34-7.38 (m, 1H), 7.24-7.26 (m, 1H), 7.12 (s, 1H), 7.04-7.08 (dd, 1H), 6.96-7.2 (m, 2H), 6.88-6.94 (m, 2H), 4.32-4.42 (q, 2H), 3.52-3.58 (m, 4H), 3.05-3.35 (m, 4H), 1.32-1.42 (m, 3H). $^{13}$C NMR (400 MHz, CDCl$_3$): 164.2, 128, 126.8, 126.6, 120.2, 118.4, 115.2, 62.5, 54.2, 50.5, 42.6, 44, 14.6.

Synthesis of 2-(4-Amino-3-heptafluoropropyl-5-methyl-pyrazol-1-yl)-1-[4-(4-chloro-phenyl)-piperazin-1-yl]-ethanone

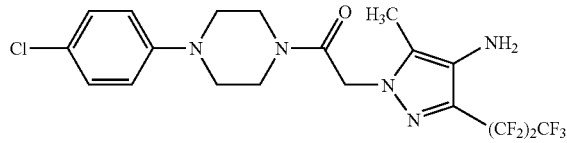

Protocol T was followed using 4-Amino-3-heptafluoropropyl-5-methyl-1H-pyrazole, $K_2CO_3$, 2-Chloro-1-[4-(4-chloro-phenyl)-piperazin-1-yl]-ethanone and DMF. Column chromatography using a solvent mixture (hexane/ethyl acetate=1/4, $R_f$=0.42) afforded the title compound as colorless oil. $^1$H NMR (400 MHz, $CDCl_3$); 6.88-6.94 (d, 2H), 7.22-7.26 (d, 2H), 4.98 (s, 2H), 3.64-3.82 (m, 4H), 3.1-3.22 (m, 4H), 2.98 (s, 2H), 2.18 (s, 3H). MS (ES) M+H) expected=501.82, found 502.1.

Synthesis of 1-[4-(4-Chloro-3-methoxy-phenyl)-piperazin-1-yl]-2-(4-chloro-5-ethyl-3-trifluoromethyl-pyrazol-1-yl)-ethanone

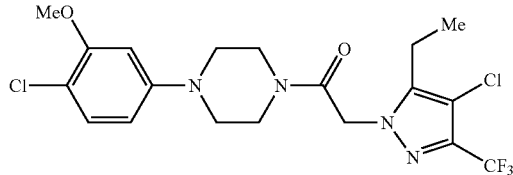

Protocol T was followed using 4-Chloro-5-ethyl-3-trifluoromethyl-1-H-pyrazol, $K_2CO_3$, 1-[4-(4-Chloro-3-methoxyphenyl)-piperazine-1-yl]-ethanone and DMF. Column chromatography using a solvent mixture (hexane/ethyl acetate=2/3, $R_f$=0.53) afforded the title compound as white solid. $^1$H NMR (400 MHz, $CDCl_3$); 7.18-7.22 (d, 2H), 6.38-6.48 (m, 2H), 4.98 (s, 2H), 3.86 (s, 3H), 3.66-3.76 (m, 4H), 3.1-3.2 (m, 4H), 2.66-2.74 (q, 2H), 1.18-1.28 (m, 3H). MS (ES) M+H) expected=464.82, found 465.

Synthesis of 2-(4-Chloro-5-isopropyl-3-trifluoromethyl-pyrazol-1-yl)-1-[4-(4-chloro-3-methoxy-phenyl)-piperazin-1-yl]-ethanone

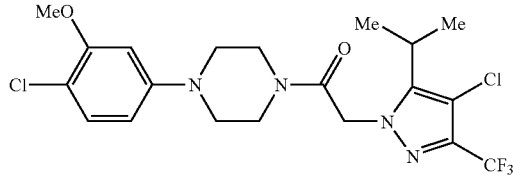

Protocol T was followed using 4-Chloro-5-isopropyl-3-trifluoromethyl-1-H-pyrazol, $K_2CO_3$, 1-[4-(4-Chloro-3-methoxyphenyl)-piperazine-1-yl]-ethanone and DMF. Column chromatography using a solvent mixture (hexane/ethyl acetate=5.5/4.5, $R_f$=0.52) afforded the title compound as white solid. $^1$H NMR (400 MHz, $CDCl_3$); 7.19-7.22 (d, 2H), 6.42-6.48 (m, 2H), 5.18 (s, 2H), 3.88 (s, 3H), 3.56-3.78 (m, 4H), 3.22-3.44 (m, 4H), 3.04-3.14 (m, 1H), 1.44-1.48 (d, 6H). $^{13}$C NMR (400 MHz, $CDCl_3$): 164.2, 154.8, 151, 130, 109.8, 102, 56.2, 54, 50.5, 50, 45.2, 42.6, 26.2, 22.1.

Synthesis of 2-(4-Chloro-3-isopropyl-5-trifluoromethyl-pyrazol-1-yl)-1-[4-(4-chloro-3-methoxy-phenyl)-piperazin-1-yl]-ethanone

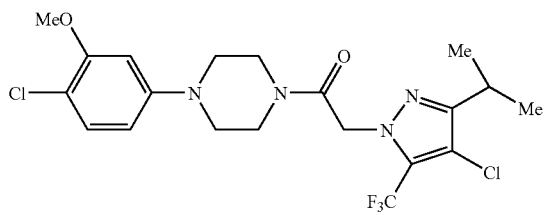

Protocol T was followed using 4-Chloro-3-isopropyl-5-trifluoromethyl-1-H-pyrazol, $K_2CO_3$, 1-[4-(4-Chloro-3-methoxyphenyl)-piperazine-1-yl]-ethanone and DMF. Column chromatography using a solvent mixture (hexane/ethyl acetate=2/3, $R_f$=0.45) afforded the title compound as white solid. $^1$H NMR (400 MHz, $CDCl_3$); 7.19-7.22 (d, 2H), 6.38-6.48 (m, 2H), 5 (s, 2H), 3.86 (s, 3H), 3.62-3.78 (m, 4H), 3.08-3.18 (m, 4H), 2.98-3.04 (m, 1H), 1.35-1.41 (d, 6H). $^{13}$C NMR (400 MHz, $CDCl_3$): 163.8, 154.8, 150.5, 130, 109.8, 102, 56.4, 52.8, 50, 49.8, 45.2, 42.6, 26.8, 20.

Synthesis of 2-(4-Chloro-3-n-propyl-5-trifluoromethyl-pyrazol-1-yl)-1-[4-(4-chloro-3-methoxy-phenyl)-piperazin-1-yl]-ethanone

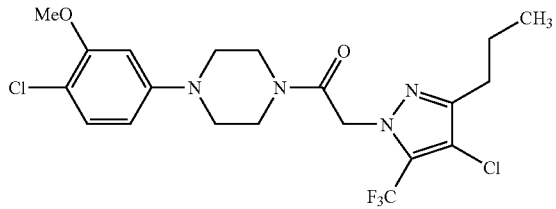

Protocol T was followed using 4-Chloro-3-n-propyl-5-trifluoromethyl-1-H-pyrazol, $K_2CO_3$, 1-[4-(4-Chloro-3-methoxyphenyl)-piperazine-1-yl]-ethanone and DMF. Column chromatography using a solvent mixture (hexane/ethyl acetate=3/7, $R_f$=0.78) afforded the title compound as white solid. $^1$H NMR (400 MHz, $CDCl_3$); 7.22-7.24 (d, 2H), 6.42-6.48 (m, 2H), 5.7 (s, 2H), 3.8 (s, 3H), 3.72-3.78 (m, 4H), 3.22-3.42 (m, 4H), 2.66-2.72 (t, 2H), 1.58-1.68 (m, 2H), 0.98-1.02 (t, 3H). $^{13}$C NMR (400 MHz, $CDCl_3$): 164, 154.8, 150.5, 130, 109.8, 102.2, 56.4, 52.8, 50, 49.8, 45.2, 42.6, 26, 21.8, 14.

Synthesis of 1-[4-(4-Chloro-3-methoxyphenyl)-piperazin-1-yl]-2-(4-bromo-3-phenyl-5-trifluoromethyl-pyrazol-1-yl)-ethanone

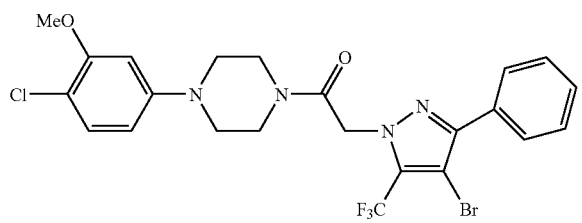

Protocol T was followed using 4-Bromo-3-phenyl-5-trifluoromethyl-1H-pyrazole, $K_2CO_3$, 2-Chloro-1-[4-(4-chloro-3-methoxy-phenyl)-piperazin-1-yl]-ethanone and DMF. Column chromatography using a solvent mixture (hexane/ethyl acetate=1/1, $R_f$=0.51) afforded the title compound as a white solid. $^1$H NMR (400 MHz, $CDCl_3$): 7.42-7.52 (m, 5H), 7.18-7.22 (d, 1H), 6.38-6.42 (dd, 1H), 6.46-6.48 (d, 1H), 4.94 (s, 2H), 3.88 (s, 3H), 3.5-3.78 (m, 4H), 3.18 (s, 4H).

Synthesis of 1-[4-(4-Chloro-3-methoxyphenyl)-piperazin-1-yl]-2-(4-chloro-5-phenyl-3-trifluoromethyl-pyrazol-1-yl)-ethanone

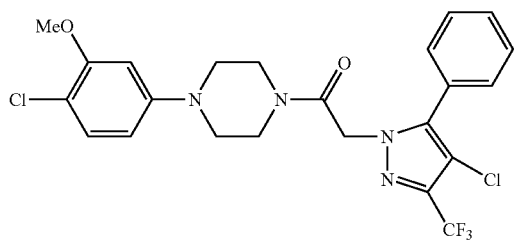

Protocol T was followed using 4-Chloro-5-phenyl-3-trifluoromethyl-1H-pyrazole, $K_2CO_3$, 2-Chloro-1-[4-(4-chloro-3-methoxy-phenyl)-piperazin-1-yl]-ethanone and DMF. Column chromatography using a solvent mixture (hexane/ethyl acetate=2/3, $R_f$=0.92) afforded the title compound as a white solid. $^1$H NMR (400 MHz, $CDCl_3$): 7.78-7.84 (m, 2H), 7.36-7.52 (m, 4H), 6.38-6.48 (m, 2H), 5.2 (s, 2H), 3.88 (s, 3H), 3.62-3.78 (m, 4H), 3.18-3.26 (s, 4H). $^{13}$C NMR (400 MHz, $CDCl_3$) 164.4, 156, 150.4, 130.4, 130, 128.6, 110.2, 102.4, 56.4, 52, 50.4, 44.6, 42.

Synthesis of 1-[4-(4-Chloro-3-methoxyphenyl)-piperazin-1-yl]-2-(4-chloro-3-[3-Fluoro-phenyl]-5-trifluoromethyl-pyrazol-1-yl)-ethanone

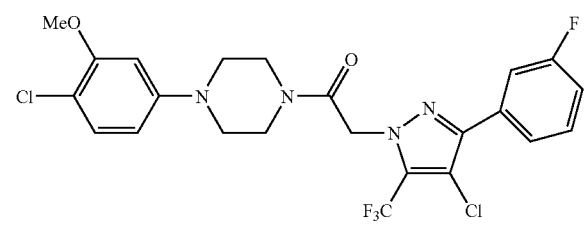

Protocol T was followed using 4-Chloro-3-[3-Fluorophenyl]-5-trifluoromethyl-1H-pyrazole, $K_2CO_3$, 2-Chloro-1-[4-(4-chloro-3-methoxy-phenyl)-piperazin-1-yl]-ethanone and DMF. Column chromatography using a solvent mixture (hexane/ethyl acetate=2/3, $R^f$=0.51) afforded the title compound as a white solid. $^1$H NMR (400 MHz, $CDCl_3$): 7.44-7.52 (m, 1H), 7.18-7.28 (m, 4H), 6.38-6.48 (m, 2H), 4.94 (s, 2H), 3.84 (s, 3H), 3.52-3.78 (m, 4H), 3.12 (s, 4H).

Synthesis of 1-[4-(4-Chloro-3-methoxyphenyl)-piperazin-1-yl]-2-(4-chloro-5-[3-Fluoro-phenyl]-3-trifluoromethyl-pyrazol-1-yl)-ethanone

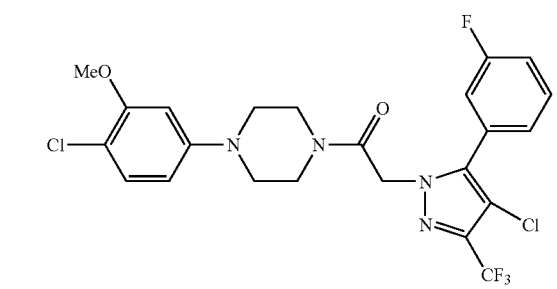

Protocol T was followed using 4-Chloro-5-[3-Fluorophenyl]-3-trifluoromethyl-1H-pyrazole, $K_2CO_3$, 2-Chloro-1-[4-(4-chloro-3-methoxy-phenyl)-piperazin-1-yl]-ethanone and DMF. Column chromatography using a solvent mixture (hexane/ethyl acetate=2/3, $R^f$=0.59) afforded the title compound as a white solid. $^1$H NMR (400 MHz, $CDCl_3$): 7.64-7.68 (d, 1H), 7.56-7.62 (d, 1H), 7.36-7.42 (m, 1H), 7.22-7.24 (m, 2H), 7.08-7.12 (m, 1H), 6.42-6.52 (m, 2H), 5.2 (s, 2H), 3.9 (s, 3H), 3.62-3.82 (m, 4H), 3.12-3.22 (m, 4H).

Protocol U: for the K$_2$CO$_3$ Mediated Coupling Reaction of Chloroacetyl Substituted Arylpiperazines with Novel Heteraryl Ring Systems Synthesis of 1-[4-(4-Fluoro-phenyl)-piperazin-1-yl]-2-[5-nitro-indazol-1-yl]-ethanone

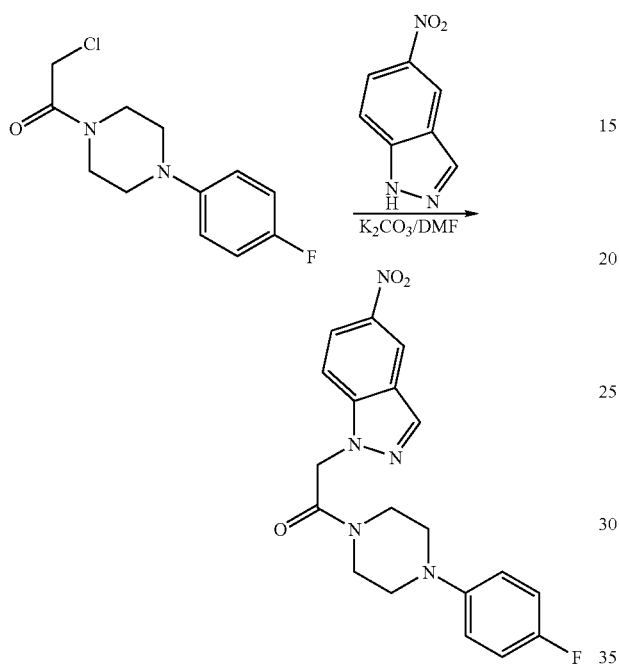

2-Chloro-1-[4-(4-fluoro-phenyl)-piperazin-1-yl]-ethanone (0.834 g, 3.3 mmol) was taken in dry DMF (15 mL) and dry potassium carbonate (1.6 g, 11.6 mmol) was added to it and the reaction mixture stirred at room temperature for 1 h under nitrogen. 5-Nitro-1H-indazole (0.5 g, 2.9 mmol) in DMF (2 mL) was then added to the mixture through a syringe. The reaction was heated at 70° C. for 14 h, cooled and then quenched with water and extracted with ethyl acetate. Drying of the organic layer with Na$_2$SO$_4$ followed by concentration afforded material that on purification on neutral alumina column (pet ether/ethyl acetate) gave title compound as a pale yellow solid.

Synthesis of 1-[4-(4-Fluoro-phenyl)-piperazin-1-yl]-2-[7-nitro-indazol-1-yl]-ethanone

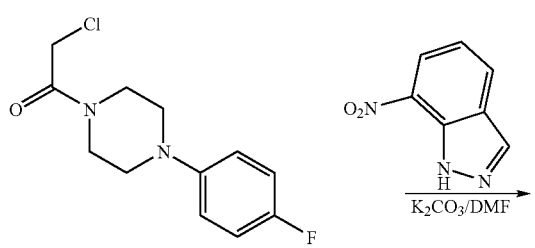

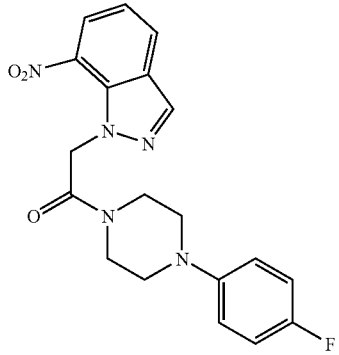

2-Chloro-1-[4-(4-fluoro-phenyl)-piperazin-1-yl]-ethanone (0.834 g, 3.3 mmol) was taken in dry DMF (15 mL) and dry potassium carbonate (1.6 g, 11.6 mmol) was added to it and the reaction mixture stirred at room temperature for 1 h under nitrogen. 7-Nitro-1H-indazole (0.5 g, 2.9 mmol) in DMF (2 mL) was then added to the mixture through a syringe. The reaction was then heated at 70° C. for 14 h, cooled and then quenched with water and extracted with ethyl acetate. Drying of the organic layer with Na$_2$SO$_4$ followed by concentration afforded material that was purified on neutral alumina column (pet ether/ethyl acetate). The resulting solid was recrystallized from DCM/pet ether to obtain pure product as a pale yellow solid.

Synthesis of 2-Benzoimidazol-1-yl-1-[4-(4-chloro-phenyl)-piperazin-1-yl]-ethanone

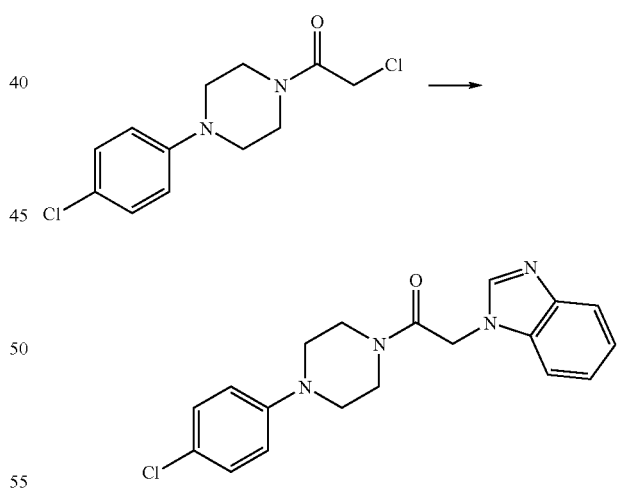

Benzimidazole (0.785 g, 0.7 mmol) was taken in dry DMF (15 ml) and dry potassium carbonate (340 mg) and KI (20 mg) was added to it and the reaction mixture stirred at room temperature for 1 h under nitrogen. 2-Chloro-1-[4-(4-chloro-phenyl)-piperazin-1-yl]-ethanone (200 mg, 1.1 mmol) in DMF (5 ml) was then added to the mixture through a syringe. The reaction was then heated at 140° C. for 14 h, cooled and then quenched with water and extracted with ethyl acetate. Drying of the organic layer with Na$_2$SO$_4$ followed by concentration gave material that on purification by flash chromatography (CHCl3/MeOH) afforded pure product: $^1$H NMR (300 MHz, CDCl$_3$): δ 8.10-7.65 (m, 4H), 7.26 (d, 2H), 6.83 (d, 2H), 4.99 (s, 2H), 3.79-3.66 (m, 4H), 3.14 (br, 4H).

Synthesis of 1-[4-(4-Chloro-phenyl)-piperazin-1-yl]-2-(2,4-dimethyl-imidazol-1-yl)-ethanone

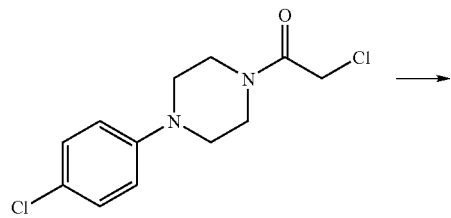

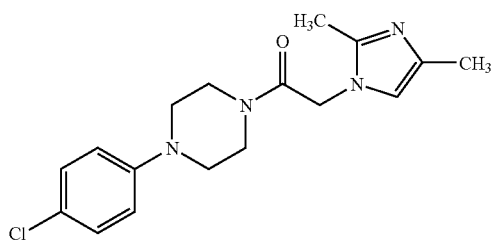

2,4-dimethylimidazole (0.633 g, 0.7 mmol) was taken up in dry DMF (15 ml) and dry potassium carbonate (340 mg) and KI (20 mg) was added and the reaction mixture was stirred at room temperature for 1 h under nitrogen. 2-Chloro-1-[4-(4-chloro-phenyl)-piperazin-1-yl]-ethanone (200 mg, 1.1 mmol) in DMF (5 ml) was then added to the mixture through a syringe. The reaction was then heated at 140° C. for 14 h, cooled and quenched with water and extracted with ethyl acetate. Drying of the organic layer with Na$_2$SO$_4$ followed by concentration gave material that was purified on a silica gel column (CHCl3/MeOH): $^1$H NMR (300 MHz, CDCl$_3$): δ 7.25 (d, 2H), 6.80 (d, 2H), 6.53 (s, 1H), 4.62 (s, 2H), 3.78 (br, 2H), 3.59 (br, 2H), 3.21 (br, 4H), 2.31 (s, 3H), 2.17 (s, 1H).

Synthesis of 2-(5-Amino-3-methylsulfanyl-[1,2,4]triazol-1-yl)-1-[4-(4-chloro-phenyl)-piperazin-1-yl]-ethanone

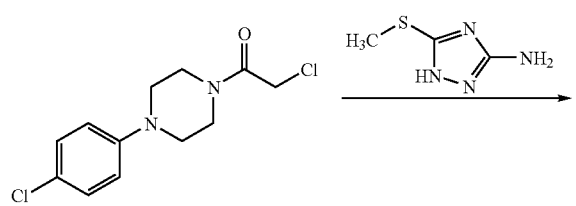

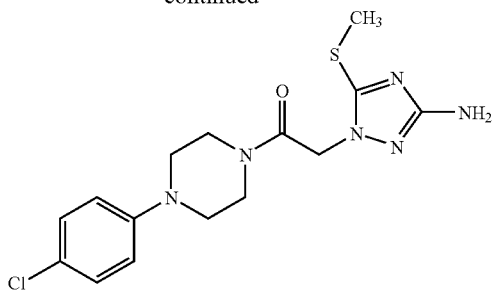

5-Methylsulfanyl-2H-[1,2,4]triazol-3-ylamine (0.216 g, 1.7 mmol) was taken in dry DMF (15 ml) and dry potassium carbonate (800 mg) and KI (20 mg) was added to it and the reaction mixture stirred at room temperature for 1 h under nitrogen. 2-Chloro-1-[4-(4-chloro-phenyl)-piperazin-1-yl]-ethanone (500 mg, 1.8 mmol) in DMF (5 ml) was then added to the mixture through a syringe. The reaction was then heated at 140° C. for 14 h, cooled and then quenched with water and extracted with ethyl acetate. Drying of the organic layer with Na$_2$SO$_4$ followed by concentration afforded crude product that was purified by column chromatography (CHCl3/MeOH): $^1$H NMR (300 MHz, DMSO-d6): δ 7.24 (d, 2H), 6.98 (d, 2H), 6.24 (s, 2H), 4.84 (s, 2H), 3.57 (m, 4H), 3.21 (m, 2H), 3.13 (m, 2H), 2.37 (s, 3H).

Synthesis of 2-[5-(2-Bromo-phenyl)-tetrazol-1-yl]-1-[4-(4-chloro-phenyl)-piperazin-1-yl]-ethanone

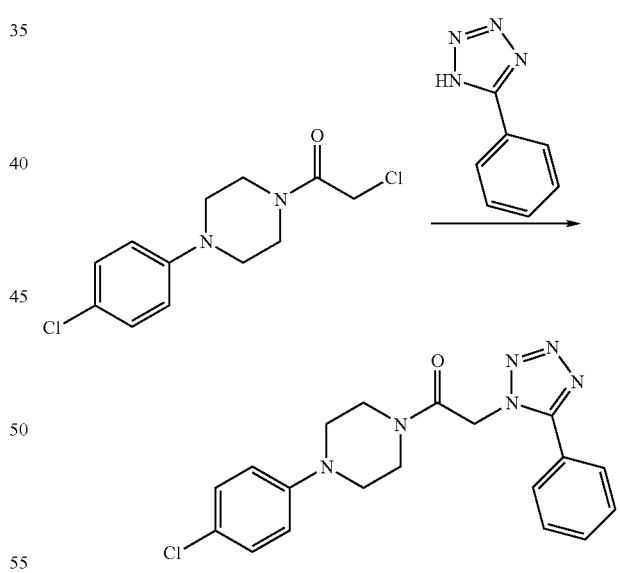

5-phenyl-1H-tetrazole (0.1216 g, 0.832 mmol) was taken in dry DMF (15 ml) and dry potassium carbonate (400 mg) and KI (20 mg) was added to it and the reaction mixture stirred at room temperature for 1 h under nitrogen. 2-Chloro-1-[4-(4-chloro-phenyl)-piperazin-1-yl]-ethanone (250 mg, 0.92 mmol) in DMF (5 ml) was then added to the mixture through a syringe. The reaction was then heated at 140° C. for 14 h, cooled and extracted with ethyl acetate. Drying of the organic layer with Na$_2$SO$_4$ followed by concentration afforded material that was further purified by flash column chromatography (ethyl acetate/pet ether): $^1$H NMR (300 MHz, CDCl$_3$): δ 8.17 (br, 2H), 7.49 (br, 3H), 7.24 (br, 2H), 6.85 (br, 2H), 5.60 (s, 2H), 3.82 (m, 2H), 3.71 (m, 2H), 3.19 (m, 4H).

Synthesis of 2-[5-(2-Bromo-phenyl)-tetrazol-1-yl]-1-[4-(4-chloro-phenyl)-piperazin-1-yl]-ethanone

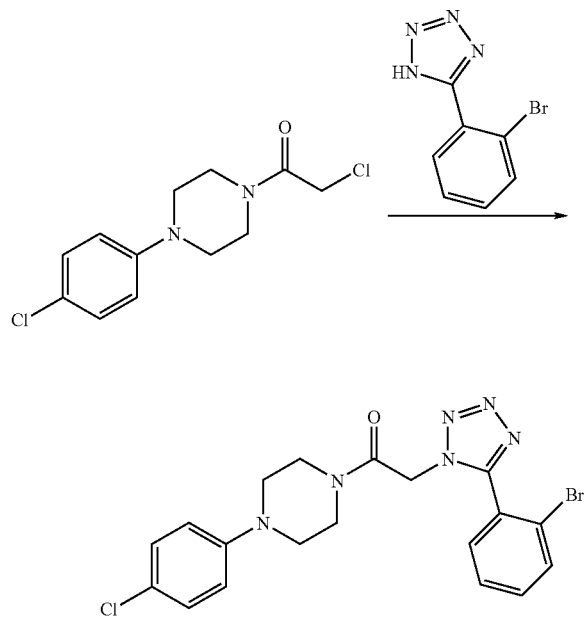

5-(2-Bromo-phenyl)-1H-tetrazole (0.374 g, 1.66 mmol) was taken in dry DMF (15 mL) and dry potassium carbonate (800 mg) and KI (20 mg) was added to it and stirred at rt for 1 h under nitrogen. 2-Chloro-1-[4-(4-chloro-phenyl)-piperazin-1-yl]-ethanone (500 mg, 1.8 mmol) in DMF (5 mL) was then added to the mixture through a syringe. The reaction was then heated at 140° C. for 14 h, cooled and quenched with water and extracted with ethyl acetate. Drying of the organic layer with Na$_2$SO$_4$ followed by concentration afforded material that was further purified by flash column chromatography (ethyl acetate/pet ether): $^1$H NMR (300 MHz, CDCl$_3$): δ 7.90 (d, 1H), 7.74 (d, 1H), 7.45 (t, 1H), 7.35 (t, 1H), 7.25 (d, 2H), 6.87 (d, 2H), 5.65 (s, 2H), 3.84 (m, 2H), 3.73 (m, 2H), 3.20 (m, 4H).

Preparation of Compounds with Modified Linker Regions
α-Substituted Acetyl Linkers Synthesis of 2-(4-Chloro-5-methyl-3-trifluoromethyl-pyrazol-1-yl)-1-[4-(4-fluoro-phenyl)-piperazin-1-yl]-propan-1-one

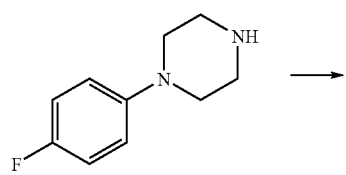

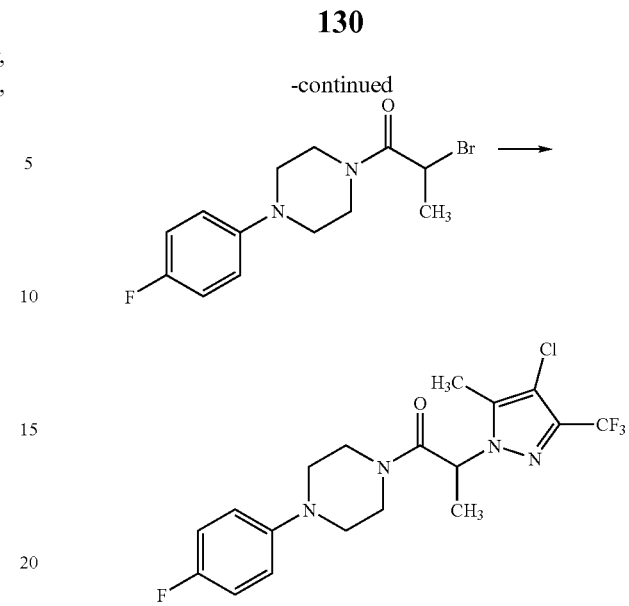

1-(4-Fluorophenyl)-piperazine (1 g, 5.5 mmol) dissolved in dry CH$_2$Cl$_2$ (20 ml) was cooled to 0° C. and triethylamine (1.66 g, 16.5 mmol) was added to it. 2-bromopropionyl chloride (1.14 g, 6.6 mol) was added slowly and the reaction mixture stirred for another 1 h at the same temperature. The mixture was washed with sodium bicarbonate and brine and dried (Na$_2$SO$_4$). Evaporation of the solvent afforded the intermediate alkyl bromide (0.68 g, 3.7 mmol) which was taken into dry DMF (20 ml). Potassium carbonate (2.1 g) was added. After stirring for 1 h at room temperature under nitrogen, 3-Methyl-4-chloro-5-trifluoromethyl-(1H)-pyrazole (1.3 g, 4.1 mmol) in DMF (5 ml) was then added to the mixture through a syringe. The reaction was then heated at 70° C. for 14 h, cooled and quenched with water and extracted with ethyl acetate. Drying of the organic layer over Na$_2$SO$_4$ followed by concentration afforded material that was purified on a neutral alumina column (chloroform/methanol).

Synthesis of 2-(4-Chloro-5-methyl-3-trifluoromethyl-pyrazol-1-yl)-1-[4-(4-chloro-phenyl)-piperazin-1-yl]-2-phenyl-ethanone

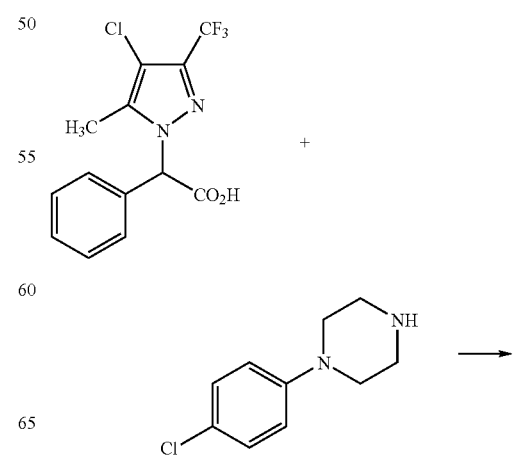

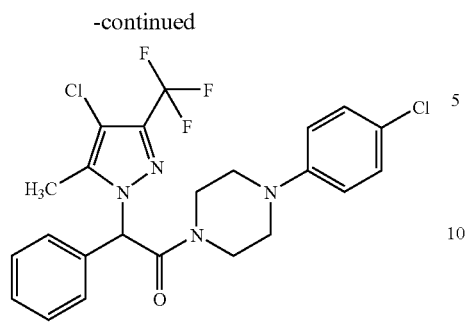

To 4-Chloro-5-methyl-3-(trifluoromethyl)-1H-pyrazol-1-yl] phenylacetic acid (0.1 g, 0.00036 mol) and 1-(4-chlorophenyl) piperazine (0.060 g, 0.00031 mol) in 20 ml of dry $CH_2Cl_2$ was added 0.2 ml of triethylamine and the reaction mixture stirred at room temperature for 30 min. TBTU (0.1 g, 0.00031 mol) was then added and the reaction mixture was stirred at room temperature for 17 h. The reaction mixture was diluted with 60 ml of $CH_2Cl_2$ and washed with saturated aqueous $NaHCO_3$ (2×50 ml), brine and then dried over sodium sulfate. The crude product obtained after concentration was purified by column chromatography to give the product as an off white solid: $^1H$ NMR (CDCl$_3$, 300 MHz) 7.40-6.61 (m, 10H), 3.99 (m, 1H), 3.80 (m, 1H), 3.50-2.81 (m, 6H), 1.90 (s, 3H) ppm; MS (ES) M+H expected=497.1, found 497.2.

Synthesis of 2-(4-Chloro-5-methyl-3-trifluoromethyl-pyrazol-1-yl)-1-[4-(4-chloro-phenyl)-piperazin-1-yl]-2-(3-methoxy-phenyl)-ethanone

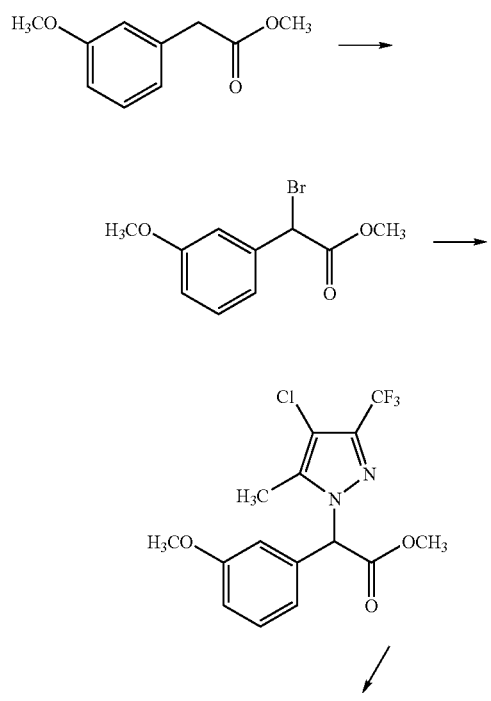

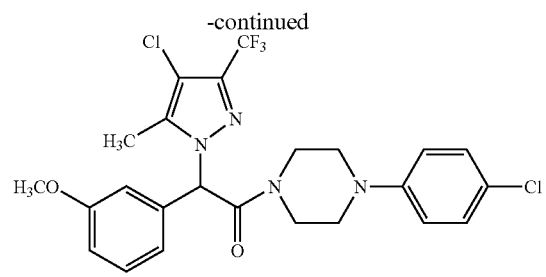

AIBN (10 mg) was added to a solution of (3-Methoxyphenyl)-acetic acid methyl ester (2 g, 11 mmol) in $CCl_4$ (30 ml). The solution was then heated to reflux and NBS (2.3 g, 13 mmol) was added in portions. After complete addition the reaction mixture was refluxed for 4 h. After cooling, solid residue was filtered off and the filtrate concentrated to yield product Bromo-(3-methoxy-phenyl)-acetic acid methyl ester, that was washed repeatedly with pet ether.

4-Chloro-3-methyl-5-trifluoromethyl-1H-pyrazole (610 mg, 3.3 mmol) was taken into dry $CH_3CN$ (15 ml), dry potassium carbonate (1.15 g) was added to this and the resulting mixture stirred at room temperature for 1 h under nitrogen. Bromo-(3-methoxy-phenyl)-acetic acid methyl ester (900 mg, 2.8 mmol) in CH3CN (5 ml) was then added to the mixture through a syringe. The reaction was then heated at reflux for 10 h, cooled and then filtered through a celite filter bed. The filtrate was concentrated to obtain (4-Chloro-5-methyl-3-trifluoromethyl-pyrazol-1-yl)-(3-methoxy-phenyl)-acetic acid ethyl ester that was purified by column chromatography on silica (pet ether/ethyl acetate)

(4-Chloro-5-methyl-3-trifluoromethyl-pyrazol-1-yl)-(3-methoxy-phenyl)-acetic acid methyl ester was then dissolved in THF (20 ml) and LiOH (0.39 g) in water (5 ml) were added. The mixture was stirred at room temperature for 4 h. After this period the THF was completely evaporated from the reaction mixture under vacuum. The remaining aqueous layer was extracted with ethyl acetate (3×5 ml) and the organic layer was discarded. The aqueous layer was cooled in ice and neutralized by using concentrated HCl. This neutral aqueous layer was extracted with ethyl acetate (3×10 ml), the organic layer dried over $Na_2SO_4$, concentrated and purified by flash chromatography (CHCl3/MeOH) to yield (4-Chloro-5-methyl-3-trifluoromethyl-pyrazol-1-yl)-(3-methoxy-phenyl)-acetic acid This compound (90 mg, 0.275 mmol) was taken into dry $CH_2Cl_2$ (10 ml) and cooled to 0° C. To this cold mixture was first added 4-chlorophenyl-piperazine (0.059 g, 0.3 mmol) followed by the addition of T3P (0.35 g, 0.55 mmol, 50% solution in EtOAc). The reaction was left overnight at room temperature. The mixture was diluted with $CH_2Cl_2$, and then washed sequentially with saturated NaHCO3 solution, brine, dried over Na2SO4, and concentrated to afford the crude product. Purification by column chromatography on neutral alumina yielded 2-(4-Chloro-5-methyl-3-trifluoromethyl-pyrazol-1-yl)-1-[4-(4-chloro-phenyl)-piperazin-1-yl]-2-(3-methoxy-phenyl)-ethanone: $^1H$ NMR (300 MHz, CDCl$_3$): δ 7.37-7.21 (m, 3H), 6.96-6.79 (m, 4H), 6.60 (s, 1H), 5.31 (s, 1H), 3.99 (m, 1H), 3.80 (s, 3H), 3.79 (m, 1H), 3.46 (m, 2H), 3.24 (m, 1H), 3.13 (m, 2H), 2.91 (m, 1H), 1.95 (s, 3H).

Example 2

This example illustrates the activity associated with representative compounds of the invention.

Materials and Methods

A. Cells

CCR1 Expressing Cells a. THP-1 cells

THP-1 cells were obtained from ATCC and cultured as a suspension in RPMI-1640 medium supplemented with 2 mM L-glutamine, 1.5 g/L sodium bicarbonate, 4.5 g/L glucose, 10 mM HEPES, 1 mM sodium pyruvate, 0.05% 2-mercaptoethanol and 10% FBS. Cells were grown under 5% $CO_2$/95% air, 100% humidity at 37° C. and subcultured twice weekly at 1:5 and harvested at $1\times10^6$ cells/ml. THP-1 cells express CCR1 and can be used in CCR1 binding and functional assays.

b. Isolated Human Monocytes

Monocytes were isolated from human buffy coats using the Miltenyi bead isolation system (Miltenyi, Auburn, Calif.). Briefly, following a Ficoll gradient separation to isolate peripheral blood mononuclear cells, cells were washed with PBS and the red blood cells lysed using standard procedures. Remaining cells were labeled with anti-CD14 antibodies coupled to magnetic beads (Miltenyi Biotech, Auburn, Calif.). Labeled cells were passed through AutoMACS (Miltenyi, Auburn, Calif.) and positive fraction collected. Monocytes express CCR1 and can be used in CCR1 binding and functional assays.

B. Assays

Inhibition of CCR1 Ligand Binding

CCR1 expressing cells were centrifuged and resuspended in assay buffer (20 mM HEPES pH 7.1, 140 mM NaCl, 1 mM $CaCl_2$, 5 mM $MgCl_2$, and with 0.2% bovine serum albumin) to a concentration of $2.2\times10^5$ cells/ml for THP-1 cells and $1.1\times10^6$ for monocytes. Binding assays were set up as follows. First, 0.09 ml of cells ($1\times10^5$ THP-1 cells/well or $5\times10^5$ monocytes) was added to the assay plates containing the compounds, giving a final concentration of 2-10 µM each compound for screening (or part of a dose response for compound $IC_{50}$ determinations). Then 0.09 ml of $^{125}I$ labeled MIP-1α (obtained from Amersham; Piscataway, N.J.) diluted in assay buffer to a final concentration of ~50 pM, yielding ~30,000 cpm per well, was added, the plates sealed and incubated for approximately 3 hours at 4° C. on a shaker platform. Reactions were aspirated onto GF/B glass filters pre-soaked in 0.3% polyethyleneimine (PEI) solution, on a vacuum cell harvester (Packard Instruments; Meriden, Conn.). Scintillation fluid (50 µl; Microscint 20, Packard Instruments) was added to each well, the plates were sealed and radioactivity measured in a Top Count scintillation counter (Packard Instruments). Control wells containing either diluent only (for total counts) or excess MIP-1α or MIP-1β (1 µg/ml, for non-specific binding) were used to calculate the percent of total inhibition for compound. The computer program Prism from GraphPad, Inc. (San Diego, Calif.) was used to calculate $IC_{50}$ values. $IC_{50}$ values are those concentrations required to reduce the binding of labeled MIP-1α to the receptor by 50%.

Calcium Mobilization

To detect the release of intracellular stores of calcium, cells (THP-1 or monocytes) were incubated with 3 µM of INDO-1AM dye (Molecular Probes; Eugene, Oreg.) in cell media for 45 minutes at room temperature and washed with phosphate buffered saline (PBS). After INDO-1AM loading, the cells were resuspended in flux buffer (Hank's balanced salt solution (HBSS) and 1% FBS). Calcium mobilization was measured using a Photon Technology International spectrophotometer (Photon Technology International; New Jersey) with excitation at 350 nm and dual simultaneous recording of fluorescence emission at 400 nm and 490 nm. Relative intracellular calcium levels were expressed as the 400 nm/490 nm emission ratio. Experiments were performed at 37° C. with constant mixing in cuvettes each containing $10^6$ cells in 2 ml of flux buffer. The chemokine ligands may be used over a range from 1 to 100 nM. The emission ratio was plotted over time (typically 2-3 minutes). Candidate ligand blocking compounds (up to 10 µM) were added at 10 seconds, followed by chemokines at 60 seconds (i.e., MIP-1α; R&D Systems; Minneapolis, Minn.) and control chemokine (i.e., SDF-1α; R&D Systems; Minneapolis, Minn.) at 150 seconds.

Chemotaxis Assays

Chemotaxis assays were performed using 5 µm pore polycarbonate, polyvinylpyrrolidone-coated filters in 96-well chemotaxis chambers (Neuroprobe; Gaithersburg, Md.) using chemotaxis buffer (Hank's balanced salt solution (HBSS) and 1% FBS). CCR1 chemokine ligands (i.e, MIP-1α, Leukotactin; R&D Systems; Minneapolis, Minn.) are use to evaluate compound mediated inhibition of CCR1 mediated migration. Other chemokines (i.e., SDF-1α, R&D Systems; Minneapolis, Minn.) are used as specificity controls. The lower chamber was loaded with 29 µl of chemokine (i.e., 0.1 nM MIP-1α) and varying amounts of compound; the top chamber contained 100,000 THP-1 or monocyte cells in 20 µl. The chambers were incubated 1-2 hours at 37° C., and the number of cells in the lower chamber quantified either by direct cell counts in five high powered fields per well or by the CyQuant assay (Molecular Probes), a fluorescent dye method that measures nucleic acid content and microscopic observation.

Identification of Inhibitors of CCR1

A. Assay

To evaluate small organic molecules that prevent the receptor CCR1 from binding ligand, an assay was employed that detected radioactive ligand (i.e, MIP-1α or leukotactin) binding to cells expressing CCR1 on the cell surface (for example, THP-1 cells or isolated human monocytes). For compounds that inhibited binding, whether competitive or not, fewer radioactive counts are observed when compared to uninhibited controls.

THP-1 cells and monocytes lack other chemokine receptors that bind the same set of chemokine ligands as CCR1 (i.e., MIP-1α, MPIF-1, Leukotactin, etc.). Equal numbers of cells were added to each well in the plate. The cells were then incubated with radiolabeled MIP-1α. Unbound ligand was removed by washing the cells, and bound ligand was determined by quantifying radioactive counts. Cells that were incubated without any organic compound gave total counts; non-specific binding was determined by incubating the cells with unlabeled ligand and labeled ligand. Percent inhibition was determined by the equation:

% inhibition=(1-[(sample cpm)-(nonspecific cpm)]/
   [(total cpm)-(nonspecific cpm)])×100.

B. Inhibitors from a Compound Library Identified Using CCR1 Expressing Cells

In a screen of a set of compounds, the normalized standard deviation was 17%, indicating that inhibitory activity of 34% or more was significant; again, a 40% threshold was used. These pooled compound plates yielded 39 wells that exhibited greater than 40% inhibition of MIP-1α binding. When screened a second time as pooled compound plates, 14 of these wells decreased ligand by greater than 40%. To determine which of the compounds in each well inhibited CCR1 ligation of MIP-1α, the pools were deconvoluted by testing each of the compounds individually for inhibitory activity in the assay. Because some compounds may act together to inhibit binding and deconvolution assays only tested compounds individually, compounds that were effective in combination but not singly were not found in this experiment. Testing the compounds singly identified inhibitory candidates:

C. Inhibitor from Compound Library Identified Using CCR1-Expressing Cells

CCX-105 was identified from the compound screening effort.

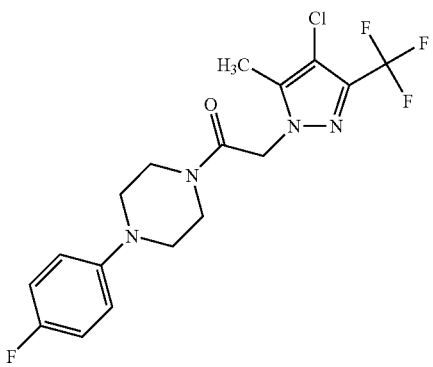

Dose Response Curves

To ascertain a candidate compound's affinity for CCR1 as well as confirm its ability to inhibit ligand binding, inhibitory activity was titered over a $1\times10^{-10}$ to $1\times10^{-4}$ M range of compound concentrations. In the assay, the amount of compound was varied; while cell number and ligand concentration were held constant. Compound CCX-105 was titered and found to be a potent inhibitor of CCR1 specific chemokine binding (see Table, for compound 1.001).

CCR1 Functional Assays

CCR1 is a seven transmembrane, G-protein linked receptor. A hallmark of signaling cascades induced by the ligation of some such receptors is the pulse-like release of calcium ions from intracellular stores. Calcium mobilization assays were performed to determine if the candidate CCR1 inhibitory compounds were able to also block aspects of CCR1 signaling. Candidate compounds able to inhibit ligand binding and signaling with an enhanced specificity over other chemokine and non-chemokine receptors were desired.

Calcium ion release in response to CCR1 chemokine ligands (i.e., MIP-1α, MPIF-1, Leukotactin, etc.) was measured using the calcium indicator INDO-1. THP-1 cells or monocytes were loaded with INDO-1/AM and assayed for calcium release in response to CCR1 chemokine ligand (i.e., MIP-1α) addition. To control for specificity, non-CCR1 ligands, specifically bradykinin, was added, which also signals via a seven transmembrane receptor. Without compound, a pulse of fluorescent signal will be seen upon MIP-1α addition. If a compound specifically inhibits CCR1-MIP-1α signaling, then little or no signal pulse will be seen upon MIP-1α addition, but a pulse will be observed upon bradykinin addition. However, if a compound non-specifically inhibits signaling, then no pulse will be seen upon both MIP-1α and bradykinin addition.

As shown below, CCX-105 was able to significantly and specifically inhibit signaling from CCR1.

TABLE 2

| | Inhibition of calcium signaling | | |
|---|---|---|---|
| Compound | MIP-1α[1] | Bradykinin[1] | Comments |
| CCX-105 | – | + | Specific inhibition |

[1]+, pulse observed, –, no pulse observed, n.s., non-specific signal (see main text)

One of the primary functions of chemokines is their ability to mediate the migration of chemokine receptor-expressing cells, such as white blood cells. To confirm that CCX-105 inhibited not only CCR1 specific binding and signaling (at least as determined by calcium mobilization assays), but also CCR1 mediated migration, a chemotaxis assay was employed. THP-1 myelomonocytic leukemia cells, which resemble monocytes, as wells as freshly isolated monocytes, were used as targets for chemoattraction by CCR1 chemokine ligands (i.e., MIP-1α, CCL15/leukotactin). Cells were place in the top compartment of a microwell migration chamber, while MIP-1α (or other potent CCR1 chemokine ligand) and increasing concentrations of CCX-105 or other candidate compound was loaded in the lower chamber. In the absence of inhibitor, cells will migrate to the lower chamber in response to the chemokine agonist; if a compound inhibited CCR1 function, then the majority of cells will remain in the upper chamber. To ascertain a candidate compound's affinity for CCR1 as well as to confirm its ability to inhibit CCR1 mediated cell migration, inhibitory activity was titered over a $1\times10^{-10}$ to $1\times10^{-4}$ M range of compound concentrations in this chemotaxis assay. In this assay, the amount of compound was varied; while cell number and chemokine agonist concentrations were held constant. After the chemotaxis chambers were incubated 1-2 hours at 37° C., the responding cells in the lower chamber were quantified by labeling with the CyQuant assay (Molecular Probes), a fluorescent dye method that measures nucleic acid content, and by measuring with a Spectrafluor Plus (Tecan). The computer program Prism from GraphPad, Inc. (San Diego, Calif.) was used to calculate $IC_{50}$ values. $IC_{50}$ values are those compound concentrations required to inhibit the number of cells responding to a CCR1 agonist by 50%.

In Vivo Efficacy

Rabbit Model of Destructive Joint Inflammation

A study was conducted to evaluate the effects of CCX-105 on inhibiting the inflammatory response of rabbits to an intra-articular injection of the bacterial membrane component lipopolysaccharide (LPS). This study design mimics the destructive joint inflammation seen in arthritis. Intra-articular injection of LPS causes an acute inflammatory response characterized by the release of cytokines and chemokines, many of which have been identified in rheumatoid arthritic joints. Marked increases in leukocytes occur in synovial fluid and in synovium in response to elevation of these chemotactic mediators. Selective antagonists of chemokine receptors have shown efficacy in this model (see Podolin, et al., *J. Immunol.* 169(11):6435-6444 (2002)).

In a rabbit LPS study conducted essentially as described in Podolin, et al. ibid., female New Zealand rabbits (approximately 2 kilograms) were treated intra-articularly in one knee with LPS (10 ng) together with either vehicle only (phosphate buffered saline with 1% DMSO) or with addition of CCX-105 (dose 1=50 μM or dose 2=100 μM) in a total volume of 1.0 mL. Sixteen hours after the LPS injection, knees were lavaged and cells counts performed. Beneficial effects of treatment were determined by histopathologic evaluation of synovial inflammation. The following inflammation scores were used for the histopathologic evaluation: 1—minimal, 2—mild, 3—moderate, 4—moderate-marked. As shown below, CCX-105 was able to significantly and specifically inhibit the inflammatory response in this in vivo assay.

TABLE 3

CCX-105 efficacy in a rabbit model of destructive joint inflammation

|  | synovium inflammation score |
|---|---|
| Vehicle | 3 |
| CCX-105 (dose 1) | 2 |
| CCX-105 (dose 2) | 1 |

Evaluation of Compound 1.028 in a Rat Model of Collagen Induced Arthritis

A 17 day developing type II collagen arthritis study was conducted to evaluate the effects of compound 1.028 on arthritis induced clinical ankle swelling. Rat collagen arthritis is an experimental model of polyarthritis that has been widely used for preclinical testing of numerous anti-arthritic agents (see Trentham, et al., *J. Exp. Med.* 146(3):857-868 (1977), Bendele, et al., *Toxicologic Pathol.* 27:134-142 (1999), Bendele, et al., *Arthritis Rheum.* 42:498-506 (1999)). The hallmarks of this model are reliable onset and progression of robust, easily measurable polyarticular inflammation, marked cartilage destruction in association with pannus formation and mild to moderate bone resorption and periosteal bone proliferation.

Female Lewis rats (approximately 0.2 kilograms) were anesthetized with isoflurane and injected with Freund's Incomplete Adjuvant containing 2 mg/ml bovine type II collagen at the base of the tail and two sites on the back on days 0 and 6 of this 17 day study. Compound 1.028 was dosed daily in a sub-cutaneous manner from day 0 till day 17 at a dose of 25 mg/kg and a volume of 1 ml/kg in the following vehicle (20% N,N-dimethylacetamide, 75% corn oil, 5% Tween-80). Caliper measurements of the ankle joint diameter were taken, and reducing joint swelling was taken as a measure of efficacy. As shown below, compound 1.028 was able to significantly and specifically inhibit the arthritis induced ankle swelling in this in vivo assay.

TABLE 4

Efficacy of compound 1.028 in a rat collagen induced arthritis assay

|  | change in joint diameter day 9-day 17 |
|---|---|
| Vehicle | 15.7% +/− 2.0% |
| Normal | 0% +/− 0.3% |
| Compound 1.028 | 9.1% +/− 1.8% |

In the table below, structures and activity are provided for representative compounds described herein. Activity is provided as follows for either or both of the chemotaxis assay and/or binding assay, described above: +, $IC_{50}$>12.5 µM; ++, 2500 nM<$IC_{50}$<12.5 µM; +++, 500 nM<$IC_{50}$<2500 nM; and ++++, $IC_{50}$<500 nM.

| Structure |
|---|
| 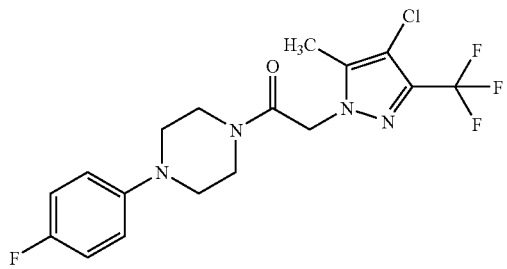<br>CCX 105<br>1.001 / ++++ |
| 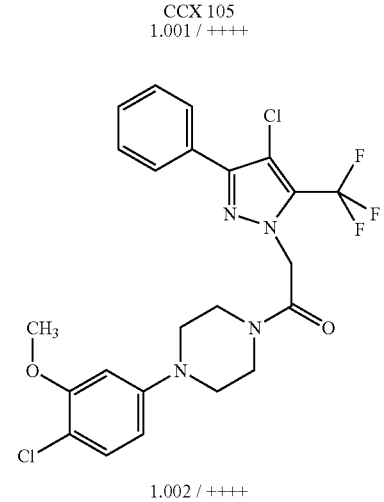<br>1.002 / ++++ |
| 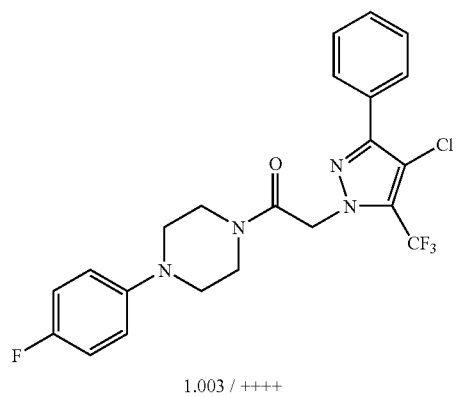<br>1.003 / ++++ |
| 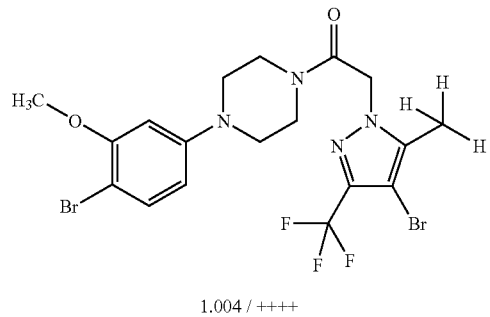<br>1.004 / ++++ |

| Structure | | Structure |
|---|---|---|
| 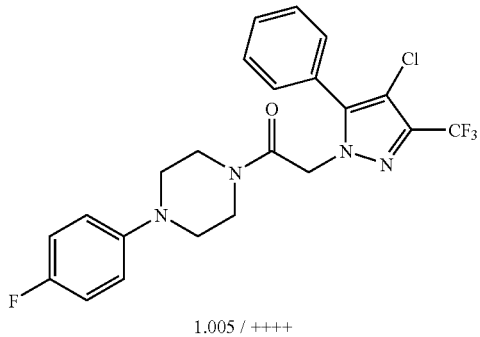
1.005 / ++++ | | 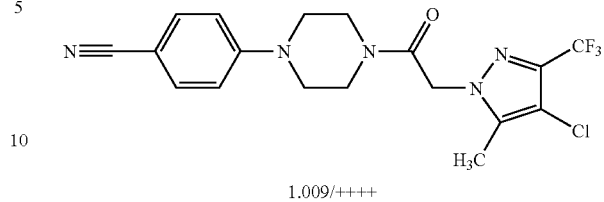
1.009/++++ |
| 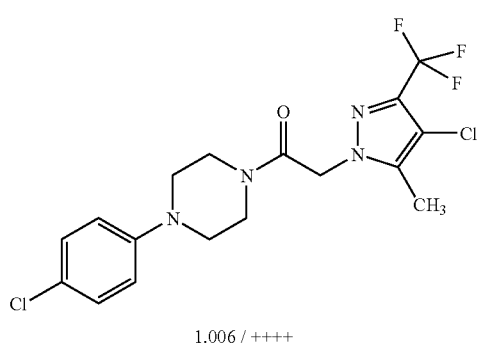
1.006 / ++++ | | 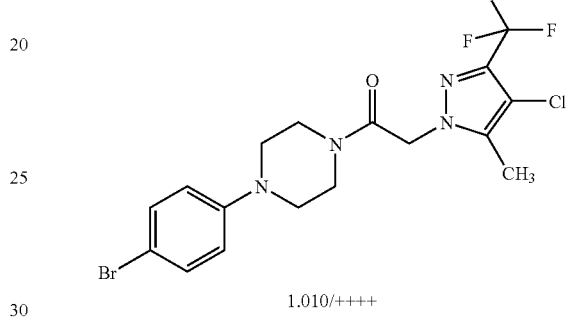
1.010/++++ |
| 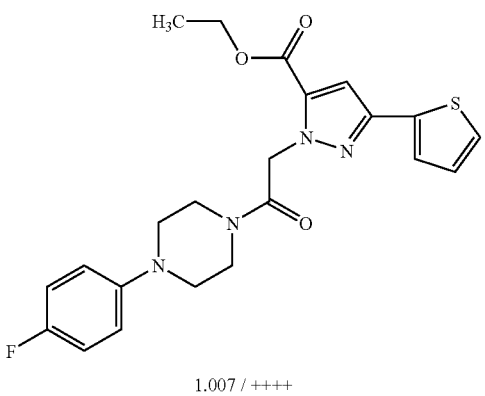
1.007 / ++++ | | 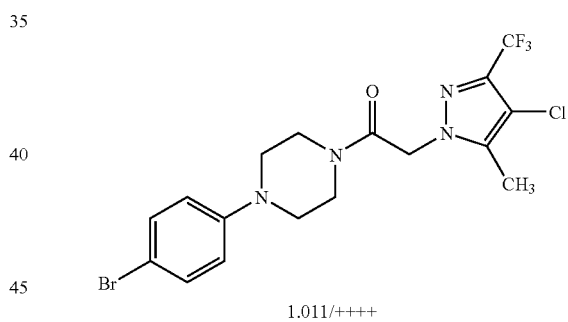
1.011/++++ |
| 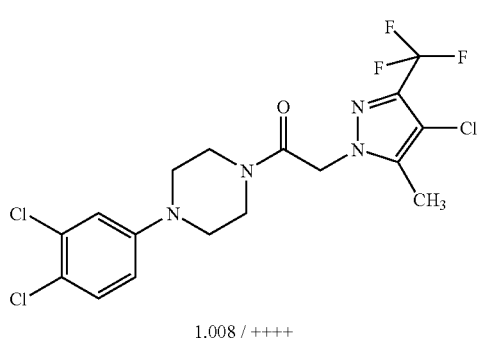
1.008 / ++++ | | 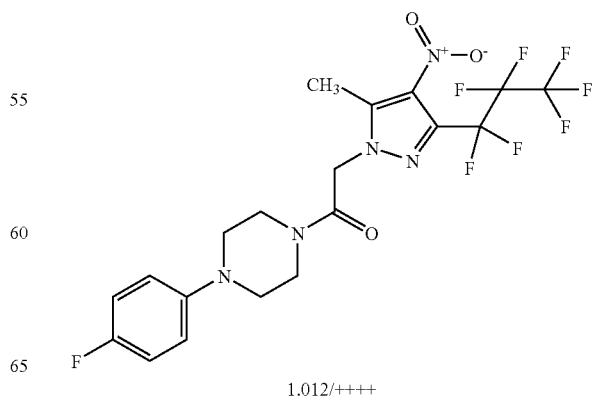
1.012/++++ |

141
-continued
Structure
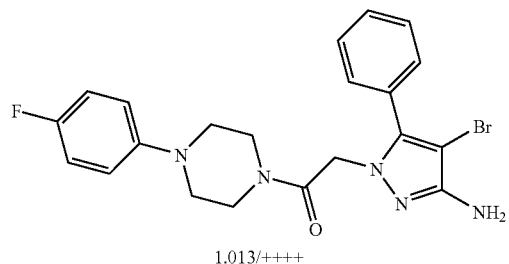
1.013/++++
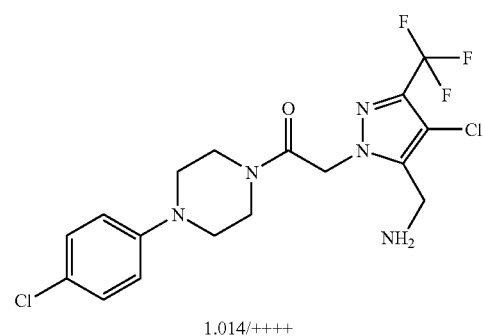
1.014/++++
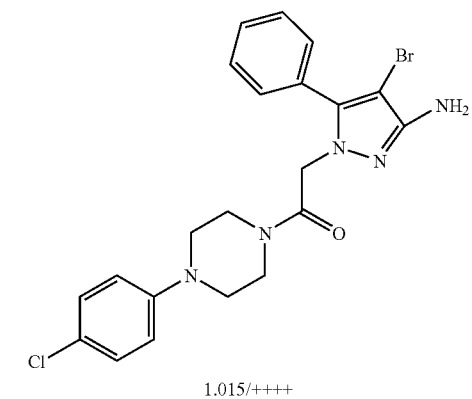
1.015/++++
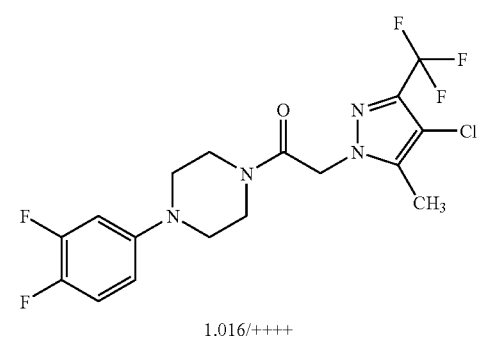
1.016/++++
142
-continued
Structure
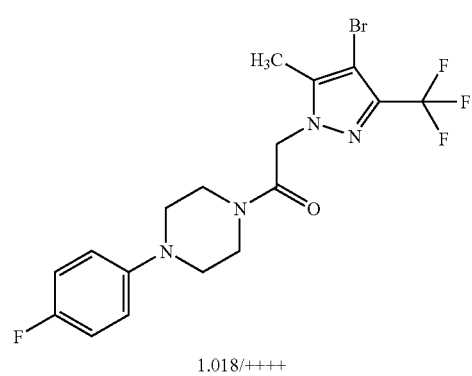
1.017/++++
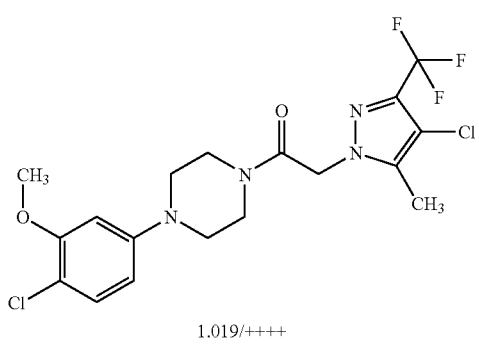
1.018/++++
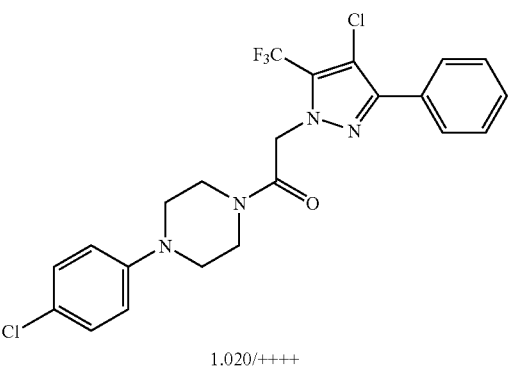
1.019/++++
1.020/++++

| Structure | | Structure |
|---|---|---|
| 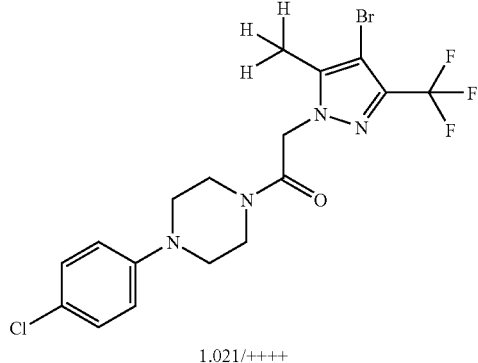<br>1.021/++++ | | 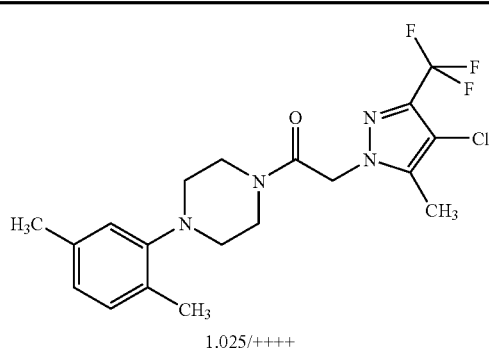<br>1.025/++++ |
| 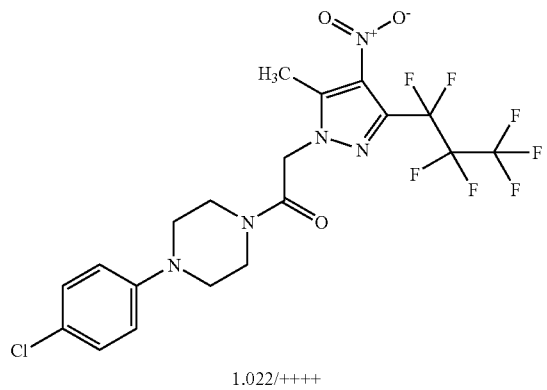<br>1.022/++++ | | 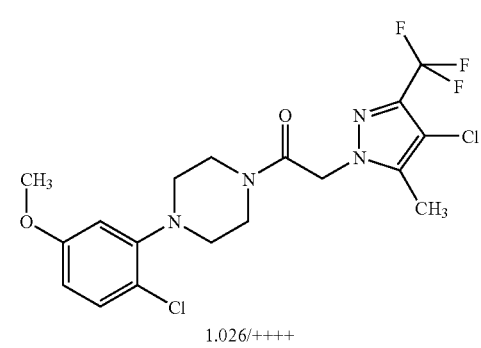<br>1.026/++++ |
| 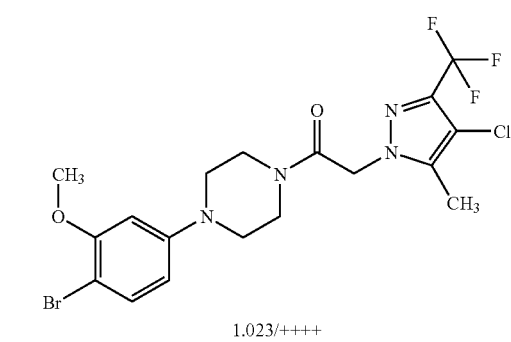<br>1.023/++++ | | 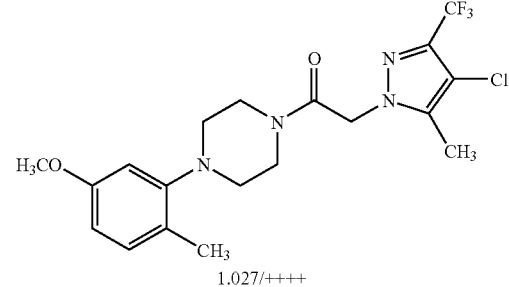<br>1.027/++++ |
| 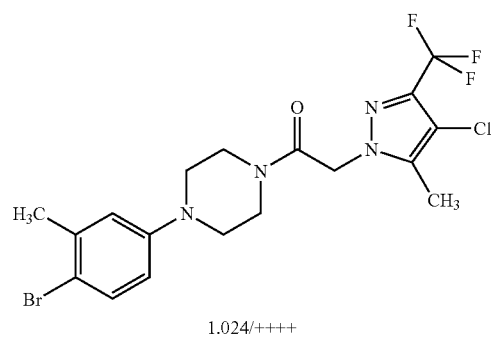<br>1.024/++++ | | 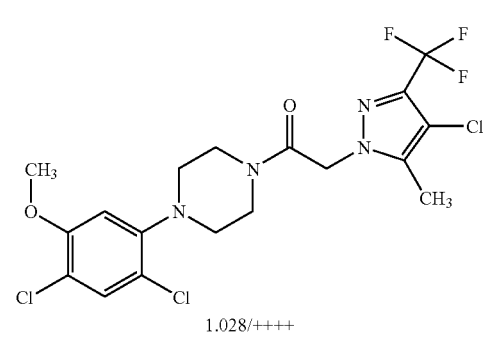<br>1.028/++++ |

-continued
| Structure |
|---|
| 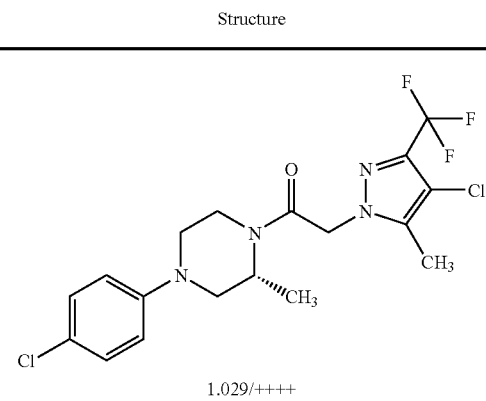
1.029/++++ |
| 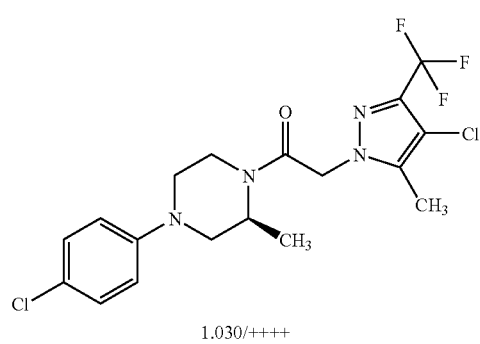
1.030/++++ |
| 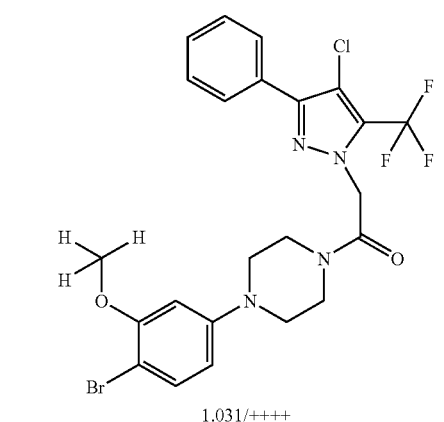
1.031/++++ |
| 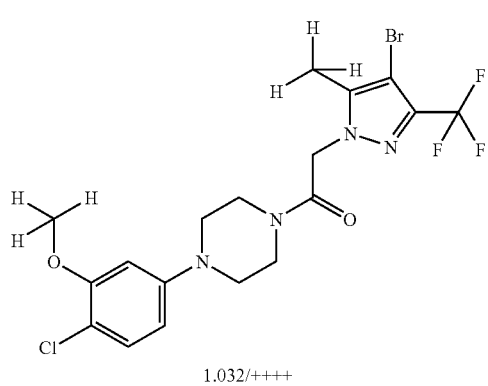
1.032/++++ |
-continued
| Structure |
|---|
| 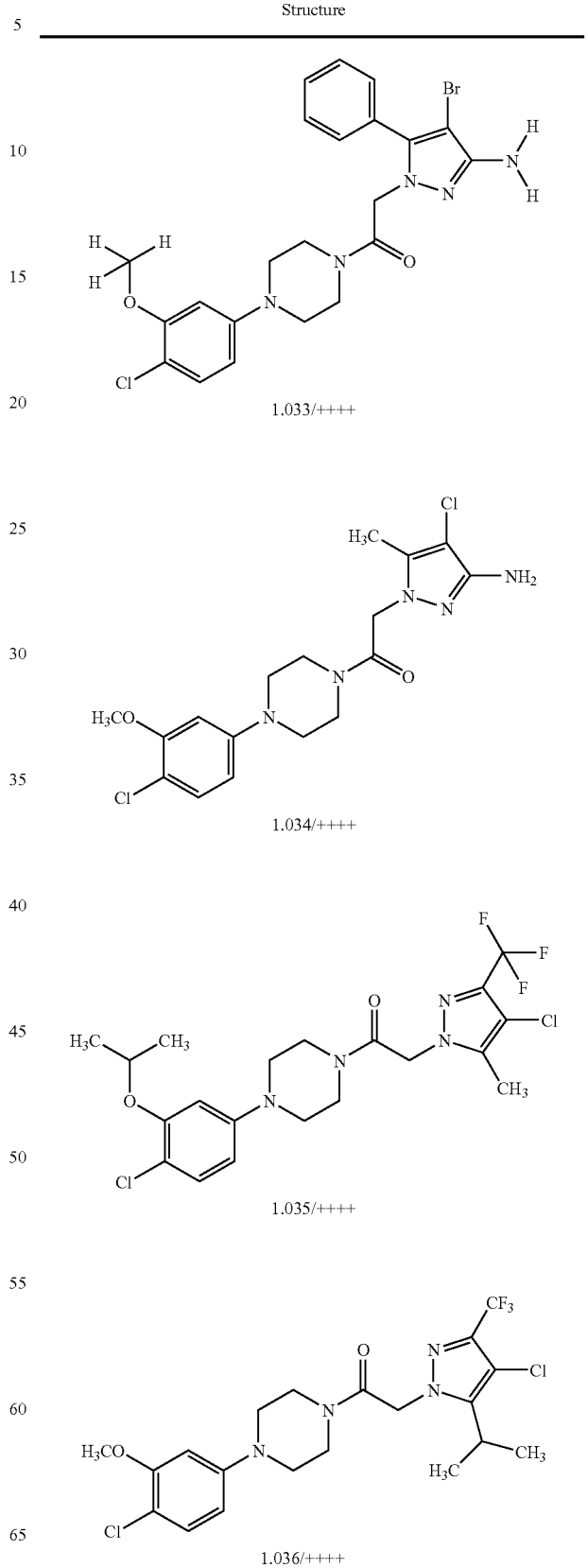 |
1.033/++++
1.034/++++
1.035/++++
1.036/++++

147
-continued
Structure
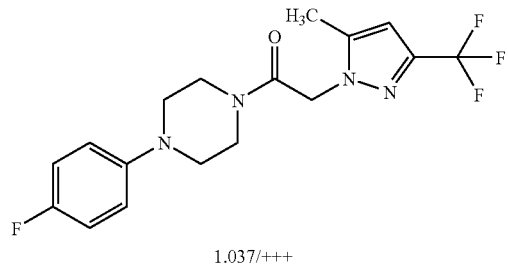
1.037/+++
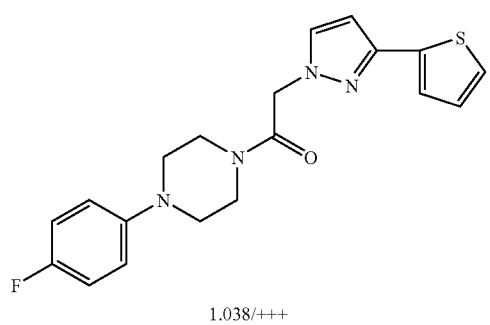
1.038/+++
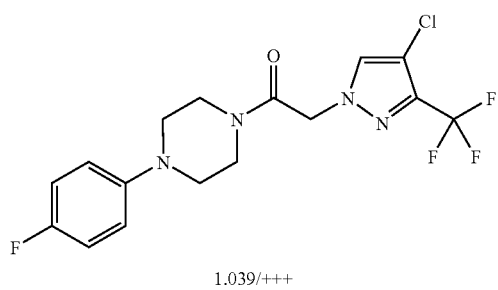
1.039/+++
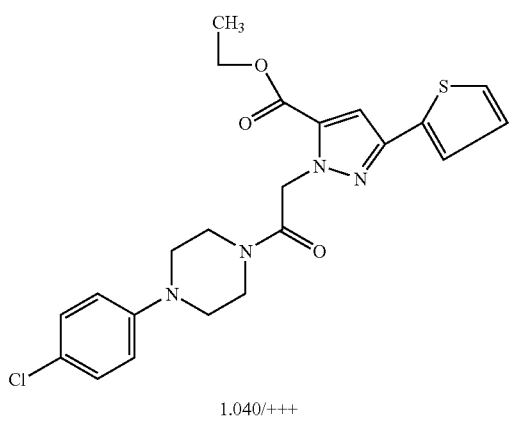
1.040/+++
148
-continued
Structure
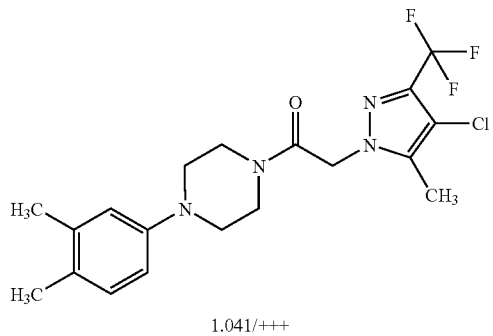
1.041/+++
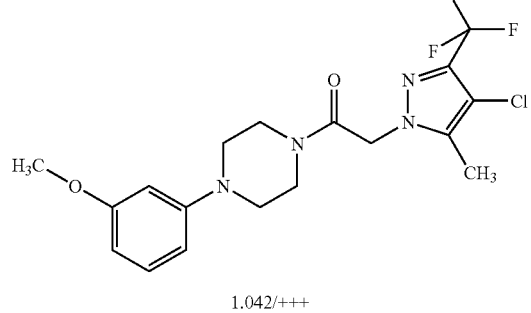
1.042/+++
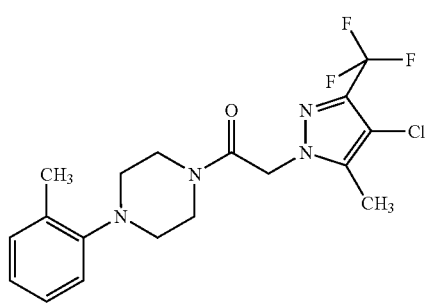
1.043/+++
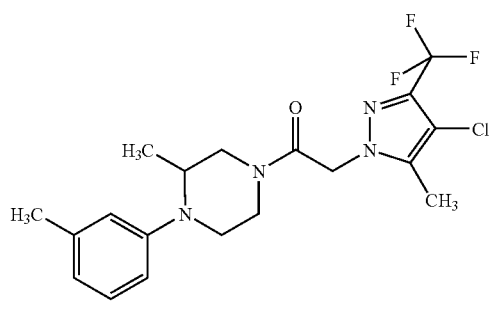
1.044/+++

| -continued | -continued |
|---|---|
| Structure | Structure |
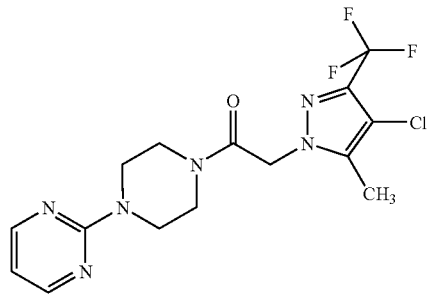
1.045/+++
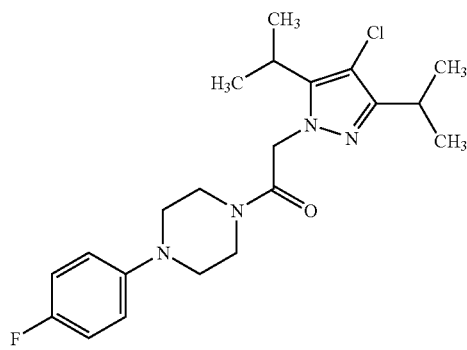
1.049/+++
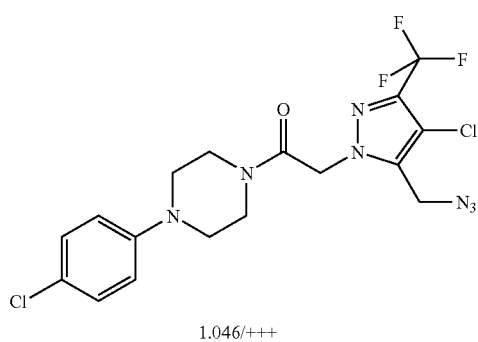
1.046/+++
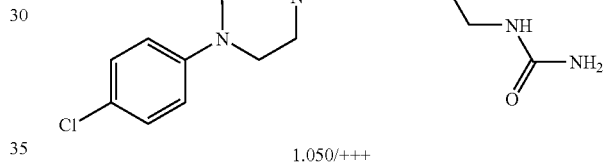
1.050/+++
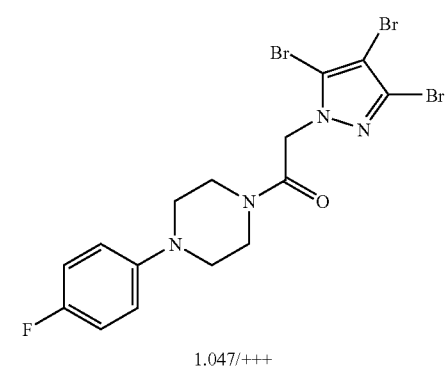
1.047/+++
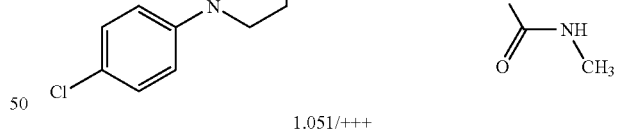
1.051/+++
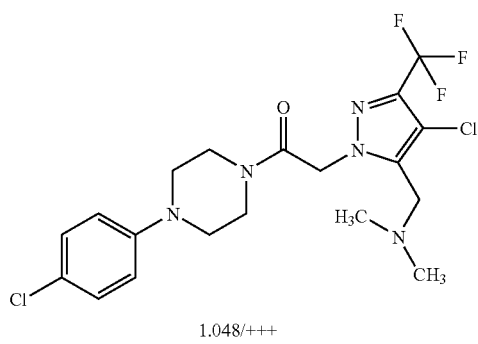
1.048/+++
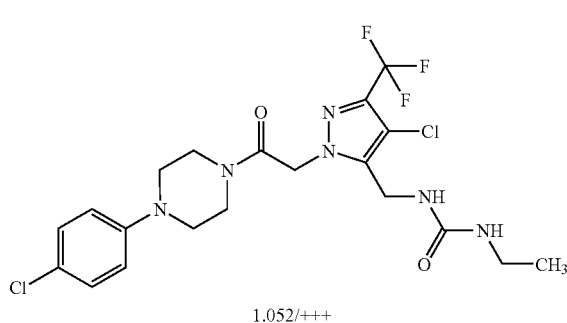
1.052/+++

151
-continued
| Structure |
|---|
| 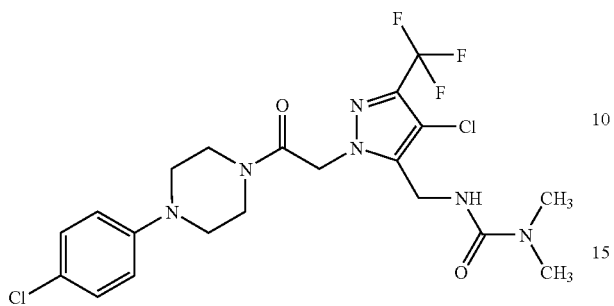<br>1.053/+++ |
| 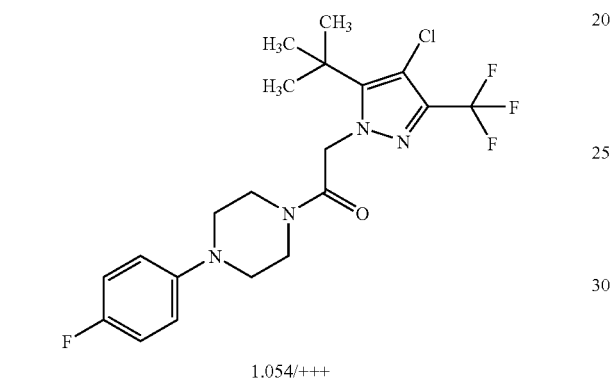<br>1.054/+++ |
| 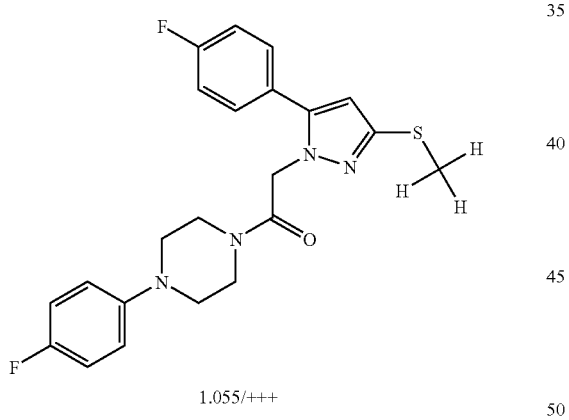<br>1.055/+++ |
| 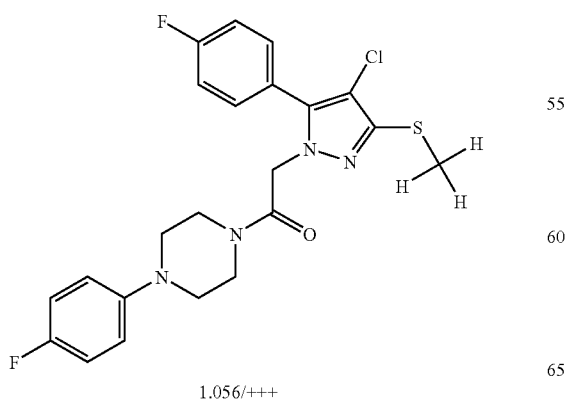<br>1.056/+++ |
152
-continued
| Structure |
|---|
| 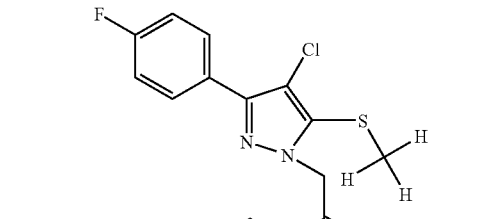<br>1.057/+++ |
| 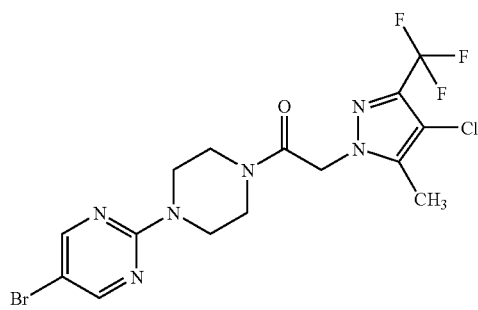<br>1.058/+++ |
| 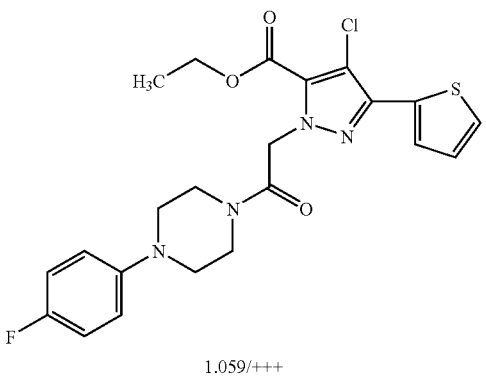<br>1.059/+++ |
| 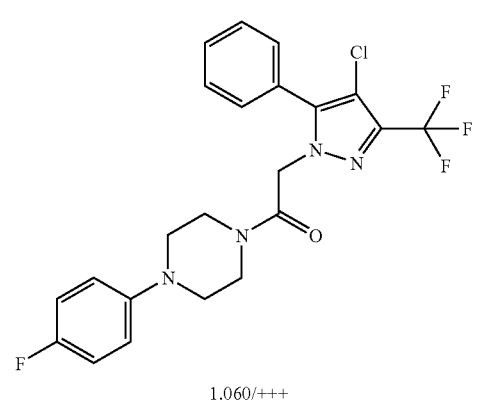<br>1.060/+++ |

| Structure | Structure |
|---|---|
| 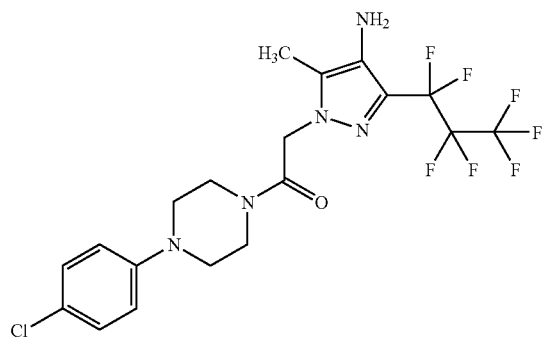<br>1.061/+++ | 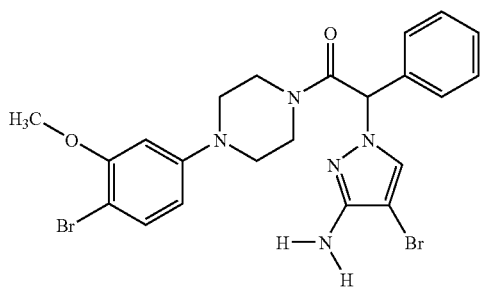<br>1.065/+++ |
| 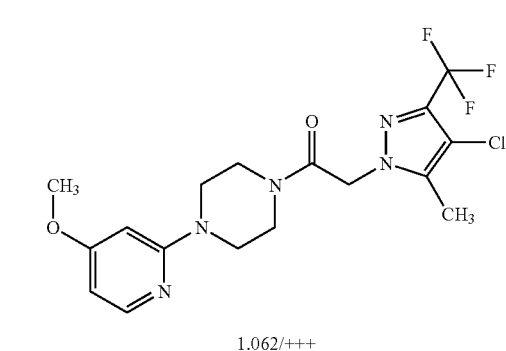<br>1.062/+++ | 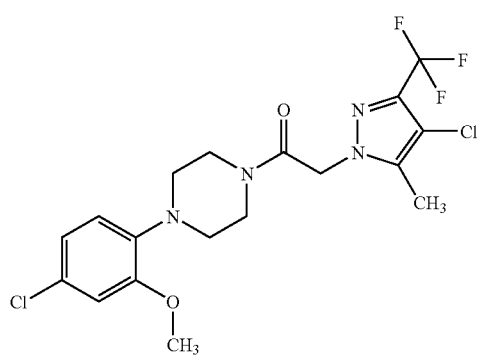<br>1.066/+++ |
| 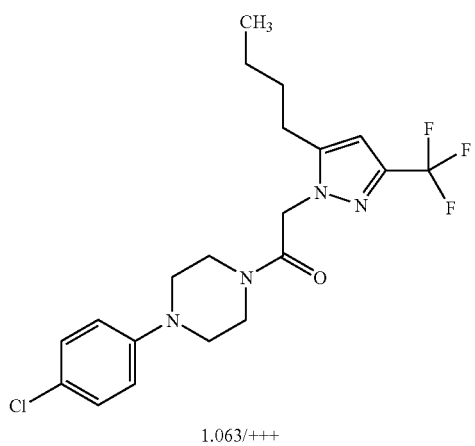<br>1.063/+++ | 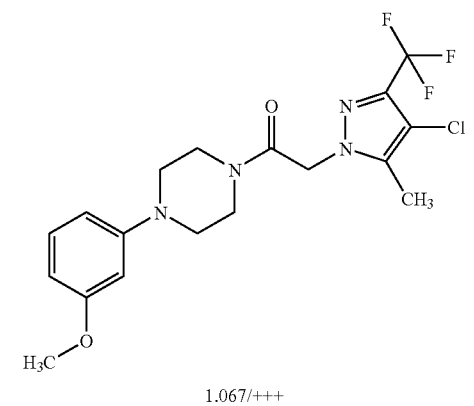<br>1.067/+++ |
| 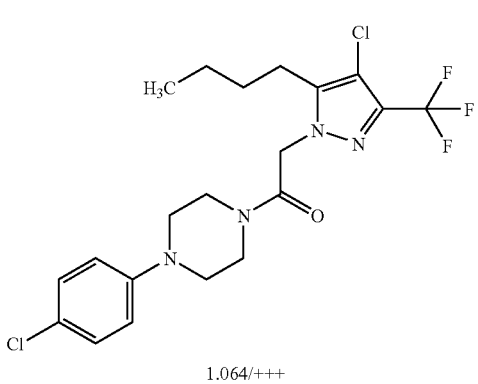<br>1.064/+++ | 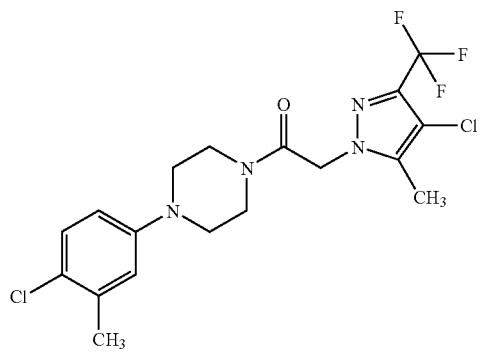<br>1.068/++++ |

-continued
| Structure |
|---|
| 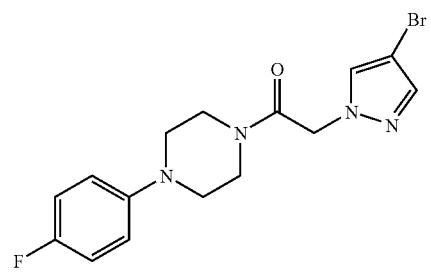
1.069/++ |
| 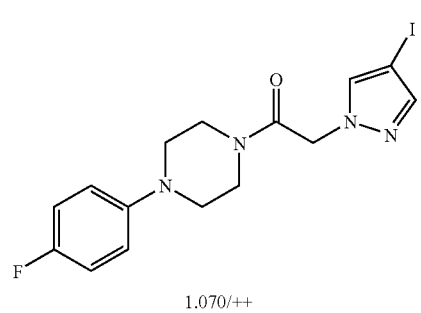
1.070/++ |
| 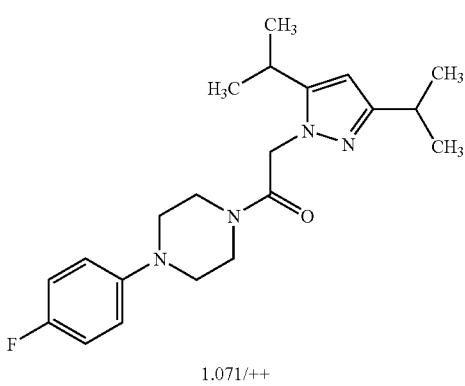
1.071/++ |
| 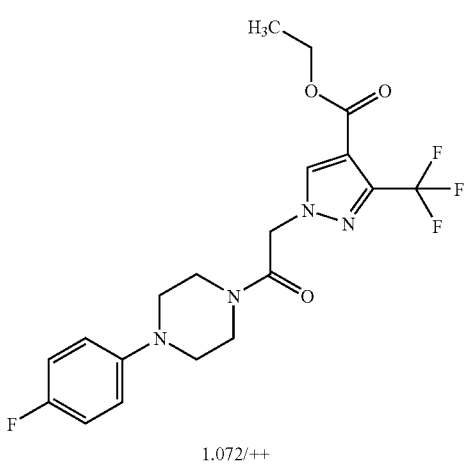
1.072/++ |
-continued
| Structure |
|---|
| 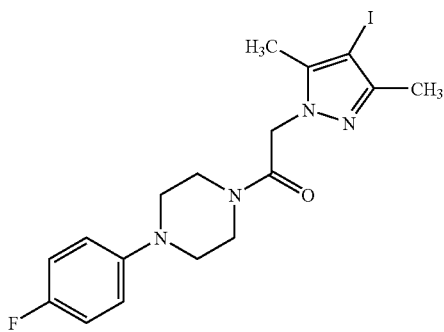
1.073/++ |
| 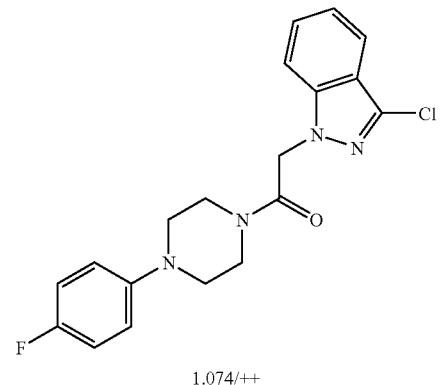
1.074/++ |
| 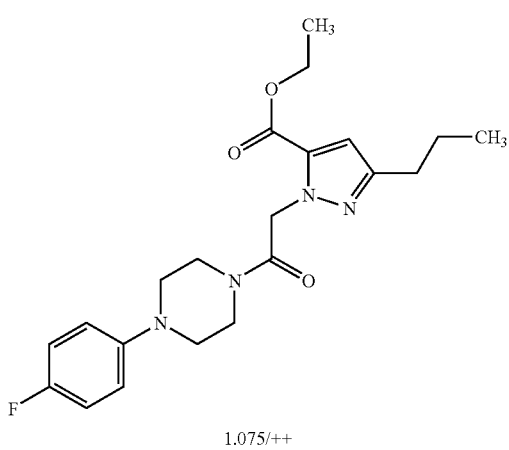
1.075/++ |

| 157 | 158 |
|---|---|
| -continued | -continued |
| Structure | Structure |
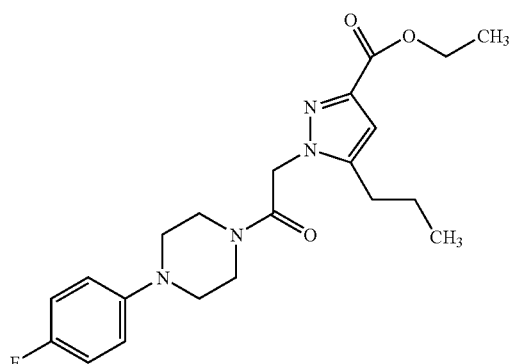
1.076/++
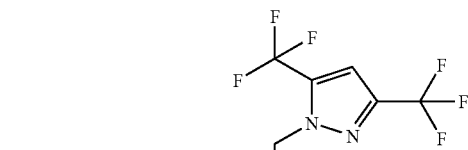
1.080/++
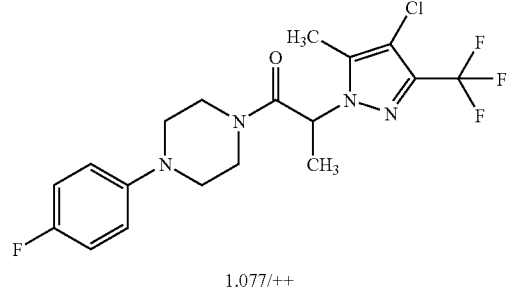
1.077/++
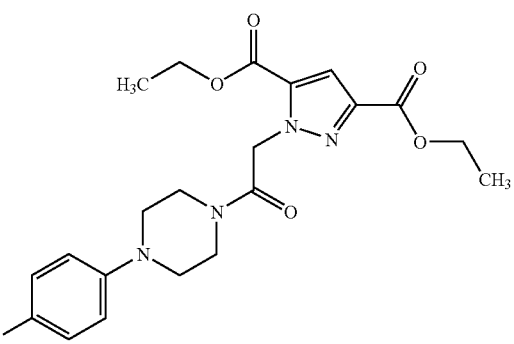
1.081/++
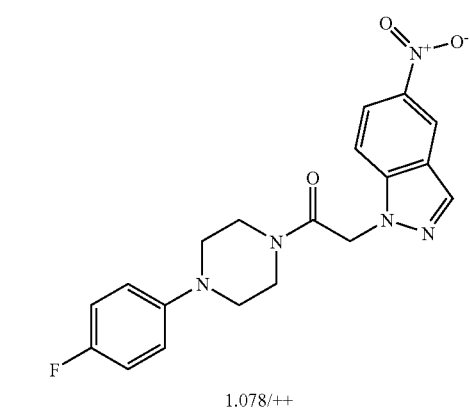
1.078/++
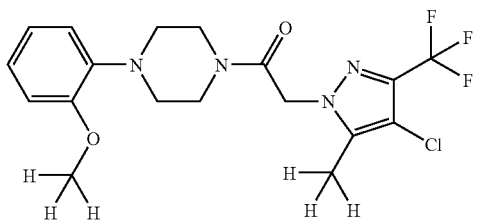
1.082/++
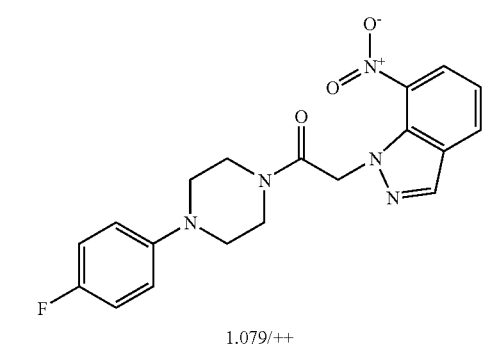
1.079/++
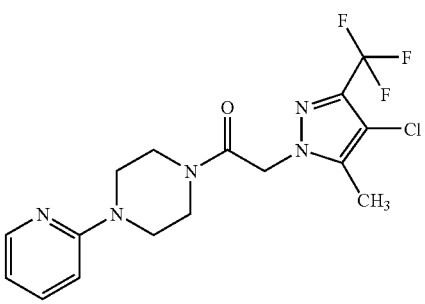
1.083/++

| 159 | 160 |
|---|---|
| -continued | -continued |
| Structure | Structure |
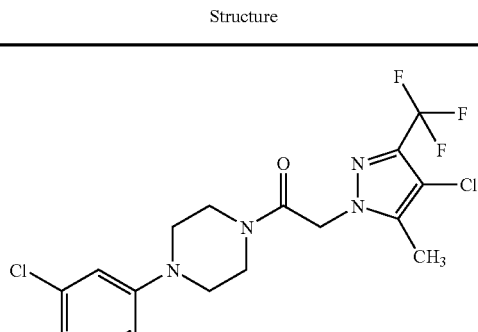
1.084/++
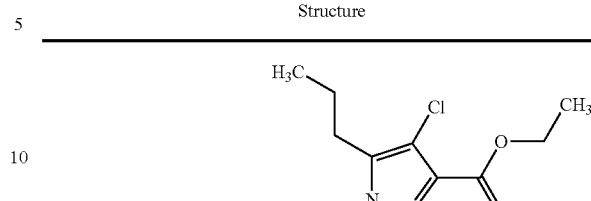
1.088/++
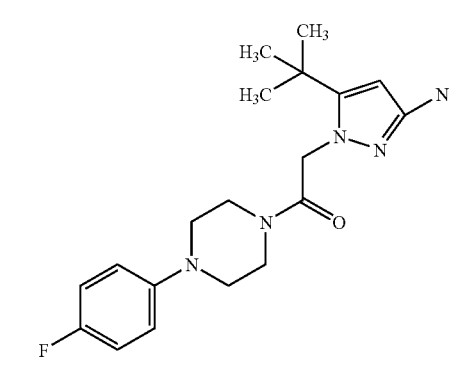
1.085/++
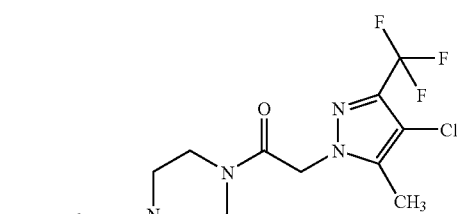
1.089/++
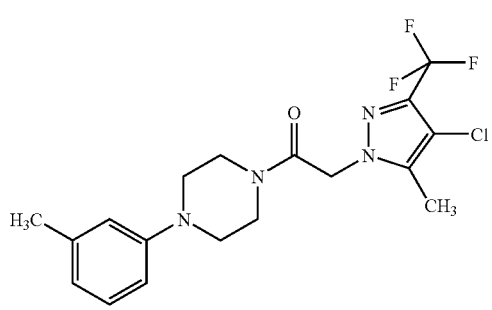
1.086/++
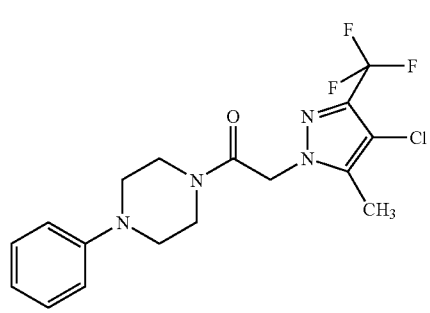
1.087/++
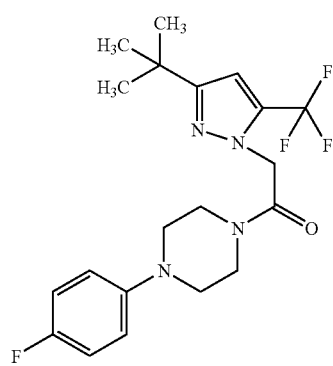
1.090/++

| 161 | 162 |
|---|---|
| -continued | -continued |
| Structure | Structure |
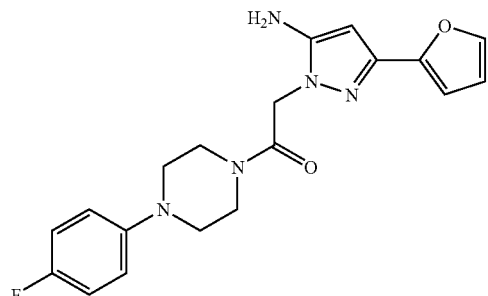
1.091/++
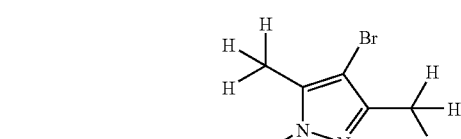
1.095/++
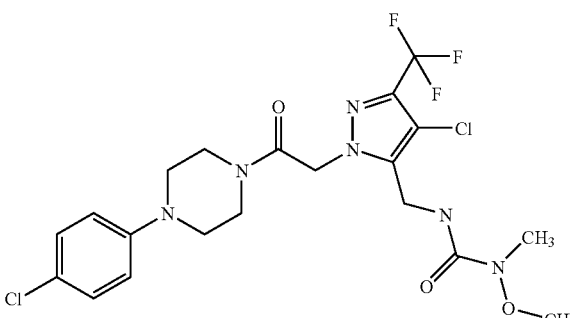
1.092/++
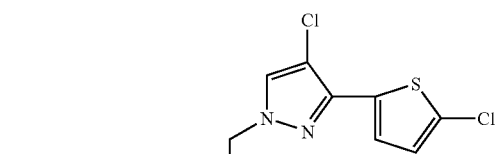
1.096/++
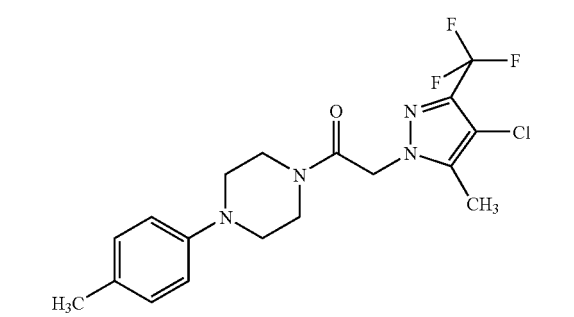
1.093/++
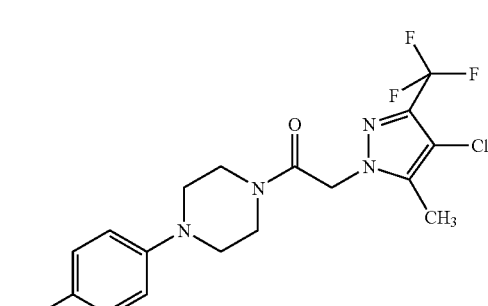
1.094/++
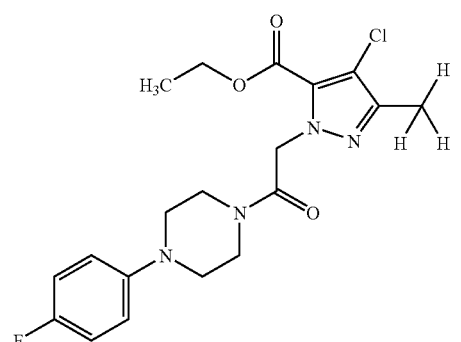
1.097/++

| 163 | 164 |
|---|---|
| -continued | -continued |
| Structure | Structure |
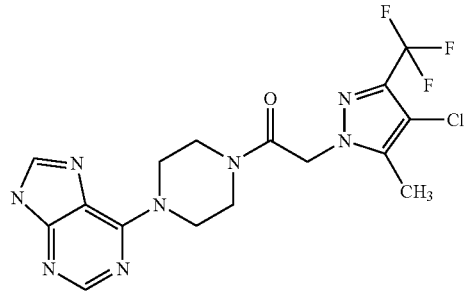
1.098/++
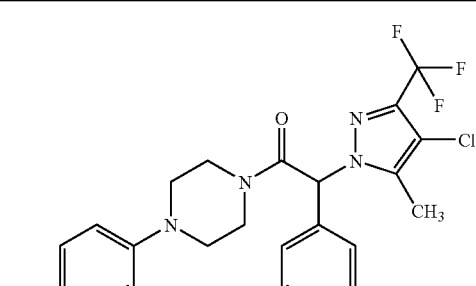
1.102/++
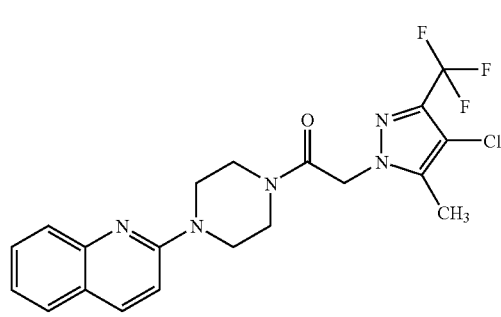
1.099/++
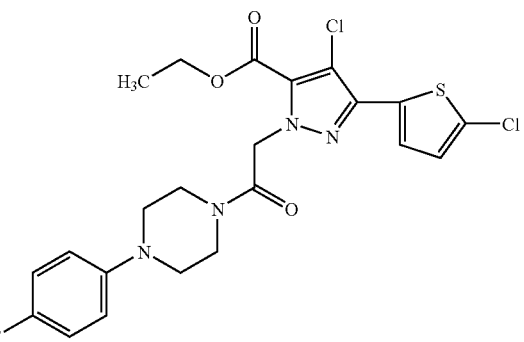
1.100/++
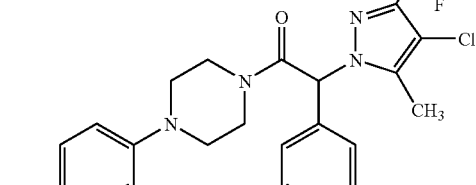
1.103/++
1.101/++
1.104/++

| 165 | 166 |
|---|---|
| -continued | -continued |
| Structure | Structure |
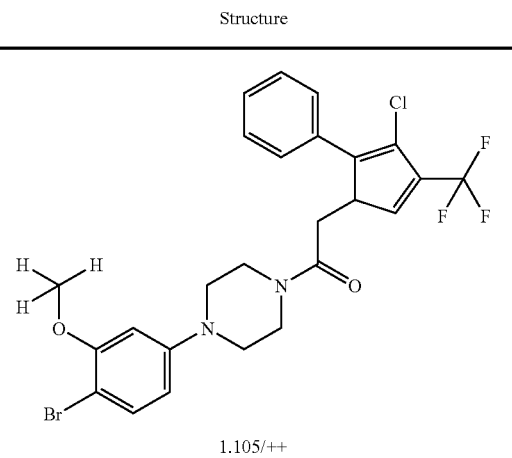
1.105/++
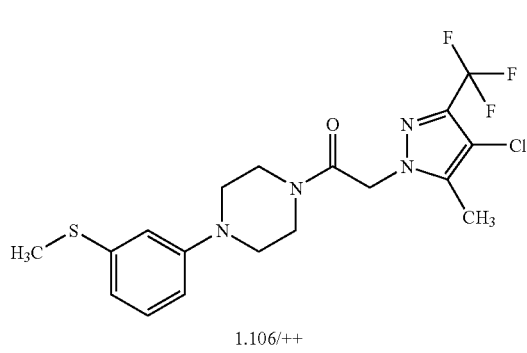
1.106/++
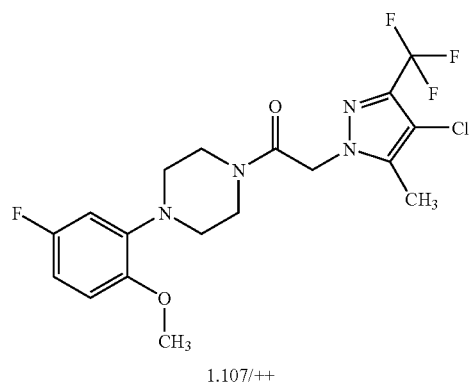
1.107/++
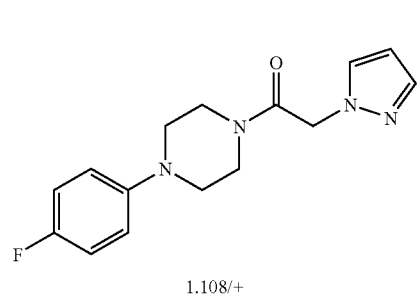
1.108/+
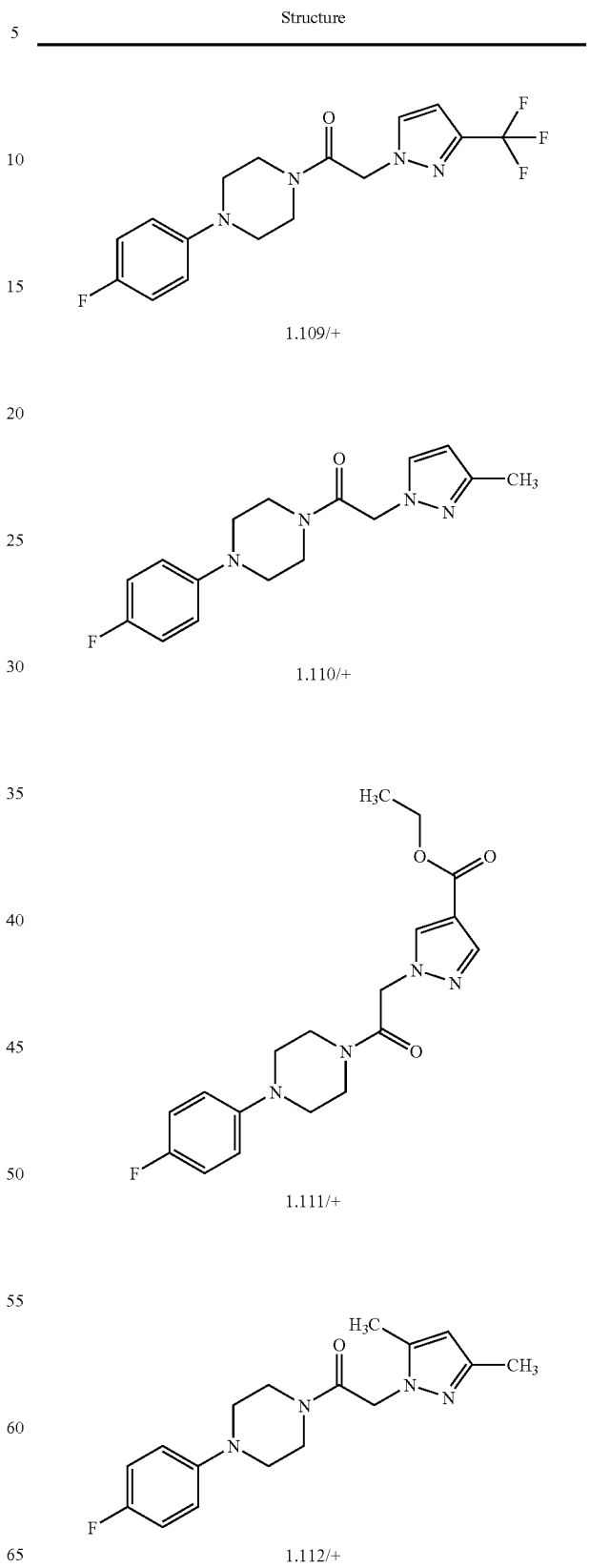
1.109/+
1.110/+
1.111/+
1.112/+

167
-continued
| Structure |
|---|
| 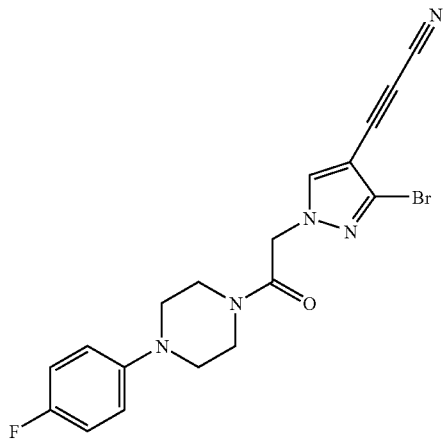 |
| 1.113/+ |
| 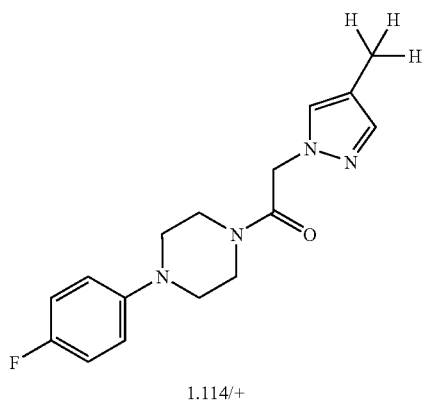 |
| 1.114/+ |
| 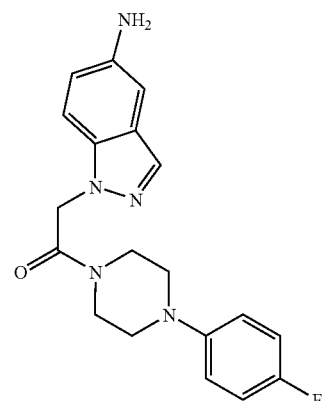 |
| 1.115/+ |
168
-continued
| Structure |
|---|
| 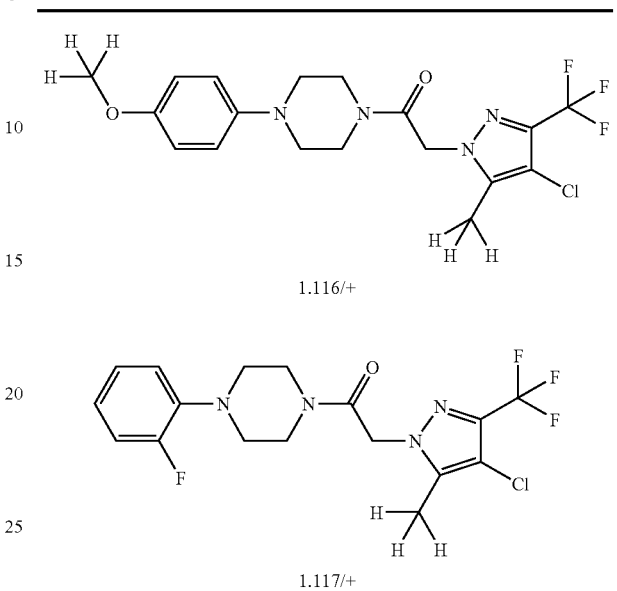 |
| 1.116/+ |
| 1.117/+ |
| 1.118/+ |
| 1.119/+ |
| 1.120/+ |

-continued
| Structure |
|---|
| 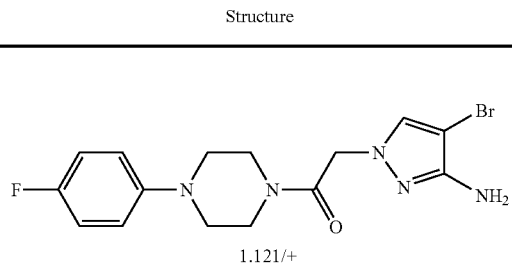 <br> 1.121/+ |
| 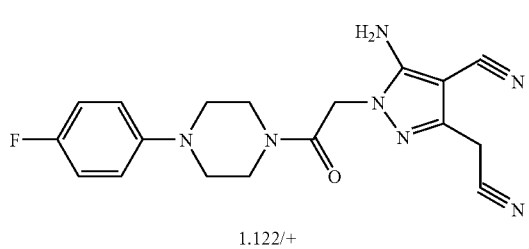 <br> 1.122/+ |
| 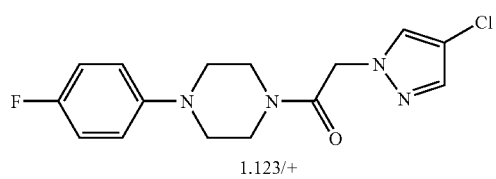 <br> 1.123/+ |
| 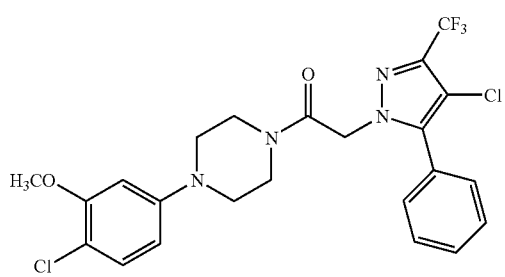 <br> 1.124/+++ |
| 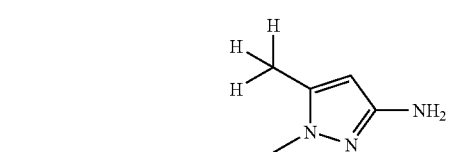 <br> 1.125/+ |
-continued
| Structure |
|---|
| 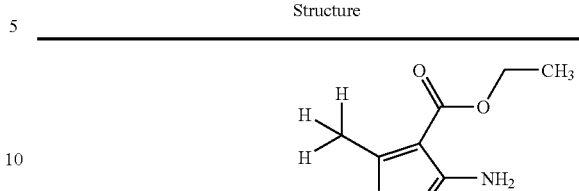 <br> 1.126/+ |
| 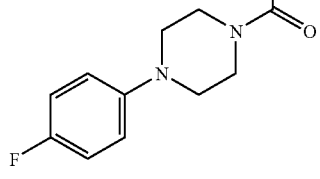 <br> 1.127/+ |
| 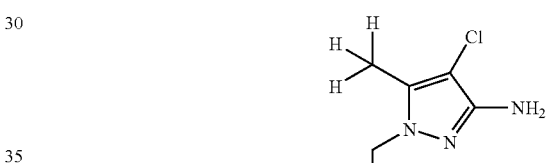 <br> 1.128/+ |

-continued
| Structure |
|---|
| 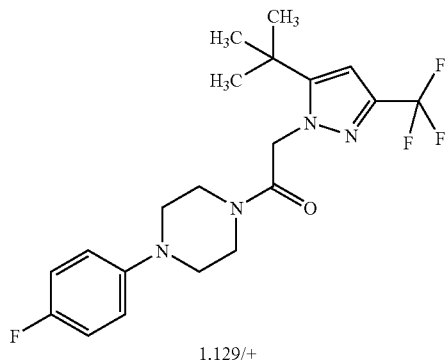 1.129/+ |
| 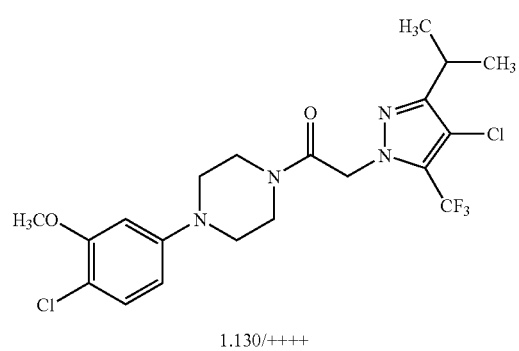 1.130/++++ |
| 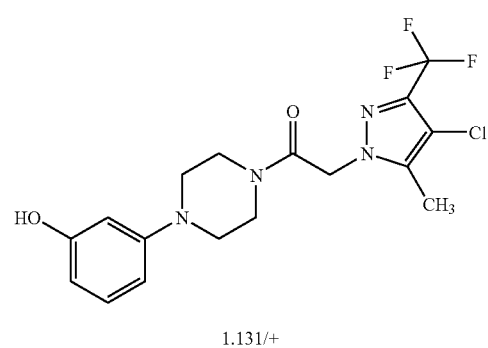 1.131/+ |
| 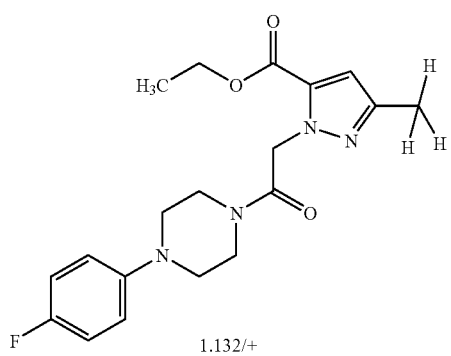 1.132/+ |
-continued
| Structure |
|---|
| 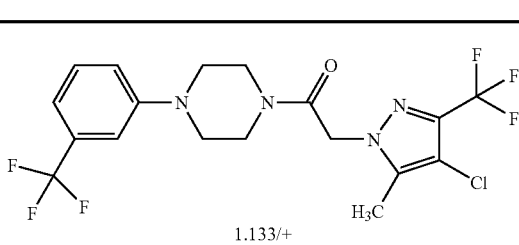 1.133/+ |
| 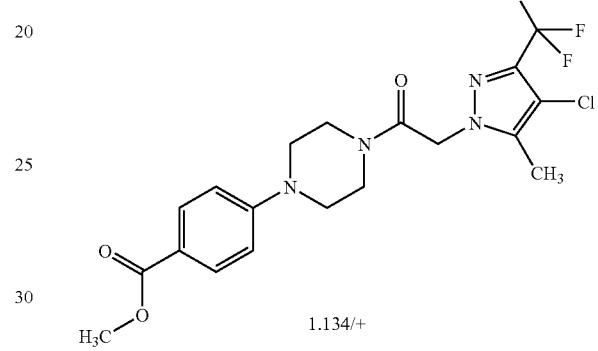 1.134/+ |
| 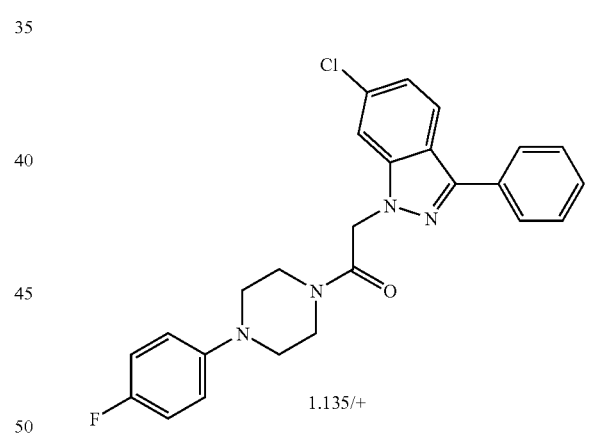 1.135/+ |
| 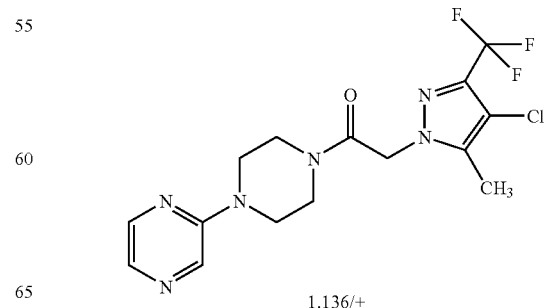 1.136/+ |

| 173 | 174 |
|---|---|
| -continued | -continued |
| Structure | Structure |
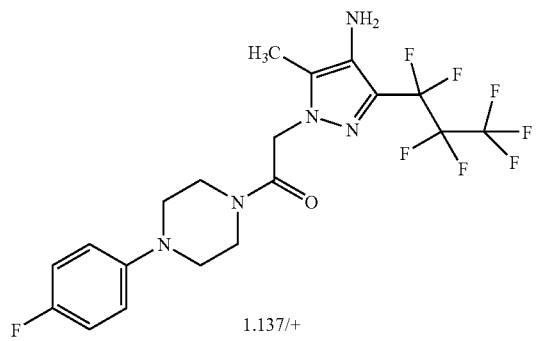
1.137/+
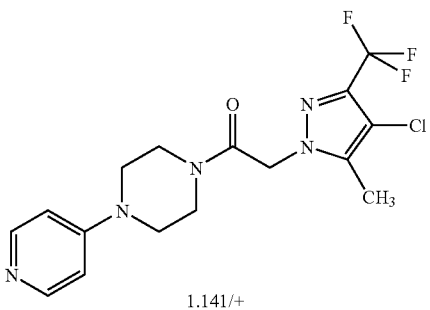
1.141/+
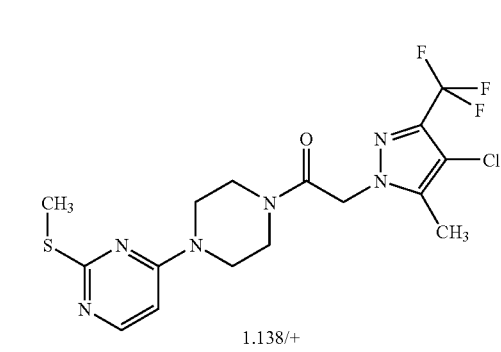
1.138/+
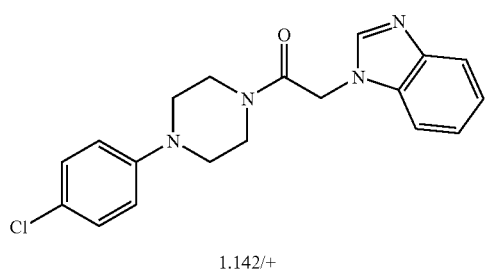
1.142/+
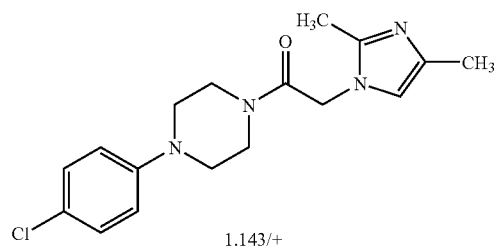
1.143/+
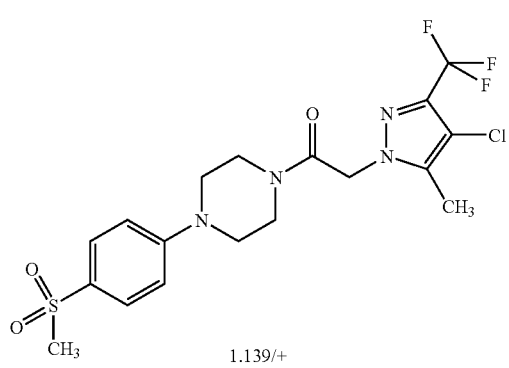
1.139/+
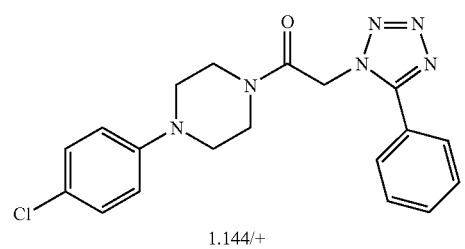
1.144/+
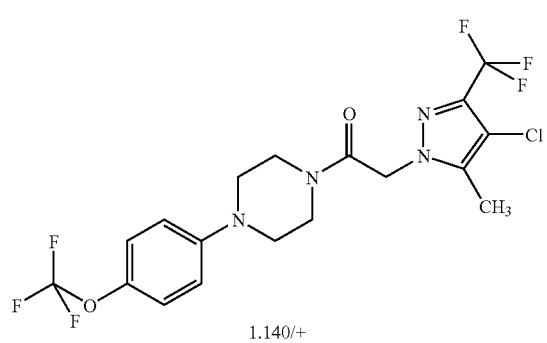
1.140/+
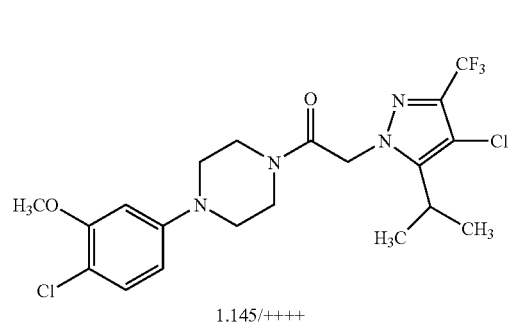
1.145/++++

-continued
Structure
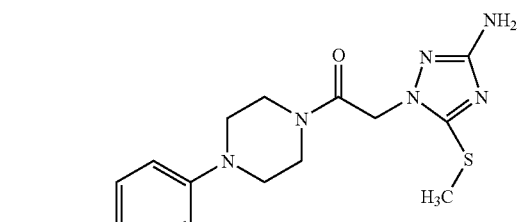
1.146/+
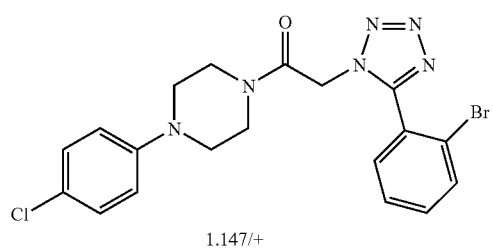
1.147/+
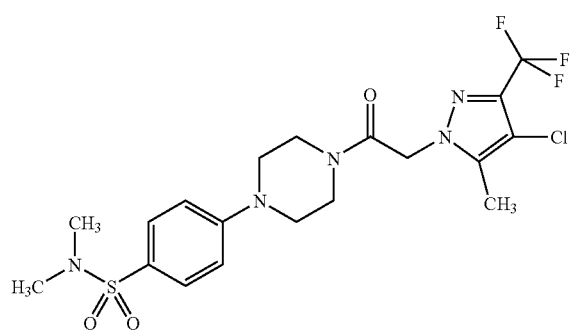
1.148/+
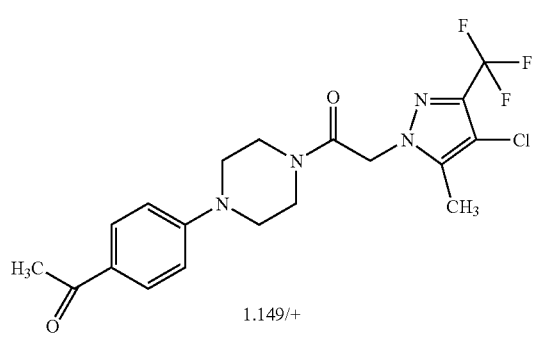
1.149/+
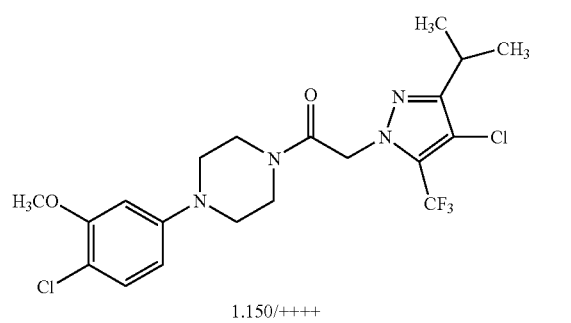
1.150/++++
-continued
Structure
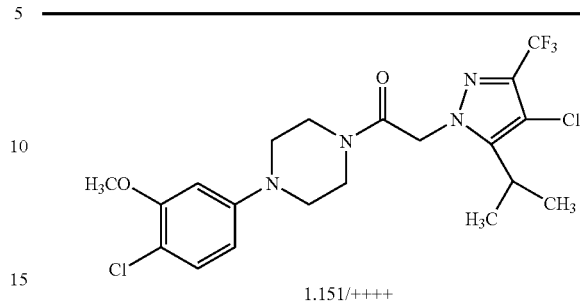
1.151/++++
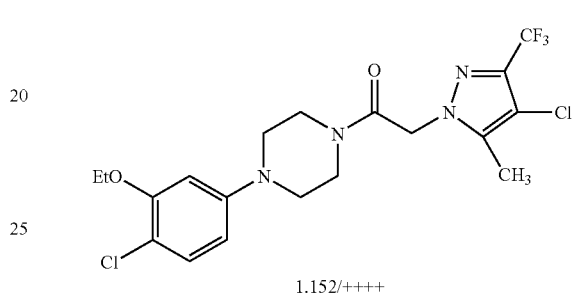
1.152/++++
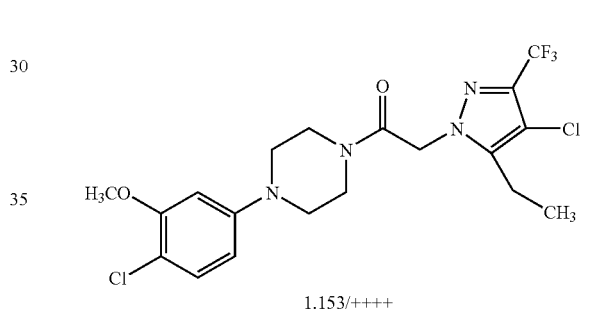
1.153/++++
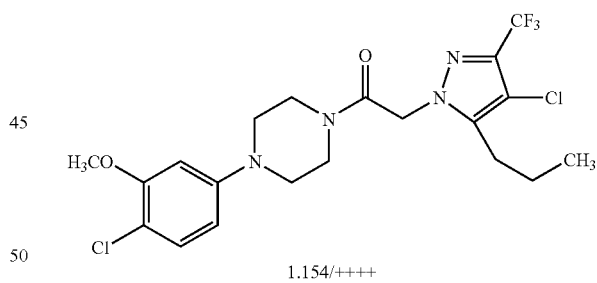
1.154/++++
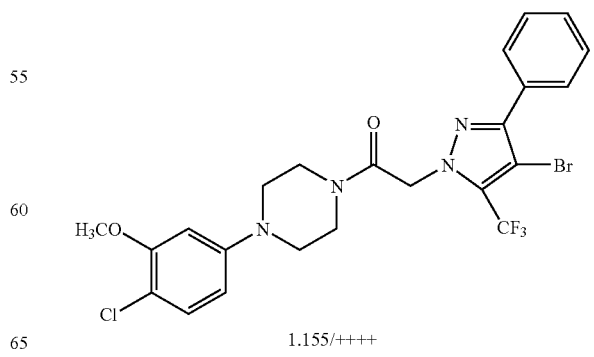
1.155/++++

-continued

Structure

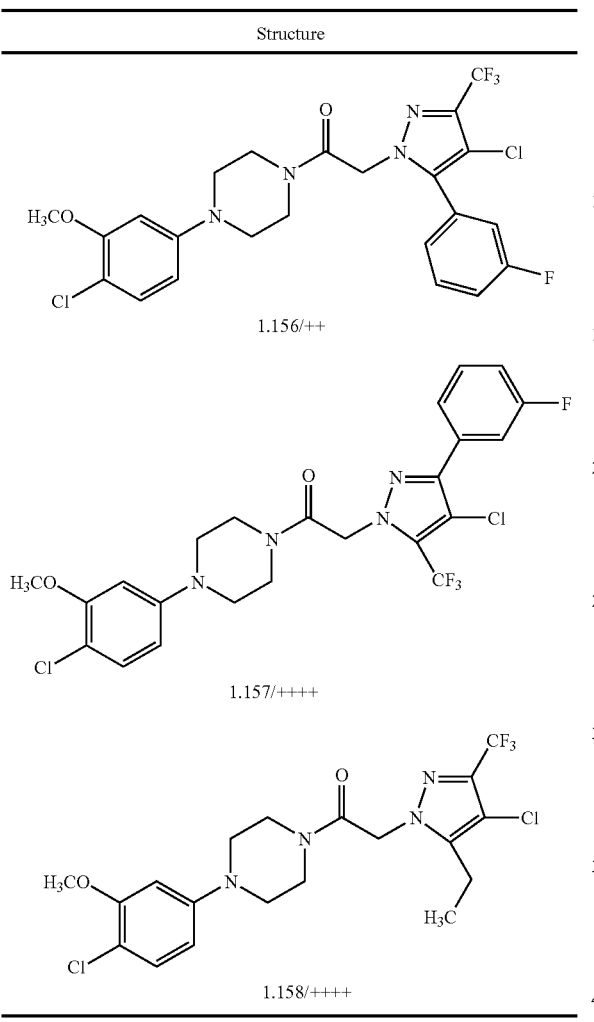

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:
1. A compound having the formula:

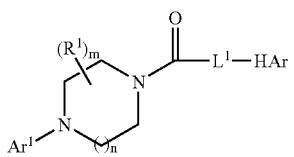

or a pharmaceutically acceptable salt thereof, wherein
the subscript n is 1;
the subscript m is an integer of from 0 to 2;
each $R^1$ is a substituent independently selected from the group consisting of $C_{1-8}$ alkyl and $C_{1-8}$ haloalkyl;

$Ar^1$ is selected from the group consisting of pyridyl, pyrazinyl, and pyridazinyl, each of which is optionally substituted with from one to three $R^2$ substituents independently selected from the group consisting of halogen, —$OR^c$, —$OC(O)R^c$, —$NR^cR^d$, —$SR^c$, —$R^e$, —CN, —$NO_2$, —$CO_2R^c$, —$CONR^cR^d$, —$C(O)R^c$, —$OC(O)NR^cR^d$, —$NR^dC(O)R^c$, —$NR^dC(O)_2R^e$, —$NR^c$—$C(O)NR^cR^d$, —$S(O)R^e$, —$S(O)_2R^e$, —$NR^cS(O)_2R^e$, —$S(O)_2NR^cR^d$, —$N_3$, —$X^2OR^c$, —$X^2OC(O)R^c$, —$X^2NR^cR^d$, —$X^2SR^c$, —$X^2CN$, —$X^2NO_2$, —$X^2CO_2R^cC$, —$X^2CONR^cR^d$, —$X^2C(O)R^c$, —$X^2OC(O)NR^cR^d$, —$X^2NR^dC(O)R^c$, —$X^2NR^dC(O)_2R^e$, —$X^2NR^cC(O)NR^cR^d$, —$X^2S(O)R^e$, —$X^2S(O)_2R^e$, —$X^2NR^cS(O)_2R^e$, —$X^2S(O)_2NR^cR^d$ and —$X^2N_3$, wherein $X^2$ is $C_{1-4}$ alkylene, and each $R^c$ and $R^d$ is independently selected from hydrogen, $C_{1-8}$ alkyl, $C_{1-8}$ haloalkyl, $C_{3-6}$ cycloalkyl, $C_{2-8}$ alkenyl, and $C_{2-8}$ alkynyl, and each $R^e$ is independently selected from the group consisting of $C_{1-8}$ alkyl, $C_{1-8}$ haloalkyl, $C_{3-6}$ cycloalkyl, $C_{2-8}$ alkenyl, and $C_{2-8}$ alkynyl, and each of $R^c$, $R^d$ and $R^e$ is optionally further substituted with from one to three members selected from the group consisting of OH, O($C_{1-8}$ alkyl), SH, S($C_{1-8}$ alkyl), CN, $NO_2$, $NH_2$, NH($C_{1-8}$ alkyl) and N($C_{1-8}$ alkyl)$_2$;

HAr is a heteroaryl group selected from the group consisting of pyrazolyl and benzopyrazolyl each of which is linked through a ring member nitrogen atom to the remainder of the molecule and is substituted with from one to three $R^3$ substituents independently selected from the group consisting of halogen, phenyl, thienyl, furanyl, pyridyl, pyrimidinyl, pyrazinyl, pyridazinyl, pyrazolyl, imidazolyl, thiazolyl, oxazolyl, isoxazolyl, isothiazolyl, triazolyl, tetrazolyl, oxadiazolyl, —$OR^f$, —$OC(O)R^f$, —$NR^fR^g$, —$SR^f$, —$R^h$, —CN, —$NO_2$, —$CO_2R^f$, —$CONR^fR^g$, —$C(O)R^f$, —$OC(O)NR^fR^g$, —$NR^gC(O)R^f$, —$NR^gC(O)_2R^h$, —$NR^f$—$C(O)NR^fR^g$, —$S(O)R^h$, —$S(O)_2R^h$, —$NR^fS(O)_2R^h$, —$S(O)_2NR^fR^g$, —$NR^fS(O)_2R^h$, —$NR^fS(O)_2NR^fR^g$, —$N_3$, —$X^3R^f$, —$X^3OC(O)R^f$, —$X^3NR^fR^g$, —$X^3SR^f$, —$X^3CN$, —$X^3NO_2$, —$X^3CO_2R^f$, —$X^3CONR^fR^g$, —$X^3C(O)R^f$, —$X^3OC(O)NR^fR^g$, —$X^3NR^gC(O)R^f$, —$X^3NR^gC(O)_2R^h$, —$X^3NR^f$—$C(O)NR^fR^g$, —$X^3S(O)R^h$, —$X^3S(O)_2R^h$, —$X^3NR^fS(O)_2R^h$, and —$X^1S(O)_2NR^fR^g$ wherein $X^3$ is $C_{1-4}$ alkylene, each $R^f$ and $R^g$ is independently selected from hydrogen, $C_{1-8}$ alkyl, $C_{1-8}$ haloalkyl, $C_{3-6}$ cycloalkyl, $C_{2-8}$ alkenyl, and $C_{2-8}$ alkynyl, and each $R^h$ is independently selected from the group consisting of $C_{1-8}$ alkyl, $C_{1-8}$ haloalkyl, $C_{3-6}$ cycloalkyl, $C_{2-8}$ alkenyl, and $C_{2-8}$ alkynyl, and wherein any phenyl, thienyl, furanyl, pyridyl, pyrimidinyl, pyrazinyl, pyridazinyl, pyrazolyl, imidazolyl, thiazolyl, oxazolyl, isoxazolyl, isothiazolyl, triazolyl, tetrazolyl or oxadiazolyl groups present are optionally substituted with from one to three substitutents selected from the group consisting of halogen, —$OR^f$, —$NR^fR^g$, —$R^h$, —CN, —$NO_2$, —$CO_2R^f$, —$CONR^fR^g$, —$C(O)R^f$, —$X^3OR^f$, —$X^3NR^fR^g$, —$X^3NR^fS(O)_2R^h$ and $X^3S(O)_2NR^fR^g$; and $L^1$ is a —$CH_2$ group.

2. A compound of claim 1, wherein $Ar^1$ is selected from the group consisting of:
(i) pyridinyl, substituted with from 1 to 3 $R^2$ groups; and
(ii) pyrazinyl, substituted with from 1 to 3 $R^2$ groups;
wherein each $R^2$ is a member independently selected from the group consisting of halogen, —$OR^c$, —$OC(O)R^c$, —$NR^cR^d$, —$SR^c$, —$R^e$, —CN, —$NO_2$, —$CO_2R^c$, —$CONR^cR^d$, —$C(O)R^c$, —$OC(O)NR^cR^d$, —$NR^dC(O)R^c$, —$NR^dC(O)_2R^e$, —$NR^c$—$C(O)NR^cR^d$, —$S(O)R^e$, —$S(O)_2R^e$, —$NR^cS$ (O)$_2$R$^e$, —S(O)$_2$NR$^c$R$^d$ and —N$_3$, wherein each R$^c$ and R$^d$ is independently selected from hydrogen, C$_{1-8}$ alkyl, C$_{1-8}$ haloalkyl, C$_{3-6}$ cycloalkyl, C$_{2-8}$ alkenyl and C$_{2-8}$ alkynyl, and each R$^e$ is independently selected from the group consisting of C$_{1-8}$ alkyl, C$_{1-8}$ haloalkyl, C$_{3-6}$ cycloalkyl, C$_{2-8}$ alkenyl and C$_{2-8}$ alkynyl.

3. A compound of claim 1, wherein Ar$^1$ is selected from the group consisting of:

(i) pyridinyl substituted with from 1 to 3 R$^2$ groups; and (ii) pyrazinyl, substituted with from 1 to 3 R$^2$ groups;

wherein each R$^2$ is a member independently selected from the group consisting of halogen, —X$^2$OR$^c$, —X$^2$OC(O)R$^c$C, —X$^2$NR$^c$R$^d$, —X$^2$SR$^c$, —X$^2$CN, —X$^2$NO$_2$, —X$^2$CO$_2$R$^c$, —X$^2$CONR$^c$R$^d$, —X$^2$C(O)R$^c$, —X$^2$OC(O)NR$^c$R$^d$, —X$^2$NR$^d$C(O)R$^e$, —X$^2$NR$^d$C(O)$_2$R$^e$, —X$^2$NR$^c$C(O)NR$^c$R$^d$, —X$^2$S(O)R$^e$, —X$^2$S(O)$_2$R$^e$, —X$^2$NR$^c$S(O)$_2$R$^e$, —X$^2$S(O)$_2$NR$^c$R$^d$ and —X$^2$N$_3$, wherein each R$^c$ and R$^d$ is independently selected from hydrogen, C$_{1-8}$ alkyl, C$_{1-8}$ haloalkyl, C$_{3-6}$ cycloalkyl, C$_{2-8}$ alkenyl and C$_{2-8}$ alkynyl, and each R$^e$ is independently selected from the group consisting of C$_{1-8}$ alkyl, C$_{1-8}$ haloalkyl, C$_{3-6}$ cycloalkyl, C$_{2-8}$ alkenyl and C$_{2-8}$ alkynyl.

4. A compound of claim 1, wherein HAr is a member selected from the group consisting of pyrazolyl and benzopyrazolyl each of which is optionally substituted with from one to three-R$^3$ groups independently selected from the group consisting of halogen, phenyl, thienyl, —OR$^f$, —COR$^f$, —CO$_2$R$^f$, —CONR$^f$R$^g$, —NO$_2$, —R$^h$, —CN, —SR$^f$, —S(O)R$^h$, —S(O)$_2$R$^h$ and —NR$^f$R$^g$, wherein R$^f$ and R$^g$ are each independently selected from the group consisting of H, C$_{1-8}$ alkyl, C$_{3-6}$ cycloalkyl and C$_{1-8}$ haloalkyl, and each R$^h$ is independently selected from the group consisting of C$_{1-8}$ alkyl, C$_{3-6}$ cycloalkyl and C$_{1-8}$ haloalkyl.

5. A compound of claim 1, wherein HAr is pyrazolyl or benzopyrazolyl, each of which is optionally substituted with from one to three R$^3$ groups independently selected from the group consisting of halogen, phenyl, thienyl, —OR$^f$, —CO$_2$R$^f$, —COR$^f$, —CONR$^f$R$^g$, —NO$_2$, —R$^h$, —CN, —SR$^f$, —S(O)R$^h$, —S(O)$_2$R$^h$ and —NR$^f$R$^g$, wherein each R$^f$ and R$^g$ is independently selected from the group consisting of H, C$_{1-8}$ alkyl and C$_{1-8}$ haloalkyl, and each R$^h$ is independently selected from the group consisting of C$_{1-8}$ alkyl and C$_{1-8}$ haloalkyl.

6. A compound of claim 1, wherein HAr is selected from the group consisting of:

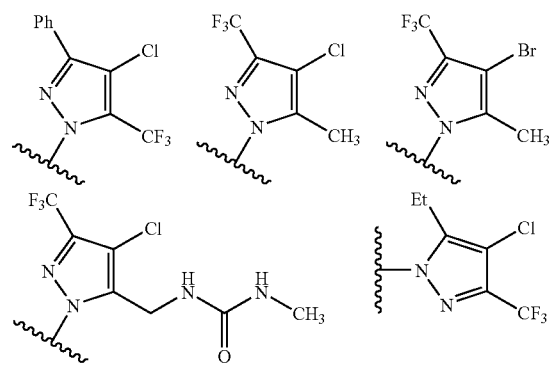

-continued

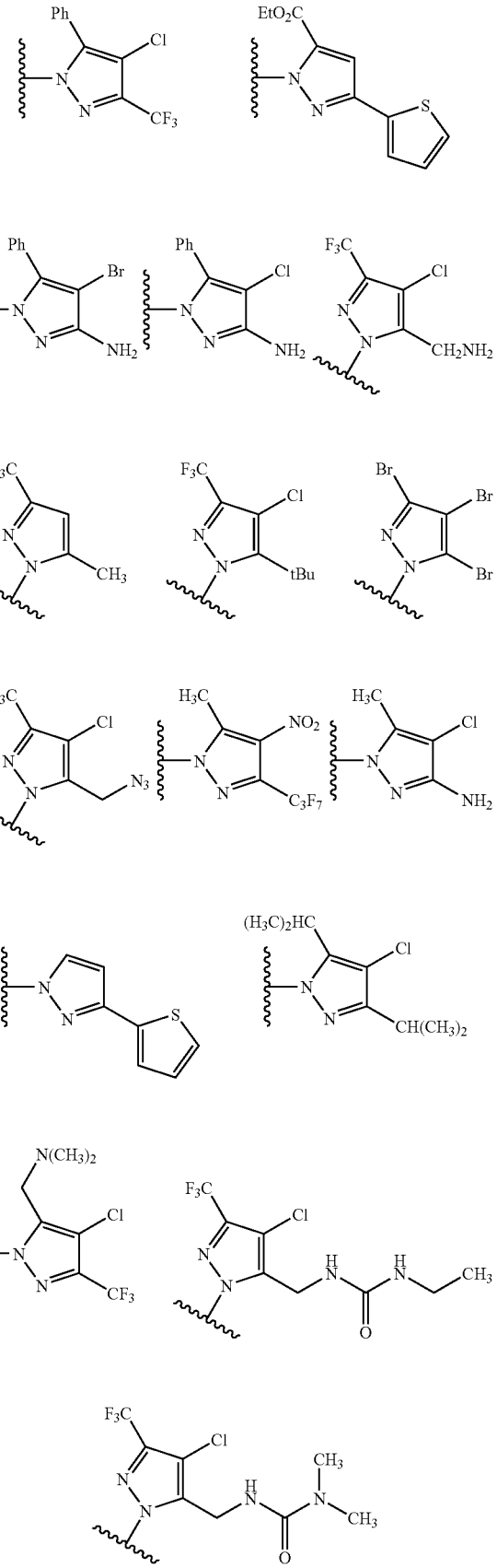

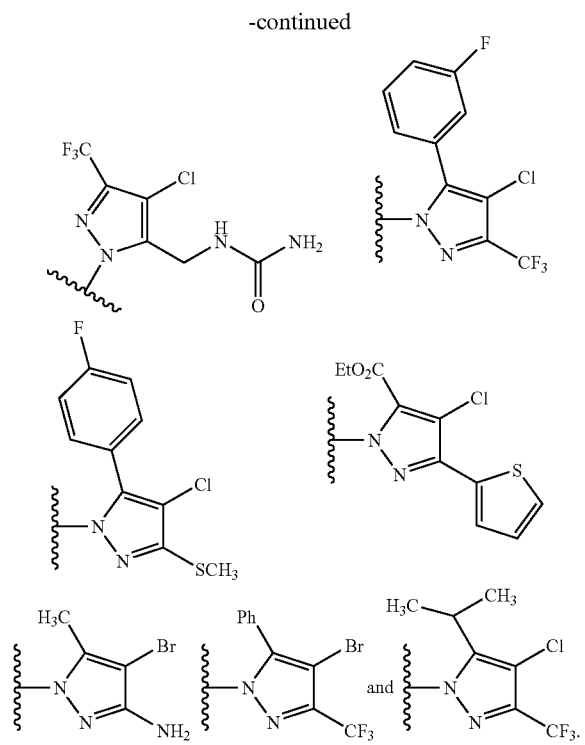
7. A compound of claim 1, wherein HAr is selected from the group consisting of:
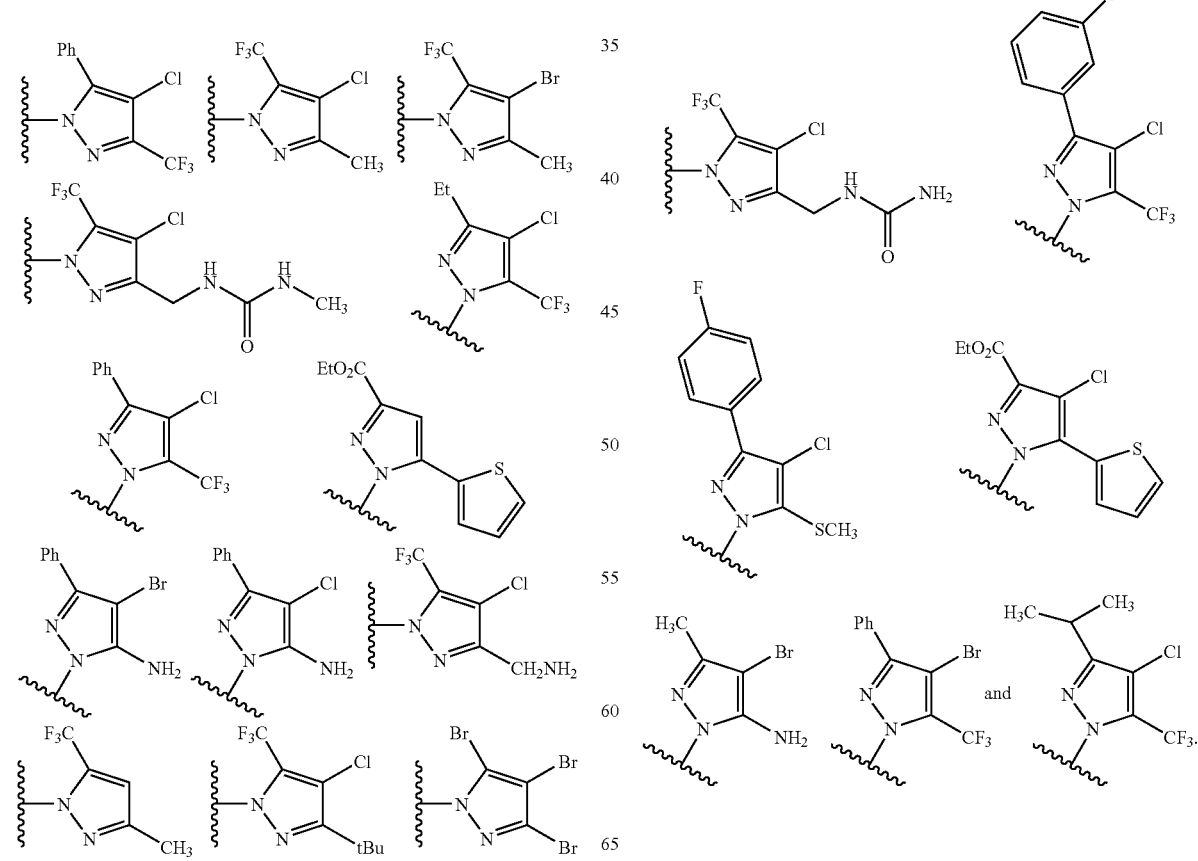
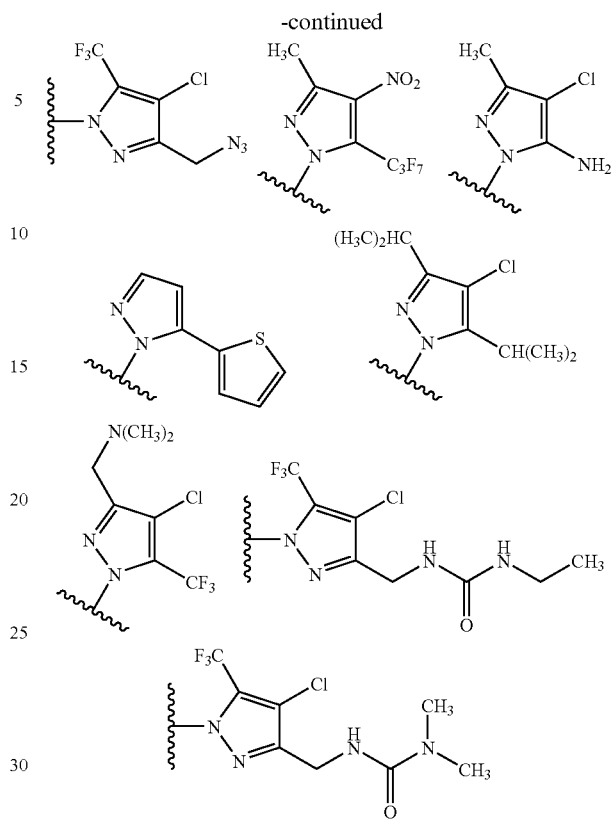

UNITED STATES PATENT AND TRADEMARK OFFICE
CERTIFICATE OF CORRECTION

PATENT NO. : 7,449,576 B1
APPLICATION NO. : 11/491540
DATED : November 11, 2008
INVENTOR(S) : Pennell et al.

It is certified that error appears in the above-identified patent and that said Letters Patent is hereby corrected as shown below:

In the Claims:

Claim 1, Column 178, Line 11: please delete "$X^2CO_2R^cC$" and insert --$X^2CO_2R^c$--

Claim 1, Column 178, Line 43: please delete "$X^1$" and insert --$X^3$--

Signed and Sealed this

Twenty-ninth Day of September, 2009

David J. Kappos
*Director of the United States Patent and Trademark Office*